United States Patent
Baryza et al.

(10) Patent No.: US 9,301,923 B2
(45) Date of Patent: Apr. 5, 2016

(54) LIPIDS, LIPID COMPOSITIONS, AND METHODS OF USING THEM

(71) Applicants: Jeremy Baryza, Cambridge, MA (US); Keith Bowman, Cambridge, MA (US); Andrew Geall, Cambridge, MA (US); Tanzina Labonte, Cambridge, MA (US); Cameron Lee, Cambridge, MA (US); Chandra Vargeese, Cambridge, MA (US); Laura West, Cambridge, MA (US); Junping Zhao, Cambridge, MA (US)

(72) Inventors: Jeremy Baryza, Cambridge, MA (US); Keith Bowman, Cambridge, MA (US); Andrew Geall, Cambridge, MA (US); Tanzina Labonte, Cambridge, MA (US); Cameron Lee, Cambridge, MA (US); Chandra Vargeese, Cambridge, MA (US); Laura West, Cambridge, MA (US); Junping Zhao, Cambridge, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/197,124

(22) Filed: Mar. 4, 2014

(65) Prior Publication Data

US 2014/0309277 A1     Oct. 16, 2014

Related U.S. Application Data

(63) Continuation of application No. 12/974,906, filed on Dec. 21, 2010, now abandoned.

(60) Provisional application No. 61/284,787, filed on Dec. 23, 2009.

(51) Int. Cl.
| | | |
|---|---|---|
| *A61K 31/575* | (2006.01) | |
| *A61K 47/06* | (2006.01) | |
| *A61K 9/127* | (2006.01) | |
| *A61K 31/7088* | (2006.01) | |
| *A61K 47/18* | (2006.01) | |
| *A61K 47/28* | (2006.01) | |
| *A61K 47/30* | (2006.01) | |
| *C07J 9/00* | (2006.01) | |
| *C07J 41/00* | (2006.01) | |
| *C07J 43/00* | (2006.01) | |
| *A61K 47/14* | (2006.01) | |
| *C07J 31/00* | (2006.01) | |

(52) U.S. Cl.
CPC .............. *A61K 9/127* (2013.01); *A61K 9/1272* (2013.01); *A61K 31/7088* (2013.01); *A61K 47/14* (2013.01); *A61K 47/18* (2013.01); *A61K 47/28* (2013.01); *A61K 47/30* (2013.01); *C07J 9/00* (2013.01); *C07J 41/0055* (2013.01); *C07J 43/003* (2013.01); *C07J 31/006* (2013.01)

(58) Field of Classification Search
CPC .... A61K 2300/00; A61K 47/18; A61K 47/30; A61K 31/7088; A61K 47/14; A61K 47/28; A61K 9/127; A61K 9/1272; C07J 31/006; C07J 41/0055; C07J 43/003; C07J 9/00
USPC ........ 514/44 A, 788, 19.3, 44, 169, 772, 785; 544/178, 400, 402; 546/184; 564/197, 564/509; 424/450, 489, 130.1, 94.1; 540/113; 549/555; 560/160; 568/675
See application file for complete search history.

(56) References Cited

U.S. PATENT DOCUMENTS

| | | |
|---|---|---|
| 4,173,641 A | 11/1979 | Kraska |
| 4,987,071 A | 1/1991 | Cech et al. |
| 5,080,896 A | 1/1992 | Visser et al. |
| 5,589,332 A | 12/1996 | Shih et al. |
| 5,741,679 A | 4/1998 | George et al. |

(Continued)

FOREIGN PATENT DOCUMENTS

| | | |
|---|---|---|
| AU | 2007247458 B2 | 11/2007 |
| CN | 1311189 A | 9/2001 |

(Continued)

OTHER PUBLICATIONS

Adinolfi et al.; "Enhancement of Glucantime Therapy of Murine Leishmania Donovani Infection by a Synthetic Immunopotentiating Compound (CP-46,665-1)"; Am. J. Trop. Med. Hyg.; 34(2):270-277 (1985).

(Continued)

*Primary Examiner* — Janet Epps-Smith
(74) *Attorney, Agent, or Firm* — Brinks Gilson & Lione

(57) ABSTRACT

Disclosed are formulation and optimization protocols for delivery of therapeutically effective amounts of biologically active agents to liver, tumors, and/or other cells or tissues. Also provided are compositions and uses for cationic lipid compounds of formula (I).

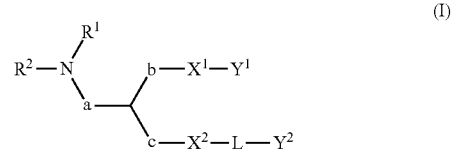

The invention also relates to compositions and uses for stealth lipids of formula (XI).

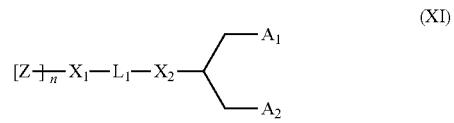

Also provided are processes for making such compounds, compositions, and formulations, plus methods and uses of such compounds, compositions, and formulations to deliver biologically active agents to cells and/or tissues.

8 Claims, No Drawings

(56) References Cited

U.S. PATENT DOCUMENTS

| | | | |
|---|---|---|---|
| 5,834,186 | A | 11/1998 | George et al. |
| 5,849,902 | A | 12/1998 | Arrow et al. |
| 5,871,914 | A | 2/1999 | Nathan |
| 5,989,912 | A | 11/1999 | Arrow et al. |
| 6,166,197 | A | 12/2000 | Cook et al. |
| 7,404,969 | B2 | 7/2008 | Chen et al. |
| 2002/0157568 | A1 | 10/2002 | Adachi et al. |
| 2006/0240554 | A1 | 10/2006 | Chen et al. |
| 2008/0020058 | A1 | 1/2008 | Chen et al. |
| 2008/0188675 | A1 | 8/2008 | Chen et al. |
| 2008/0214437 | A1 | 9/2008 | Mohapatra et al. |
| 2009/0048197 | A1* | 2/2009 | Chen et al. ............... 514/44 |

FOREIGN PATENT DOCUMENTS

| | | |
|---|---|---|
| CN | 101468203 A | 7/2009 |
| EP | 0187702 A1 | 7/1986 |
| EP | 0188311 A2 | 7/1986 |
| EP | 1946761 A1 | 10/2005 |
| GB | 2005248 A | 4/1979 |
| JP | 51-79734 A | 7/1976 |
| JP | 2000281569 A | 3/1999 |
| JP | 2002-212477 A | 7/2002 |
| WO | 9748712 A1 | 12/1997 |
| WO | 9827104 A1 | 6/1998 |
| WO | 9841214 A1 | 9/1998 |
| WO | 9907409 A1 | 2/1999 |
| WO | 9929842 A1 | 6/1999 |
| WO | 9932619 A1 | 7/1999 |
| WO | 9933791 A1 | 7/1999 |
| WO | 0001846 A2 | 1/2000 |
| WO | 0024931 A2 | 5/2000 |
| WO | 0026226 A1 | 5/2000 |
| WO | 0030444 A1 | 6/2000 |
| WO | 0044895 A1 | 8/2000 |
| WO | 0044914 A1 | 8/2000 |
| WO | 0129058 A1 | 4/2001 |
| WO | 0136646 A1 | 5/2001 |
| WO | 2005121348 A1 | 12/2005 |
| WO | 2006007712 A1 | 1/2006 |
| WO | 2006016097 A2 | 2/2006 |
| WO | WO 2007/076328 A2 | 7/2007 |
| WO | 2007128477 A2 | 11/2007 |
| WO | 2008103276 A2 | 8/2008 |
| WO | WO 2008096690 A1 * | 8/2008 |
| WO | WO 2008103276 A2 * | 8/2008 |
| WO | 2008137758 A2 | 11/2008 |
| WO | 2008147438 A2 | 12/2008 |
| WO | 2009086558 A1 | 7/2009 |
| WO | WO 2009/082817 A1 | 7/2009 |
| WO | 2009129387 A2 | 10/2009 |
| WO | 2010009065 A9 | 1/2010 |
| WO | 2010054384 A1 | 5/2010 |
| WO | 2010054401 A1 | 5/2010 |
| WO | 2010054405 A1 | 5/2010 |
| WO | 2010054406 A1 | 5/2010 |
| WO | WO 2010054401 A1 * | 5/2010 |
| WO | 2011022460 A1 | 2/2011 |

OTHER PUBLICATIONS

Akhtar et al.; "Cellular uptake and intracellular fate of antisense oligonucleotides"; Trends in Cell Biology; 2 (5):139-144 (1992)[Abstract only].

Akhtar et al.; "Nonviral delivery of synthetic siRNAs in vivo"; The Journal of Clinical Investigation—Review series; 117(12):3623-3632 (2007).

Allshire; "RNAi and Heterochromatin—a Hushed-Up Affair"; Science; 297:1818-1819 (2002).

Bailey et al.; "Modulation of Membrane Fusion by Asymmetric Transbilayer Distributions of Amino Lipids"; Biochemistry; 33:12573-12580 (1994).

Bangham et al.; "Diffusion of univalent ions across the lamellae of swollen phospholipids"; Journal of Molecular Biology; 13(1):238-252 (1965) [Abstract only].

Bass; "The short answer"; Nature-news and views; 411:428-429 (2001).

Behlke; "Progress Towards in Vivo Use of siRNAs"; Molecular Therapy—Review Article; 13(4):644-670 (2006).

Berdel et al.; "Lack of therapeutic activity of the lipoidal amine CP-46.665 in rodent tumors and human nonseminomatous germ cell tumors growing in nude mice"; Cancer Letters; 38(1-2):191-197 (1987)[Abstract only].

Berdel et al.; "Cytotoxicity of the Alkyl-linked Lipoidal Amine 4-Aminomethyl-1-[2.3-(di-n-decyloxy)-n-propyl]-4-phenylpiperidine (CP-46,665) in Cells from Human Tumors and Leukemias"; Cancer Research; 45:1206-1213 (1985).

Berdel et al.; "Ether lipid derivatives: antineoplastic activity in vitro and the structure-activity relationship"; Lipids; 21 (4):301-304 (1986)[Abstract only].

Berdel et al.; "Studies on the Role of Ether Lipids as Purging Agents in Autologous Bone Marrow Transplantation" In the Pharmacological Effect of Lipids III (The American Oil Chemists' Society, Champaign, IL); pp. 338-360 (1989).

Berens et al.; "Effects of structural modifications of ether lipids on antiproliferative activity against human glioma cell lines"; Anticancer Research; 13(2):401-405 (1993)[Abstract only].

Brigham et al.; "In vivo Transfection of Murine Lungs with a Functioning Prokaryotic Gene Using a Liposome Vehicle"; American Journal of the Medical Sciences; 298(4):278 (1989)[Abstract only].

Brody et al.; "Aptamers as therapeutic and diagnostic agents"; J. Biotechnol.; 74(1):5-13 (2000)[Abstract only].

Cech; "Ribozymes and their medical implications"; JAMA; 260(20):3030-3034 (1988)[Abstract only].

Cook; "Medicinal chemistry of antisense oligonucleotides—future opportunities"; Anticancer Drug Des.; 6(6):585-607 (1991)[Abstract only].

Crooke; "Advances in Understanding the Pharmacological Properties of Antisense Oligonucleotides"; Adv. Pharmacal.; 40:1-49 (1997)[Abstract only].

Crooke; "Antisense Therapeutics"; Biotechnol. Genet. Eng. Rev.; 15:121-157 (1998).

Crooke; "Progress in Antisense Technology: The End of the Beginning"; Methods in Enzymology; 313:3-45 (2000).

Danhauser et al.; "Structure-cytoloxicity studies on alkyllysophospholipids and some analogs in leukemic blasts of human origin in vitro"; Lipids; 22(11):911-915 (1987)[Abstract only].

Database: XP-002633767—Preparation and formulation of cholesteryl-containing cationic lipid nanoparticle used for delivering various bioi. active mols. to cells (2008).

Database: XP-002633768—RN: 1050504-57-8 (Compound) Registry (2008).

Delgado et al.; "The uses and properties of PEG-linked proteins"; Cril. Rev. Ther. Drug Carrier Syst.; 9(3-4):249-304 (1992)[Abstract only].

Delihas et al.; "Natural Antisense RNA/target RNA interactions: Possible models for antisense oligonucleotide drug design"; Nature Biotechnology—Review; 15(8):751-753 (1997).

Ding et al.; "Non-ionic Surfactant Modified Cationic Liposomes Mediated Gene Transfection in Vitro and in the Mouse Lung"; Bioi. Pharm. Bull.; 32(2):311-315 (2009).

Duda et al.; "Reversal of Chemotherapeutically Induced Defective Wound Healing With CP-46,665"; Surgical Forum; 36:419-421 (1985).

Duval-Valentin et al.; "Specific inhibition of transcription by triple helix-forming oligonucleotides"; Proc. Nail. Acad. Sci. USA; 89:504-508 (1992).

Egholm et al.; "PNA hybridizes to complementary oligonucleotides obeying the Watson-Crick hydrogen-bonding rules"; Nature—Letters to Nature; 365:566-568 (1993).

Elbashir et al.; "Duplexes of 21-nucleotide RNAs mediate RNA interference in cultured mammalian cells"; Nature—Letter to Nature; 411:494-498 (2001).

(56) References Cited

OTHER PUBLICATIONS

Felgner; "Particulate systems and polymers for in vitro and in vivo delivery of polynucleotides"; Advanced Drug Delivery Reviews; 5(3):163-187 (1990)[Abstract only].

Felgner; "Cationic Lipid/Polynucleotide Condensates for in Vitro and in Vivo Polynucleotide Delivery—The Cytofectins"; J. Liposome Res.; 3:3-6 (1993).

Felgner et al.; "Lipofection: A highly efficient. lipid-mediated DNA-transfection procedure"; Proc. Natl. Acad. Sci. USA; 84:7413-7417 (1987).

Fox; "Targeting DNA with triplexes"; Curr. Med. Chem.; 7(1):17-37 (2000)[Abstract only].

Freier et al.; "Improved free-energy parameters for predictions of RNA duplex stability"; Proc. Natl. Acad. Sci. USA; 83:9373-9377 (1986).

Gold et al.; "Diversity of Oligonucleotide Functions"; Annual Review of Biochemistry; 64:763-797 (1995)[Abstract only].

Greenhalgh et al.; "Immunomodulators and wound healing"; J. Trauma; 27(5):510-514 (1987)[Abstract only].

Hall et al.; "Establishment and Maintenance of a Heterochromatin Domain"; Science; 297:2232-2237 (2002).

Hammann et al.; "Length Variation of Helix III in a Hammerhead Ribozyme and Its Influence on Cleavage Activity"; Antisense & Nucleic Acid Drug Development; 9:25-31 (1999).

Hassani et al.; "Lipid-mediated siRNA delivery down-regulates exogenous gene expression in the mouse brain at picomolar levels"; J. Gene Med.; 7:198-207 (2005).

Hegemann et al.; "Changes of epidermal cell morphology and keratin expression induced by inhibitors of protein kinase C"; Journal of Dermatological Science; 3(2):103-110 (1992)[Abstract only].

Hermann et al.; "Adaptive Recognition by Nucleic Acid Aptamers"; Science—Review: Biochemistry; 287:820-825 (2000).

Heyes et al.; "Cationic lipid saturation influences intracellular delivery of encapsulated nucleic acids"; Journal of Controlled Release; 107:276-287 (2005).

Huang et al.; "Sterol-Modified Phospholipids: Cholesterol and Phospholipid Chimeras with Improved Biomembrane Properties"; J. Am. Chem. Soc.; 130(46):15702-15712 (2008).

Huang et al.; "Disterolphospholipids: Nonexchangeable Lipids and Their Application to Liposomal Drug Delivery"; Angew. Chem. Int. Ed.—Communications, Drug Nanocarriers; 48:4146-4149 (2009).

Janowski et al.; "A microRNA in a Multiple-Turnover RNAi Enzyme Complex"; Nature Chemical Biology; 1 (4):216-222 (2005).

Jayasena; "Aptamers: An Emerging Class of Molecules That Rival Antibodies in Diagnostics"; Clinical Chemistry; 45 (9):1628-1650 (1999).

Jensen et al.; "Exploring the immunotherapeutic potential of two lipoidal amines" In Human Cancer Immunology: Nev. immunomodulating agents and biological response modifiers; Serrou, et al. editors [NY: Elsevier Science Publishing Company Inc.]; 3:55-63 (1982).

Jenuwein; "An RNA-Guided Pathway for the Epigenome"; Science; 297:2215-2218 (2002).

Kusser; "Chemically modified nucleic acid aptamers for in vitro selections: evolving evolution"; J. Biotechnol.; 74 (1):27-38 (2000)[Abstract only].

Leinweber; "Possible Physiological Roles of Carboxylic Ester Hydrolases"; Drug Metabolism Reviews; 18 (4):379-439 (1987).

Liang et al.; "Chemically modified nucleic acid aptamers for in vitro selections: evolving evolution"; Expert Opin. Ther. Patents; 11(6):981-986 (2001).

Livingston et al.; "The Serologic Response to Meth a Sarcoma Vaccines After Cyclophosphamide treatment is Additionally Increased by Various Adjuvants"; The Journal of Immunology; 135(2):1505-1509 (1985).

Lorenz et al.; "Steroid and lipid conjugates of siRNAs to enhance cellular uptake and gene silencing in liver cells"; Bioorganic & Medicinal Chemistry Letters; 14:4975-4977 (2004).

Maslov et al.; "Synthesis of alkyl glycerolipids with various cationic groups linked directly to the glycerol backbone"; Russian Chemical Bulletin; 48(7):1369-1372 (1999).

McManus et al.; "Gene silencing using micro-RNA designed hairpins"; RNA; 8:842-850 (2002).

Modest et al.; "Pharmacological Effects and Anticancer Activity of New Ether Phospholipid Analogs" In the Pharmacological Effect of Lipids III: Role of Lipids in Cancer Research; Kabara, et al. editors (The American Oil Chemists' Society-Champaign, IL); pp. 330-337 (1989).

Morrissey et al.; "Potent and persistent in vivo anti-HBV activity of chemically modified siRNAs"; Nature Biotechnology-Letters; 23(8):1002-1007 (2005).

Noseda et al.; "In Vitro Antiproliferative Activity of Combinations of Ether Lipid Analogues and DNA-interactive Agents against Human Tumor Cells"; Cancer Research; 48:1788-1791 (1988).

Okamoto et al.; "Elimination of Leukemic Cells by the Combined Use of Ether Lipids in Vitro"; Cancer Research; 47:2599-2603 (1987).

Ouchi et al.; "Synthesis and antitumor activity of poly(ethylene glycol)s linked to 5-fluorouracil via a urethane or urea bond"; Drug Des. Discov.; 9(1):93-105 (1992)[Abstract only].

Pal-Bhadra et al.; "Heterochromatic Silencing and HP1 Localization in Drosophila Are Dependent on the RNAi Machinery"; Science—Reports; 303:669-672 (2004).

Player et al.; "The 2-5A System: Modulation of Viral and Cellular Processes Through Acceleration of RNA Degradation"; Pharmacal. Ther.; 78(2):55-113 (1998).

Praseuth et al.; "Triple helix formation and the antigene strategy for sequence-specific control of gene expression"; Biochimica et Biophysica Acta (Gene Structures); 1489:181-206 (1999).

Ravasio et al.; "Selective Hydrogenations Promoted by Copper Catalysts. 1. Chemoselectivity. Regioselectivity, and Stereoselectivity in the Hydrogenation of 3-Substituted Steroids"; J. Org. Chem.; 56:4329-4333 (1991).

Reinhart et al.; "MicroRNAs in plants"; Genes Dev.; 16:1616-1626 (2002).

Reinhart et al.; "Small RNAs Correspond to Centromere Heterochromatic Repeats"; Science-Molecular Biology; 297:1831 (2002).

Rejman et al.; "Characterization and transfection properties of lipoplexes stabilized with novel exchangeable polyethylene glycol-lipid conjugates"; Biochimica et Biophysica Acta; 1660:41-52 (2004).

Romberg et al.; "Sheddable Coatings for Long-Circulating Nanoparticles"; Pharmaceutical Research; 25(1):55-71 (2007).

Schick et al.; "Cytotoxic effects of ether lipids and derivatives in human nonneoplastic bone marrow cells and leukemic cells in vitro"; Lipids; 22(11):904-910 (1987)[Abstract only].

Schmajuk et al.; "Antisense Oligonucleotides with Different Backbones"; The Journal of Biological Chemistry; 274 (31):21783-21789 (1999).

Semple et al.; "Efficient encapsulation of antisense oligonucleotides in lipid vesicles using ionizable aminolipids: formation of novel small multilamellar vesicle structures"; Biochimica et Biophysica Acta; 1510:152-166 (2001).

Semple et al.; "Rational design of cationic lipids for siRNA delivery"; Nature Biotechnology-Letters; 28(2):172-176 (2010).

Shoji et al.; "Inhibition of phospholipid/Ca2+-dependent protein kinase and phosphorylation of leukemic cell proteins by CP-46, 665-1, a novel antineoplastic lipoidal amine"; Biochemical and Biophysical Research Communications; 127 (2):590-595 (1985)[Abstract only].

Silverman et al.; "Selective RNA Cleavage by Isolated RNase L Activated with 2-5A Antisense Chimeric Oligonucleotides"; Methods in Enzymology; 313:522-533 (2000).

Spagnou et al.; "Lipidic Carriers of siRNA: Differences in the Formulation, Cellular Uptake, and Delivery with Plasmid DNA"; Biochemistry; 43:13348-13356 (2004).

Stein et al.; "A Specificity Comparison of Four Antisense Types: Morpholino, 2'-0-Methyl RNA, DNA, and Phosphorothioate DNA"; Antisense & Nucleic Acid Drug Development; 7:151-157 (1997).

(56) References Cited

OTHER PUBLICATIONS

Stein et al.; "Antisense Oligonucleotides as Therapeutic Agents Is the Bullet Really Magical?"; Science; 261:1004-1012 (1993).
Stinnett et al.; "Synthetic Immunomodulators for Prevention of Fatal Infections in a Burned Guinea Pig Model"; Annals of Surgery 198(1):53-57 (1983).
Storme et al.; "Effect of lipid derivatives on invasion in vitro and on surface glycoproteins of three rodent cell types"; Lipids; 22(11):847-850 (1987)[Abslract only].
Sullenger et al.; "Overexpression of TAR Sequences Renders Cells Resistant to Human Immunodeficiency Virus Replication"; Cell; 63:601-608 (1990).
Sun; "Technology evaluation: SELEX, Gilead Sciences Inc"; Curr. Opin. Mol. Ther.; 2(1):100-105 (2000)[Abslract only].
Torrence et al.; "Targeting RNA for degradation with a (2'-5')oligoadenylate-antisense chimera"; Proc. Nail. Acad. Sci. USA, 90:1300-1304 (1993).
Turner et al.; "Improved Parameters for Prediction of RNA Structure"; Cold Spring Harbor Symposia on Quantitative Biology; vol. LII:123-133 (1987).
Turner et al.; "Free Energy Increments for Hydrogen Bonds in Nucleic Acid Base Pairs"; J. Am. Chern. Soc. 109:3783-3785 (1987).
Vaughn et al.; "It's a Small RNA World, After All"; Science—Special Section (Viewpoint); 309:1525-1526 (2005).
Verdel et al.; "RNAi-Medialed Targeting of Heterochromatin by the RITS Complex"; Science; 303:672-676 (2004).
Vogler et al.; "Comparison of selective cytotoxicity of alkyllysophospholipids"; Lipids; 26(12):1418-1423 (1991) [Abstract only].
Volger et al.; "Experimental Studies on the Role of Alkyl Lysophospholipids in Autologous Bone Marrow Transplantation"; Lipids; 22(11):919-924 (1987).
Volpe et al.; "Regulation of Heterochromatic Silencing and Histone H3 Lysine-9 Methylation by RNAi"; Science; 297:1833-1837 (2002).
Waymack et al.; "Effect of Two New Immunomodulators on Normal and Burn Injury Neutrophils and Macrophages"; Journal of Burn Care Rehabilitation; 8(1):9-14 (1987).
Waymack et al.; "Effect of Immunomodulators on Macrophage Function in Burned Animals"; Surgical Forum; 36:110-112 (1985).
Waymack et al.; "Mechanisms of action of two new immunomodulators"; Arch. Surg.; 120(1):43-48 (1985)[Abstract only].
Wermuth; "Designing Prodrugs and Bioprecursors"; The Practice of Medicinal Chemistry: Designing Prodrugs and Bioprecursors [2nd Edition][ISBN:0-12-744481-5][Eisevier]. pp. 561-585 (2003).
Werner et al.; "The effect of base mismatches in the substrate recognition helices of hammerhead ribozymes on binding and catalysis"; Nucleic Acids Research; 23(12):2092-2096 (1995).
Wolff et al.; "CP-46,665-1: A Novel Lipoidal Amine with Antimetastatic and Immunomodulatory Properties"; Cancer Immunol. Immunother.; 12:97-103 (1982).
Xie et al.; "Harnessing in vivo siRNA delivery for drug discovery and therapeutic development"; Drug Discovery Today; 11(1-2):67-73 (2006).
Xu et al.; "Mechanism of DNA Release from Cationic Liposome/DNA Complexes Used in Cell Transfection"; Biochemistry—Accelerated Publications; 35:5616-5623 (1996).
Zamore et al.; "RNAi: Double-Stranded RNA Directs the ATP-Dependent Cleavage of mRNA at 21 to 23 Nucleotide Intervals"; Cell; 101:25-33 (2000).
Zamore et al.; "Ribo-gnome: The Big World of Small RNAs"; Science—Special Section—RNA Review; 309:1519-1524 (2005).
Zhang et al.; "Ionization Behavior of Amino Lipids for siRNA Delivery: Determination of Ionization Constants. SAR, and the Impact of Lipid pka on Cationic Lipid-Biomembrane Interactions"; Langmuir; 27(5):1907-1914 (2011).
Hutvagner et al., "A microRNA in a Multiple-Turnover RNAi Enzyme Complex," Science 297:2056-2060 (2002).
Xu, H.; Deng, Y.; Chen, D.; Hong, W.; Lu, Y.; Dong, X. "Esterase-catalyzed dePETylation of pH-sesitive vesicles modified with cleavable PET-lipid derivatives," *Journal of Controlled Release*, 2008, 130, 238-245.
Abstract of CN1311189A.
Abstract of CN101468203A.
Partial Translation of JP 51-79734.

* cited by examiner

SEQUENCE LISTING

```
<160> NUMBER OF SEQ ID NOS: 4

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 2'-O-methyl-nucleotide
<220> FEATURE:
<221> NAME/KEY: modified_base
<222> LOCATION: (13)..(13)
<223> OTHER INFORMATION: 2'-O-methyl-nucleotide
<220> FEATURE:
<221> NAME/KEY: modified_base
<222> LOCATION: (18)..(18)
<223> OTHER INFORMATION: 2'-O-methyl-nucleotide
```

-continued

```
<220> FEATURE:
<221> NAME/KEY: modified_base
<222> LOCATION: (20)..(21)
<223> OTHER INFORMATION: 2'-O-methyl-nucleotides

<400> SEQUENCE: 1
uuuaauugaa accaagacau u                                           21

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl-nucleotide
<220> FEATURE:
<221> NAME/KEY: modified_base
<222> LOCATION: (3)..(6)
<223> OTHER INFORMATION: 2'-O-methyl-nucleotides
<220> FEATURE:
<221> NAME/KEY: modified_base
<222> LOCATION: (9)..(12)
<223> OTHER INFORMATION: 2'-O-methyl-nucleotides
<220> FEATURE:
<221> NAME/KEY: modified_base
<222> LOCATION: (15)..(16)
<223> OTHER INFORMATION: 2'-O-methyl-nucleotides
<220> FEATURE:
<221> NAME/KEY: modified_base
<222> LOCATION: (20)..(21)
<223> OTHER INFORMATION: 2'-O-methyl-nucleotides

<400> SEQUENCE: 2
ugucuugguu ucaauuaaau u                                           21

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: 2'-O-methyl-nucleotide
<220> FEATURE:
<221> NAME/KEY: modified_base
<222> LOCATION: (17)..(17)
<223> OTHER INFORMATION: 2'-O-methyl-nucleotide
<220> FEATURE:
<221> NAME/KEY: modified_base
<222> LOCATION: (20)..(21)
<223> OTHER INFORMATION: 2'-O-methyl-nucleotides

<400> SEQUENCE: 3
uauuuaagga gggugaucuu u                                           21

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(7)
<223> OTHER INFORMATION: 2'-O-methyl-nucleotides
```

```
<220> FEATURE:
<221> NAME/KEY: modified_base
<222> LOCATION: (11)..(14)
<223> OTHER INFORMATION: 2'-O-methyl-nucleotides
<220> FEATURE:
<221> NAME/KEY: modified_base
<222> LOCATION: (19)..(21)
<223> OTHER INFORMATION: 2'-O-methyl-nucleotides

<400> SEQUENCE: 4
agaucacccu ccuuaaauau u                                          21
```

LIPIDS, LIPID COMPOSITIONS, AND METHODS OF USING THEM

SEQUENCE LISTING

The instant application contains a Sequence Listing which has been submitted electronically in ASCII format and is hereby incorporated by reference in its entirety. Said ASCII copy, created on Jun. 17, 2014, is named PAT054004-US-DIV_SL.txt and is 2,584 bytes in size.

FIELD OF THE INVENTION

This invention relates to cationic lipid compounds, stealth lipid compounds and to compositions comprising such compounds. The invention also relates to processes for making such compounds and compositions, and to methods and uses of such compounds and compositions, e.g., to deliver biologically active agents to cells and tissues. The invention describes optimized pKa ranges for cationic lipids for use in lipid formulations to deliver biologically active agents to specific cell types, including especially liver and tumors, and methods for optimizing the formulations.

BACKGROUND TO THE INVENTION

The delivery of biologically active agents (including therapeutically relevant compounds) to subjects is often hindered by difficulties in the compounds reaching the target cell or tissue. In particular, the trafficking of many biologically active agents into living cells is highly restricted by the complex membrane systems of the cells. These restrictions can result in the need to use much higher concentrations of biologically active agents than is desirable to achieve a result, which increases the risk of toxic effects and side effects. One solution to this problem is to utilise specific carrier molecules which are allowed selective entry into the cell. Lipid carriers, biodegradable polymers and various conjugate systems can be used to improve delivery of biologically active agents to cells.

One class of biologically active agents that is particularly difficult to deliver to cells is a biotherapeutic (including nucleosides, nucleotides, polynucleotides, nucleic acids and derivatives). In general, nucleic acids are stable for only a limited duration in cells or plasma. The development of RNA interference, RNAi therapy, RNA drugs, antisense therapy and gene therapy, among others, has increased the need for effective means of introducing active nucleic acid agents into cells. For these reasons, compositions that can stabilise and deliver nucleic acid-based agents into cells are of particular interest.

The most well-studied approaches for improving the transport of foreign nucleic acids into cells involve the use of viral vectors or cationic lipids. Viral vectors can be used to transfer genes efficiently into some cell types, but they generally cannot be used to introduce chemically synthesized molecules into cells.

An alternative approach is to use delivery compositions incorporating cationic lipids which interact with a biologically active agent at one part and interact with a membrane system at another part (for a review, see Feigner, 1990, Advanced Drug Delivery Reviews, 5, 162-187 and Felgner, 1993, J. Liposome Res., 3, 3-16). Such compositions are reported to contain liposomes.

Since the first description of liposomes in 1965 by Bangham (J. Mol. Biol. 13, 238-252), there has been a sustained interest and effort in developing lipid-based carrier systems for the delivery of biologically active agents. The process of introducing functional nucleic acids into cultured cells by using positively charged liposomes is first described by Philip Felgner et al. *Proc. Natl. Acad. Sci., USA,* 84, 7413-7417 (1987). The process was later demonstrated in vivo by K. L. Brigham et al., *Am. J. Med. Sci.,* 298, 278-281 (1989).

Liposomes are attractive carriers since they protect biological molecules from degradation while improving their cellular uptake. Out of the various classes of liposome, liposomes which contain cationic lipids are commonly used for delivering polyanions (e.g. nucleic acids). Such liposomes can be formed using cationic lipids alone and optionally including other lipids and amphiphiles such as phosphatidylethanolamine. It is well known in the art that both the composition of the lipid formulation as well as its method of preparation affect the structure and size of the resultant aggregate.

The use of cationic lipids for cellular delivery of biologically active agents has several advantages. The encapsulation of anionic compounds using cationic lipids is essentially quantitative due to electrostatic interaction. In addition, it is believed that the cationic lipids interact with the negatively charged cell membranes initiating cellular membrane transport (Akhtar et al., 1992, Trends Cell Bio., 2, 139; Xu et al., 1996, Biochemistry 35, 5616).

Following Felgner's early work on introducing functional nucleic acids into cultured cells by using positively charged liposomes, cationic lipid compounds based on general formula I have been disclosed in patent application EP 0 187 702.

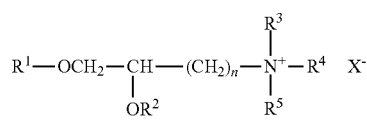

(I)

These cationic lipid compounds generally consist of two alkyl or alkenyl chains linked to the nitrogen containing "head" group. There is also the disclosure of two or three of $R^3$, $R^4$ and $R^5$ taken together being quinuclidino, piperidino, pyrrolidino or morpholino.

Since EP 0 187 702, various other researchers have disclosed cationic lipid compounds. A relevant patent application is WO00/030444 which describes synthetic cationic lipids and liposomes. The application discloses cationic lipid compounds with a variety of different head groups; some examples feature more than one head group. Amongst the compounds disclosed are compounds of formula (II).

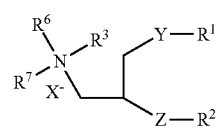

(II)

WO 2005/121348 discloses lipid-based formulations. The nucleic acid-lipid particles disclosed therein comprise an interference RNA molecule, a cationic lipid with alkyl side chains from about 10 to 20 carbon atoms having more than a single site of unsaturation, a noncationic lipid and a conjugated lipid that inhibits aggregation of the particle such as a polyethyleneglycol (PEG)-lipid conjugate or a polyamide (ATTA)-conjugate. Specific cationic lipid compounds disclosed in this patent application include DSDMA, DODMA, DLinDMA, DLenDMA.

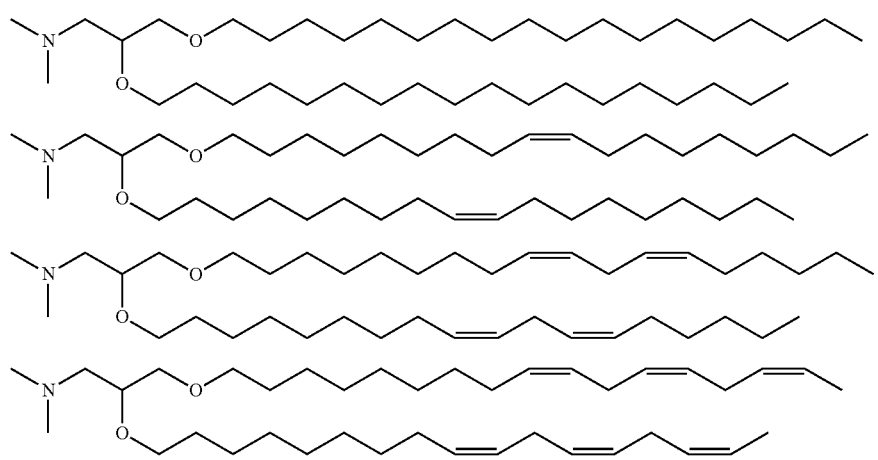

Cullis and Bailey, Biochemistry 1994, 33, 12573-12580, reports liposomes which comprise amino lipids such as the following.

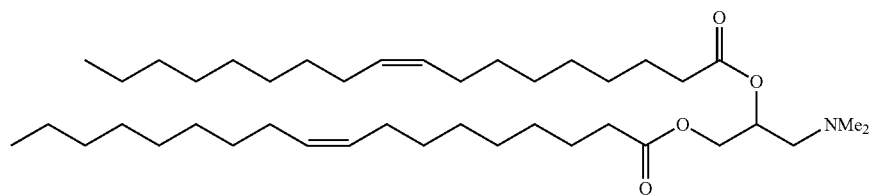 [SMILES: CCCCCCCC/C=C\CCCCCCCC(=O)OCC(CN(C)C)OC(=O)CCCCCCC/C=C\CCCCCCCC]

Another recent publication concerning new cationic lipid compounds is WO2008/137758 which describes a range of amino acid lipid compounds reported as being useful for drug delivery and diagnosis.

US 2006/0240554 and related applications US 2008/0020058 and US 2009/0048197 also relate to cationic lipids. These lipids are reported to be capable of delivering biologically active agents, including small nucleic acid molecules such as short interfering nucleic acids (siNA) to cells and/or tissues.

US2006/0240554, US2008/0020058 and US2009/0048197 describe the use of the cationic lipid CLinDMA, in combination with cholesterol and PEG-DAG for delivering siRNA to cells. The structure of CLinDMA is set out below; at the "head" of the molecule is the —N(Me)$_2$ group. ClinDMA is also referenced herein as E0173.

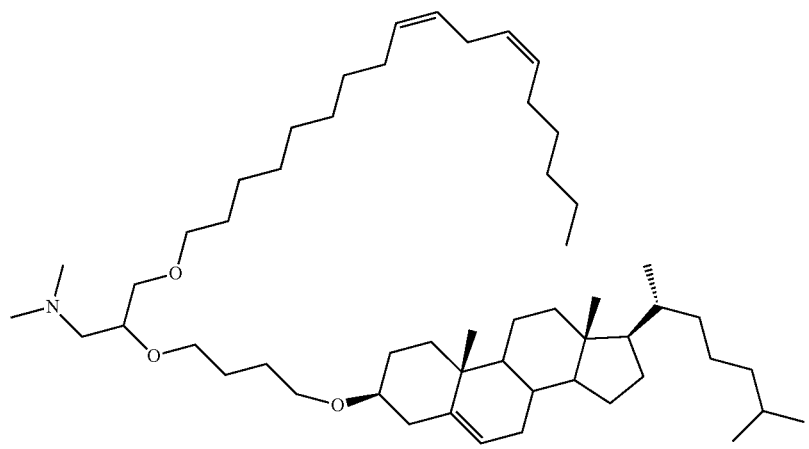 [SMILES: CCCCC/C=C\C/C=C\CCCCCCCCOCC(CN(C)C)OCCCCO[C@H]1CC[C@@]2(C)C(=CCC3C2CC[C@@]2(C)C3CC[C@@H]2[C@H](C)CCCC(C)C)C1]

WO2009/086558 discloses the following compounds:

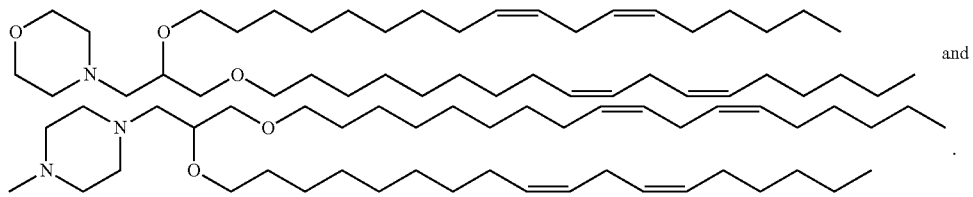

and

It also discloses amino lipids having the following general formula (in which $R^3$ and $R^4$ may join to form an optionally substituted heterocyclic ring of 4 to 6 carbon atoms and 1 or 2 heteroatoms chosen from nitrogen and oxygen):

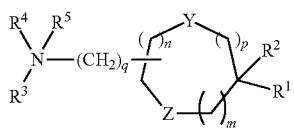

There is a need for further cationic lipids which facilitiate the systemic and local delivery of biologically active agents to cells. There is also a need for cationic lipids which, relative to those cationic lipids that are known in the art, improve the systemic and local delivery of biologically active agents to cells. There is a further need for lipid formulations that have optimized physical characteristics for improved systemic and local delivery of biologically active agents to specific organs and to tumors, especially tumors outside the liver.

SUMMARY OF THE INVENTION

The invention provides novel cationic lipids and stealth lipids, and formulations containing them, and their methods of use. Also provided are formulations for use of such lipids for delivery of therapeutically effective amounts of drugs, including especially RNAi constructs, for delivery to subject in need thereof. Particular formulations containing cationic lipids with a pKa within specific ranges are provided for administering therapeutically effective amounts of drugs to the liver and/or to tumor in the somatic tissues of a subject. As a general rule (to which there are exceptions), formulations that are the most effective for delivery to tumors (as described in greater detail below) contain cationic lipids with a pKa of about 6.1 or below, although particular ranges include from about 5.0 to about 6.7, including especially from about 5.2 to about 6.3, or from about 5.4 to about 6.2, or from about 5.8 to about 6.1, depending on tumor type; whereas formulations that are the most effective for delivery to liver (as described in greater detail below) contain cationic lipids with a pKa of of about 6.1 or above, although particular ranges include from about 5.1 to about 7.4, including from about 5.3 to about 7.3, and including especially from about 5.9 to about 7.0, and in one embodiment is from about 6.2 to about 6.8.

Formulations may be further optimized by one skilled in the art by adjusting other aspects of the formulation, including but not limited to individual selection of, e.g., the pKa of the cationic lipid optimized for the type of cell or organ being targeted, the cationic lipid used, the stealth lipid used, the helper lipid, the neutral lipid used, including whether the neutral lipid is present or absent, the ratio of the selected helper lipid, optional neutral lipid, stealth lipid and cationic lipid, the N/P ratio, the particle size, the dosage regimen, the dose given, the formulation method, and the like.

This invention provides cationic lipids (also referred to herein as "compounds") and compositions comprising such lipids. The invention also provides processes for making such compounds and compositions, and methods and uses of such compounds and compositions to deliver biologically active (including therapeutic) agents to cells (including in vivo delivery) and for optimizing such formulations for delivery in vivo to specific cell types and tissues. This invention also provides stealth lipids.

In one embodiment, the invention provides a compound of formula (I):

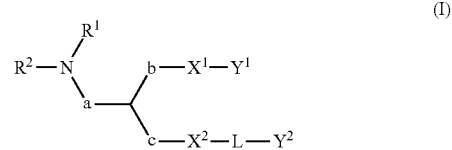

(I)

or a pharmaceutically acceptable derivative thereof, wherein:
$R^1$ and $R^2$ together with the nitrogen atom to which they are attached form an optionally substituted $C_{3-20}$-heterocycloalkyl, $C_{3-20}$-heterocycloalkenyl, $C_{3-20}$-heterocycloalkynyl or $C_{5-20}$-heteroaryl group;
a is absent or optionally substituted $C_{1-4}$ alkylene;
b is absent or optionally substituted $C_{1-4}$ alkylene;
c is absent or optionally substituted $C_{1-4}$ alkylene;
$X^1$ is O or S;
$X^2$ is O or S;
$Y^1$ is optionally substituted $C_{10-30}$alkenyl, $C_{10-30}$alkynyl, $C_{10-30}$heteroalkenyl or $C_{10-30}$heteroalkynyl;
L is absent or $-(L^a)_d-(L^b)_e-(L^c)_f-$, wherein
  $L^a$ is optionally substituted $C_{1-15}$alkylene, $C_{1-15}$alkenylene, $C_{1-15}$alkynylene, $C_{1-15}$heteroalkylene, $C_{1-15}$heteroalkenylene or $C_{1-15}$heteroalkynylene;
  $L^b$ is optionally substituted $C_{6-14}$arylene or $C_{5-13}$heteroarylene;
  $L^c$ is optionally substituted $C_{1-15}$alkylene, $C_{1-15}$alkenylene, $C_{1-15}$alkynylene, $C_{1-15}$heteroalkylene, $C_{1-15}$heteroalkenylene or $C_{1-15}$heteroalkynylene;
  d is 0 or 1;
  e is 0 or 1; and
  f is 0 or 1; and
$Y^2$ is an optionally substituted steroid.

The present invention also provides a pharmaceutical composition comprising a compound of formula (I). These compositions may comprise a biologically active agent, optionally in combination with other lipid components.

The present invention also provides a pharmaceutical composition comprising a compound of formula (XI). These compositions may comprise a biologically active agent, optionally in combination with other lipid components.

In one embodiment, the invention provides a compound of formula (XI):

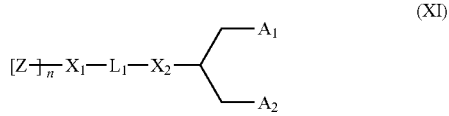

or a salt or pharmaceutically acceptable derivative thereof, wherein:
- Z is a hydrophilic head group component selected from PEG and polymers based on poly(oxazoline), poly(ethylene oxide), poly(vinyl alcohol), poly(glycerol), poly(N-vinyl pyrrolidone), poly[N-(2-hydroxypropyl)methacrylamide] and poly(amino acid)s, wherein the polymer may be linear or branched, and wherein the polymer may be optionally substituted;
- wherein Z is polymerized by n subunits;
- n is a number-averaged degree of polymerization between 10 and 200 units of Z, wherein n is optimized for different polymer types;
- $L_1$ is an optionally substituted $C_{1-10}$ alkylene or $C_{1-10}$ heteroalkylene linker including zero, one, two or more of an ether (e.g., —O—), ester (e.g., —C(O)O—), succinate (e.g., —O(O)C—CH$_2$—CH$_2$—C(O)O—)), carbamate (e.g., —OC(O)—NR'—), carbonate (e.g., —OC(O)O—), ketone (e.g., —C—C(O)—C—); carbonyl (e.g., —C(O)—); urea (e.g., —NRC(O)NR'—), amine (e.g., —NR'—), amide (e.g., —C(O)NR'—), imine (e.g., —C(NR')—), thioether (e.g., —S—), xanthate (e.g., —OC(S)S—), and phosphodiester (e.g., —OP(O)$_2$O—); any of which may be substituted by zero, one or more Z groups;
- wherein R' is independently selected from —H, —NH—, —NH$_2$, —O—, —S—, a phosphate or an optionally substituted $C_{1-10}$ alkylene;
- $X_1$ and $X_2$ are independently selected from a carbon or a heteroatom selected from —NH—, —O—, —S— or a phosphate;
- $A_1$ and $A_2$ are independently selected from a $C_{6-30}$ alkyl, $C_{6-30}$ alkenyl, and $C_{6-30}$ alkynyl, wherein $A_1$ and $A_2$ may be the same or different,
- or wherein $A_1$ and $A_2$ together with the carbon atom to which they are attached form an optionally substituted steroid.

Compositions containing lipids of the invention are useful, e.g., in delivering therapeutic compounds (e.g., one or more biologically active agents) for the treatment of disorders or diseases, including especially those disorders or diseases that respond to modulation of gene expression in a patient or administration of a therapeutic to a targeted cell or tissue. As such, the compounds and compositions of the present invention can be used to treat diseases and conditions in a patient. In particular, the compounds can be utilised in liposomes and/or lipid nanoparticle formulation compositions to deliver biologically active agents, including, e.g., antibodies, low molecular weight compositions, protein therapeutics and nucleic acid compositions such as siRNA for RNAi, to cells or tissues.

In a method of the invention the biologically active agents are delivered, utilising the described cationic lipids, to cells, during which process they may cross epithelial and endothelial tissues, such as skin, mucous membranes, vascular tissues, gastrointestinal tissues, blood brain barrier tissues, opthalmological tissues, pulmonary tissues, liver tissues, cardiac tissues, kidney tissues, tumor tissues, etc. The compounds and compositions can be used for both local and systemic delivery of the biologically active agents.

DETAILED DESCRIPTION OF THE INVENTION

To date, the therapeutic potential of the RNAi field has not been met because of issues with delivery of therapeutically effective amounts of RNAi composition to most somatic tissues. RNAi therapeutics have some effectiveness when directed to tissues in the eye, skin, lungs and liver. A need remains for compositions and methods for delivery of therapeutically effective amounts of RNAi for the treatment of all other somatic tissues and for cancer, including metastatic cancers.

A discovery described herein is that the optimal pKa range of cationic lipids in formulations for delivery to tumors is lower than that for the liver. As a general rule (to which there are exceptions), formulations with the most effective lipids for delivery to tumors (as described in greater detail below) contain cationic lipids with a pKa of from about 5.0 to about 6.7, including especially from about 5.8 to about 6.1, depending on tumor type, whereas formulations with the most effective lipids for delivery to liver (as described in greater detail below) contain cationic lipids with a pKa of from about 5.1 to about 7.4, including especially from about 5.9 to about 7.0. In one embodiment, a cationic lipid with a pKa of about 6.1 or below is more effective in a formulation for delivery of a biologically active agent to a tumor or tumor cell; whereas a cationic lipid with a pKa of about 6.1 or above is more effective in a formulation for delivery of a biologically active agent to the liver or a liver cell.

Provided herein are novel cationic lipids, stealth lipids, and formulations containing them; plus methods of use. Exemplary cationic lipids of a particular pKa range are described, wherein formulations containing these cationic lipids may deliver therapeutically effective amounts of RNAi compositions to tumors when administered to a subject in vivo. Other formulations made with cationic lipids of another pKa range are described, wherein formulations containing these cationic lipids may deliver therapeutically effective amounts of RNAi compositions to liver when administered to a subject in vivo.

Cationic Lipids of the Invention

In one embodiment, the invention provides a compound of formula (I):

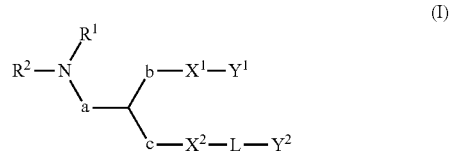

or a pharmaceutically acceptable derivative thereof, wherein:
- $R^1$ and $R^2$ together with the nitrogen atom to which they are attached form an optionally substituted $C_{3-20}$-heterocycloalkyl, $C_{3-20}$-heterocycloalkenyl, $C_{3-20}$-heterocycloalkynyl or $C_{5-20}$-heteroaryl group;
- a is absent or optionally substituted $C_{1-4}$ alkylene;
- b is absent or optionally substituted $C_{1-4}$ alkylene;
- c is absent or optionally substituted $C_{1-4}$ alkylene;
- $X^1$ is O or S;

$X^2$ is O or S;

$Y^1$ is optionally substituted $C_{10-30}$alkenyl, $C_{10-30}$alkynyl, $C_{10-30}$heteroalkenyl or $C_{10-30}$heteroalkynyl;

L is absent or $-(L^a)_d-(L^b)_e-(L^c)_f-$, wherein $L^a$ is optionally substituted $C_{1-15}$alkylene, $C_{1-15}$alkenylene, $C_{1-15}$alkynylene, $C_{1-15}$heteroalkylene, $C_{1-15}$heteroalkenylene or $C_{1-15}$heteroalkynylene;

$L^b$ is optionally substituted $C_{6-14}$arylene or $C_{5-13}$heteroarylene;

$L^c$ is optionally substituted $C_{1-15}$alkylene, $C_{1-15}$alkenylene, $C_{1-15}$alkynylene, $C_{1-15}$heteroalkylene, $C_{1-15}$heteroalkenylene or $C_{1-15}$heteroalkynylene;

d is 0 or 1;

e is 0 or 1; and f is 0 or 1; and $Y^2$ is an optionally substituted steroid.

In one embodiment of formula I, a is an optionally substituted $C_{1-2}$ alkylene. In one embodiment of formula I, a is an optionally substituted $C_1$ alkylene. In one embodiment of formula I, b is an optionally substituted $C_{0-2}$ alkylene. In one embodiment of formula I, b is an optionally substituted $C_1$ alkylene. In one embodiment of formula I, c is absent or is an optionally substituted $C_1$ alkylene. In one embodiment of formula I, a, b and c are unsubstituted. In one embodiment of formula I, c is absent.

In one embodiment of formula I, $R^1$ and $R^2$ together with the nitrogen atom to which they are attached form an optionally substituted $C_{3-20}$-heterocycloalkyl, $C_{3-20}$-heterocycloalkenyl or $C_{3-20}$-heterocycloalkynyl group. In one embodiment of formula I, $R^1$ and $R^2$ together with the nitrogen atom to which they are attached form an optionally substituted $C_{3-20}$-heterocycloalkyl group. In one embodiment of formula I, $R^1$ and $R^2$ together with the nitrogen atom to which they are attached form an optionally substituted $C_{5-16}$ group. In one embodiment of formula I, $R^1$ and $R^2$ together with the nitrogen atom to which they are attached form an optionally substituted $C_{5-12}$ group.

In one embodiment of formula I, $R^1$ and $R^2$ together with the nitrogen atom to which they are attached form an optionally substituted $C_5$ group, $C_6$ group or $C_7$ group. In one embodiment of formula I, $R^1$ and $R^2$ together with the nitrogen atom to which they are attached form an optionally substituted $C_5$ group or $C_6$ group.

In one embodiment of formula I, $R^1$ and $R^2$ together with the nitrogen atom to which they are attached are selected from $H^1$ to $H^{52}$.

In one embodiment of formula I, $X^1$ is O. In one embodiment of formula I, $X^2$ is O.

In one embodiment of formula I, L comprises at least one heteroatom. In one embodiment of formula I, L comprises at least one O atom. In one embodiment of formula I, L comprises at least two heteroatoms. In one embodiment of formula I, L comprises at least two substitutions of O atoms. In one embodiment of formula I, $L^c$ is an optionally substituted $C_{1-15}$alkylene or $C_{1-15}$heteroalkylene. In one embodiment of formula I, $L^c$ is selected from any one or more of formulae $L^{c-i}$ to $L^{c-xxxxiii}$.

In one embodiment of formula I, $L^c$ is an optionally substituted $C_{1-15}$heteroalkylene. In one embodiment of formula I, $L^c$ is an optionally substituted $C_{1-11}$ group. In one embodiment of formula I, $L^c$ is an optionally substituted $C_{1-9}$ group. In one embodiment of formula I, $L^c$ is an optionally substituted $C_{3-8}$ group. In one embodiment of formula I, $L^c$ is an optionally substituted $C_{4-7}$ group. In one embodiment of formula I, $L^c$ is an optionally substituted $C_5$, $C_6$ or $C_7$ group.

In one embodiment of formula I, d is 0; e is 0, and f is 1.

In one embodiment of formula I, $Y^1$ is a $C_{12-28}$ group. In one embodiment of formula I, $Y^1$ is a $C_{14-26}$ group. In one embodiment of formula I, $Y^1$ is a $C_{16-24}$ group. In one embodiment of formula I, $Y^1$ is a $C_{16-22}$ group. In one embodiment of formula I, $Y^1$ has at least one alkene group. In one embodiment of formula I, $Y^1$ has 1, 2 or 3 alkene groups. In one embodiment of formula I, $Y^1$ has an alkene group at the omega-3 position. In one embodiment of formula I, $Y^1$ has an alkene group at the omega-6 position. In one embodiment of formula I, $Y^1$ has an alkene group at the omega-9 position.

In one embodiment of formula I, $Y^1$ has at least one cis unsaturated alkene group. In one embodiment of formula I, $Y^1$ has at least two cis unsaturated alkene groups. In one embodiment of formula I, $Y^1$ has at least three cis unsaturated alkene groups. In one embodiment of formula I, $Y^1$ is selected from $Y^{1-i}$ to $Y^{1-vii}$.

In one embodiment of formula I, $Y^2$ is linked to L via an oxygen atom on the optionally substituted steroid. In one embodiment of formula I, $Y^2$ is linked to L via an oxygen atom on the 3-position of the A steroid ring. In one embodiment of formula I, $Y^2$ is a sterol in which the hydrogen atom of the hydroxy group at the 3-position of the A steroid ring has been removed. In one embodiment of formula I, the sterol is cholesterol.

A second embodiment of the invention is represented by a compound of formula (II):

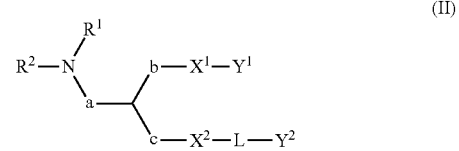

(II)

or a pharmaceutically acceptable derivative thereof, wherein:

$R^1$ and $R^2$ together with the nitrogen atom to which they are attached form an optionally substituted $C_{3-20}$-heterocycloalkyl, $C_{3-20}$-heterocycloalkenyl, $C_{3-20}$-heterocycloalkynyl or $C_{5-20}$-heteroaryl group;

a is absent or optionally substituted $C_{1-4}$ alkylene;

b is absent or optionally substituted $C_{1-4}$ alkylene;

c is absent or optionally substituted $C_{1-4}$ alkylene;

$X^1$ is O or S;

$X^2$ is O or S;

$Y^1$ is optionally substituted $C_{10-30}$alkenyl, $C_{10-30}$alkynyl, $C_{10-30}$heteroalkenyl or $C_{10-30}$heteroalkynyl;

L is $-(L^a)_d-(L^b)_e-(L^c)_f-$, wherein $L^a$ is optionally substituted $C_{1-15}$alkylene, $C_{1-15}$alkenylene, $C_{1-15}$alkynylene, $C_{1-15}$heteroalkylene, $C_{1-15}$heteroalkenylene or $C_{1-15}$heteroalkynylene;

$L^b$ is optionally substituted $C_{6-14}$arylene or $C_{5-13}$heteroarylene;

$L^c$ is optionally substituted $C_{1-15}$alkylene, $C_{1-15}$alkenylene, $C_{1-15}$alkynylene, $C_{1-15}$heteroalkylene, $C_{1-15}$heteroalkenylene or $C_{1-15}$heteroalkynylene;

d is 0 or 1;

e is 0 or 1; and f is 0 or 1;

provided that L comprises one or more heteroatoms, and $Y^2$ is an optionally substituted steroid.

A third embodiment of the invention is represented by a compound of formula (III):

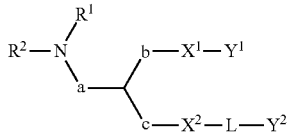

(III)

or a pharmaceutically acceptable derivative thereof, wherein:
$R^1$ and $R^2$ together with the nitrogen atom to which they are attached form an optionally substituted $C_{3-20}$-heterocycloalkyl, $C_{3-20}$-heterocycloalkenyl, $C_{3-20}$-heterocycloalkynyl or $C_{5-20}$-heteroaryl group;
a is methylene;
b is methylene;
c is absent;
$X^1$ is O or S;
$X^2$ is O or S;
$Y^1$ is optionally substituted $C_{10-30}$alkenyl, $C_{10-30}$alkynyl, $C_{10-30}$heteroalkenyl or $C_{10-30}$heteroalkynyl;
L is $-(L^a)_d-(L^b)_e-(L^c)_f-$, wherein
$L^a$ is optionally substituted $C_{1-15}$alkylene, $C_{1-15}$alkenylene, $C_{1-15}$alkynylene, $C_{1-15}$heteroalkylene, $C_{1-15}$heteroalkenylene or $C_{1-15}$heteroalkynylene;
$L^b$ is optionally substituted $C_{6-14}$arylene or $C_{5-13}$heteroarylene;
$L^c$ is optionally substituted $C_{1-15}$alkylene, $C_{1-15}$alkenylene, $C_{1-15}$alkynylene, $C_{1-15}$heteroalkylene, $C_{1-15}$heteroalkenylene or $C_{1-15}$heteroalkynylene;
d is 0 or 1;
e is 0 or 1; and
f is 0 or 1; and
$Y^2$ is an optionally substituted steroid.

A fourth embodiment of the invention is represented by a compound of formula (IV):

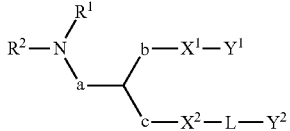

(IV)

or a pharmaceutically acceptable derivative thereof, wherein:
$R^1$ and $R^2$ together with the nitrogen atom to which they are attached form an optionally substituted $C_{3-20}$-heterocycloalkyl, $C_{3-20}$-heterocycloalkenyl, $C_{3-20}$-heterocycloalkynyl or $C_{5-20}$-heteroaryl group;
a is methylene;
b is methylene;
c is absent;
$X^1$ is O or S;
$X^2$ is O or S;
$Y^1$ is optionally substituted $C_{10-30}$alkenyl, $C_{10-30}$alkynyl, $C_{10-30}$heteroalkenyl or $C_{10-30}$heteroalkynyl;
L is $-(L^a)_d-(L^b)_e-(L^c)_f-$, wherein
$L^a$ is optionally substituted $C_{1-15}$alkylene, $C_{1-15}$alkenylene, $C_{1-15}$alkynylene, $C_{1-15}$heteroalkylene, $C_{1-15}$heteroalkenylene or $C_{1-15}$heteroalkynylene;
$L^b$ is optionally substituted $C_{6-14}$arylene or $C_{5-13}$heteroarylene;
$L^c$ is optionally substituted $C_{1-15}$alkylene, $C_{1-15}$alkenylene, $C_{1-15}$alkynylene, $C_{1-15}$heteroalkylene, $C_{1-15}$heteroalkenylene or $C_{1-15}$heteroalkynylene;
d is 0 or 1;
e is 0 or 1; and
f is 0 or 1;
provided that L comprises one or more heteroatoms, and $Y^2$ is an optionally substituted steroid.

A fifth embodiment of the invention is represented by a compound of formula (V):

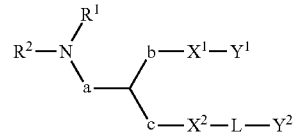

(V)

or a pharmaceutically acceptable derivative thereof, wherein:
$R^1$ and $R^2$ together with the nitrogen atom to which they are attached form an optionally substituted $C_{3-20}$-heterocycloalkyl, $C_{3-20}$-heterocycloalkenyl, $C_{3-20}$-heterocycloalkynyl or $C_{5-20}$-heteroaryl group;
a is methylene;
b is methylene;
c is absent;
$X^1$ is O;
$X^2$ is O;
$Y^1$ is optionally substituted $C_{10-30}$alkenyl, $C_{10-30}$alkynyl, $C_{10-30}$heteroalkenyl or $C_{10-30}$heteroalkynyl;
L is $-(L^a)_d-(L^b)_e-(L^c)_f-$, wherein
$L^a$ is optionally substituted $C_{1-15}$alkylene, $C_{1-15}$alkenylene, $C_{1-15}$alkynylene, $C_{1-15}$heteroalkylene, $C_{1-15}$heteroalkenylene or $C_{1-15}$heteroalkynylene;
$L^b$ is optionally substituted $C_{6-14}$arylene or $C_{5-13}$heteroarylene;
$L^c$ is optionally substituted $C_{1-15}$alkylene, $C_{1-15}$alkenylene, $C_{1-15}$alkynylene, $C_{1-15}$heteroalkylene, $C_{1-15}$heteroalkenylene or $C_{1-15}$heteroalkynylene;
d is 0 or 1;
e is 0 or 1; and
f is 0 or 1;
provided that L comprises one or more heteroatoms, and $Y^2$ is an optionally substituted steroid.

A sixth embodiment of the invention is represented by a compound of formula (VI):

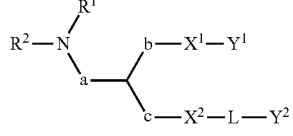

(VI)

or a pharmaceutically acceptable derivative thereof, wherein:
$R^1$ and $R^2$ together with the nitrogen atom to which they are attached form an optionally substituted $C_{3-20}$-heterocycloalkyl, $C_{3-20}$-heterocycloalkenyl, $C_{3-20}$-heterocycloalkynyl or $C_{5-20}$-heteroaryl group;
a is methylene;

b is methylene;
c is absent;
$X^1$ is O;
$X^2$ is O;
$Y^1$ is optionally substituted $C_{10-30}$alkenyl, $C_{10-30}$alkynyl, $C_{10-30}$heteroalkenyl or $C_{10-30}$heteroalkynyl;
L is —$L^c$—, wherein
  $L^c$ is optionally substituted $C_{1-15}$heteroalkylene, $C_{1-15}$heteroalkenylene or $C_{1-15}$heteroalkynylene; and
$Y^2$ is an optionally substituted steroid.

A seventh embodiment of the invention is represented by a compound of formula (VII):

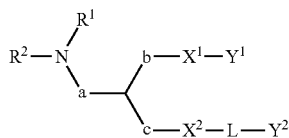

(VII)

or a pharmaceutically acceptable derivative thereof, wherein:
  $R^1$ and $R^2$ together with the nitrogen atom to which they are attached form an optionally substituted $C_{3-20}$-heterocycloalkyl, $C_{3-20}$-heterocycloalkenyl, $C_{3-20}$-heterocycloalkynyl or $C_{5-20}$-heteroaryl group;
  a is methylene;
  b is methylene;
  c is absent;
  $X^1$ is O;
  $X^2$ is O;
  $Y^1$ is an optionally substituted $C_{16-22}$ alkenyl group;
  L is —$L^c$—, wherein
    $L^c$ is optionally substituted $C_{1-15}$heteroalkylene, $C_{1-15}$heteroalkenylene or $C_{1-15}$heteroalkynylene; and
  $Y^2$ is an optionally substituted steroid.

An eighth embodiment of the invention is represented by a compound of formula (VIII):

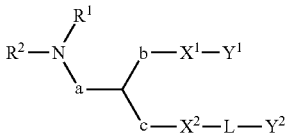

(VIII)

or a pharmaceutically acceptable derivative thereof, wherein:
  $R^1$ and $R^2$ together with the nitrogen atom to which they are attached form an optionally substituted $C_{3-20}$-heterocycloalkyl, $C_{3-20}$-heterocycloalkenyl, $C_{3-20}$-heterocycloalkynyl or $C_{5-20}$-heteroaryl group;
  a is methylene;
  b is methylene;
  c is absent;
  $X^1$ is O;
  $X^2$ is O;
  $Y^1$ is an optionally substituted $C_{16-22}$ alkenyl group;
  L is —$L^c$—, wherein
    $L^c$ is optionally substituted $C_{1-15}$heteroalkylene, $C_{1-15}$heteroalkenylene or $C_{1-15}$heteroalkynylene; and
  $Y^2$ is cholesterol connected through the hydroxy group at the 3-position of the A steroid ring, the hydrogen atom of said hydroxy group being absent.

A ninth embodiment of the invention is represented by a compound of formula (IX):

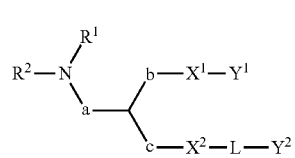

(IX)

or a pharmaceutically acceptable derivative thereof, wherein:
  $R^1$ and $R^2$ together with the nitrogen atom to which they are attached form an optionally substituted $C_{3-20}$-heterocycloalkyl, $C_{3-20}$-heterocycloalkenyl, $C_{3-20}$-heterocycloalkynyl or $C_{5-20}$-heteroaryl group;
  a is methylene;
  b is methylene;
  c is absent;
  $X^1$ is O or S;
  $X^2$ is O or S;
  $Y^1$ is optionally substituted $C_{10-30}$alkenyl, $C_{10-30}$alkynyl, $C_{10-30}$heteroalkenyl or $C_{10-30}$heteroalkynyl;
  L is —$(L^a)_d$—$(L^b)_e$—$(L^c)_f$—, wherein
    $L^a$ is optionally substituted $C_{1-15}$alkylene, $C_{1-15}$alkenylene, $C_{1-15}$alkynylene, $C_{1-15}$heteroalkylene, $C_{1-15}$heteroalkenylene or $C_{1-15}$heteroalkynylene;
    $L^b$ is optionally substituted $C_{6-14}$arylene or $C_{5-13}$heteroarylene;
    $L^c$ is optionally substituted $C_{1-15}$alkylene, $C_{1-15}$alkenylene, $C_{1-15}$alkynylene, $C_{1-15}$heteroalkylene, $C_{1-15}$heteroalkenylene or $C_{1-15}$heteroalkynylene;
    d is 0 or 1;
    e is 0 or 1; and
    f is 0 or 1;
    provided that L comprises one or more heteroatoms, and
  $Y^2$ is an optionally substituted steroid; and
wherein the pKa of the compound is from about 5.1 to about 7.4.

A tenth embodiment of the invention is represented by a compound of formula (X):

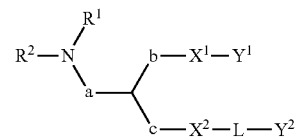

(X)

or a pharmaceutically acceptable derivative thereof, wherein:
  $R^1$ and $R^2$ together with the nitrogen atom to which they are attached form an optionally substituted $C_{3-20}$-heterocycloalkyl, $C_{3-20}$-heterocycloalkenyl, $C_{3-20}$-heterocycloalkynyl or $C_{5-20}$-heteroaryl group;
  a is methylene;
  b is methylene;
  c is absent;
  $X^1$ is O or S;
  $X^2$ is O or S;
  $Y^1$ is optionally substituted $C_{10-30}$alkenyl, $C_{10-30}$alkynyl, $C_{10-30}$heteroalkenyl or $C_{10-30}$heteroalkynyl;

L is —(L$^a$)$_d$—(L$^b$)$_e$—(L$^c$)$_f$—, wherein
  L$^a$ is optionally substituted C$_{1-15}$alkylene, C$_{1-15}$alkenylene, C$_{1-15}$alkynylene, C$_{1-15}$heteroalkylene, C$_{1-15}$heteroalkenylene or C$_{1-15}$heteroalkynylene;
  L$^b$ is optionally substituted C$_{6-14}$arylene or C$_{5-13}$heteroarylene;
  L$^c$ is optionally substituted C$_{1-15}$alkylene, C$_{1-15}$alkenylene, C$_{1-15}$alkynylene, C$_{1-15}$heteroalkylene, C$_{1-15}$heteroalkenylene or C$_{1-15}$heteroalkynylene;
  d is 0 or 1;
  e is 0 or 1; and
  f is 0 or 1;
provided that L comprises one or more heteroatoms, and
  Y$^2$ is an optionally substituted steroid; and
wherein the pKa of the compound is from about 5.0 to about 6.7.

Stealth Lipids

Included in the present invention are "stealth lipids" containing a hydrophilic head group linked to a lipid moiety. Further characterization of stealth lipids is provided below.

In one embodiment is provided a stealth lipid composition of formula (XI):

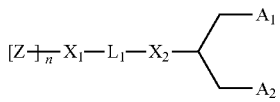

(XI)

or a salt or pharmaceutically acceptable derivative thereof, wherein:
  Z is a hydrophilic head group component selected from PEG and polymers based on poly(oxazoline), poly(ethyleneoxide), poly(vinyl alcohol), poly(glycerol), poly(N-vinylpyrrolidone), poly[N-(2-hydroxypropyl)methacrylamide] and poly(amino acid)s, wherein the polymer may be linear or branched, and wherein the polymer may be optionally substituted;
  wherein Z is polymerized by n subunits;
  n is a number-averaged degree of polymerization between 10 and 200 units of Z, wherein n is optimized for different polymer types;
  L$_1$ is an optionally substituted C$_{1-10}$ alkylene or C$_{1-10}$ heteroalkylene linker including zero, one, two or more of an ether (e.g., —O—), ester (e.g., —C(O)O—), succinate (e.g., —O(O)C—CH$_2$—CH$_2$—C(O)O—)), carbamate (e.g., —OC(O)—NR'—), carbonate (e.g., —OC(O)O—), ketone (e.g., —C—C(O)—C—), carbonyl (e.g., —C(O)—), urea (e.g., —NRC(O)NR'—), amine (e.g., —NR'—), amide (e.g., —C(O)NR'—), imine (e.g., —C(NR')—), thioether (e.g., —S—), xanthate (e.g., —OC(S)S—), and phosphodiester (e.g., —OP(O)$_2$O—); any of which may be substituted by zero, one or more Z groups;
  wherein R' is independently selected from —H, —NH—, —NH$_2$, —O—, —S—, a phosphate or an optionally substituted C$_{1-10}$ alkylene;
  X$_1$ and X$_2$ are independently selected from a carbon or a heteroatom selected from —NH—, —O—, —S— or a phosphate;
  A$_1$ and A$_2$ are independently selected from a C$_{6-30}$ alkyl, C$_{6-30}$ alkenyl, and C$_{6-30}$ alkynyl, wherein A$_1$ and A$_2$ may be the same or different,
  or wherein A$_1$ and A$_2$ together with the carbon atom to which they are attached form an optionally substituted steroid.

In one embodiment, the invention provides a stealth lipid of formula (XII)

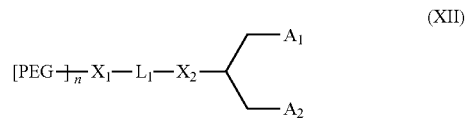

(XII)

or a salt or pharmaceutically acceptable derivative thereof, wherein
  PEG is a poly(ethylene glycol) subunit, wherein the PEG may be linear or branched;
  n is a number-averaged degree of polymerization between 10 and 200 units of PEG, preferably about 23 units, about 45 units or about 68 units;
  L$_1$ is an optionally substituted C$_{1-10}$ alkylene or C$_{1-10}$ heteroalkylene linker containing one, two or more of an ether, ester, succinate, carbamate, carbonate, ketone, carbonyl, urea, amine, amide, imine, thioether, xanthate, and phosphodiester; any of which may be substituted by zero, one or more PEG groups;
  X$_1$ and X$_2$ are independently selected from carbon or oxygen;
  A$_1$ and A$_2$ are independently selected from a C$_{6-30}$ alkyl, C$_{6-30}$ alkenyl, and C$_{6-30}$ alkynyl, wherein A$_1$ and A$_2$ may be the same or different,
  or wherein A$_1$ and A$_2$ together with the carbon atom to which they are attached form an optionally substituted steroid.

The stealth lipids of formulae (XI) and (XII), when formulated with e.g., the cationic lipids of formula (I), provide lipid nanoparticles with increased in vivo potency compared to previous comparable stealth lipids. Therefore the invention provides stealth lipids having the potential to improve efficacy and toxicity. Provided herewith is a composition containing these stealth lipids and the use of these stealth lipids to deliver biologically active agents to cells.

As provided in Table 8, two exemplary lipid nanoparticles formulated using the same process and with otherwise identical compositions, but differing in the stealth lipids, are delivered to the liver. The lipid nanoparticle containing the prior art stealth lipid S010 and delivering an siRNA construct specific to factor VII ("FVII") demonstrates an in vivo inhibition of 72.2% when administered to the liver, while the lipid nanoparticle containing the stealth lipid S006 in comparison demonstrated an in vivo Factor VII inhibition of 83.8%.

In another example provided in Table 9, for delivery in vivo to subcutaneous tumors, six lipid nanoparticles with otherwise identical compositions except for the PEG/stealth lipid are compared for effective delivery of an siRNA specific to Polo-Like Kinase 1 ("PLK1"). The lipid nanoparticle containing the prior art stealth lipid S011 demonstrates an in vivo PLK1 inhibition of 46% in the tumor tissue, while lipid nanoparticles containing the stealth lipids S004, S007, S009, S008, and S005 demonstrate in vivo PLK1 inhibitions of 56%, 65%, 64%, 60%, and 52%, respectively, in the tumor tissue.

The stealth lipids S001 through S009 and S012 through S026 individually and as a class thereby demonstrate improved characteristics when used in formulations and therapeutic composition for use in delivery of biologically active agents, in this case for one or more siRNA.

Novel stealth lipids are provided in the invention. In one embodiment of the invention, the stealth lipid is S001. In one embodiment, the stealth lipid is S002. In one embodiment, the stealth lipid is S003. In one embodiment, the stealth lipid is S004. In one embodiment, the stealth lipid is S005. In one embodiment, the stealth lipid is S006. In one embodiment, the stealth lipid is S007. In one embodiment, the stealth lipid is S008. In one embodiment, the stealth lipid is S009. In one embodiment, the stealth lipid is S012. In one embodiment, the stealth lipid is S013. In one embodiment, the stealth lipid is S014. In one embodiment, the stealth lipid is S015. In one embodiment, the stealth lipid is S016. In one embodiment, the stealth lipid is S017. In one embodiment, the stealth lipid is S018. In one embodiment, the stealth lipid is S019. In one embodiment, the stealth lipid is S020. In one embodiment, the stealth lipid is S021. In one embodiment, the stealth lipid is S022. In one embodiment, the stealth lipid is S023. In one embodiment, the stealth lipid is S024. In one embodiment, the stealth lipid is S025. In one embodiment, the stealth lipid is S026.

Formulations for Delivery of Biologically Active Agents

In general, whereas in the prior art the tissue dependent efficacy was controlled by varying the stealth lipid alone, we have found that efficacy with respect to a particular tissue can surprisingly be controlled by varying the cationic lipid. As discussed below, it has been discovered that lipid formulations for delivery of biologically active agents can be adjusted to preferentially target one cell type or organ over another by alterring only the cationic lipid included in the formulations. For example, cationic lipids whose pKa is about 6.1 or above are much more effective in formulations targeting the liver compared to formulations containing cationic lipids whose pKa is about 6.1 or lower, which are comparatively more effective in formulation targeting tumors in vivo. As a general rule (to which there are exceptions), formulations with the most effective lipids for delivery to tumors (as described in greater detail below) contain cationic lipids with a pKa of from about 5.0 to about 6.7, including especially from about 5.2 to about 6.3, or from about 5.4 to about 6.2, or from about 5.8 to about 6.1, depending on tumor type; whereas formulations with the most effective lipids for delivery to liver (as described in greater detail below) contain cationic lipids with a pKa of from about 5.1 to about 7.4, including from about 5.3 to about 7.3, including from about 5.9 to about 7.0, and in one embodiment including from about 6.2 to about 6.8.

In one embodiment, further optimization is possible by one skilled in the art by combining cationic lipids with the desired pKa range, stealth lipids, helper lipid, optional alkyl resorcinol based lipids and optional neutral lipids into formulations, including, e.g., liposome formulations, liponanoparticle (LNP) formulations, and the like for delivery to specific cells and tissues in vivo. In one embodiment, further optimization is obtained by adjusting the lipid molar ratio between these various types of lipids. In one embodiment, further optimization is obtained by adjusting one or more of: the desired particle size, N/P ratio, formulation methods and/or dosing regimen (e.g., number of doses administered over time, actual dose in mg/kg, timing of the doses, combinations with other therapeutics, etc.). The various optimization techniques known to those of skill in the art pertaining to the above listed embodiments are considered as part of this invention.

In one embodiment, cationic lipids of the invention are provided wherein formulation for delivery of therapeutically effective amounts of biologically active agents comprise at least one each of a cationic lipid, a helper lipid, and a stealth lipid. In one embodiment, such a formulation further comprises at least one neutral lipid. In one embodiment the formulation is optimized for delivery of a biologically active agent for delivery to a tumor. In one embodiment the formulation is optimized for delivery of a biologically active agent for delivery to liver. In one embodiment the formulation is optimized for delivery of a particular type of biologically active agent. Exemplary types of biologically active agents include, but are not limited to, e.g., antibodies, cholesterol, hormones, antivirals, peptides, polypeptides, proteins, nucleoproteins, chemotherapeutics, low molecular weight drugs, vitamins, co-factors, nucleosides, nucleoside derivatives, nucleotides, oligonucleotides, enzymatic nucleic acids, antisense nucleic acids, triplex forming oligonucleotides, 2,5-A antisense chimeras, allozymes, aptamers, ribozyme, decoy RNA molecules and analogs thereof, and small nucleic acid molecules, such as short interfering nucleic acid (siRNA), short interfering RNA (siRNA), double-stranded RNA (dsRNA), micro-RNA (miRNA), and short hairpin RNA (shRNA). Such biologically active agents may be optionally optimized with one or more further chemical and biologic agents to increase their therapeutic value, e.g., modifications that modulate biological properties such as, e.g., stability, half-life, potency, and/or immunogenicity.

For delivery of therapeutic agents to tumors, preferred formulations are selected from those that deliver sufficient amounts of a biologically active agent to effectively modulate the activity of the therapeutic target in a subject in need of such administration.

Where the biologically active agent is an RNAi construct, an effective amount of an RNAi, siRNA, siNA, or shRNA is the amount that provides a knock down (KD) at least 20% or greater, 50% or greater, 60% or greater, 70% or greater, 75% or greater, 80% or greater, 85% or greater, 90% or greater, 95% or greater, or up to 100% of the target mRNA expressed in the target cell. In general, choice of which therapeutically relevant KD range is needed for effective treatment may vary by the pathway being targetted, by cell type or tissue, and/or by the disease or disorder being treated.

Cationic lipids of the type described above, wherein $R^1$ and $R^2$ together with the nitrogen atom to which they are attached form a cyclic "headgroup", are reported herein to be effective cationic lipids for use in lipid formulations. Furthermore, it is now reported that the presence of the cyclic headgroup unexpectedly alters the behaviour of a lipid formulation and, in particular, that it changes the influence of the other substituents.

The headgroup (i.e., $R^1$—N—$R^2$) of the cationic lipid compounds of the invention contains a tertiary amine group. This feature causes the compounds to behave differently, e.g., from if they had, e.g., quaternary (cationic) amine groups because quaternization of the nitrogen puts a fixed charge on the atom, removing its pH responsiveness and causing a compound to behave very differently.

In one specific instance, the presence of a cyclic head group in inventive compounds E0027 and E0014 altered the ability of the cationic lipid as a whole to act as an effective delivery agent in a formulation as compared to lipids E0173 and E0172, which differs only in the head group. For example, as described in greater detail below, a formulation containing a particular cationic lipid (E0173, CLinDMA) with the —N(Me)$_2$ headgroup, when used in a formulation for delivery of an RNAi construct specific to Factor VII, demonstrates an in vivo Factor VII inhibition of 98.5%. When that compound is modified by replacing the L alkylene substituent with an L heteroalkylene substituent (marked with an arrow below), the activity of the compound (E0172) is found to decrease: an in vivo Factor VII inhibition of 40.8% is found.

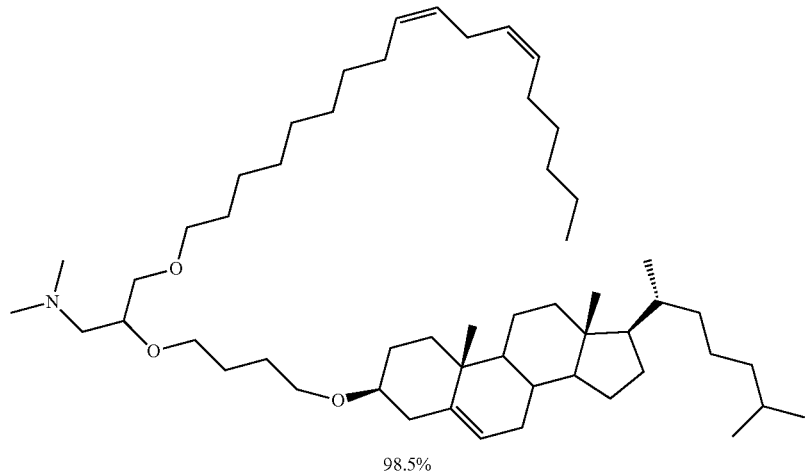
(E0173)
98.5%
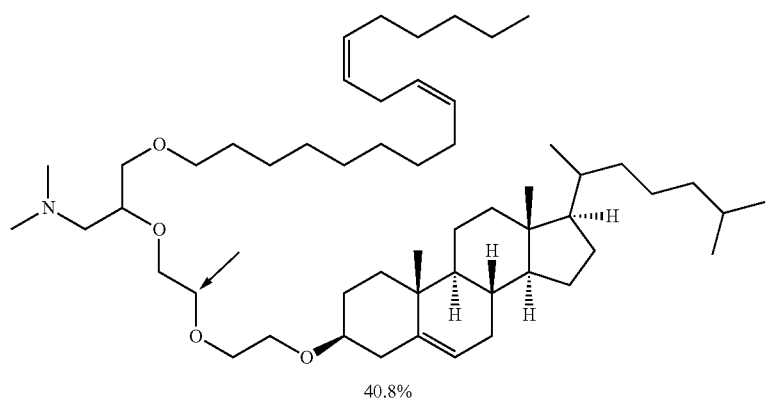
(E0172)
40.8%
In contrast, the present inventors have found that, when a cyclic headgroup is present, changing the L alkylene to an L heteroalkylene substituent has the opposite effect: the efficacy of the compound increases. For example:
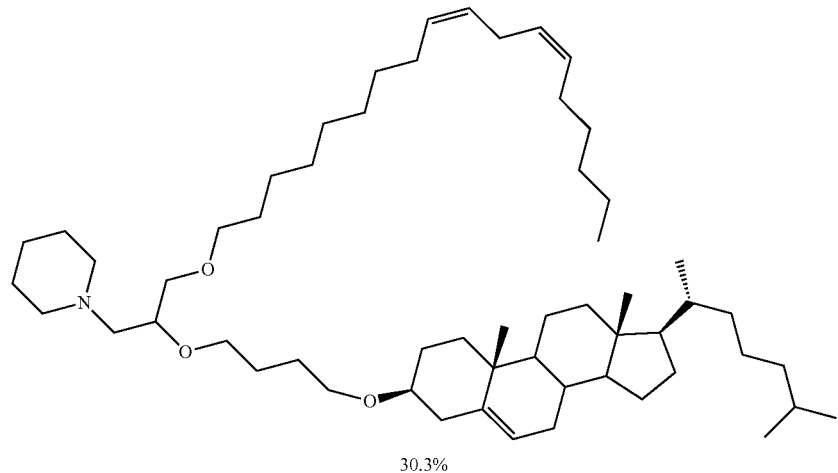
(E0027)
30.3%

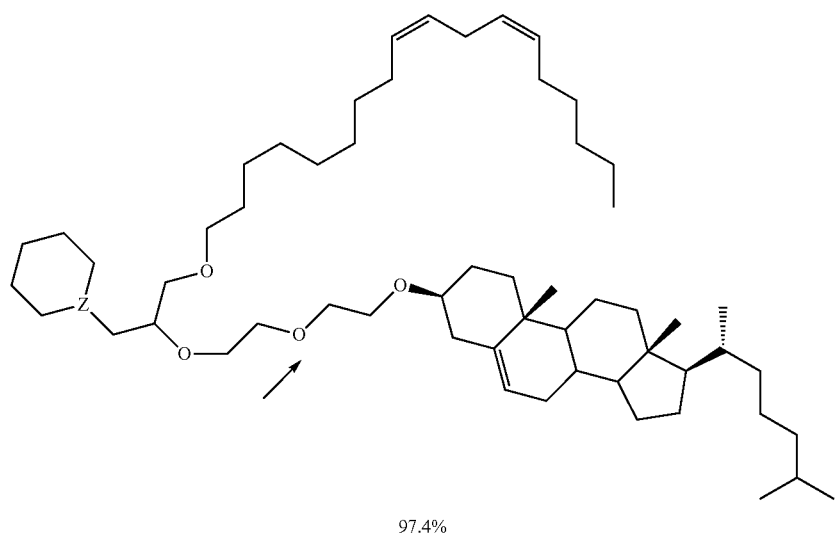

(E0014)

97.4%

Thus, one embodiment of the invention comprises those compounds wherein L comprises one or more heteroatoms. The skilled person would not arrive at such compounds starting from the disclosure of CLinDMA because, as noted above, the skilled person starting from compounds with a CLinDMA headgroup would have discovered that an L group comprising two or more heteroatoms reduces the efficacy of the final compounds, and so would not have provided a compound which comprises such a group.

Without wishing to be bound by any theory, one possibility is that the efficacy of the lipid formulations of the invention is related to pKa. The pKa of a cationic lipid can be adjusted by altering the structure, e.g. by varying the number of heteroatoms in L or by varying the nature of the headgroup.

In one example, referring to the in vivo siRNA experiments, e.g., in Table 8, using the formulations mentioned above (containing cationic lipids E0172, E0171, E0027 and E0014) which resulted in Factor-VII inhibitions in the liver of 98.5%, 40.8%, 30.3% and 97.4% respectively, their pKa values are found to be 6.7, 8.5, 5.7 and 6.4, respectively.

With respect to delivery of agents to the liver, for one embodiment of the invention, it is thought that, as a general rule (to which there are exceptions), the most effective cationic lipids for use in such formulations have a pKa of from about 5.1 to about 7.4. In one embodiment, cationic lipids with a pKa of from about 5.3 to about 7.3 are provided for formulation of this invention for liver delivery. In one embodiment, cationic lipids with a pKa of from about 5.9 to about 7.0 are provided for formulation of this invention for liver delivery. In one embodiment, preferred lipids have a pKa range of about 6.2 to about 6.8 for use in formulation for delivery of biologically active agents to the liver.

A surprising discovery of the invention is that tumor tissues have different optimal pKa ranges for efficacy. Thus, the pKa ranges in the previous paragraph apply to the extent that the lipids are intended to deliver biologically active agents to liver cells.

With respect to delivery of biologically active agents to a tumor, it is thought that, as a general rule (to which there are exceptions), the most effective cationic lipids of the invention for use in such formulations have a pKa of from about 5.0 to about 6.7, and thus are preferred lipids for delivery to tumors in one embodiment.

In one general embodiment, cationic lipids with a pKa of from about 5.0 to about 6.7 are provided for formulation of this invention for use in delivery of biologically active agents to one or more tumors. In one embodiment, cationic lipids with a pKa of from about 5.2 to about 6.3 are provided for formulation of this invention for use in delivery of biologically active agents to one or more tumors. In one embodiment, cationic lipids with a pKa of from about 5.4 to about 6.2 are provided for formulation of this invention for use in delivery of biologically active agents to one or more tumors. In one embodiment, cationic lipids with a pKa of from about 5.8 to about 6.1 are provided for formulation of this invention for use in delivery of biologically active agents to one or more tumors.

In one embodiment, the cationic lipid used in the formulation has a pKa optimized for delivery of a biologically active agent to a particular tumor or cell type. Tumor types may be primary tumors or may be metastatic.

In one specific embodiment, formulations optimized for delivery to Hep3B-like tumors contain cationic lipids with a pKa of from about 5.0 to about 6.7. In one specific embodiment, formulations optimized for delivery to Hep3B-like tumors contain cationic lipids with a pKa of from about 5.3 to about 6.3. In one specific embodiment, formulations optimized for delivery to Hep3B-like tumors contain cationic lipids with a pKa of from about 5.4 to about 5.9. In one specific embodiment, formulations optimized for delivery to Hep3B-like tumors contain cationic lipids with a pKa of from about 5.8 to about 5.9.

In one specific embodiment, formulations optimized for delivery to HepG2-like tumors contain cationic lipids with a pKa of from about 5.2 to about 6.2. In one specific embodiment, formulations optimized for delivery to Hep3B-like tumors contain cationic lipids with a pKa of from about 5.3 to about 6.2. In one specific embodiment, formulations optimized for delivery to Hep3B-like tumors contain cationic lipids with a pKa of from about 5.6 to about 6.1. In one specific embodiment, formulations optimized for delivery to HepG2-like tumors contain cationic lipids with a pKa of about 6.1.

In one specific embodiment, formulations optimized for delivery to 786-0-like renal tumors, or their metastases, contain cationic lipids with a pKa of about 6.1.

It is reasonable to postulate that other tissues, indications, tumor types or administration routes may possess preferred lipid pKa ranges. For liposome or LNP formulations, it is also reasonable to postulate that various tissues, indications, tumor types or administration routes may possess preferred cationic lipid pKa ranges, N/P ratios, particle size, cationic lipid used, stealth lipid used, helper lipid used, optional use of a selected neutral lipid, relative molar ratios of each lipid component, formulation method, biologically active agent to be delivered, and dosage regimen including dose given. Optimizing each of these aspects, either independently or in a coordinated manner, is described below, and many specific aspects of such optimization is believed to be within the ability of one skilled in the art without requiring undue experimentation.

Formulations may be optimized by one skilled in the art by adjusting other aspects of the formulation, including but not limited to individual selection of, e.g., the pKa of the cationic lipid optimized for the type of cell or organ being targeted; the cationic lipid used; the stealth lipid used; the helper lipid used; whether a neutral lipid is present or absent; the choice of neutral lipid used if present; the molar ratio of the selected helper lipid, optional neutral lipid, stealth lipid and cationic lipid; the N/P ratio; the particle size; the dosage regimen; the dose given; the formulation method; and the like.

Embodiments of the Compounds of Formulae (I) Through (X)

a, b and c

In one embodiment, a is optionally substituted $C_{1-2}$ alkylene. In one embodiment, a is optionally substituted $C_1$ alkylene.

In one embodiment, b is optionally substituted $C_{0-2}$ alkylene. In one embodiment, b is optionally substituted $C_1$ alkylene.

In one embodiment, c is absent or is optionally substituted $C_1$ alkylene. In one embodiment, c is absent.

In one embodiment, a, b and c are, if present, unsubstituted.

The Headgroup for Cationic Lipids

In one embodiment, $R^1$ and $R^2$ together with the nitrogen atom to which they are attached form an optionally substituted $C_{3-20}$-heterocycloalkyl, $C_{3-20}$-heterocycloalkenyl, $C_{3-20}$-heterocycloalkynyl group, $C_5$-heteroaryl or $C_6$-heteroaryl group. In one embodiment, $R^1$ and $R^2$ together with the nitrogen atom to which they are attached form an optionally substituted $C_{3-20}$-heterocycloalkyl, $C_{3-20}$-heterocycloalkenyl or $C_{3-20}$-heterocycloalkynyl group. In one embodiment, $R^1$ and $R^2$ together with the nitrogen atom to which they are attached form an optionally substituted $C_{3-20}$-heterocycloalkyl group.

In one embodiment, $R^1$ and $R^2$ together with the nitrogen atom to which they are attached form an optionally substituted cyclic $C_{5-16}$ group. In one embodiment, $R^1$ and $R^2$ together with the nitrogen atom to which they are attached form an optionally substituted cyclic $C_{5-12}$ group. In one embodiment, $R^1$ and $R^2$ together with the nitrogen atom to which they are attached form an optionally substituted cyclic $C_5$ group, cyclic $C_6$ group or cyclic $C_7$ group. In one embodiment, $R^1$ and $R^2$ together with the nitrogen atom to which they are attached form an optionally substituted cyclic $C_5$ group or cyclic $C_6$ group.

In one embodiment of this invention, $R^1$ and $R^2$ together with the nitrogen atom to which they are attached forms a cyclic species which comprises at least one oxygen atom.

In one embodiment, $R^1$ and $R^2$ together with the nitrogen atom to which they are attached are selected from at least one of the headgroups $H^1$ to $H^{52}$ as provided in Table 1.

TABLE 1

Moieties named $H^1$ to $H^{52}$

| | Structure |
|---|---|
| $H^1$ | (morpholine structure) |
| $H^2$ | (Boc-piperazine structure) |
| $H^3$ | (piperazine structure) |
| $H^4$ | (N-methylpiperazine structure) |
| $H^5$ | (piperidine structure) |
| $H^6$ | (4,4-difluoropiperidine structure) |
| $H^7$ | (pyrrolidine structure) |
| $H^8$ | (1,4-dioxa-8-azaspiro[4.5]decane structure) |
| $H^9$ | (2-phenylpyrrolidine structure) |
| $H^{10}$ | (4-(piperidin-1-yl)piperidine structure) |
| $H^{11}$ | (4-methoxypiperidine structure) |

TABLE 1-continued

Moieties named H¹ to H⁵²

| | Structure |
|---|---|
| H¹² | (2-methylpyrrolidinyl) |
| H¹³ | (2,6-dimethylmorpholinyl) |
| H¹⁴ | (azepanyl) |
| H¹⁵ | (1,2,3,4-tetrahydroisoquinolinyl) |
| H¹⁶ | (1,2,3,6-tetrahydropyridinyl) |
| H¹⁷ | (2-methylpiperidinyl) |
| H¹⁸ | (4,4-dimethylpiperidinyl) |
| H¹⁹ | (1,4-dioxa-8-azaspiro[4.5]decanyl) |
| H²⁰ | (2,5-dihydro-1H-pyrrolyl) |
| H²¹ | (decahydroisoquinolinyl) |
| H²² | (decahydroquinolinyl) |
| H²³ | (decahydroisoquinolinyl) |
| H²⁴ | (octahydrocyclopenta[c]pyrrolyl) |
| H²⁵ | (3-methylpiperidinyl) |
| H²⁶ | (2-methylpyrrolidinyl) |
| H²⁷ | (3-propylpyrrolidinyl) |
| H²⁸ | (3,3-dimethylpyrrolidinyl) |
| H²⁹ | (isoindolinyl) |
| H³⁰ | (1,4,7-trioxa-10-azacyclododecanyl) |

TABLE 1-continued

Moieties named $H^1$ to $H^{52}$

| | Structure |
|---|---|
| $H^{31}$ | thiomorpholine (N-linked) |
| $H^{32}$ | octahydropyrrolo[3,4-b]pyridine with N-Boc |
| $H^{33}$ | 4-(2-methoxyethyl)piperidine (N-linked) |
| $H^{34}$ | 2,2-dimethyl-hexahydro-[1,3]dioxolo[4,5-c]pyridine (N-linked) |
| $H^{35}$ | 3-methoxypyrrolidine (N-linked) |
| $H^{36}$ | 3-morpholinopyrrolidine (N-linked) |
| $H^{37}$ | 3-(dimethylamino)pyrrolidine (N-linked) |
| $H^{38}$ | 3-methylpyrrolidine (N-linked) |
| $H^{39}$ | 3-((tert-butyldimethylsilyl)oxy)pyrrolidine (N-linked) |
| $H^{40}$ | 1H-imidazole (N-linked) |
| $H^{41}$ | 3-hydroxypyrrolidine (N-linked) |
| $H^{42}$ | 2,5-dimethylpyrrolidine (N-linked) |
| $H^{43}$ | 4-methylpiperidine (N-linked) |
| $H^{44}$ | (S)-2-(methoxymethyl)pyrrolidine (N-linked) |
| $H^{45}$ | (S)-3-methylpyrrolidine (N-linked) |
| $H^{46}$ | (R)-3-methylpyrrolidine (N-linked) |
| $H^{47}$ | (S)-2-methylpiperidine (N-linked) |
| $H^{48}$ | (S)-3-(dimethylamino)pyrrolidine (N-linked) |
| $H^{49}$ | ethyl piperidine-4-carboxylate (N-linked) |
| $H^{50}$ | methyl piperidine-4-carboxylate (N-linked) |

TABLE 1-continued

Moieties named H¹ to H⁵²

| | Structure |
|---|---|
| $H^{51}$ | (oxetane-spiro-piperidine structure with O and N) |
| $H^{52}$ | (morpholine with methyl substituent and N attachment) | pKa for Cationic Lipids

In one embodiment, cationic lipids herein with pKa ranges in the desired range are preferred, including especially for formulations for delivery of biologically active agents.

As mentioned above, and shown below, a cationic lipid with a pKa of from about 5.1 to about 7.4 are generally effective when used in a formulation for targetting liver. In one embodiment, the pKa of a cationic lipid is from about 5.1 to about 7.4 for delivery to liver. In one embodiment, a cationic lipid with a pKa from about 5.3 to about 7.3 for use in formulations specific for targeting the liver. Thus, in one embodiment, the pKa of a cationic lipid is from about 5.3 to about 7.3 for delivery to liver. In one embodiment, the pKa of a cationic lipid is from about 5.9 to about 7.0 for delivery to liver. In one embodiment, the pKa of the cationic lipid is from about 6.2 to about 6.8 for delivery to liver.

As mentioned above and illustrated experimentally below, a cationic lipid with a pKa of from about 5.0 to about 6.7 is particularly effective when used in a formulation for delivery of a biologically active agent to a tumor. Thus, in one embodiment, the pKa of a cationic lipid is from about 5.0 to about 6.7 for delivery to tumors. In one embodiment, the pKa of a cationic lipid is from about 5.2 to about 6.3 for delivery to tumors. In one embodiment, the pKa of a cationic lipid is from about 5.4 to about 6.2 for delivery to tumors. In one embodiment, the pKa of the cationic lipid is from about 5.8 to about 6.1 for delivery to tumors. In a general embodiment, the pKa of a cationic lipid is from about 6.1 or below for delivery of a biologically active agent to a tumor or tumor cell.

The pKa of the cationic lipid for use in a formulation for delivery of a biologically active agent may be further optimized depending on tumor type. For example, as provided in Tables 9, 10 and 11, RNAi constructs specific to PLK1 mRNA are differentially delivered to Hep3B, HepG2 and 786-0 renal tumors injected into the flank of a mouse, in a manner that correlates with the pKa of the cationic lipid in the LNP formulation. Upon further analysis, it is apparent that the optimal pKa range for knockdown of PLK1 in Hep3B tumors in vivo differs from the optimal pKa range for HepG2 and 786-0 tumors, although both ranges fall within the general range of 5.0 to 6.7 as listed in the above paragraph, and all ranges in general include cationic lipids with a lower pKa than is optimal for delivery to liver.

Therefore, in one embodiment for delivery of a biologically active agent to Hep3B-like tumors in vivo, the cationic lipids of the invention have pKa ranges from about 5.0 to about 6.7. In one embodiment, the pKa of a cationic lipid is from about 5.3 to about 6.3 for delivery to Hep3B-like tumors. In one embodiment, the pKa of a cationic lipid is from about 5.4 to about 5.9 for delivery to Hep3B-like tumors. In one embodiment, the pKa of a cationic lipid is from about 5.8 to about 5.9 for delivery to Hep3B-like tumors.

Furthermore, in one embodiment for delivery of a biologically active agent to HepG2-like tumors in vivo, the cationic lipids of the invention have pKa ranges from about 5.2 to about 6.2. In one embodiment, the pKa of a cationic lipid is from about 5.3 to about 6.2 for delivery to HepG2-like tumors. In one embodiment, the pKa of a cationic lipid is from about 5.6 to about 6.1 for delivery to HepG2-like tumors. In one embodiment, the pKa of a cationic lipid is about 6.1 to HepG2-like tumors or to 786-0 renal tumor-like tumors.

$X^1$ and $X^2$

In one embodiment, $X^1$ is O. In another embodiment, $X^2$ is O. In one embodiment, both $X^1$ and $X^2$ are O.

Linker

In one embodiment, L comprises at least one heteroatom. This means that the chain which provides a direct link between $X^2$ and $Y^2$ has at least one heteroatom. In other words, any heteroatom in a substituent on L does not count for these purposes. In one embodiment, L comprises at least one O atom.

In one embodiment, L comprises at least two heteroatoms. In one embodiment, L comprises at least two O atoms.

In one embodiment, $L^c$ is optionally substituted $C_{1-15}$alkylene or $C_{1-15}$heteroalkylene. In one embodiment, $L^c$ is optionally substituted $C_{1-15}$alkylene or $C_{1-15}$heteroalkylene and d and e are both zero (0).

In one embodiment, $L^c$ is selected from one of formulae $L^{c-i}$ to $L^{c-xxxxiii}$. In one embodiment, $L^c$ is selected from one of formulae $L^{c-i}$ to $L^{c-xxxxiii}$ and d and e are both zero (0).

| | |
|---|---|
| $L^{c-i}$ | —(CH₂)₂O(CH₂)₂— |
| $L^{c-ii}$ | —(CH₂)₄— |
| $L^{c-iii}$ | —CO(CH₂)₂CO— |
| $L^{c-iv}$ | —CO— |
| $L^{c-v}$ | —COCH₂OCH₂CO— |
| $L^{c-vi}$ | —(CH₂)₂O(CH₂)₂NHCO— |
| $L^{c-vii}$ | —(CH₂)₃O(CH₂)₃— |
| $L^{c-viii}$ | —(CH₂)₂— |
| $L^{c-ix}$ | —(CH₂)₂O(CH₂)₂O(CH₂)₂O(CH₂)₂— |
| $L^{c-x}$ | —(CH₂)₂O(CH₂)₂O(CH₂)₂— |
| $L^{c-xi}$ | (structure with O-CH₂CH₂-O-CH₂CH₂-NH-C(=O)-CH₂CH₂-C(=O)) |
| $L^{c-xii}$ | (structure with O-CH₂CH₂-O-CH₂CH₂-NH-C(=O)-CH₂-O-CH₂-C(=O)) |
| $L^{c-xiii}$ | (structure with O-CH₂CH₂-NH-C(=O)-CH₂CH₂-C(=O)) |
| $L^{c-xiv}$ | (structure with O-CH₂CH₂-O-CH₂CH₂-NH-C(=O)-) |
| $L^{c-xv}$ | —(CH₂)₂O(CH₂)₂OCH(CH₃)— |
| $L^{c-xvi}$ | —(CH₂)₂O(CH₂)₂OC(=O)(CH₂)₂CO— |
| $L^{c-xvii}$ | —(CH₂)₂OC(=O)(CH₂)₂CO— |
| $L^{c-xviii}$ | —(CH₂)₂O(CH₂)₂OCO— |
| $L^{c-xix}$ | —(CH₂)₂NHC(=O)CH₂OCH₂C(=O)— |

| | |
|---|---|
| $L^{c-xx}$ | —(CH$_2$)$_2$NHC(=O)(CH$_2$)$_2$C(=O)— |
| $L^{c-xxi}$ | —(CH$_2$)$_2$NHC(=O)— |
| $L^{c-xxii}$ | —(CH$_2$)$_2$NHC(=O)CH$_2$NHC(=O)— |
| $L^{c-xxiii}$ | —(CH$_2$)$_2$NHC(=O)CH(side-chain-1)NHC(=O)—, wherein | side-chain-1 represents the group 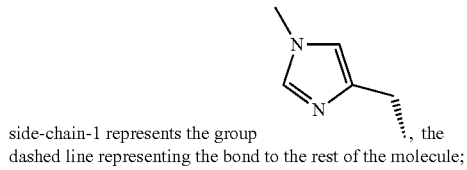, the dashed line representing the bond to the rest of the molecule;

| | |
|---|---|
| $L^{c-xxiv}$ | —(CH$_2$)$_2$OC(=O)— |
| $L^{c-xxv}$ | —(CH$_2$)$_2$O(CH$_2$)$_2$OC(=O)CH$_2$— |
| $L^{c-xxvi}$ | —(CH$_2$)$_2$OC(=O)CH$_2$— |
| $L^{c-xxvii}$ | —(CH$_2$)$_2$OC(=O)CH$_2$NHC(=O)— |
| $L^{c-xxviii}$ | —(CH$_2$)$_2$OC(=O)(CH$_2$)$_2$NHC(=O)— |

$L^{c-xxix}$ 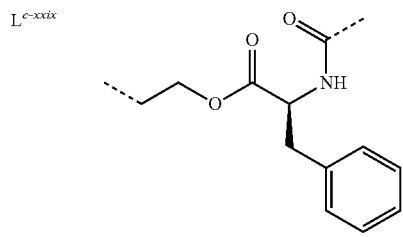

$L^{c-xxx}$ 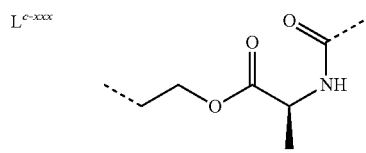

$L^{c-xxxi}$ 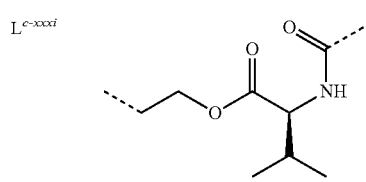

$L^{c-xxxii}$ 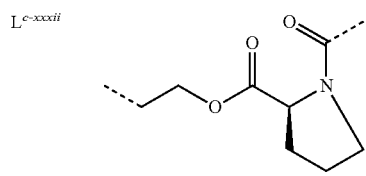

$L^{c-xxxiii}$ 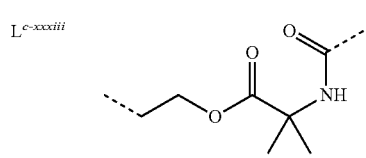

$L^{c-xxxiv}$ 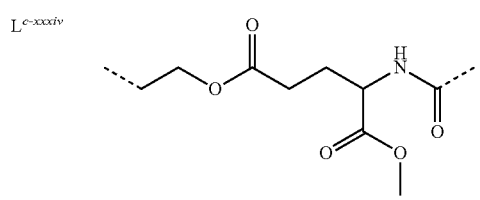

$L^{c-xxxv}$ 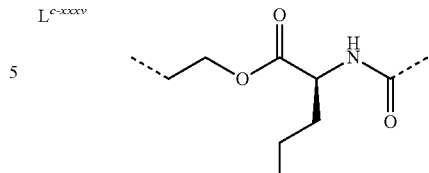

| | |
|---|---|
| $L^{c-xxxvi}$ | —(CH$_2$)$_2$OCO$_2$(CH$_2$)$_2$— |
| $L^{c-xxxvii}$ | —(CH$_2$)$_2$OC(=O)CH$_2$OCH$_2$C(=O)— |
| $L^{c-xxxviii}$ | —(CH$_2$)$_2$OC(=O)(CH$_2$)$_3$C(=O)— |
| $L^{c-xxxix}$ | —(CH$_2$)$_3$OC(=O)(CH$_2$)$_2$C(=O)— |

$L^{c-xxxx}$ 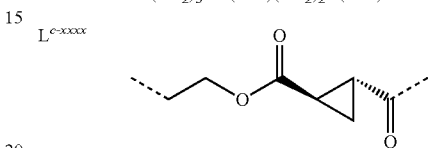

$L^{c-xxxxi}$ 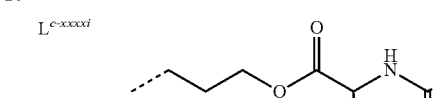

| | |
|---|---|
| $L^{c-xxxxii}$ | —(CH$_2$)$_2$OCH$_2$C(=O)—; and |

$L^{c-xxxxiii}$ 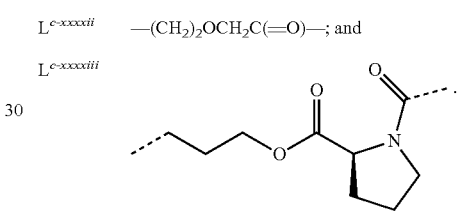

Since groups in which L comprises at least one heteroatom are preferred, $L^c$ is preferably selected from $L^{c-i}$, $L^{c-iv}$ to $L^{c-vii}$ and $L^{c-ix}$ to $L^{c-xxxxiii}$.

In one embodiment, $L^c$ is optionally substituted $C_{1-15}$heteroalkylene.

In one embodiment, $L^c$ is an optionally substituted $C_{1-11}$ group. In one embodiment, $L^c$ is an optionally substituted $C_{1-9}$ group. In one embodiment, $L^c$ is an optionally substituted $C_{3-8}$ group. In one embodiment, wherein $L^c$ is an optionally substituted $C_{4-7}$ group. In one embodiment, $L^c$ is an optionally substituted $C_5$, $C_6$ or $C_7$ group.

In one embodiment, d is 0; e is 0, and f is 1. In one embodiment, d is 0; e is 0, and f is 1 and $L^c$ is, within the chain lengths set out above, heteroalkylene.

$Y^1$ for Cationic Lipids

In one embodiment, $Y^1$ is a $C_{12-28}$ group. In one embodiment, $Y^1$ is an optionally substituted $C_{14-26}$ group. In one embodiment, $Y^1$ is an optionally substituted $C_{16-24}$ group. In one embodiment, $Y^1$ is an optionally substituted $C_{16-22}$ group. In one embodiment, the optionally substituted $Y^1$ chain is 18, 19, 20 or 21 atoms long.

Within the carbon ranges set out above, $Y^1$ is preferably alkenyl or heteroalkenyl.

In one embodiment, $Y^1$ has at least one alkene group. In one embodiment, $Y^1$ has 1, 2 or 3 alkene groups.

In one embodiment, $Y^1$ has an alkene group at the omega-3 position. In another embodiment, $Y^1$ has an alkene group at the omega-6 position. In another embodiment, $Y^1$ has an alkene group at the omega-9 position. In one embodiment, $Y^1$ has an alkene group at two or three of the omega-3, omega-6 and omega-9 positions. In one embodiment, $Y^1$ is unsaturated at the omega-6 and omega-9 positions. In another embodiment, $Y^1$ is unsaturated at the omega-3, omega-6 and omega-9 positions. In one embodiment, $Y^1$ is unsaturated at the omega-9 position.

In one embodiment, $Y^1$ has at least one cis unsaturated alkene group. In one embodiment, $Y^1$ has at least two cis unsaturated alkene groups. In one embodiment, $Y^1$ has at least three cis unsaturated alkene groups. The at least one cis unsaturated alkene group may be at one, two or three of the omega-3, omega-6 and omega-9 positions. Unsaturation in lipid chains is discussed in MacLachlan et al., Journal of Controlled Release 107 (2005) 276-287.

In one embodiment $Y^1$ is selected from $Y^{1-i}$ to $Y^{1-vii}$ as provided in Table 2.

TABLE 2

| Name | Structure |
|---|---|
| $Y^{1-i}$ | 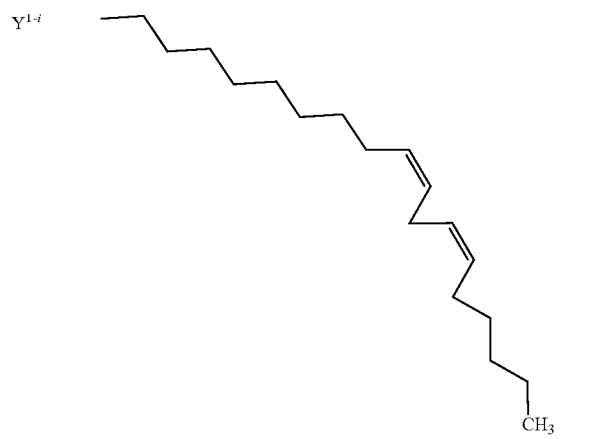 |
| $Y^{1-ii}$ | 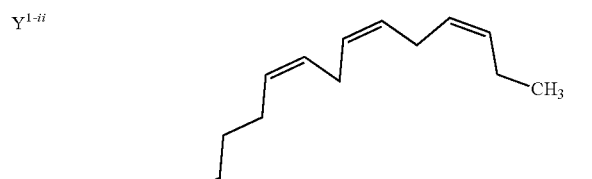 |

TABLE 2-continued

| Name | Structure |
|---|---|
| $Y^{1-iii}$ | 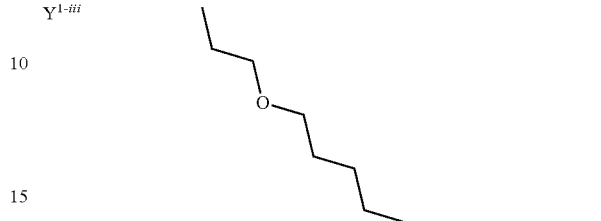 |
| $Y^{1-iv}$ | 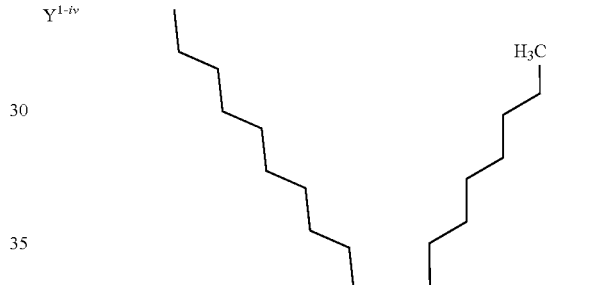 |
| $Y^{1-v}$ | 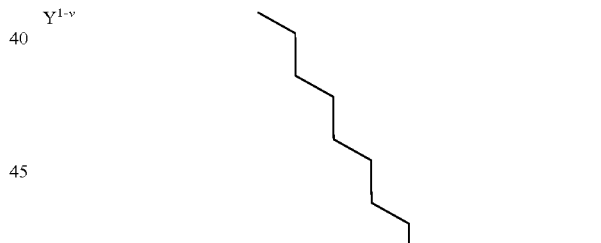 |
| $Y^{1-vi}$ | 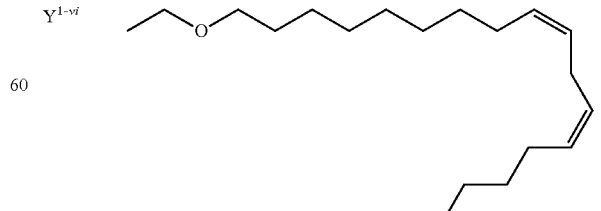 |

TABLE 2-continued

Y¹ related Moieties named $Y^{1-i}$ to $Y^{1-vii}$

| Name | Structure |
|---|---|
| $Y^{1-vii}$ | 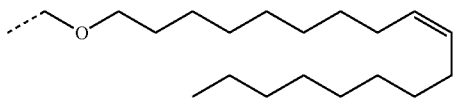 |

$Y^2$

In one embodiment, $Y^2$ is linked to L via an oxygen atom on the optionally substituted steroid. In one embodiment, $Y^2$ is linked to L via an oxygen atom on the 3-position of the A steroid ring. In one embodiment $Y^2$ is a sterol in which the hydrogen atom of the hydroxy group at the 3-position of the A steroid ring has been removed (and the connection to L is through the oxygen atom of said hydroxy group).

In one embodiment said sterol is selected from the group consisting of:

| | | | |
|---|---|---|---|
| annasterol; | avenasterol; | beta-sitosterol; | brassicasterol; |
| calciferol; | campesterol; | chalinosterol; | chinasterol; |
| cholestanol; | cholesterol; | coprostanol; | cycloartenol; |
| dehydrocholesterol; | desmosterol; | dihydrocalciferol; | dihydrocholesterol; |
| dihydroergosterol; | dinosterol; | epicholesterol; | ergosterol; |
| fucosterol; | hexahydrolumisterol; | hexaol; | hydroxycholesterol; |
| lanosterol; | lumisterol; | parkeol; | poriferasterol; |
| saringosterol; | sitostanol; | sitosterol; | stigmastanol; |
| stigmasterol; | weinbersterol; | zymosterol; | | a sterol bile acid (such as cholic acid; chenodeoxycholic acid; glycocholic acid; taurocholic acid; deoxycholic acid, and lithocholic acid);
and/or a pharmaceutically relevant salt or a pharmaceutically acceptable derivative thereof.

In one embodiment, the sterol is cholesterol.

Specific Lipids for Use in Delivery of a Biologically Active Agent

The novel cationic lipids and stealth lipids of the invention may be used for the delivery of therapeutically acceptable agents including, e.g., biologically active agents. Formulations containing cationic lipids, stealth lipids, and other types of lipids are described throughout this disclosure. Whereas the lipids disclosed herein are believed novel and useful, certain characteristics are preferred over others for therapeutic use, as detailed further in the exemplary and nonbinding disclosure provided below. In one embodiment, the liposome, lipid nanoparticle or other such lipid formulation further comprises a biological effective agent. In one embodiment, the liposome, lipid nanoparticle or other such lipid formulation is empty.

In one embodiment, the separate lipid components for use in a formulation are provided in a kit. In one embodiment, the kit contains instructions for generation of the lipid formulation. The kit may comprise a ready-made formulation or separate or partial components that require mixing prior to administration. A kit may further provide additional components such as, but not limited to, controls, buffers, containers, and delivery components, or may be limited to those inventive lipids and components as described herein.

In one embodiment, the kit contains at least a liposome or liposome components including but not limited to one or more of a cationic lipid, a stealth lipid, a helper lipid, and/or an optional neutral lipid. In one embodiment, the kit further comprises a biologically active agent. In one embodiment, the kit further comprises one or more control lipids, or control agents, a control liposome formulation, stains, buffers, instructions for use, and the like. In one alternative, the liposome formulation is premixed. One or more of the kit's chemical components may be provided in a dehydrated form or in a hydrated form. Any of the various methods known in the art for dehydration on lyophilization of the various compounds and compositions described herein may be used.

In one aspect of the invention, there is provided any one of the specific compounds exemplified below or a pharmaceutically acceptable derivative thereof.

In one embodiment, the compound is for delivery of a biologically active agent to the liver and the compound is selected from one or more of E0024, E0014, E0052, E0118, E0175, E0177 or E0083. In one embodiment, a composition for delivery of a biologically active agent to the liver comprises one or more of compounds selected from E0024, E0014, E0052, E0118 or E0083. In one embodiment, a composition for delivery of a biologically active agent to the liver comprises compound E0024. In one embodiment, a composition for delivery of a biologically active agent to the liver comprises compound E0014. In one embodiment, a composition for delivery of a biologically active agent to the liver comprises compound E0052. In one embodiment, a composition for delivery of a biologically active agent to the liver comprises compound E0118. In one embodiment, a composition for delivery of a biologically active agent to the liver comprises compound E0083.

In one embodiment, the compound is for delivery of a biologically active agent to a tumor and the compound is selected from one or more of E0011, E0008, E0025, E0026, E0076, E0077, E0085 or E0088. In one embodiment, a composition for delivery of a biologically active agent to a tumor comprises one or more of compounds selected from E0011, E0008, E0025, E0026, E0076, E0077, E0085 or E0088. In one embodiment, a composition for delivery of a biologically active agent to a tumor comprises compound E0011. In one embodiment, a composition for delivery of a biologically active agent to a tumor comprises compound E0008. In one embodiment, a composition for delivery of a biologically active agent to a tumor comprises compound E0025. In one embodiment, a composition for delivery of a biologically active agent to a tumor comprises compound E0026. In one embodiment, a composition for delivery of a biologically active agent to a tumor comprises compound E0076. In one embodiment, a composition for delivery of a biologically active agent to a tumor comprises compound E0077. In one embodiment, a composition for delivery of a biologically active agent to a tumor comprises compound E0085. In one embodiment, a composition for delivery of a biologically active agent to a tumor comprises compound E0088.

Liposomes, lipid nanoparticles and other such lipid formulations containing one or more of the lipids described herein are useful for delivery of nucleic acid compositions to a cell or tissue, either in vitro or in vivo. Therapeutically relevant nucleic acid compositions include RNAi agents that are specific to one or more genes associated with a disease or disorder, wherein targetting the endogenous sequence in the cell or tissue with the RNAi agent leasts to a therapeutic or prophylactic effect.

As a general non-binding rule, therapeutically effective amounts of target inhibition for delivery of biologically active agents, including especially RNAi agents, result in target inhibition of at least 70% where the target is expressed in the liver. In one embodiment, cationic lipids of the invention provide at least 70% target inhibition when provided in a formulation for delivery of an RNAi to the liver. Cationic lipids that provide at least 70% KD when formulated for liver include, but are not limited to, E0007, E0008, E0011, E0014, E0015, E0016, E0017, E0018, E0019, E0022, E0024, E0025, E0026, E0032, E0034, E0040, E0042, E0043, E0045, E0048, E0049, E0051, E0052, E0053, E0054, E0055 and E0118. In one embodiment, cationic lipids of the invention provide at least 80% target inhibition when provided in a formulation for delivery of an RNAi to the liver. Cationic lipids that provide at least 80% KD when formulated for liver include, but are not limited to, E0008, E0011, E0014, E0016, E0017, E0018, E0019, E0022, E0024, E0025, E0026, E0032, E0034, E0040, E0042, E0043, E0045, E0048, E0052, E0053, E0054, E0055 and E0118. In one embodiment, cationic lipids of the invention provide at least 90% target inhibition when provided in a formulation for delivery of an RNAi to the liver. Cationic lipids that provide at least 90% KD when formulated for liver include, but are not limited to, E0011, E0014, E0017, E0018, E0024, E0025, E0026, E0040, E0043, E0045, E0052, E0053, E0054, E0055 and E0118. In one embodiment, cationic lipids of the invention provide at least 95% target inhibition when provided in a formulation for delivery of an RNAi to the liver. Cationic lipids that provide at least 95% KD when formulated for liver include, but are not limited to, E0014, E0017, E0018, E0024, E0026, E0040, E0043, E0052, E0054, E0055 and E0118. In one embodiment, cationic lipids of the invention provide at least 98% target inhibition when provided in a formulation for delivery of an RNAi to the liver. Cationic lipids that provide at least 98% KD when formulated for liver include, but are not limited to, E0014, E0017, E0018, E0024, E0052, E0054 and E0118.

As a general non-binding rule, therapeutically effective amounts of target inhibition for delivery of biologically active agents, including especially RNAi agents, result in target inhibition of at least 50% where the target is a tumor. In one embodiment, cationic lipids of the invention provide at least 50% target inhibition when provided in a formulation for delivery of an RNAi to a tumor or tumor cells. Cationic lipids that provide at least 50% KD when formulated for tumors or tumor cells include, but are not limited to, E0008, E0011, E0025, E0026, E0075, E0076, E0077, E0085, E0088, E0095, E0104, E0178 and E0179. In one embodiment, cationic lipids of the invention provide at least 60% target inhibition when provided in a formulation for delivery of an RNAi to a tumor or tumor cells. Cationic lipids that provide at least 60% KD when formulated for tumors or tumor cells include, but are not limited to, E0008, E0011, E0025, E0026, E0075, E0076, E0077, E0085 and E0088. In one embodiment, cationic lipids of the invention provide at least 70% target inhibition when provided in a formulation for delivery of an RNAi to a tumor or tumor cells. Cationic lipids that provide at least 70% KD when formulated for tumors or tumor cells include, but are not limited to, E0011, E0025, E0026, E0075, E0076, E0077 and E0088. In one embodiment, cationic lipids of the invention provide at least 80% target inhibition when provided in a formulation for delivery of an RNAi to the tumor to a tumor or tumor cells. Cationic lipids that provide at least 80% KD when formulated for tumors or tumor cells include, but are not limited to, E0008, E0025 and E0076.

In a specific embodiment, therapeutically effective amounts of target inhibition for delivery of biologically active agents, including especially RNAi agents, result in target inhibition of at least 30% where the target is a HepG2-like tumor or a 786-0-like tumor. In one specific embodiment, cationic lipids of the invention provide at least 30% target inhibition when provided in a formulation for delivery of an RNAi to a HepG2-like tumor or a 786-0-like tumor, and include E0056, E0076, E0085, E0104, E0175, E0176 and E0177. In one specific embodiment, cationic lipids of the invention provide at least 30% target inhibition when provided in a formulation for delivery of an RNAi to a HepG2-like tumor or a 786-0-like tumor, and include E0085, E0175 and E0177.

Specific Cationic Lipids for Delivery to Liver

In one embodiment, a preferred cationic lipid is E0014. In one embodiment, a preferred cationic lipid is E0017. In one embodiment, a preferred cationic lipid is E0018. In one embodiment, a preferred cationic lipid is E0024. In one embodiment, a preferred cationic lipid is E0052. In one embodiment, a preferred cationic lipid is E0054. In one embodiment, a preferred cationic lipid is E0118.

In one embodiment, a preferred formulation for delivery of a biologically active agent to liver contains a cationic lipid with a pKa of from about 5.1 to about 7.4. In one embodiment, a preferred formulation for delivery of a biologically active agent to liver contains a cationic lipid with a pKa of from about 5.3 to about 7.3. In one embodiment, a preferred formulation for delivery of a biologically active agent to liver contains a cationic lipid with a pKa of from about 5.9 to about 7.0. In one embodiment, a preferred formulation for delivery of a biologically active agent to liver contains a cationic lipid with a pKa of from about 6.2 to about 6.8. In one embodiment, a preferred formulation for delivery of a biologically active agent to liver contains a cationic lipid with a pKa of about 6.1 or higher.

Specific Cationic Lipids for Delivery to Tumors

In one embodiment, a preferred cationic lipid is E0008. In one embodiment, a preferred cationic lipid is E0025. In one embodiment, a preferred cationic lipid is E0076. In one embodiment, a preferred cationic lipid is E0085. In one embodiment, a preferred cationic lipid is E0175. In one embodiment, a preferred cationic lipid is E0177.

In one embodiment, a preferred formulation for delivery of a biologically active agent to a tumor in vivo contains a cationic lipid with a pKa of from about 5.0 to about 6.7. In one embodiment, a preferred formulation for delivery of a biologically active agent to a tumor in vivo contains a cationic lipid with a pKa of from about 5.2 to about 6.3. In one embodiment, a preferred formulation for delivery of a biologically active agent to a tumor in vivo contains a cationic lipid with a pKa of from about 5.4 to about 6.2. In one embodiment, a preferred formulation for delivery of a biologically active agent to a tumor in vivo contains a cationic lipid with a pKa of from about 5.8 to about 6.1. In one embodiment, a preferred formulation for delivery of a biologically active agent to a tumor or tumor cell contains a cationic lipid with a pKa of about 6.1 or lower.

Pharmaceutical Compositions and Formulations

The present invention provides a pharmaceutical composition comprising at least one cationic lipid compound of the invention. The present invention provides a pharmaceutical composition comprising at least one stealth lipid compound of the invention. In one embodiment, at least one other lipid component is present. Such compositions may also contain a biologically active agent, optionally in combination with one or more other lipid components. In one embodiment, the one or more components, compositions and/or agents are provided in a kit. Compositions containing lipids of the invention in combination with one or more biologically active agents in one embodiment are provided as formulations for use, e.g., in the delivery of therapeutically effective amounts of one or more biologically active agents to a cell or tissue. In one embodiment, the cell or tissue is in a subject in need of treatment or prophylaxis. In one embodiment, the subject is a patient in need of therapeutically effective amounts of the biologically active agent. As used herein, subjects include both humans and non-human animals.

The other lipid component(s) may be one or more selected from the group consisting of cationic lipids, (optional) neutral lipids, helper lipids, stealth lipids and alkyl resorcinol based lipids. In one embodiment, the invention provides a composition comprising: (a) a cationic lipid, e.g., compounds of any one of Formulas I through X, and/or E0001-E0171 and E0175-E0180 of the invention; (b) an optional neutral lipid, e.g. DSPC; (c) a helper lipid, e.g. one containing cholesterol; (d) a stealth lipid, e.g., one of either Formula XI or XII or any one or more of S001-S009 and S012-S026, or 1,2-dimyristoyl-sn-glycero-3-phosphoethanolamine-N-[methoxy (polyethylene glycol)-2000] (catalog # 880150P from Avanti Polar Lipids). In one embodiment, the lipid components are in a liposome formulation, e.g., a nanoparticle or the like. In one embodiment, the liposome formulation further comprises a biologically active agent. In one embodiment, the liposome formulation further comprises a therapeutically effectve amount of a biologically active agent.

The other lipid component(s) may, e.g., be one or more selected from the group of known cationic lipids consisting of N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N,N-dimethyl-2,3-dioleyloxy)propylamine (DODMA), 1,2-Dioleoyl-3-Dimethylammonium -propane (DODAP), 1,2-Dioleoylcarbamyl -3-Dimethylammonium-propane (DOCDAP), 1,2-Dilineoyl-3-Dimethylammonium-propane (DLINDAP), dilauryl($C_{12:0}$) trimethyl ammonium propane (DLTAP), Dioleoyloxy-N-[2-sperminecarboxamido)ethyl}-N,N-dimethyl-1-propanaminiumtrifluoroacetate (DOSPA), Dioctadecylamidoglycyl spermine (DOGS), DC-Chol, 1,2-Dimyristyloxypropyl-3-dimethyl-hydroxyethyl ammonium bromide (DMRIE), 3-Dimethylamino-2-(Cholest-5-en -3-beta-oxybutan-4-oxy) -1-(cis,cis-9,12-octadecadienoxy)propane (CLinDMA), 2-[5'-(cholest-5-en-3[beta]-oxy)-3'-oxapentoxy) -3-dimethyl-1-(cis,cis-9',12'-octadecadienoxy) propane (CpLinDMA) and N,N-Dimethyl-3,4-dioleyloxybenzylamine (DMOBA), dioleoyl phosphatidylethanolamine (DOPE), 1,2-N,N'-Dioleylcarbamyl-3-dimethylaminopropane (DOcarbDAP). In one embodiment the other lipid component(s) is DOTAP or DLTAP.

In one embodiment, the cationic lipid is selected from a lipid of Formula I. In one embodiment, the cationic lipid is selected from a lipid of Formula II. In one embodiment, the cationic lipid is selected from a lipid of Formula III. In one embodiment, the cationic lipid is selected from a lipid of Formula IV. In one embodiment, the cationic lipid is selected from a lipid of Formula V. In one embodiment, the cationic lipid is selected from a lipid of Formula VI. In one embodiment, the cationic lipid is selected from a lipid of Formula VII. In one embodiment, the cationic lipid is selected from a lipid of Formula VIII. In one embodiment, the cationic lipid is selected from a lipid of Formula IX. In one embodiment, the cationic lipid is selected from a lipid of Formula X. In one embodiment, the cationic lipid is selected from the list of E0001 through E0171 (E0001-E0171) and E0175 through E0180 (E0175-E0180).

The other lipid component(s) may, e.g., be (a) neutral lipid(s). The neutral lipid(s) may, in one embodiment, be one or more selected from any of a variety of neutral uncharged or zwitterionic lipids. Examples of neutral phospholipids for the present invention include: 5-heptadecylbenzene-1,3-diol (resorcinol), cholesterol hemisuccinate (CHEMS), dipalmitoylphosphatidylcholine (DPPC), distearoylphosphatidylcholine (DSPC), phosphocholine (DOPC), dimyristoylphosphatidylcholine (DMPC), phosphatidylcholine (PLPC), phosphatidylethanolamine (PE), egg phosphatidylcholine (EPC), dilauryloylphosphatidylcholine (DLPC), dimyristoylphosphatidylcholine (DMPC), 1-myristoyl-2-palmitoyl phosphatidylcholine (MPPC), 1-palmitoyl-2-myristoyl phosphatidylcholine (PMPC), 1,2-diarachidoyl-sn-glycero-3-phosphocholine (DBPC), 1-palmitoyl-2-stearoyl phosphatidylcholine (PSPC), 1-stearoyl-2-palmitoyl phosphatidylcholine (SPPC), 1,2-distearoyl-sn-glycero-3-phosphocholine (DAPC), 1,2-dieicosenoyl-sn-glycero -3-phosphocholine (DEPC), palmitoyloleoyl phosphatidylcholine (POPC), lysophosphatidyl choline, dilinoleoylphosphatidylcholine distearoylphophatidylethanolamine (DSPE), dimyristoyl phosphatidylethanolamine (DMPE), dipalmitoyl phosphatidylethanolamine (DPPE), palmitoyloleoyl phosphatidylethanolamine (POPE), lysophosphatidylethanolamine or a combination thereof. In one embodiment, the neutral phospholipid is selected from the group consisting of distearoylphosphatidylcholine (DSPC) and dimyristoyl phosphatidyl ethanolamine (DMPE).

The other lipid component(s) may, e.g., be (a) anionic lipid(s), e.g. anionic lipids capable of producing a stable complex. Examples of anionic lipids are phosphatidylglycerol, cardiolipin, diacylphosphatidylserine, diacylphosphatidic acid, N-dodecanoyl phosphatidyl ethanoloamine, N-succinyl phosphatidylethanolamine, N-glutaryl phosphatidylethanolamine and lysylphosphatidylglycerol.

Suitable neutral and anionic lipids also include those described in US 2009/0048197, paragraph [0119].

The total amount of lipid in the composition being administered is, in one embodiment, from about 5 to about 30 mg lipid per mg biologically active agent (e.g. siRNA), in another embodiment from about 5 to about 25 mg lipid per mg biologically active agent (e.g. siRNA), in another embodiment from about 7 to about 25 mg lipid per mg biologically active agent (e.g. siRNA) and in one embodiment from about 7 to about 15 mg lipid per mg biologically active agent (e.g. siRNA).

Various methods for loading biologically active agents into lipid compositions, such as liposomes and liponanoparticles are available in the art, including both passive and active loading methods. Either are contemplated as being within the scope of the invention. The exact method used may be chosen based one multiple factors that include, but are not limited to, e.g., the biologically active agent to be loaded, the storage method to be used once loaded, the size of the resulting particle, and the dosage regimen contemplated. Methods include, e.g., mechanical mixing of the drug and lipids at the time the liposomes are formed or reconstituted, dissolving all components in an organic solvent and concentrating them into a dry film, forming a pH or ion gradient to draw the active agent into the interior of the liposome, creating a transmembrane potential, and ionophore mediated loading. See, e.g., at least Examples 68, 69 and 77 below, PCT Publication No. WO 95/08986, U.S. Pat. No. 5,837,282, U.S. Pat. No. 5,837,282, and U.S. Pat. No. 7,811,602.

The dose of biologically active agent administered will depend on a number of factors such as the identity of the biologically active agent and the target patient (e.g. species of animal). The concentration of biologically active agent will be adjusted accordingly but, when siRNA is being administered to an animal, a concentration of from 0.1 mg/ml to 10 mg/ml is typical per dose.

The total amount of siRNA can be measured by several methods. HPLC methods include anion exchange, reverse phase (RP) or size exclusion (SEC). Fluorescent methods may also be used. In all of these methods the nanoparticles must be lysed to release the siRNA from the nanoparticle prior to measuring the total siRNA content.

In one embodiment, the composition comprises a cationic lipid component which forms from about 10% to about 80%, from about 20% to about 70% or from about 30% to about 60% of the total lipid present in the composition. These percentages are mole percentages relative to the total moles of lipid components in the final lipid particle.

In one embodiment, the composition comprises a neutral lipid component which forms from about 0% to about 50%, from about 0% to about 30% or from about 10% to about 20% of the total lipid present in the composition. In one embodiment, the neutral lipid component of the composition is optional. In one embodiment, the composition has no neutral lipid component. These percentages are mole percentages relative to the total moles of lipid components in the final lipid particle.

In one embodiment, the composition comprises a helper lipid component which forms from about 5% to about 80%, from about 20% to about 70% or from about 30% to about 50% of the total lipid present in the composition. These percentages are mole percentages relative to the total moles of lipid components in the final lipid particle.

In one embodiment, the composition comprises a stealth lipid component which forms from about 0% to about 10%, from about 1% to about 6%, or from about 2% to about 5% of the total lipid present in the composition. These percentages are mole percentages relative to the total moles of lipid components in the final lipid particle.

In one embodiment, the composition comprises a cationic lipid component forming from about 30 to about 60% of the total lipid present in the formulation, a neutral lipid comprising forming from about 0 to about 30% of the total lipid present in the formulation, a helper lipid forming from about 18 to about 46% of the total lipid present in the formulation and a stealth lipid forming from about 2 to about 4% of the total lipid present in the formulation. These percentages are mole percentages relative to the total moles of lipid components in the final lipid particle.

Liposomal compositions of the invention are administered in any of a number of ways, including parenteral, intravenous, systemic, local, oral, intratumoral, intramuscular, subcutaneous, intraperitoneal, inhalation, or any such method of delivery. In one embodiment, the compositions are administered parenterally, i.e., intraarticularly, intravenously, intraperitoneally, subcutaneously, or intramuscularly. In a specific embodiment, the liposomal compositions are administered by intravenous infusion or intraperitoneally by a bolus injection.

Liposomal compositions of the invention may be formulated as pharmaceutical compositions suitable for delivery to a subject. The pharmaceutical compositions of the invention will often further comprise one or more buffers (e.g., neutral buffered saline or phosphate buffered saline), carbohydrates (e.g., glucose, mannose, sucrose, dextrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

Suitable formulations for use in the present invention can be found, e.g., in Remington's Pharmaceutical Sciences, Mack Publishing Company, Philadelphia, Pa., 17.sup.th Ed. (1985). Often, intravenous compositions will comprise a solution of the liposomes suspended in an acceptable carrier, such as an aqueous carrier.

Method for Delivering Biologically Active Agents and Related Uses

The cationic and stealth lipids of the invention are useful for formulations used for delivery of biologically active agents. Formulations containing the novel lipids of the invention may be in various forms, including but not limited to particle forming delivery agents including microparticles, nanoparticles and trasfection agents that are useful for delivering various molecules to cells. Specific formulations are effective at transfecting or delivering biologically active agents, such as antibodies (e.g., monoclonal, chimeric, humanized, nanobodies, and fragments thereof etc.), cholesterol, hormones, peptides, proteins, chemotherapeutics and other types of antineoplastic agents, low molecular weight drugs, vitamins, co-factors, nucleosides, nucleotides, oligonucleotides, enzymatic nucleic acids, antisense nucleic acids, triplex forming oligonucleotides, antisense DNA or RNA compositions, chimeric DNA:RNA compositions, allozymes, aptamers, ribozyme, decoys and analogs thereof, plasmids and other types of expression vectors, and small nucleic acid molecules, RNAi agents, short interfering nucleic acid (siNA), short interfering RNA (siRNA), double-stranded RNA (dsRNA), micro-RNA (miRNA), and short hairpin RNA (shRNA) molecules, to relevant cells and/or tissues, such as in a cell culture, subject or organism. The above list of biologically active agents is exemplary only, and is not intended to be limiting. Such compounds may be purified or partially purified, and may be naturally occuring or synthetic, and may be chemically modified.

Such formulations containing biologically active agents are useful, e.g., in providing compositions to prevent, inhibit, or treat diseases, conditions, or traits in a cell, subject or organism. Diseases, conditions or traits include, but are not limited to, proliferative diseases, including cancer, inflammatory disease, transplant and/or tissue rejection, autoimmune diseases or conditions, age-related disease, neurological or neurodegenerative disease, respiratory disease, cardiovacular disease, ocular disease, metabolic disease, dermatological disease, auditory disease, a liver disease, a kidney or renal disease, etc.

The amount of active agent administered per dose is an amount above the minimal therapeutic dose but below a toxic dose. The actual amount per dose may be determined by a physician depending on a number of factors, such as the medical history of the patient, the use of other therapies, the biologically active agent to be provided, and the nature of the disease. The amount of biologically active agent administered may be adjusted throughout treatment, depending on the patient's response to treatment and the presence or severity of any treatment-associated side effects. Exemplary dosages and treatment for compounds that have been approved by an appropriate regulatory agency are known and available to those skilled in the art. See, e.g., Physician's Desk Reference, 64th ed., Physician's Desk Reference Inc. (2010), Remington's Pharmaceutical Sciences, Mack Publishing Company, Philadelphia, Pa. (1985), and Remington The Science and Practice of Pharmacy, 21st ed., Lippincott Williams & Williams Publishers (2005).

In one embodiment, a single dose is administered of a biologically active agent to a patient in need thereof. In one embodiment, multiple doses are administered, wherein the multiple doses may be administered concurrently, sequentially or alternating. In one embodiment, the same formulation is administered over multiple doses. In one embodiment, the formulations differ over multiple doses. In various embodiments, the doses may be administered once a day, or for one, two, three, four or more consecutive days. In one embodiment, the doses are administered once a week. In one embodiment, the doses are administered once every other week. In one embodiment, patients receive at least two courses of a treatment regimen, and potentially more, depending on the response of the patient to the treatment. In single agent regimens, total courses of treatment are determined by the patient and physician based on observed responses and toxicity. The above dosage regimens are to be considered as exemplary. Other dosage regimens are contemplated as being within the scope of the invention, and depend on the therapeutic effect desired.

In one embodiment, the invention provides a method for delivering a biologically active agent to a cell comprising administering a composition, which comprises the biologically active agent and a compound of the present invention, to the cell.

The cell may be in vitro or in vivo.

The invention provides a compound of formula (I) for use in therapy. It also provides subsets of compounds of formula I that are further distinguished in forumulas II to X. Compounds of formulas I through X are generally referred to herein as cationic lipids.

The invention further provides a compound of formula (XI) for use in therapy. It also provides a subset of compound of formula XI that are further distinguished in forumula XII. Compounds of formulas XI and XII are generally referred to herein as stealth lipids.

The invention further provides a method for the treatment of a disease or condition, comprising the step of administering a therapeutically effective amount of a composition containing at least one compound of formula (I) to a patient in combination with a biologically active agent that treats the disease or condition. The invention also provides a composition containing at least one compound of formula (XI) for use in treating a disease or condition.

The invention also provides the use of a compound of formula (I) in the manufacture of a medicament for the treatment of a disease or condition. In one embodiment, the medicament contains a biologically active agent that treats the disease or condition. The invention also provides the use of a biologically active agent which treats a disease or condition in the manufacture of a medicament for the treatment of the disease or condition, wherein the medicament also contains a compound of formula (I) or formula XI.

The invention also provides a method for the treatment of a disease or condition comprising the step of administering a therapeutically effective amount of a biologically active agent in a formulation containing at least one composition of the invention to a patient. In one embodiment, the disease or condition is a disease of the liver, a tumor or a disease. In one embodiment, the disease or condition is treatable by administering an siRNA agent.

The invention also provides a composition of the invention for use in treating a disease or condition in a patient. In one embodiment, the disease or condition is a disease of the liver, a tumor or a disease mediated by a protein encoded by a mRNA.

The invention also provides a product containing a compound of formula (I) and/or formula XI. In one embodiment, the product further comprises a biologically active agent as a combined preparation for simultaneous, separate or sequential use in therapy.

Administration & Formulation

General

For pharmaceutical use, the compounds and compositions of the invention may be administered as at least one portion of a medicament by enteral or parenteral routes, including intravenous, intramuscular, subcutaneous, transdermal, airway (aerosol), oral, intranasal, rectal, vaginal, buccal, nasopharangeal, gastrointestinal or sublingual administration. The administration may be systemic or topical. Topical administration may involve, e.g., catheterization, implantation, osmotic pumping, direct injection, dermal/transdermal application, stenting, ear/eye drops or portal vein administration. The compounds of formula (I) and/or formula XI should be assessed for their biopharmaceutical properties, such as solubility and solution stability (across pH), permeability, etc., in order to select the most appropriate dosage form and route of administration for treatment of the proposed indication.

The compounds and compositions of the invention will generally, but not necessarily, be administered as a formulation in association with one or more pharmaceutically acceptable excipients. The term "excipient" includes any ingredient other than the compound(s) of the invention, the other lipid component(s) and the biologically active agent. An excipient may impart either a functional (e.g drug release rate controlling) and/or a non-functional (e.g. processing aid or diluent) characteristic to the formulations. The choice of excipient will to a large extent depend on factors such as the particular mode of administration, the effect of the excipient on solubility and stability, and the nature of the dosage form.

Typical pharmaceutically acceptable excipients include:
diluents, e.g. lactose, dextrose, sucrose, mannitol, sorbitol, cellulose and/or glycine;
lubricants, e.g. silica, talcum, stearic acid, its magnesium or calcium salt and/or polyethyleneglycol;
binders, e.g. magnesium aluminum silicate, starch paste, gelatin, tragacanth, methylcellulose, sodium carboxymethylcellulose and/or polyvinylpyrrolidone;
disintegrants, e.g. starches, agar, alginic acid or its sodium salt, or effervescent mixtures; and/or
absorbants, colorants, flavors and/or sweeteners.

The excipient may be an aqueous solution carrier which may optionally contain a buffer (e.g. a PBS buffer) and/or a sugar.

A thorough discussion of pharmaceutically acceptable excipients is available in Gennaro, *Remington: The Science and Practice of Pharmacy* 2000, 20th edition (ISBN: 0683306472).

Oral Administration

The compounds and compositions of the invention may be administered orally. Oral administration may involve swallowing, so that the compound enters the gastrointestinal tract, and/or buccal, lingual, or sublingual administration by which the compound enters the blood stream directly from the mouth.

Parenteral Administration

The compounds and compositions of the invention can be administered parenterally. The compounds and compositions of the invention may be administered directly into the blood stream, into subcutaneous tissue, into muscle, or into an internal organ. Suitable means for administration include intravenous, intraarterial, intrathecal, intraventricular, intraurethral, intrasternal, intracranial, intramuscular, intrasynovial and subcutaneous. Suitable devices for administration include needle (including microneedle) injectors, needle-free injectors and infusion techniques.

Parenteral formulations are typically aqueous or oily solutions. Where the solution is aqueous, excipients such as sugars (including but restricted to glucose, mannitol, sorbitol, etc.) salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water (WFI).

Parenteral formulations may include implants derived from degradable polymers such as polyesters (i.e. polylactic acid, polylactide, polylactide-co-glycolide, polycapro-lactone, polyhydroxybutyrate), polyorthoesters and polyanhydrides. These formulations may be administered via surgical incision into the subcutaneous tissue, muscular tissue or directly into specific organs.

The preparation of parenteral formulations under sterile conditions, e.g., by lyophilisation, may readily be accomplished using standard pharmaceutical techniques well known to the skilled person.

The solubility of the compounds and compositions used in the preparation of parenteral solutions may be increased by the use of appropriate formulation techniques, such as the incorporation of co-solvents and/or solubility-enhancing agents such as surfactants, micelle structures and cyclodextrins.

Inhalation & Intranasal Administration

The compounds and compositions of the invention can be administered intranasally or by inhalation, typically in the form of a dry powder (either alone, as a mixture, e.g., in a dry blend with lactose, or as a mixed component particle, e.g., mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, e.g., chitosan or cyclodextrin.

The pressurised container, pump, spray, atomizer, or nebuliser contains a solution or suspension of the compound(s) of the invention comprising, e.g., ethanol, aqueous ethanol, or a suitable alternative agent for dispersing, solubilising, or extending release of the compositions of the invention, a propellant(s) as solvent and an optional surfactant, such as sorbitan trioleate, oleic acid, or an oligolactic acid.

Prior to use in a dry powder or suspension formulation, the compound or composition is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, e.g., from gelatin or hydroxypropylmethylcellulose), blisters and cartridges for use in an inhaler or insufflator may be formulated to contain a powder mix of the compound or composition of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

Formulations for inhaled/intranasal administration may be formulated to be immediate and/or modified release using, e.g., PGLA. Modified release formulations include delayed-, sustained-, pulsed-, controlled-, targeted and programmed release.

Transdermal Administration

Suitable formulations for transdermal application include a therapeutically effective amount of a compound or composition of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Cells and Organs Targeted by the Invention

The compounds, compositions, methods and uses of the invention can be used to deliver a biologically active agent to one or more of the following in a patient:
  the liver or liver cells (e.g. hepatocytes);
  a kidney or kidney cells;
  a tumor or tumor cells;
  the CNS or CNS cells (Central Nervous System, e.g. brain and/or spinal cord);
  the PNS or PNS cells (Peripheral Nervous System);
  a lung or lung cells;
  the vasculature or vascular cells;
  the skin or skin cells (e.g. dermis cells and/or follicular cells);
  an eye or ocular cells (e.g. macula, fovea, cornea, retina), and
  an ear or cells of the ear (e.g. cells of the inner ear, middle ear and/or outer ear).

In one embodiment, the invention the compounds, compositions, methods and uses of the invention are for delivering a biologically active agent to liver cells (e.g. hepatocytes). In one embodiment, the invention the compounds, compositions, methods and uses of the invention are for delivering a biologically active agent to a tumor or to tumor cells (e.g. a primary tumor or metastatic cancer cells).

For delivery of a biologically active agent to the liver or liver cells, in one embodiment a compound or composition of the invention is contacted with the liver or liver cells of the patient as is generally known in the art, such as via parental administration (e.g. intravenous, intramuscular, subcutaneous administration) or local administration (e.g. direct injection, portal vein injection, catheterization, stenting), to facilitate delivery.

For delivery of a biologically active agent to the kidney or kidney cells, in one embodiment a compound or composition of the invention is contacted with the kidney or kidney cells of the patient as is generally known in the art, such as via parental administration (e.g. intravenous, intramuscular, subcutaneous administration) or local administration (e.g. direct injection, catheterization, stenting), to facilitate delivery.

For delivery of a biologically active agent to a tumor or tumor cells, in one embodiment a compound or composition of the invention is contacted with the tumor or tumor cells of the patient as is generally known in the art, such as via parental administration (e.g. intravenous, intramuscular, subcutaneous administration) or local administration (e.g. direct injection, catheterization, stenting), to facilitate delivery.

For delivery of a biologically active agent to the CNS or CNS cells (e.g. brain cells and/or spinal cord cells), in one embodiment a compound or composition of the invention is contacted with the CNS or CNS cells (e.g. brain cells and/or spinal cord cells) of the patient as is generally known in the art, such as via parental administration (e.g. intravenous, intramuscular, subcutaneous administration) or local administration (e.g. direct injection, catheterization, stenting, osmotic pump administration (e.g. intrathecal or ventricular)), to facilitate delivery.

For delivery of a biologically active agent to the PNS or PNS cells, in one embodiment a compound or composition of the invention is contacted with the PNS or PNS cells of the patient as is generally known in the art, such as via parental administration (e.g. intravenous, intramuscular, subcutaneous administration) or local administration (e.g. direct injection), to facilitate delivery.

For delivery of a biologically active agent to a lung or lung cells, in one embodiment a compound or composition of the invention is contacted with the lung or lung cells of the patient as is generally known in the art, such as via parental administration (e.g. intravenous, intramuscular, subcutaneous administration) or local administration (e.g. pulmonary administration directly to lung tissues and cells), to facilitate delivery.

For delivery of a biologically active agent to the vasculature or vascular cells, in one embodiment a compound or composition of the invention is contacted with the vasculature or vascular cells of the patient as is generally known in the art, such as via parental administration (e.g. intravenous, intramuscular, subcutaneous administration) or local administration (e.g. clamping, catheterization, stenting), to facilitate delivery.

For delivery of a biologically active agent to the skin or skin cells (e.g. dermis cells and/or follicular cells), in one embodiment a compound or composition of the invention is contacted with the skin or skin cells (e.g. dermis cells and/or follicular cells) of the patient as is generally known in the art, such as via parental administration (e.g. intravenous, intramuscular, subcutaneous administration) or local administration (e.g. direct dermal application, iontophoresis), to facilitate delivery.

For delivery of a biologically active agent to an eye or ocular cells (e.g. macula, fovea, cornea, retina), in one embodiment a compound or composition of the invention is contacted with the eye or ocular cells (e.g. macula, fovea, cornea, retina) of the patient as is generally known in the art, such as via parental administration (e.g. intravenous, intramuscular, subcutaneous administration) or local administration (e.g. direct injection, intraocular injection, periocular injection, iontophoresis, use of eyedrops, implants), to facilitate delivery.

For delivery of a biologically active agent to an ear or cells of the ear (e.g. cells of the inner ear, middle ear and/or outer ear), in one embodiment a compound or composition of the invention is contacted with the ear or cells of the ear (e.g. cells of the inner ear, middle ear and/or outer ear) of the patient as is generally known in the art, such as via parental administration (e.g. intravenous, intramuscular, subcutaneous administration) or local administration (e.g. direct injection), to facilitate delivery.

Treatment of Diseases or Conditions

The diseases or conditions which may be treated by this invention include those related to modulation in a patient of a gene, gene expression, protein, protein activity, cellular pathway, and the like. The disease or condition treated by this invention may be one or more selected from the group consisting of: a proliferative disease (e.g. a tumor); an inflammatory disease; transplant and/or tissue rejection (allograft rejection); an autoimmune disease; an infectious disease; an age-related disease; a neurologic or neurodegenerative disease (e.g. Huntington's disease); a metabolic disease; a cardiovascular disease; a respiratory disease; an ocular disease; a dermatological disease; an auditory disease (e.g. hearing loss, deafness); a liver disease (e.g. hepatitis, HCV, HBV, diabetis, cirrhosis, hepatocellular carcinoma), and a kidney/renal disease (e.g. polycystic kidney disease). In one particular embodiment, the invention treats a proliferative disease, e.g. a tumor or tumor cell. In one particular embodiment, the invention treats a liver disease, e.g. hepatitis, HCV, HBV, diabetis, cirrhosis and certain hepatocellular carcinomas.

The skilled person would be able to select a biologically active agent which in combination with a compound of the present invention delivers a therapeutically effective amount of the agent. Where the agent is a RNAi therapeutic, the desired therapeutic effect is modulating expression of a target gene implicated in the disease or condition of interest. In one embodiment, the reduction of gene expression and thus reduction in the level of the respective protein/RNA relieves, to some extent, the symptoms of the disease or condition.

Efficacy

The compounds, compositions, methods and uses may involve administration conditions suitable for reducing or inhibiting, or ameliorating a disease or disorder. In one embodiment, a therapeutically effective amount of an RNAi agent is administered to a patient in need thereof, wherein the level of target gene expression is reduced in the patient compared to an untreated patient.

In one embodiment, the expression of a target gene implicated in the disease or condition of interest is reduced by about 10%, more preferably about 20%, more preferably about 30%, more preferably about 40%, more preferably about 50%, more preferably about 60%, more preferably about 70%, more preferably about 80%, more preferably about 90%, more preferably about 95%, more preferably about 98%, and most preferably about 100% relative to an untreated patient.

Definitions

As used throughout this disclosure, articles such as "a" and "an" refer to one or more than one (at least one) of the grammatical object of the article.

Compounds of Formulae (I), (II), (III), (IV), (V), (VI), (VII), (VIII), (IX), (X), (XI) and (XII) and Derivatives Thereof As used herein, the terms "(lipid) compound of the invention", "(lipid) compound of formula (I)", "(lipid) compound", "cationic lipid" etc. (i.e. all references to the cationic lipids of the invention, and/or "stealth lipids" include pharmaceutically acceptable derivatives thereof and polymorphs, isomers and isotopically labelled variants thereof. Furthermore, said terms include compounds of formula (II), (III), (IV), (V), (VI), (VII), (VIII), (IX) and (X) for cationic lipids; and formulas (XI) and (XII) for stealth lipids; and embodiments thereof disclosed herein.

Pharmaceutically Acceptable Derivatives

The term "pharmaceutically acceptable derivative" includes any pharmaceutically acceptable salt, solvate or hydrate of a compound of formula (I). In one embodiment, the pharmaceutically acceptable derivatives are pharmaceutically acceptable salts, solvates or hydrates of a compound of formula (I).

Pharmaceutically Acceptable Salts

The term "pharmaceutically acceptable salt" includes a salt prepared from pharmaceutically acceptable non-toxic acids or bases including inorganic or organic acids and bases. For a review of pharmaceutically acceptable salts, see Stahl and Wermuth, Handbook of Pharmaceutical Salts: Properties, Selection and Use (Wiley-VCH, Weinheim, Germany, 2002).

Solvates & Hydrates

The compounds of the invention may exist in both unsolvated and solvated forms. The term "solvate" includes molecular complexes comprising a compound of the invention and one or more pharmaceutically acceptable solvent molecules such as water or $C_{1-6}$ alcohols, e.g. ethanol. The term "hydrate" means a "solvate" where the solvent is water.

Isomeric Forms

Compounds of the invention may exist in one or more geometrical, optical, enantiomeric, diastereomeric and tautomeric forms, including but not limited to cis- and trans-forms, E- and Z-forms, R-, S- and meso-forms, keto-, and enol-forms. All such isomeric forms are included within the invention. The isomeric forms may be in isomerically pure or enriched form, as well as in mixtures of isomers (e.g. racemic or diastereomeric mixtures).

Accordingly, the invention provides at least, e.g.:
stereoisomeric mixtures of compounds of formula (I);
a diastereomerically enriched or diastereomerically pure isomer of a compound of formula (I); or
an enantiomerically enriched or enantiomerically pure isomer of a compound of formula (I).

Where appropriate isomers can be separated from their mixtures by the application or adaptation of known methods (e.g. chromatographic techniques and recrystallisation techniques). Where appropriate isomers can be prepared by the application or adaptation of known methods (e.g. asymmetric synthesis).

Isotopic Labeling

The invention includes pharmaceutically acceptable isotopically-labelled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$. Certain isotopically-labelled compounds of formula (I), e.g., those incorporating a radioactive isotope, are useful in drug and/or substrate tissue distribution studies. The radioactive isotopes $^{3}H$ and $^{14}C$ are particularly useful for this purpose in view of their ease of incorporation and ready means of detection.

Substitution with positron emitting isotopes, such as $^{11}C$, $^{18}F$, $^{15}O$ and $^{13}N$, can be useful in Positron Emission Topography (PET) studies.

Isotopically-labelled compounds of formula (I) can generally be prepared by conventional techniques known to the skilled person or by processes analogous to those described herein using an appropriate isotopically-labelled reagent in place of the non-labelled reagent previously employed.

Therapeutic Definitions

As used herein, "treatment" includes ameliorative, curative and prophylactic treatment. As used herein, a "patient" means an animal, preferably a mammal, preferably a human, in need of treatment.

The "biologically active agent" is preferably a therapeutic compound, i.e. a compound that is useful for the treatment or prevention of a disease or a condition.

The biologically active agent includes but are not limited to, e.g., antibodies, cholesterol, hormones, antivirals, peptides, polypeptides, proteins, nucleoproteins, chemotherapeutics, low molecular weight drugs, vitamins, co-factors, nucleosides, nucleoside derivatives, nucleotides, oligonucleotides, enzymatic nucleic acids, antisense nucleic acids, triplex forming oligonucleotides, 2,5-A antisense chimeras, allozymes, aptamers, ribozyme, decoy RNA molecules and analogs thereof, and small nucleic acid molecules, such as an RNA inhibitor (RNAi) including, e.g., short interfering nucleic acid (siNA), short interfering RNA (siRNA), double-stranded RNA (dsRNA), micro-RNA (miRNA), and short hairpin RNA (shRNA). In one embodiment the biologically active agent is preferably a nucleoside or nucleoside derivative, e.g. a nucleic acid, an oligonucleotide, a polynucleotide (e.g. siNA, miRNA, RNAi, antisense, aptamer, ribozyme, decoy, ribozyme, 2-5A, triplex forming oligonucleotide), and preferably an siRNA, miRNA, siRNA inhibitor or an miRNA inhibitor.

In one embodiment, the biologically active agent is an siNA (short interfering nucleic acid) molecule. In one embodiment, the siNA is siDNA. In one embodiment, the siNA is siRNA. In one embodiment, the siNA is miRNA.

In one embodiment, the biologically active agent is a small nucleic acid molecule, referred to below for convenience purposes only as a "siNA" molecule, down-regulates expression of a target gene, e.g. wherein the target gene comprises a target encoding sequence or wherein the target gene comprises a target non-coding sequence or regulatory elements involved in target gene expression.

The siNA can be single, double, or multiple stranded. In one embodiment, it is double stranded.

In one embodiment, the siNA comprises unmodified nucleotides and/or non-nucleotides. In one embodiment, the siNA comprises at least one, or more than one, modified nucleotides and/or non-nucleotides. In one embodiment, the modified nucleotide comprises a modified base portion. In one embodiment, the modified nucleotide comprises a modified sugar portion. In one embodiment, the modified nucleotide comprises a modified backbone portion. In one embodiment, the siNA comprises one or more of a modified base portion, a modified sugar portion, and/or a modified backbone portion.

In one embodiment, the siNA molecule comprises about 15 to about 40 (e.g. about 15, 16, 17, 18, 19, 20, 21, 22, 23, 24, 25, 26, 27, 28, 29, 30, 31, 23, 33, 34, 35, 36, 37, 38, 39, or 40) base pairs, in a sub-embodiment about 15 to about 30 (e.g. about 15, 16, 17, 18, 19, 20, 21, 22, 23, 24, 25, 26, 27, 28, 29, or 30) base pairs, in a sub-embodiment about 15 to about 28 base pairs, in a sub-embodiment about 17 to about 25 base pairs, in a sub-embodiment about 18 to about 23 base pairs, in a further sub-embodiment about 19 to about 22 base pairs. In one embodiment the siNA comprises about 17 base pairs. In one embodiment the siNA comprises about 18 base pairs. In one embodiment the siNA comprises about 19 base pairs. In one embodiment the siNA comprises about 20 base pairs. In one embodiment the siNA comprises about 21 base pairs.

In one embodiment, each of the two strands of the siNA molecule independently comprises about 15 to about 40 (e.g. about 15, 16, 17, 18, 19, 20, 21, 22, 23, 24, 25, 26, 27, 28, 29, 30, 31, 23, 33, 34, 35, 36, 37, 38, 39, or 40) nucleotides, in a sub-embodiment about 15 to about 30 (e.g. about 15, 16, 17, 18, 19, 20, 21, 22, 23, 24, 25, 26, 27, 28, 29, or 30) nucleotides, in a sub-embodiment about 15 to about 28 nucleotides, in a sub-embodiment about 17 to about 25 nucleotides, in a sub-embodiment about 18 to about 23 nucleotides, in a further sub-embodiment about 19 to about 22 nucleotides. In one embodiment each strand is about 17 nucleotides long. In one embodiment each strand is about 18 nucleotides long. In one embodiment each strand is about 19 nucleotides long. In one embodiment each strand is about 20 nucleotides long. In one embodiment each strand is about 21 nucleotides.

In one embodiment, the siNA molecule directs cleavage of a target RNA via the RISC complex, i.e., RNA interference (RNAi).

In one embodiment, the siNA molecule comprises a first and a second strand, the first strand of the siNA comprising a nucleotide sequence having sufficient complementarity to the target RNA for the siNA molecule to direct cleavage of the target RNA via RNA interference, and the second strand of said siNA molecule comprising a nucleotide sequence that is complementary to the first strand.

In one embodiment, the short interfering nucleic acid (siNA) molecule is a chemically synthesized double stranded molecule.

In one embodiment, the siNA inhibits the expression of target genes or a target gene family, wherein the genes or gene family sequences share sequence homology. Such homologous sequences can be identified as is known in the art, e.g., using sequence alignments. Such siNA molecules can be designed to target such homologous sequences, e.g., using perfectly complementary sequences or by incorporating non-canonical base pairs, e.g., mismatches and/or wobble base pairs that can provide additional target sequences.

In one embodiment, the double-stranded siNA molecule does not contain any ribonucleotides. In another embodiment, the double-stranded siNA molecule comprises one or more ribonucleotides.

In one embodiment, the siNA molecule which down-regulates expression of a target gene comprises an antisense region, wherein the antisense region comprises a nucleotide sequence that is complementary to a nucleotide sequence of the target gene or a portion thereof, and a sense region, wherein the sense region comprises a nucleotide sequence substantially similar to the nucleotide sequence of the target gene or a portion thereof. In one embodiment, the antisense region and the sense region independently comprise about 15 to about 30 (e.g. about 15, 16, 17, 18, 19, 20, 21, 22, 23, 24, 25, 26, 27, 28, 29, or 30) nucleotides. In one embodiment, the antisense region comprises a nucleotide sequence that is complementary to a nucleotide sequence of RNA encoded by the target gene or a portion thereof, and the sense region comprises a nucleotide sequence that is complementary to the antisense region.

In one embodiment, the siNA molecule comprises one blunt end. In one embodiment, the siNA molecule comprises two blunt ends, i.e., a symmetric terminus without any overhanging unpaired nucleotides.

In one embodiment, all nucleotides of each fragment of the siNA molecule are base-paired to complementary nucleotides on the other strand of the siNA molecule.

In one embodiment, the siNA molecule comprises one or more of the following features: a mismatch, a bulge, a loop and a wobble base pair, each of which may modulate the activity of the siNA molecule to mediate RNA interference.

In one embodiment the sense region is connected to the antisense region via a linker molecule, such as a polynucleotide linker or a non-nucleotide linker.

In one embodiment, the siNA molecule has one or more modified pyrimidine and/or purine nucleotides. In one embodiment, the pyrimidine nucleotides in the sense region are 2'-O-methylpyrimidine nucleotides or 2'-deoxy-2'-fluoro pyrimidine nucleotides and the purine nucleotides present in the sense region are 2'-deoxy purine nucleotides. In another embodiment, the pyrimidine nucleotides in the sense region are 2'-deoxy-2'-fluoro pyrimidine nucleotides and the purine nucleotides present in the sense region are 2'-O-methyl purine nucleotides. In another embodiment, the pyrimidine nucleotides in the sense region are 2'-deoxy-2'-fluoro pyrimidine nucleotides and the purine nucleotides present in the sense region are 2'-deoxy purine nucleotides. In one embodiment, the pyrimidine nucleotides in the antisense region are 2'-deoxy-2'-fluoro pyrimidine nucleotides and the purine nucleotides present in the antisense region are 2'-O-methyl or 2'-deoxy purine nucleotides.

In one embodiment, the sense strand has a non-complementary region. Optionally, the nucleotides present in said non-complementary region are all 2'-deoxy nucleotides.

In one embodiment, the polynucleotide comprising the sense region includes a terminal cap moiety at the 5'-end, the 3'-end, or both of the 5' and 3' ends of the strand. In one embodiment, the polynucleotide comprising the antisense strand includes a terminal cap moiety at the 5'-end, the 3'-end, or both of the 5' and 3' ends of the strand. In one embodiment, the terminal cap moiety is an inverted deoxy abasic moiety or glyceryl moiety. Other examples of terminal cap moieties are known in the art, e.g., WO 2005/021749 and WO 2007/128477.

In one embodiment, the siNA has phosphite, phosphodiester, phosphorothioate and/or phosphorodithioate linkages in the polynucleotide backbone. In one embodiment, the siNA has at least one phosphorothioate linkage. In one embodiment, the siNA has at least one phosphorodithioate linkage.

In one embodiment, the nucleotide modification(s) are present at specifically selected locations in the siNA that are sensitive to cleavage by ribonucleases, such as locations having pyrimidine nucleotides.

In one embodiment, each of the two 3' terminal nucleotides of each strand of the siNA molecule is a 2'-deoxy-pyrimidine nucleotide, such as a 2'-deoxy-thymidine.

The amount of the compound of the invention and the biologically active agent (e.g. the therapeutic compound) administered should be a therapeutically effective amount where used for the treatment of a disease or condition, and a prophylactically effective amount where used for the prevention of a disease or condition.

The term "therapeutically effective amount" refers to the amount of the compound of the invention and the biologically active agent (e.g. the therapeutic compound) needed to treat or ameliorate a targeted disease or condition. The term "prophylactically effective amount" used herein refers to the amount of the compound of the invention and the biologically active agent (e.g. the therapeutic compound) needed to prevent a targeted disease or condition. The exact dosage will generally be dependent on the patient's status at the time of administration. Factors that may be taken into consideration when determining dosage include the severity of the disease state in the patient, the general health of the patient, the age, weight, gender, diet, time, frequency and route of administration, identity of the biologically active agent (e.g. the therapeutic compound), reaction sensitivities and the patient's tolerance or response to therapy. The precise amount can be determined by routine experimentation, but may ultimately lie with the judgement of the clinician. Generally, an effective dose will be from 0.01 mg/kg/day (mass of drug compared to mass of patient) to 1000 mg/kg/day, e.g. 1 mg/kg/day to 100 mg/kg/day. Compositions may be administered individually to a patient or may be administered in combination with other agents, drugs or hormones.

In any of the methods of treatment or associated uses, the compound or composition of the invention can be administered to the patient as a course of treatment, e.g., administration at various time intervals, such as once per day over the course of treatment, once every two days over the course of treatment, once every three days over the course of treatment, once every four days over the course of treatment, once every five days over the course of treatment, once every six days over the course of treatment, once per week over the course of treatment, once every other week over the course of treatment, once per month over the course of treatment, etc. In one embodiment, the course of treatment is once every 1, 2, 3, 4, 5, 6, 7, 8, 9, or 10 weeks. In one embodiment, the course of treatment is from about one to about 52 weeks or longer (e.g. indefinitely). In one embodiment, the course of treatment is from about one to about 48 months or longer (e.g. indefinitely).

In one embodiment, a course of treatment involves an initial course of treatment, such as once every 1, 2, 3, 4, 5, 6, 7, 8, 9, 10 or more weeks for a fixed interval (e.g. 1×, 2×, 3×, 4×, 5×, 6×, 7×, 8×, 9×, 10× or more) followed by a maintenance course of treatment, such as once every 4, 6, 8, 10, 15, 20, 25, 30, 35, 40, or more weeks for an additional fixed interval (e.g. 1×, 2×, 3×, 4×, 5×, 6×, 7×, 8×, 9×, 10× or more).

By "proliferative disease" as used herein is meant any disease, condition, trait, genotype or phenotype characterized by unregulated cell growth or replication as is known in the art. In one embodiment, the proliferative disease is cancer. In one embodiment, the proliferative disease is a tumor. In one embodiment, the proliferative disease includes, but are not limited to, e.g., liquid tumors such as, e.g., leukemias, e.g., acute myelogenous leukemia (AML), chronic myelogenous leukemia (CML), acute lymphocytic leukemia (ALL), multiple myeloma, and chronic lymphocytic leukemia; and solid tumors, e.g., AIDS related cancers such as Kaposi's sarcoma; breast cancers; bone cancers; brain cancers; cancers of the head and neck, non-Hodgkins lymphoma, adenoma, squamous cell carcinoma, laryngeal carcinoma, gallbladder and bile duct cancers, cancers of the retina, cancers of the esophagus, gastrointestinal cancers, ovarian cancer, uterine cancer, thyroid cancer, testicular cancer, endometrial cancer, melanoma, colorectal cancer, lung cancer, bladder cancer, prostate cancer, lung cancer (including non-small cell lung carcinoma), pancreatic cancer, sarcomas, Wilms' tumor, cervical cancer, head and neck cancer, skin cancers, nasopharyngeal carcinoma, liposarcoma, epithelial carcinoma, renal cell carcinoma, gallbladder adeno carcinoma, endometrial sarcoma, multidrug resistant cancers. In one embodiment, the proliferative disease includes neovascularization associated with tumor angiogenesis, macular degeneration (e.g. wet/dry age related macular degeneration), corneal neovascularization, diabetic retinopathy, neovascular glaucoma, myopic degeneration. In one embodiment, the proliferative disease includes restenosis and polycystic kidney disease.

By "inflammatory disease" as used herein is meant any disease, condition, trait, genotype or phenotype characterized by an inflammatory or allergic process as is known in the art. Inflammatory diseases include, but are not limited to, e.g., inflammation (e.g. acute and/or chronic inflammation), respiratory disease, atherosclerosis, psoriasis, dermatitis, restenosis, asthma, allergic rhinitis, atopic dermatitis, septic shock, rheumatoid arthritis, inflammatory bowel disease, inflammatory pelvic disease, pain, ocular inflammatory disease, celiac disease, tuberculosis, silicosis and other pneumoconioses.

By "autoimmune disease" as used herein is meant any disease, condition, trait, genotype or phenotype characterized by autoimmunity as is known in the art. Autoimmune diseases include, but are not limited to, e.g., multiple sclerosis, diabetes mellitus, lupus, scleroderms, fibromyalgia, transplantation rejection (e.g. prevention of allograft rejection), pernicious anemia, rheumatoid arthritis, systemic lupus erythematosus, dermatomyositis, myasthenia gravis, lupus erythematosus, multiple sclerosis, and Grave's disease.

By "infectious disease" is meant any disease, disorder or condition associated with an infectious agent, such as a virus, bacteria, fungus, prion or parasite.

By "neurologic disease" is meant any disease, disorder, or condition affecting the central or peripheral nervous system. Neurologic diseases include, but are not limited to, diseases or disorders of either the peripheral or the central nervous system including, e.g., Alzheimer's Disease, Aneurysm, Brain Injury, Carpal Tunnel Syndrome, Cerebral Aneurysm, Chronic Pain, Creutzfeldt-Jakob Disease, Epilepsy, Huntington's Disease, Meningitis, Seizure Disorders, and other neurologic diseases, disorders and syndromes.

By "respiratory disease" is meant any disease or condition affecting the respiratory tract. Respiratory diseases include, but are not limited to, e.g., asthma, chronic obstructive pulmonary disease (COPD), allergic rhinitis, sinusitis, allergies, impeded respiration, respiratory distress syndrome, cystic fibrosis, pulmonary hypertension or vasoconstriction and emphysema.

By "cardiovascular disease" is meant and disease or condition affecting the heart and vasculature. Cardiovascular diseases include, but are not limited to, e.g., coronary heart disease (CHD), cerebrovascular disease (CVD), aortic stenosis, peripheral vascular disease, myocardial infarction (heart attack), arrhythmia, and congestive heart failure.

By "ocular disease" as used herein is meant any disease, condition, trait, genotype or phenotype of the eye and related structures. Ocular diseases include, but are not limited to, e.g., cystoid macular edema, diabetic retinopathy, lattice degeneration, retinal vein occlusion, retinal artery occlusion, macular degeneration (e.g. age related macular degeneration such as wet AMD or dry AMD), toxoplasmosis, retinitis pigmentosa, conjunctival laceration, corneal laceration, glaucoma, and the like.

By "metabolic disease" is meant any disease or condition affecting metabolic pathways. Metabolic disease can result in an abnormal metabolic process, either congenital due to inherited enzyme abnormality (inborn errors of metabolism) or acquired due to disease of an endocrine organ or failure of a metabolically important organ such as the liver. In one embodiment, metabolic disease includes obesity, insulin resistance, and diabetes (e.g. type I and/or type II diabetes).

By "dermatological disease" is meant any disease or condition of the skin, dermis, or any substructure therein such as a hair, a follicle, etc. Dermatological diseases, disorders, conditions, and traits can include psoriasis, ectopic dermatitis, skin cancers such as melanoma and basal cell carcinoma, hair loss, hair removal and alterations in pigmentation.

By "auditory disease" is meant any disease or condition of the auditory system, including the ear, such as the inner ear, middle ear, outer ear, auditory nerve, and any substructures therein. Auditory diseases, disorders, conditions, and traits can include hearing loss, deafness, tinnitus, vertigo, balance and motion disorders.

In one embodiment, the disease or condition is a disease of the liver, a tumor, a disease mediated by FVII, and/or a disease mediated by PLK1. Diseases mediated by FVII include abnormal blood coagulation and tumors; such diseases thus include thrombosis (e.g. venous thromboembolisms, pulmonary embolisms and strokes).

Biochemical Terms and Definitions

The term "lipid" refers to a group of organic compounds that includes, but is not limited to, esters of fatty acids and are characterised by being insoluble in water, but soluble in many organic solvents. Lipids can be divided into at least three classes (1) "simple lipids" which include fats and oils as well as waxes; (2) "compound lipids" which include phospholipids and glycolipids, and (3) "derived lipids" such as steroids.

The term "cationic lipid" as used herein is meant any lipophilic compound having a cationic charge, such as a compound having formula (I)

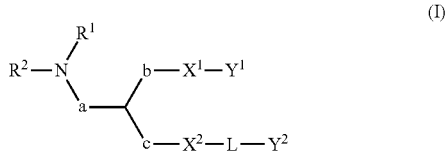

wherein the definitions are as set out elsewhere herein. Other examples of cationic lipids are set out above under the heading "compositions".

Helper Lipids

The term "helper lipid" as used herein is meant a lipid that enhances transfection (e.g. transfection of the nanoparticle including the biologically active agent) to some extent. The mechanism by which the helper lipid enhances transfection may include, e.g., enhancing particle stability and/or enhancing membrane fusogenicity. Helper lipids include steroids and alkyl resorcinols. Examples of helper lipids are cholesterol, 5-heptadecylresorcinol, and cholesterol hemisuccinate Stealth Lipids The term "stealth lipid" as used herein is meant a lipid that increases the length of time for which the nanoparticles can exist in vivo (e.g. in the blood). In one embodiment, a stealth lipid comprises a hydrophilic polymer head group operably linked to a lipid moiety. In one embodiment stealth lipids in a liposome formulation shield the nanoparticle surface and thereby reduce opsonisation by blood proteins and uptake by the macrophages of the mononuclear phagocyte system. Structures of stealth lipids suitable for use in the present invention include but are not limited to, e.g., compounds as provided in formula XI and formula XII. Other contemplated stealth lipids and information about the biochemistry of such lipids can be found in Romberg et al., Pharmaceutical Research, Vol. 25, No. 1, 2008, p. 55-71 and Hoekstra et al., Biochimica et Biophysica Acta 1660 (2004) 41-52.

In one embodiment, the stealth lipid comprises a group selected from PEG (sometimes referred to as poly(ethylene oxide) and polymers based on poly(oxazoline), poly(vinyl alcohol), poly(glycerol), poly(N-vinylpyrrolidone), polyaminoacids and poly[N-(2-hydroxypropyl) methacrylamide]. In one embodiment the helper lipid is able to "shed" as described in Romberg et al. Specific stealth lipids of the invention are provided, e.g., in formula XI and formula XII, which may be further substituted by one skilled in the art. Additional suitable PEG lipids are disclosed, e.g., in WO 2006/007712.

Specific suitable stealth lipids include polyethyleneglycol-diacylglycerol or polyethyleneglycol-diacylglycamide (PEG-DAG) conjugates including those comprising a dialkylglycerol or dialkylglycamide group having alkyl chain length independently comprising from about $C_4$ to about $C_{40}$ saturated or unsaturated carbon atoms. The dialkylglycerol or dialkylglycamide group can further comprise one or more substituted alkyl groups. In any of the embodiments described herein, the PEG conjugate can be selected from PEG-dilaurylglycerol, PEG-dimyristylglycerol (catalog # GM-020 from NOF), PEG-dipalmitoylglycerol, PEG-disterylglycerol, PEG-dilaurylglycamide, PEG-dimyristylglycamide, PEG-dipalmitoylglycamide, and PEG-disterylglycamide, PEG-cholesterol (1-[8'-(Cholest-5-en-3[beta]-oxy)carboxamido-3',6'-dioxaoctanyl]carbamoyl-[omega]-methyl-poly(ethylene glycol), PEG-DMB (3,4-Ditetradecoxylbenzyl-[omega]-methyl-poly(ethylene glycol) ether), S001, S002, S003, S004, S005, S006, S007, S008, S009, S010, S011, S012, S013, S014, S015, S016, S017, S018, S019, S020, S021, S022, S023, S024, S025, S026, 1,2-dimyristoyl-sn-glycero-3-phosphoethanolamine-N-[methoxy(polyethylene glycol)-2000] (catalog # 880150P from Avanti Polar Lipids). S010 and S011 are disclosed in WO 2009/086558 under the labels IVa and IVc, respectively.

Unless otherwise indicated, the term "PEG" as used herein means any polyethylene glycol or other polyalkylene ether polymer. In one embodiment, PEG is an optionally substituted linear or branched polymer of ethylene glycol or ethylene oxide. In one embodiment PEG is unsubstituted. In one embodiment the PEG is substituted, e.g., by one or more alkyl, alkoxy, acyl or aryl groups. In one embodiment, the term includes PEG copolymers such as PEG-polyurethane or PEG-polypropylene (see, e.g., J. Milton Harris, Poly(ethylene glycol) chemistry: biotechnical and biomedical applications (1992)); in another embodiment, the term does not include PEG copolymers. In one embodiment, the PEG has a molecular weight of from about 130 to about 50,000, in a sub-embodiment about 150 to about 30,000, in a sub-embodiment about 150 to about 20,000, in a sub-embodiment about 150 to about 15,000, in a sub-embodiment about 150 to about 10,000, in a sub-embodiment about 150 to about 6000, in a sub-embodiment about 150 to about 5000, in a sub-embodiment about 150 to about 4000, in a sub-embodiment about 150 to about 3000, in a sub-embodiment about 300 to about 3000, in a sub-embodiment about 1000 to about 3000, and in a sub-embodiment about 1500 to about 2500.

In certain embodiments the PEG is a "PEG-2K", also termed "PEG 2000", which has an average molecular weight of about 2000 daltons. PEG-2K is represented herein by the following formula (XIIa), wherein n is 45, meaning that the number-averaged degree of polymerization comprises about 45 subunits. However, other PEG embodiment known in the art may be used, including, e.g., those where the number-averaged degree of polymerization comprises about 23 subunits (n=23) and/or 68 subunits (n=68).

(XIIa)

Definitions for RNA Interference and RNAi Formulations

By "lipid nanoparticle" is meant a particle that comprises a plurality of (i.e. more than one) lipid molecules physically associated with each other by intermolecular forces. The lipid nanoparticles may be, e.g., microspheres (including unilamellar and multilamellar vesicles, e.g. liposomes), a dispersed phase in an emulsion, micelles or an internal phase in a suspension.

The lipid nanoparticles have a size of about 1 to about 2,500 nm, about 1 to about 1,500 nm, about 1 to about 1,000 nm, in a sub-embodiment about 50 to about 600 nm, in a sub-embodiment about 50 to about 400 nm, in a sub-embodiment about 50 to about 250 nm, and in a sub-embodiment about 50 to about 150 nm. Unless indicated otherwise, all sizes referred to herein are the average sizes (diameters) of the fully formed nanoparticle, as measured by dynamic light scattering on a Malvern Zetasizer. The nanoparticle sample is diluted in phosphate buffered saline (PBS) so that the count rate is approximately 200-400 kcts. The data is presented as a weighted average of the intensity measure.

In one embodiment, the biologically active agent is associated with the lipid nanoparticle (e.g. vesicle), and is preferably encapsulated thereby.

In one embodiment, the lipid nanoparticle comprises a biologically active agent, a compound of the invention, a neutral lipid, a helper lipid and a stealth lipid.

In one embodiment, the liposome particles are stable in serum.

The term "short interfering nucleic acid" (siNA) as used herein refers to any nucleic acid molecule capable of inhibiting or down regulating gene expression or viral replication by mediating RNA interference (RNAi) or gene silencing in a sequence-specific manner. It includes short interfering RNA (siRNA), microRNA (miRNA), short interfering oligonucleotides and chemically-modified short interfering nucleic acid molecules. siRNAs are responsible for RNA interference, the process of sequence-specific post-transcriptional gene silencing in animals and plants. siRNAs are generated by ribonuclease III cleavage from longer double-stranded RNA (dsRNA) which are homologous to, or specific to, the silenced gene target.

By "RNA interference" (RNAi) is meant a biological process of inhibiting or down regulating gene expression in a cell as is generally known in the art, see e.g., Zamore and Haley, 2005, Science, 309, 1519-1524; Zamore et al., 2000, Cell, 101, 25-33; Elbashir et al., 2001, Nature, 411, 494-498; and Kreutzer et al., PCT Publication WO 00/44895; Fire, PCT Publication WO 99/32619; Mello and Fire, PCT Publication WO 01/29058; and the like.

As used herein, RNAi is equivalent to other terms used to describe sequence specific RNA interference, such as post transcriptional gene silencing, translational inhibition, transcriptional inhibition, or epigenetics. For example, the formulations containing lipids of the invention can be used in conjunction with siNA molecules to epigenetically silence genes at both the post-transcriptional level and/or the pre-transcriptional level. In a non-limiting example, modulation of gene expression by siNA molecules can result from siNA mediated cleavage of RNA (either coding or non-coding RNA) via RISC, or alternately, translational inhibition as is known in the art. In another embodiment, modulation of gene expression by siNA can result from transcriptional inhibition such as is reported e.g., in Janowski et al., 2005, Nature Chemical Biology, 1, 216-222.

By "RNAi inhibitor" is meant any molecule that can down modulate (e.g. reduce or inhibit) RNA interference function or activity in a cell or patient. An RNAi inhibitor can down regulate, reduce or inhibit RNAi (e.g. RNAi mediated cleavage of a target polynucleotide, translational inhibition, or transcriptional silencing) by interaction with or interfering with the function of any component of the RNAi pathway, including protein components such as RISC, or nucleic acid components such as miRNAs or siRNAs. An RNAi inhibitor can be a siNA molecule, an antisense molecule, an aptamer, or a small molecule that interacts with or interferes with the function of RISC, a miRNA, or a siRNA or any other component of the RNAi pathway in a cell or patient. By inhibiting RNAi (e.g. RNAi mediated cleavage of a target polynucleotide, translational inhibition, or transcriptional silencing), an RNAi inhibitor can be used to modulate (e.g, up-regulate or down regulate) the expression of a target gene. In one embodiment, an RNA inhibitor is used to up-regulate gene expression by interfering with (e.g. reducing or preventing) endogenous down-regulation or inhibition of gene expression through translational inhibition, transcriptional silencing, or RISC mediated cleavage of a polynucleotide (e.g. mRNA). By interfering with mechanisms of endogenous repression, silencing, or inhibition of gene expression, RNAi inhibitors of the invention can therefore be used to up-regulate gene expression for the treatment of diseases or conditions resulting from a loss of function. The term "RNAi inhibitor" is used in interchangeably with the term "siNA" in various embodiments herein.

The term "enzymatic nucleic acid" as used herein refers to a nucleic acid molecule that has complementarity in a substrate binding region to a specified gene target, and also has an enzymatic activity that acts to specifically cleave a target RNA, thereby inactivating the target RNA molecule. The complementary regions allow sufficient hybridization of the enzymatic nucleic acid molecule to the target RNA and thus permit cleavage. Complementarity of 100% is preferred, but complementarity as low as 50-75% can also be useful in this invention (see e.g., Werner and Uhlenbeck, 1995, Nucleic Acids Research, 23, 2092-2096; Hammann et al., 1999, Antisense and Nucleic Acid Drug Dev., 9, 25-31). The nucleic acids can be modified at the base, sugar, and/or phosphate groups. The term enzymatic nucleic acid is used interchangeably with phrases such as ribozymes, catalytic RNA, enzymatic RNA, catalytic DNA, aptazyme or aptamer-binding ribozyme, regulatable ribozyme, catalytic oligonucleotides, nucleozyme, DNAzyme, RNA enzyme, endoribonuclease, endonuclease, minizyme, leadzyme, oligozyme or DNA enzyme. All of these terminologies describe nucleic acid molecules with enzymatic activity. The key features of an enzymatic nucleic acid molecule are that it has a specific substrate binding site that is complementary to one or more of the target nucleic acid regions, and that it has nucleotide sequences within or surrounding that substrate binding site that impart a nucleic acid cleaving and/or ligation activity to the molecule (see, e.g., Cech et al., U.S. Pat. No. 4,987,071; Cech et al., 1988, 260 JAMA 3030). Ribozymes and enzymatic nucleic acid molecules of the invention can be chemically modified, e.g., as described in the art and elsewhere herein.

The term "antisense nucleic acid", as used herein, refers to a non-enzymatic nucleic acid molecule that binds to target RNA by means of RNA-RNA or RNA-DNA or RNA-PNA (protein nucleic acid; Egholm et al., 1993 Nature 365, 566) interactions and alters the activity of the target RNA (for a review, see Stein and Cheng, 1993 Science 261, 1004 and Woolf et al., U.S. Pat. No. 5,849,902). Antisense DNA can be synthesized chemically or expressed via the use of a single stranded DNA expression vector or equivalent thereof. Antisense molecules of the invention can be chemically modified, e.g. as described in the art.

The term "RNase H activating region" as used herein, refers to a region (generally greater than or equal to 4-25 nucleotides in length, preferably from 5-11 nucleotides in length) of a nucleic acid molecule capable of binding to a target RNA to form a non-covalent complex that is recognized by cellular RNase H enzyme (see e.g., Arrow et al., U.S. Pat. No. 5,849,902; Arrow et al., U.S. Pat. No. 5,989,912). The RNase H enzyme binds to the nucleic acid molecule-target RNA complex and cleaves the target RNA sequence.

The term "2-5A antisense chimera" as used herein, refers to an antisense oligonucleotide containing a 5'-phosphorylated 2'-5'-linked adenylate residue. These chimeras bind to target RNA in a sequence-specific manner and activate a cellular 2-5A-dependent ribonuclease that, in turn, cleaves the target RNA (Torrence et al., 1993 Proc. Natl. Acad. Sci. USA 90, 1300; Silverman et al., 2000, Methods Enzymol., 313, 522-533; Player and Torrence, 1998, Pharmacol. Ther., 78, 55-113). 2-5A antisense chimera molecules can be chemically modified, e.g. as described in the art.

The term "triplex forming oligonucleotides" as used herein, refers to an oligonucleotide that can bind to a double-stranded DNA in a sequence-specific manner to form a triple-strand helix. Formation of such triple helix structure has been shown to inhibit transcription of the targeted gene (Duval-Valentin et al., 1992 Proc. Natl. Acad. Sci. USA 89, 504; Fox, 2000, Curr. Med. Chem., 7, 17-37; Praseuth et. al., 2000, Biochim. Biophys. Acta, 1489, 181-206). Triplex forming oligonucleotide molecules of the invention can be chemically modified, e.g. as described in the art.

The term "decoy RNA" as used herein, refers to an RNA molecule or aptamer that is designed to preferentially bind to a predetermined ligand. Such binding can result in the inhibition or activation of a target molecule. The decoy RNA or aptamer can compete with a naturally occurring binding target for the binding of a specific ligand. Similarly, a decoy RNA can be designed to bind to a receptor and block the binding of an effector molecule, or can be designed to bind to receptor of interest and prevent interaction with the receptor. Decoy molecules of the invention can be chemically modified, e.g. as described in the art.

The term "single stranded DNA" (ssDNA) as used herein refers to a naturally occurring or synthetic deoxyribonucleic acid molecule comprising a linear single strand, e.g., a ssDNA can be a sense or antisense gene sequence or EST (Expressed Sequence Tag).

The term "allozyme" as used herein refers to an allosteric enzymatic nucleic acid molecule, including e.g., U.S. Pat. Nos. 5,834,186, 5,741,679, 5,589,332, 5,871,914, and PCT publication Nos. WO 00/24931, WO 00/26226, WO 98/27104, and WO 99/29842.

By "aptamer" as used herein is meant a polynucleotide composition that binds specifically to a target molecule, wherein the polynucleotide has a sequence that differs from a sequence normally recognized by the target molecule in a cell. Alternately, an aptamer can be a nucleic acid molecule that binds to a target molecule where the target molecule does not naturally bind to a nucleic acid. The target molecule can be any molecule of interest. Aptamer molecules of the invention can be chemically modified, e.g. as described in the art.

By "modulate" is meant that the expression of the gene, or level of RNA molecule or equivalent RNA molecules encoding one or more proteins or protein subunits, or activity of one or more proteins or protein subunits is up regulated or down regulated, or is absent, such that expression, level, or activity is greater than or less than that observed without the modulator. For example, in one embodiment, the term "modulate" means "inhibit". In one embodiment, modulation of a pathway denotes, within the terms of the invention, an up-regulation or a down-regulation of a therapeutically meaningful component and/or endpoint of a biological pathway that contains, or is regulated by, e.g., the protein, enzyme, or substance being targetted or encoded by the target mRNA.

By "inhibit", "down-regulate", or "reduce", it is meant that the expression of the gene, or level of RNA molecules or equivalent RNA molecules encoding one or more proteins or protein subunits, or activity of one or more proteins or protein subunits, is reduced below that observed in a natural environment, e.g. in the absence of the nucleic acid molecules (e.g. siNA). In one embodiment, inhibition, down-regulation or reduction with a siNA molecule is below that level observed in the presence of an inactive or attenuated molecule. In one embodiment, inhibition, down-regulation, or reduction with siNA molecules is below that level observed in the presence of, e.g., a siNA molecule with scrambled sequence or with mismatches. In one embodiment, inhibition, down-regulation, or reduction of gene expression with a nucleic acid molecule is greater in the presence of the nucleic acid molecule than in its absence. In one embodiment, inhibition, down regulation, or reduction of gene expression is associated with post transcriptional silencing, such as RNAi mediated cleavage of a target nucleic acid molecule (e.g. RNA) or inhibition of translation. In one embodiment, inhibition, down regulation, or reduction of gene expression is associated with pretranscriptional silencing.

By "up-regulate", or "promote", it is meant that the expression of the gene, or level of RNA molecules or equivalent RNA molecules encoding one or more proteins or protein subunits, or activity of one or more proteins or protein subunits, is increased above that observed in a natural environment, e.g. in the absence of the nucleic acid molecules (e.g. siNA). In one embodiment, up-regulation or promotion of gene expression with an siNA molecule is above that level observed in the presence of an inactive or attenuated molecule. In one embodiment, up-regulation or promotion of gene expression with siNA molecules is above that level observed in the presence of, e.g., an siNA molecule with scrambled sequence or with mismatches. In one embodiment, up-regulation or promotion of gene expression with a nucleic acid molecule is greater in the presence of the nucleic acid molecule than in its absence. In one embodiment, up-regulation or promotion of gene expression is associated with inhibition of RNA mediated gene silencing, such as RNAi mediated cleavage or silencing of a coding or non-coding RNA target that down regulates, inhibits, or silences the expression of the gene of interest to be up-regulated.

By "gene", or "target gene", is meant a nucleic acid that encodes RNA, e.g., nucleic acid sequences including, but not limited to, structural genes encoding a polypeptide. A gene or target gene can also encode a functional RNA (FRNA) or non-coding RNA (ncRNA), such as small temporal RNA (stRNA), micro RNA (miRNA), small nuclear RNA (snRNA), short interfering RNA (siRNA), small nucleolar RNA (snRNA), ribosomal RNA (rRNA), transfer RNA (tRNA) and precursor RNAs thereof. Such non-coding RNAs can serve as target nucleic acid molecules for siNA mediated RNA interference in modulating the activity of FRNA or ncRNA involved in functional or regulatory cellular processes. Aberrant FRNA or ncRNA activity leading to disease can therefore be modulated by siNA molecules.

By "target" as used herein is meant any target protein, peptide, or polypeptide encoded by a target gene. The term "target" also refers to nucleic acid sequences encoding any target protein, peptide, or polypeptide having target activity, such as encoded by target RNA. The term "target" is also meant to include other target encoding sequence, such as other target isoforms, mutant target genes, splice variants of target genes, and target gene polymorphisms. By "target nucleic acid" is meant any nucleic acid sequence whose expression or activity is to be modulated. The target nucleic acid can be DNA or RNA.

By "non-canonical base pair" is meant any non-Watson Crick base pair, such as mismatches and/or wobble base.

By "sense region" is meant a nucleotide sequence of a siNA molecule having complementarity to an antisense region of the siNA molecule. In addition, the sense region of a siNA molecule can comprise a nucleic acid sequence having homology with a target nucleic acid sequence. In one embodiment, the sense region of the siNA molecule is referred to as the sense strand or passenger strand.

By "antisense region" is meant a nucleotide sequence of a siNA molecule having complementarity to a target nucleic acid sequence. In addition, the antisense region of a siNA molecule can optionally comprise a nucleic acid sequence having complementarity to a sense region of the siNA molecule. In one embodiment, the antisense region of the siNA molecule is referred to as the antisense strand or guide strand.

By "target nucleic acid" or "target polynucleotide" is meant any nucleic acid sequence whose expression or activity is to be modulated. The target nucleic acid can be DNA or RNA. In one embodiment, a target nucleic acid of the invention is target RNA. In one embodiment, a target nucleic acid of the invention is target DNA.

By "complementarity" is meant that a nucleic acid can form hydrogen bond(s) with another nucleic acid sequence by either traditional Watson-Crick or other non-traditional types such as Hoogsteen base pairing. In one embodiment, a double stranded nucleic acid molecule of the invention, such as an siNA molecule, wherein each strand is between 15 and 40 nucleotides in length, comprises between about 10% and about 100% (e.g. about 10%, 20%, 30%, 40%, 50%, 60%, 70%, 80%, 90%, 95%, 98%, or 100%) complementarity between the two strands of the double stranded nucleic acid molecule. A percent complementarity indicates the percentage of contiguous residues in a nucleic acid molecule that can pair through the formation of hydrogen bonds (e.g. Watson-Crick base pairing) with a second nucleic acid sequence.

Chemical Terms and Definitions

For purposes of interpreting this specification, the following definitions will apply and whenever appropriate, terms used in the singular will also include the plural and vice versa.

Halo

As used herein, the term "halogen" or "halo" refers to fluoro, chloro, bromo, and iodo. The term "halogen" (or "halo") includes fluorine, chlorine, bromine and iodine.

As used herein, the term "haloalkyl" refers to an alkyl as defined herein that is substituted by one or more halo groups as defined herein. The haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

Alkyl, Alkylene, Alkenyl, Alkynyl, Cycloalkyl etc.

The terms "alkyl", "alkylene", "alkenyl" and "alkynyl" are used herein to refer to both straight and branched chain acyclic forms. Cyclic analogs thereof are referred to as cycloalkyl, cycloalkenyl, etc.

The term "alkyl" includes monovalent, straight or branched, saturated, acyclic hydrocarbyl groups. As used herein, the term "alkyl" refers to a fully saturated branched or unbranched hydrocarbon moiety having up to 50 carbon atoms. Unless otherwise provided, alkyl refers to hydrocarbon moieties having 1 to 50 carbon atoms, 1 to 40 carbon atoms, 1 to 30 carbon atoms, 1 to 20 carbon atoms, 1 to 16 carbon atoms, 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tedbutyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. In one embodiment alkyl is $C_{1-10}$alkyl, in another embodiment $C_{1-6}$alkyl, in another embodiment $C_{1-4}$alkyl, such as methyl, ethyl, n-propyl, i-propyl or t-butyl groups.

The term "cycloalkyl" includes monovalent, saturated, cyclic hydrocarbyl groups. In one embodiment cycloalkyl is $C_{3-10}$cycloalkyl, in another embodiment $C_{3-6}$cycloalkyl such as cyclopentyl and cyclohexyl.

The term "alkoxy" means alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Typically, alkoxy groups have about 1-7, more preferably about 1-4 carbons.

The term "alkenyl" includes monovalent, straight or branched, unsaturated, acyclic hydrocarbyl groups having at least one carbon-carbon double bond and, in one embodiment, no carbon-carbon triple bonds. As used herein, the term "alkylene" refers to divalent alkyl group as defined herein above having 1 to 50 carbon atoms. It comprises 1 to 50 carbon atoms, Unless otherwise provided, alkylene refers to moieties having 1 to 50 carbon atoms, 1 to 40 carbon atoms, 1 to 30 carbon atoms, 1 to 20 carbon atoms, 1 to 16 carbon atoms, 1 to 10 carbon atoms, 1 to 7 carbon atoms, or 1 to 4 carbon atoms. Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, n-decylene and the like. In one embodiment alkenyl is $C_{2-10}$alkenyl, in another embodiment $C_{2-6}$alkenyl, in another embodiment $C_{2-4}$alkenyl.

The term "cycloalkenyl" includes monovalent, partially unsaturated, cyclic hydrocarbyl groups having at least one carbon-carbon double bond. In one embodiment cycloalkenyl is $C_{3-10}$cycloalkenyl, in another embodiment $C_{5-10}$cycloalkenyl, e.g. cyclohexenyl.

The term "alkynyl" includes monovalent, straight or branched, unsaturated, acyclic hydrocarbyl groups having at least one carbon-carbon triple bond and, in one embodiment, no carbon-carbon double bonds. In one embodiment, alkynyl is $C_{2-10}$alkynyl, in another embodiment $C_{2-6}$alkynyl, in another embodiment $C_{2-4}$alkynyl.

The term "cycloalkynyl" includes monovalent, partially unsaturated, cyclic hydrocarbyl groups having at least one carbon-carbon triple bond. In one embodiment cycloalkynyl is $C_{6-10}$cycloalkenyl, in another embodiment $C_{8-10}$cycloalkynyl.

The term "alkylene" includes divalent, straight or branched, saturated, acyclic hydrocarbyl groups. In one embodiment alkylene is $C_{1-10}$alkylene, in another embodiment $C_{1-6}$alkylene, in another embodiment $C_{1-4}$alkylene, such as methylene, ethylene, n-propylene, i-propylene or t-butylene groups.

The term "alkenylene" includes divalent, straight or branched, unsaturated, acyclic hydrocarbyl groups having at least one carbon-carbon double bond and, in one embodiment, no carbon-carbon triple bonds. In one embodiment alkenylene is $C_{2-10}$alkenylene, in another embodiment $C_{2-6}$alkenylene, in another embodiment $C_{2-4}$alkenylene.

The term "alkynylene" includes divalent, straight or branched, unsaturated, acyclic hydrocarbyl groups having at least one carbon-carbon triple bond. In one embodiment alkynylene is $C_{2-10}$alkynylene, in another embodiment $C_{2-6}$alkynylene, in another embodiment $C_{2-4}$alkynylene.

Heteroalkyl etc.

As used herein, the term "hetero atoms" refers to nitrogen (N), oxygen (O), phosphorus (P) or sulfur (S) atoms, in particular nitrogen or oxygen.

The term "heteroalkyl" includes alkyl groups in which up to six carbon atoms, in one embodiment up to five carbon atoms, in another embodiment up to four carbon atoms, in another embodiment up to three carbon atoms, in another embodiment up to two carbon atoms, in another embodiment one carbon atom, are each replaced independently by O, $S(O)_q$, N, $P(O)_r$ or Si (and preferably O, $S(O)_q$ or N), provided at least one of the alkyl carbon atoms remains. The heteroalkyl group may be C-linked or hetero-linked, i.e. it may be linked to the remainder of the molecule through a carbon atom or through O, $S(O)_q$, N, $P(O)_r$ or Si. Note that $S(O)_q$ and $P(O)_r$ are defined below.

The term "heterocycloalkyl" includes cycloalkyl groups in which up to six carbon atoms, in one embodiment up to five carbon atoms, in another embodiment up to four carbon atoms, in another embodiment up to three carbon atoms, in another embodiment up to two carbon atoms, in another embodiment one carbon atom, are each replaced independently by O, $S(O)_q$ or N, provided at least one of the cycloalkyl carbon atoms remains. Examples of heterocycloalkyl groups include oxiranyl, thiaranyl, aziridinyl, oxetanyl, thiatanyl, azetidinyl, tetrahydrofuranyl, tetrahydrothiophenyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thieazepanyl and 1,4-diazepanyl. The heterocycloalkyl group may be C-linked or N-linked, i.e. it may be linked to the remainder of the molecule through a carbon atom or through a nitrogen atom.

The term "heteroalkenyl" includes alkenyl groups in which up to three carbon atoms, in one embodiment up to two carbon atoms, in another embodiment one carbon atom, are each replaced independently by O, $S(O)_q$ or N, provided at least one alkenyl carbon-carbon double bond remains. The heteroalkenyl group may be C-linked or hetero-linked, i.e. it may be linked to the remainder of the molecule through a carbon atom or through O, $S(O)_q$ or N.

The term "heterocycloalkenyl" includes cycloalkenyl groups in which up to three carbon atoms, in one embodiment up to two carbon atoms, in another embodiment one carbon atom, are each replaced independently by O, $S(O)_q$ or N, provided at least one cycloalkenyl carbon-carbon double bond remains. Examples of heterocycloalkenyl groups include 3,4-dihydro-2H-pyranyl, 5-6-dihydro-2H-pyranyl, 2H-pyranyl, 1,2,3,4-tetrahydropyridinyl and 1,2,5,6-tetrahydropyridinyl. The heterocycloalkenyl group may be C-linked or N-linked, i.e. it may be linked to the remainder of the molecule through a carbon atom or through a nitrogen atom. In one embodiment, heterocycloalkenyl groups of the invention include $C_3$-$C_{10}$ cycloalkenyl groups. In one embodiment, heterocycloalkenyl groups of the invention include $C_5$-$C_{10}$ cycloalkenyl groups.

The term "heteroalkynyl" includes alkynyl groups in which up to three carbon atoms, in one embodiment up to two carbon atoms, in another embodiment one carbon atom, are each replaced independently by O, $S(O)_q$ or N, provided at least one alkynyl carbon-carbon triple bond remains. The heteroalkynyl group may be C-linked or hetero-linked, i.e. it may be linked to the remainder of the molecule through a carbon atom or through O, $S(O)_q$ or N.

The term "heterocycloalkynyl" includes cycloalkynyl groups in which up to three carbon atoms, in one embodiment up to two carbon atoms, in another embodiment one carbon atom, are each replaced independently by O, $S(O)_q$ or N, provided at least one of the cycloalkynyl carbon-carbon triple bonds remains. The heterocycloalkynyl group may be C-linked or N-linked, i.e. it may be linked to the remainder of the molecule through a carbon atom or through a nitrogen atom. An example of a heterocycloalkynyl group includes azacyclooct-4-yne. In one embodiment, the invention includes $C_3$-$C_{10}$ heterocycloalkynyl groups. In one embodiment, the invention includes $C_5$-$C_{10}$ heterocycloalkynyl groups.

The term "heteroalkylene" includes alkylene groups in which up to three carbon atoms, in one embodiment up to two carbon atoms, in another embodiment one carbon atom, are each replaced independently by O, $S(O)_q$ or N, provided at least one alkylene carbon-carbon bond remains.

The term "heteroalkenylene" includes alkenylene groups in which up to three carbon atoms, in one embodiment up to two carbon atoms, in another embodiment one carbon atom, are each replaced independently by O, $S(O)_q$ or N, provided at least one alkenylene carbon-carbon double bond remains.

The term "heteroalkynylene" includes alkynylene groups in which up to three carbon atoms, in one embodiment up to two carbon atoms, in another embodiment one carbon atom, are each replaced independently by O, $S(O)_q$ or N, provided at least one alkynylene carbon-carbon triple bond remains.

Aryl

The term "aryl" includes monovalent, aromatic, cyclic hydrocarbyl groups, such as phenyl or naphthyl (e.g. 1-naphthyl or 2-naphthyl). In general, the aryl groups may be monocyclic or polycyclic fused ring aromatic groups. Preferred aryl are $C_6$-$C_{14}$aryl. As used herein the term "aryl" refers to an aromatic hydrocarbon group having 6-20 carbon atoms in the ring portion. Typically, aryl is monocyclic, bicyclic or tricyclic aryl having 6-20 carbon atoms and includes one or more aromatic rings fused to one or more non-aromatic hydrocarbon rings. Non-limiting examples include phenyl, naphthyl or tetrahydronaphthyl.

Other examples of aryl groups are monovalent derivatives of aceanthrylene, acenaphthylene, acephenanthrylene, anthracene, azulene, chrysene, coronene, fluoranthene, fluorene, as-indacene, s-indacene, indene, naphthalene, ovalene, perylene, phenalene, phenanthrene, picene, pleiadene, pyrene, pyranthrene and rubicene.

The term "arylalkyl" means alkyl substituted with an aryl group, e.g. benzyl.

The term "arylene" includes divalent aromatic, cyclic hydrocarbyl groups, such as phenylene. In general, the arylene groups may be monocyclic or polycyclic fused ring aromatic groups. Preferred arylene are $C_6$-$C_{14}$arylene. Other examples of arylene groups are divalent derivatives of aceanthrylene, acenaphthylene, acephenanthrylene, anthracene, azulene, chrysene, coronene, fluoranthene, fluorene, as-indacene, s-indacene, indene, naphthalene, ovalene, perylene, phenalene, phenanthrene, picene, pleiadene, pyrene, pyranthrene and rubicene.

Heteroaryl

The term "heteroaryl" includes monovalent, heteroaromatic, cyclic hydrocarbyl groups additionally containing one or more heteroatoms independently selected from O, S, N and $NR^N$, where $R^N$ is defined below (and in one embodiment is H or alkyl (e.g., $C_{1-6}$alkyl)). As used herein, the term "heteroaryl" refers to a 5-14 membered monocyclic- or bicyclic- or tricyclic-aromatic ring system, having 1 to 8 heteroatoms selected from N, O or S. Typically, the heteroaryl is a 5-10 membered ring system (e.g., 5-7 membered monocycle or an 8-10 membered bicycle) or a 5-7 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2, 3-triazolyl, tetrazolyl, 2-, 3-, or 4-pyridyl, 3- or 4-pyridazinyl, 3-, 4-, or 5-pyrazinyl, 2-pyrazinyl, and 2-, 4-, or 5-pyrimidinyl.

The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include those head groups provided herein as $H^{15}$ and $H^{29}$.

In general, the heteroaryl groups may be monocyclic or polycyclic (e.g., bicyclic) fused ring heteroaromatic groups. In one embodiment, heteroaryl groups contain 5-13 ring members (e.g., 5-10 members) and 1, 2, 3 or 4 ring heteroatoms independently selected from O, S, N and $NR^N$. In one embodiment, a heteroaryl group may be 5, 6, 9 or 10 membered, e.g., 5-membered monocyclic, 6-membered monocyclic, 9-membered fused-ring bicyclic or 10-membered fused-ring bicyclic.

Monocyclic heteroaromatic groups include heteroaromatic groups containing 5-6 ring members and 1, 2, 3 or 4 heteroatoms selected from O, S, N or $NR^N$.

In one embodiment, 5-membered monocyclic heteroaryl groups contain 1 ring member which is a —$NR^N$-group, an —O-atom or an —S-atom and, optionally, 1-3 ring members (e.g. 1 or 2 ring members) which are =N-atoms (where the remainder of the 5 ring members are carbon atoms).

Examples of 5-membered monocyclic heteroaryl groups are pyrrolyl, furanyl, thiophenyl, pyrazolyl, imidazolyl, isoxazolyl, oxazolyl, isothiazolyl, thiazolyl, 1,2,3 triazolyl, 1,2,4 triazolyl, 1,2,3 oxadiazolyl, 1,2,4 oxadiazolyl, 1,2,5 oxadiazolyl, 1,3,4 oxadiazolyl, 1,3,4 thiadiazolyl, pyridyl, pyrimidinyl, pyridazinyl, pyrazinyl, 1,3,5 triazinyl, 1,2,4 triazinyl, 1,2,3 triazinyl and tetrazolyl.

Examples of 6-membered monocyclic heteroaryl groups are pyridinyl, pyridazinyl, pyrimidinyl and pyrazinyl.

In one embodiment, 6-membered monocyclic heteroaryl groups contain 1 or 2 ring members which are =N-atoms (where the remainder of the 6 ring members are carbon atoms).

Bicyclic heteroaromatic groups include fused-ring heteroaromatic groups containing 9-13 ring members and 1, 2, 3, 4 or more heteroatoms selected from O, S, N or $NR^N$.

In one embodiment, 9-membered bicyclic heteroaryl groups contain 1 ring member which is a —$NR^N$-group, an —O-atom or an —S-atom and, optionally, 1-3 ring members (e.g. 1 or 2 ring members) which are =N-atoms (where the remainder of the 9 ring members are carbon atoms).

Examples of 9-membered fused-ring bicyclic heteroaryl groups are benzofuranyl, benzothiophenyl, indolyl, benzimidazolyl, indazolyl, benzotriazolyl, pyrrolo[2,3-b]pyridinyl, pyrrolo[2,3-c]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-c]pyridinyl, pyrazolo[3,4-b]pyridinyl, isoindolyl, indazolyl, purinyl, indolininyl, imidazo[1,2-a]pyridinyl, imidazo[1,5-a]pyridinyl, pyrazolo[1,2-a]pyridinyl, pyrrolo[1,2-b]pyridazinyl and imidazo[1,2-c]pyrimidinyl.

The term "heteroarylalkyl" means alkyl substituted with a heteroaryl group.

The term "heteroarylene" includes divalent heteroaromatic, cyclic hydrocarbyl groups additionally containing one or more heteroatoms independently selected from O, S, N and $NR^N$, where $R^N$ is defined below (and in one embodiment is H or alkyl (e.g. $C_{1-6}$alkyl)). In general, the heteroarylene groups may be monocyclic or polycyclic (e.g. bicyclic) fused ring heteroaromatic groups. In one embodiment, heteroarylene groups contain 5-13 ring members (preferably 5-10 members) and 1, 2, 3 or 4 ring heteroatoms independently selected from O, S, N and $NR^N$. In one embodiment, a heteroarylene group may be 5, 6, 9 or 10 membered, e.g. 5-membered monocyclic, 6-membered monocyclic, 9-membered fused-ring bicyclic or 10-membered fused-ring bicyclic. The term "heteroarylene" includes divalent derivatives of each of the heteroaryl groups discussed above.

The terms "aryl", "aromatic", "heteroaryl" and "heteroaromatic" also include groups that are partially reduced. Thus, e.g., "heteroaryl" includes fused species in which one of the rings has been reduced to a saturated ring (e.g., 1,2,3,4-tetrahydro-1,8-naphthyridin-2-yl).

General

Unless indicated explicitly otherwise, where combinations of groups are referred to herein as one moiety, e.g. arylalkyl, the last mentioned group contains the atom by which the moiety is attached to the rest of the molecule.

Where reference is made to a carbon atom of an alkyl group or other group being replaced by O, $S(O)_q$, N or $P(O)_r$, what is intended is that:

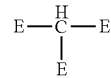

is replaced by

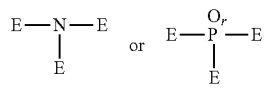

(wherein E cannot be H);
—CH= is replaced by —N= or —$P(O)_r$=;
≡C—H is replaced by ≡N or ≡$P(O)_r$; or
—$CH_2$— is replaced by —O—, —$S(O)_q$—, —$NR^N$— or —$P(O)_rR^N$—, where $R^N$ is H or optionally substituted $C_{1-6}$alkyl, $C_{1-6}$heteroalkyl, $C_{3-6}$cycloalkyl, $C_{3-6}$heterocycloalkyl, $C_{2-6}$alkenyl, $C_{2-6}$heteroalkenyl, $C_{3-6}$cycloalkenyl, $C_{3-6}$heterocycloalkenyl, phenyl, or heteroaryl containing 5 or 6 ring members. $R^N$ is preferably H, $C_{1-6}$alkyl or $C_{3-6}$cycloalkyl.

q is independently 0, 1 or 2. In one embodiment, q is 0.

r is independently 0 or 1. In one embodiment, r is 0.

Where reference is made to a carbon atom being replaced by Si, what is intended is that the carbon atom is swapped for a silicon atom but that the bonds otherwise remain the same.

Thus, e.g., —CH$_2$— is replaced by —SiH$_2$—; —CH= is replaced by —SiH=; and ≡C—H is replaced by ≡Si—H.

By way of clarification, in relation to the above mentioned heteroatom containing groups (such as heteroalkyl etc.), where a numerical of carbon atoms is given, for instance C$_{3-6}$heteroalkyl, what is intended is a group based on C$_{3-6}$alkyl in which one or more of the 3-6 chain carbon atoms is replaced by O, S(O)$_q$ or N. Accordingly, a C$_{3-6}$heteroalkyl group would, e.g., contain less than 3-6 chain carbon atoms. As another example, a pyridyl group would be classed as a C$_6$ heteroaryl group even though it contains 5 carbon atoms.

Wherein reference is made to a specific functional group or chemical moiety provided below, the intended chemical entity is as follows:

ether (e.g., —O—); ester (e.g., —C(O)O—); succinate (e.g., —O(O)C—CH$_2$—CH$_2$—C(O)O—)); carbamate (e.g., —OC(O)—NR'—); carbonate (e.g., —OC(O)O—); ketone (e.g., —C—C(O)—C—); carbonyl (e.g., —C(O)—); urea (e.g., —NRC(O)NR'—); amine (e.g., —NR'—); amide (e.g., —C(O)NR'—); imine (e.g., —C(NR')—); thioether (e.g., —S—); xanthate (e.g., —OC(S)S—); phosphodiester (e.g., —OP(O)$_2$O—); wherein R' may be independently selected from H, —NH—, —O—, —S—, a phosphate or an optionally substituted C$_{1-10}$ alkylene.

pKa

Unless explicitly indicated otherwise, all pKas referred to herein are measured in water at standard temperature and pressure. Also, unless otherwise indicated, all references to pKa are references to pKa measured using the following technique.

2 mM solution of lipid in ethanol are prepared by weighing the lipid and then dissolving in ethanol. 0.3 mM solution of fluorescent probe TNS in ethanol:methanol 9:1 is prepared by first making 3 mM solution of TNS in methanol and then diluting to 0.3 mM with ethanol.

An aqueous buffer containing sodium phosphate, sodium citrate sodium acetate and sodium chloride, at the concentrations 20 mM, 25 mM, 20 mM and 150 mM, respectively, is prepared. The buffer is split into eight parts and the pH adjusted either with 12N HCl or 6N NaOH to 4.44-4.52, 5.27, 6.15-6.21, 6.57, 7.10-7.20, 7.72-7.80, 8.27-8.33 and 10.47-11.12. 400 uL of 2 mM lipid solution and 800 uL of 0.3 mM TNS solution are mixed.

Using the Tecan Genesis RSP150 high throughput liquid handler and Gemini Software, 7.5 uL of probe/lipid mix are added to 242.5 uL of buffer in a 1 mL 96 well plate (model NUNC 260252, Nalgae Nunc International). This is done with all eight buffers.

After mixing in 1 mL 96 well plate, 100 uL of each probe/lipid/buffer mixture is transferred to a 250 uL black with clear bottom 96 well plate (model COSTAR 3904, Corning).

The fluorescence measurements are carried out on the SpectraMax M5 spectrophotometer using software SoftMax pro 5.2 and following parameters:

Read Mode: Fluorescence, Top read
Wavelengths: Ex 322 nm, Em 431 nm, Auto Cutoff On 420 nm
Sensitivity: Readings 6, PMT: Auto
Automix: Before: Off
Autocalibrate: On
Assay plate type: 96 Well Standard clrbtm
Wells to read: Read entire plate
Settling time: Off
Column Wav. Priority: Column priority
Carriage Speed: Normal
Auto read: Off After the measurement, the background fluorescence value of an empty well on the 96 well plate is subtracted from each probe/lipid/buffer mixture. The fluorescence intensity values are then normalized to the value at lowest pH. The normalized fluorescence intensity vs. pH chart is then plotted in the Microsoft Excel software. The eight points are connected with a smooth line.

The point on the line at which the normalized fluorescence intensity is equal to 0.5 is found. The pH corresponding to normalized fluorescence intensity equal to 0.5 is found and is considered the pKa of the lipid.

The pKa determined using this method is precise to about 0.2 pKa units.

Absent Groups

When group a, b or c in formula (I) is "absent", what is meant is that a single bond is present instead, i.e. that the two groups either side of group a, b or c are directly bonded to each other.

Substitution

As used herein, the term "optionally substituted" as applied to any of an aryl, heteroaryl, cycloalkyl or heterocyclyl group, unless otherwise specified, refers to such a group that is unsubstituted or is substituted by one or more, typically 1, 2, 3, 4 or 5 suitable non-hydrogen substituents, each of which is independently selected from the group consisting of:

(a) alkyl;
(b) hydroxy (or protected hydroxy);
(c) halo;
(d) oxo, i.e., =O or alkylimino, i.e. =N-alkyl;
(e) amino, alkylamino or dialkylamino;
(f) alkoxy;
(g) cycloalkyl;
(h) carboxyl;
(i) heterocyclooxy, wherein heterocyclooxy denotes a heterocyclic group bonded through an oxygen bridge;
(j) alkyl-O—C(O)—;
(k) mercapto;
(l) nitro;
(m) cyano;
(n) sulfamoyl or sulfonamido;
(o) aryl;
(p) alkyl-C(O)—O—;
(q) aryl-C(O)—O—;
(r) aryl-S—;
(s) aryloxy;
(t) alkyl-S—;
(u) formyl, i.e., HC(O)—;
(v) carbamoyl;
(w) aryl-alkyl-; and
(x) aryl substituted with alkyl, cycloalkyl, alkoxy, hydroxy, amino, alkyl-C(O)—NH—, alkylamino, dialkylamino or halogen.

As used herein, the term "optionally substituted" as applied to any of an alkyl or a group containing an alkyl, unless otherwise specified, refers to such a group that is unsubstituted or is substituted by one or more, typically 1, 2 or 3 suitable non-hydrogen substituents, each of which is independently selected from the group consisting of: halo, hydroxy (or protected hydroxy) or alkoxy groups.

Groups of the compounds of the invention (e.g. alkyl, cycloalkyl, alkoxy, alkenyl, cycloalkenyl, alkynyl, alkylene, alkenylene, heteroalkyl, heterocycloalkyl, heteroalkenyl, heterocycloalkenyl, heteroalkynyl, heteroalkylene, heteroalkenylene aryl, arylalkyl, arylheteroalkyl, heteroaryl, heteroarylalkyl or heteroarylheteroalkyl groups etc.) may be substituted or unsubstituted, in one embodiment unsubstituted. Typically, substitution involves the notional replacement of a hydrogen atom with a substituent group, or two hydrogen atoms in the case of substitution by =O.

Where substituted, there will generally be 1 to 5 substituents on each group, in one embodiment 1 to 3 substituents, in one embodiment 1 or 2 substituents, in one embodiment 1 substituent. One embodiment includes more than one substituent on the same atom, e.g. an acetal group.

In one embodiment, the substituent(s) is/are independently $Sub^1$ or $Sub^2$ (in one embodiment $Sub^2$) wherein:

$Sub^1$ is independently $Sub^1$ is independently halogen, trihalomethyl, trihaloethyl, —$NO_2$, —CN, —$N^+(R^s)_2O^-$, —$CO_2H$, —$CO_2R^s$, —$SO_3H$, —$SOR^s$, —$SO_2R^s$, —$SO_3R^s$, —OC(=O)O $R^s$, —C(=O)H, —C(=O)$R^s$, —OC(=O)$R^s$, =O, —$NR^s_2$, —C(=O)$NH_2$, —C(=O)$NR^s_2$, —N($R^s$)C(=O)$OR^s$, —N($R^s$)C(=O)$NR^s_2$, —OC(=O)$NR^s_2$, —N($R^s$) C(=O)$R^s$, —C(=S)$NR^s_2$, —$NR^sC$(=S)$R^s$, —$SO_2NR^s_2$, —$NR^sSO_2R^s$, —N($R^s$)C(=S)$NR^s_2$, —N($R^s$)$SO_2NR^s_2$, —$R^s$ or —$Z^sR^s$, wherein;

$Z^s$ is independently O, S or $NR^s$;

$R^s$ is independently H or $C_{1-6}$alkyl, $C_{1-6}$heteroalkyl, —(Alk$^a$)$_f$—$C_{3-6}$cycloalkyl, —(Alk$^a$)$_f$—$C_{3-6}$heterocycloalkyl, $C_{2-6}$alkenyl, $C_{2-6}$heteroalkenyl, —(Alk$^a$)$_f$—$C_{3-6}$cycloalkenyl, —(Alk$^3$)$_f$—$C_{3-6}$heterocycloalkenyl, $C_{2-6}$alkynyl, $C_{2-6}$heteroalkynyl, —(Alk$^a$)$_f$—$C_{6-14}$aryl, —(Alk$^a$)$_f$—$C_{6-14}$aryl or —(Alk$^a$)$_f$-heteroaryl (where heteroaryl contains 5-13 ring members), where f is 0 or 1;

Alk$^a$ is $C_{1-6}$alkylene or $C_{1-6}$heteroalkylene; and $R^s$ is optionally substituted itself (in one embodiment unsubstituted) by 1 to 3 substituents $Sub^2$;

$Sub^2$ is independently halogen, trihalomethyl, trihaloethyl, —$NO_2$, —CN, —$N^+(C_{1-6}$alkyl$)_2O^-$, —$CO_2H$, —$CO_2C_{1-6}$alkyl, —$SO_3H$, —$SOC_{1-6}$alkyl, —$SO_2C_{1-6}$alkyl, —$SO_3C_{1-6}$alkyl, —OC(=O)$OC_{1-6}$alkyl, —C(=O)H, —C(=O)$C_{1-6}$alkyl, —OC(=O)$C_{1-6}$alkyl, =O, —N($C_{1-6}$alkyl$)_2$, —C(=O)$NH_2$, —C(=O)N($C_{1-6}$alkyl$)_2$, —N($C_{1-6}$alkyl)C(=O)O($C_{1-6}$alkyl), —N($C_{1-6}$alkyl)C(=O)N($C_{1-6}$alkyl$)_2$, —OC(=O)N($C_{1-6}$alkyl$)_2$, —N($C_{1-6}$alkyl)C(=O)$C_{1-6}$alkyl, —C(=S)N($C_{1-6}$alkyl$)_2$, —N($C_{1-6}$alkyl)C(=S)$C_{1-6}$alkyl, —$SO_2N(C_{1-6}$alkyl$)_2$, —N($C_{1-6}$alkyl)$SO_2C_{1-6}$alkyl, —N($C_{1-6}$alkyl)C(=S)N($C_{1-6}$alkyl$)_2$, —N($C_{1-6}$alkyl)$SO_2N(C_{1-6}$alkyl$)_2$, —$C_{1-6}$alkyl, —$C_{1-6}$heteroalkyl, —$C_{3-6}$cycloalkyl, —$C_{3-6}$heterocycloalkyl, —$C_{2-6}$alkenyl, —$C_{2-6}$heteroalkenyl, —$C_{3-6}$cycloalkenyl, —$C_{3-6}$heterocycloalkenyl, —$C_{2-6}$alkynyl, —$C_{2-6}$heteroalkynyl, —$C_{6-14}$aryl, —$C_{5-13}$heteroaryl, —$Z^t$—$C_{1-6}$alkyl, —$Z^t$—$C_{3-6}$cycloalkyl, —$Z^t$—$C_{2-6}$alkenyl, —$Z^t$—$C_{3-6}$cycloalkenyl, or —$Z^t$—$C_{2-6}$alkynyl; and $Z^t$ is independently O, S, NH or N($C_{1-6}$alkyl).

While $R^s$ in $Sub^1$ can be optionally substituted by 1 to 3 substituents $Sub^2$, $Sub^2$ is unsubstituted. However, in one embodiment, $R^s$ is unsubstituted.

In one embodiment, $R^s$ is H or $C_{1-6}$alkyl, optionally substituted by 1 to 3 substituents $Sub^2$.

In one embodiment, $Sub^2$ is independently halogen, trihalomethyl, trihaloethyl, —$NO_2$, —CN, —$N^+(C_{1-6}$alkyl$)_2O^-$, —$CO_2H$, —$SO_3H$, —$SOC_{1-6}$alkyl, —$SO_2C_{1-6}$alkyl, —C(=O)H, —C(=O)$C_{1-6}$alkyl, =O, —N($C_{1-6}$alkyl$)_2$, —C(=O)$NH_2$, —$C_{1-6}$alkyl, —$C_{3-6}$cycloalkyl, —$C_{3-6}$heterocycloalkyl, —$Z^t$—$C_{1-6}$alkyl or —$Z^t$—$C_{3-6}$cycloalkyl.

In one embodiment, where the substituted group is acyclic (e.g. alkyl, heteroalkyl, alkenyl etc.), $Sub^1$ is not —$R^s$ and $Sub^2$ is not —$C_{1-6}$alkyl, —$C_{1-6}$heteroalkyl, —$C_{2-6}$alkenyl, —$C_{2-6}$heteroalkenyl, —$C_{2-6}$alkynyl or —$C_{2-6}$heteroalkynyl.

Where a group other than $Sub^2$ has at least 2 positions which may be substituted, the group may be substituted by both ends of an alkylene, alkenylene, alkynylene, heteroalkylene, heteroalkenylene or heteroalkynylene chain (in one embodiment containing 1 to 6 atoms, in one embodiment 3 to 6 atoms, and in one embodiment 3 or 4 atoms) to form a cyclic moiety. That chain is optionally substituted by 1 to 3 substituents $Sub^2$. In one embodiment that chain is not substituted. Thus, the terms optionally substituted "cycloalkyl", "cycloalkenyl", "cycloalkynyl", "heterocycloalkyl", "heterocycloalkenyl", "heterocycloalkynyl", "aryl" and "heteroaryl" include fused species. E.g. "optionally substituted cycloalkyl" includes a species in which two cycloalkyl rings are fused, and "optionally substituted heteroaryl" includes a species in which a heterocycloalkyl ring is fused to the aromatic ring (e.g. 5,6,7,8-tetrahydro-1,8-naphthyridin-2-yl).

Where a group other than $Sub^2$ has an atom which may be substituted twice, that atom may be substituted by both ends of an alkylene, alkenylene, alkynylene, heteroalkylene, heteroalkenylene or heteroalkynylene chain (in one embodiment containing 2 to 8 atoms, in one embodiment 3 to 6 atoms, and in one embodiment 4 or 5 atoms) to form a cyclic moiety. That chain is optionally substituted by 1 to 3 substituents $Sub^2$. In one embodiment that chain is not substituted. Thus, the terms optionally substituted "cycloalkyl", "cycloalkenyl", "cycloalkynyl", "heterocycloalkyl", "heterocycloalkenyl", "heterocycloalkynyl", "aryl" and "heteroaryl" include spiro species.

By way of clarification, when a group has a heteroatom, a substituent may be bonded to the heteroatom. Thus, e.g., "optionally substituted heteroalkyl" includes —$CH_2$—N($Sub^1$)—$CH_2$—, —CH($Sub^1$)—NH—$CH_2$— and —CH ($Sub^1$)—N($Sub^1$)—$CH_2$— etc.

Modifier Terms

When a list is preceded by a modifier, it is intended that the modifier is to be understood as applying to each of the items in the list. For example, the phrase "optionally substituted $C_{3-20}$-heterocycloalkyl, $C_{3-20}$-heterocycloalkenyl, $C_{3-20}$-heterocycloalkynyl or $C_{5-20}$-heteroaryl group" means that each of the four items in the list, namely the $C_{3-20}$-heterocycloalkyl group, the $C_{3-20}$-heterocycloalkenyl group, the $C_{3-20}$-heterocycloalkynyl group and the $C_{6-20}$-heteroaryl group, may be optionally substituted.

When a group is characterised by a first modifier and then, later on, the same group is characterised by a subsequent modifier, what is meant is that the group is characterised by both modifiers simultaneously. For example, if a group is described as a "$C_{3-20}$-heterocycloalkynyl" (the first modifier) group and then later the same group is described as a "$C_{5-16}$" (the subsequent modifier) group, what is meant is a $C_{5-16}$ heterocycloalkynyl group.

Steroids

As used herein, the term "steroid" refers to any group comprising the following structure (which structure is referred to herein as the "steroid skeleton").

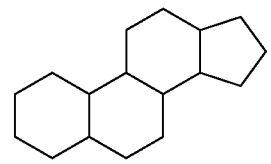 [SMILES: C1CCC2C(C1)CCC1C3CCCC3CCC21]

Purely for the purposes of illustration, the steroid skeleton has been drawn above as fully saturated. The term steroid, however, is also intended to cover instances where there is unsaturation in the steroid skeleton. For example, the term steroid covers a group which comprises the fully unsaturated (mancude) basic skeleton, 15H-cyclopenta[a]phenanthrene:

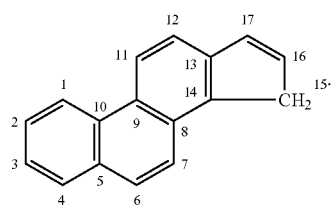

The term steroid also covers a group which comprises a partially unsaturated steroid skeleton.

The term steroid also covers "seco" derivatives of the steroid skeleton, i.e. groups in which ring cleavage has been effected; "nor" and "homo" derivatives of the steroid skeleton which involve ring contraction and expansion, respectively (see Systemic Nomenclature of Organic Chemistry, by D. Hellwinkel, published by Springer, 2001, ISBN: 3-540-41138-0, page 203 for "seco" and page 204 for "nor" and "homo"). In one embodiment, however, such "seco" derivatives are not encompassed by the term "steroid". In another embodiment, such "nor" derivatives are not encompassed by the term "steroid". In another embodiment, such "homo" derivatives are not encompassed by the term "steroid". Thus in one embodiment, such seco, nor and homo derivatives are not encompassed by the term "steroid".

The term steroid also covers instances where one or more of the carbon atoms in the structure labelled steroid skeleton is replaced by a heteroatom. In one such embodiment, up to six carbon atoms, in one embodiment up to five carbon atoms, in another embodiment up to four carbon atoms, in another embodiment up to three carbon atoms, in another embodiment up to two carbon atoms, in another embodiment one carbon atom, are each replaced independently by O, $S(O)_q$, N, $P(O)_r$ or Si (and preferably O, $S(O)_q$ or N). In one embodiment, however, the term "steroid" comprises species in which the "steroid basic skeleton" contains no heteroatoms.

A steroid ring system is numbered according to the convention set out below.

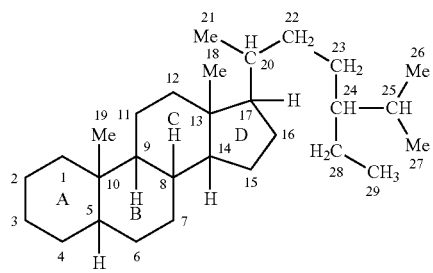

The term steroid encompasses sterols, steroid hormones, bile acids and salts of bile acids. A sterol is any steroid with a hydroxyl group at the 3-position of the A-ring.

Unsaturation

In accordance with standard use, the omega-3 position refers to the third bond from the (methyl) terminal of the chain; the omega-6 position refers to the sixth bond from the (methyl) terminal of the chain and the omega-9 position refers to the ninth bond from the (methyl) terminal of the chain.

PDI

The acronym PDI stands for polydispersity index. Unless indicated otherwise, all PDIs referred to herein are the PDI of the fully formed nanoparticle, as measured by dynamic light scattering on a Malvern Zetasizer. The nanoparticle sample is diluted in phosphate buffered saline (PBS) so that the count rate is approximately 200-400 kcts.

General Definitions

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, e.g., x±10%. In one embodiment, in relation to all numerical values disclosed, the term "about" is absent.

For the avoidance of doubt any feature that is explicitly disclosed in the context of a compound, composition, method or use is also hereby implicitly disclosed in the context of compounds, compositions, methods and uses. For example, if it is herein explicitly disclosed that an inventive compound has feature "A", then there is herein implicitly disclosed a method of treatment according to the invention which involves the compound of the invention with feature "A".

Moreover, various embodiments of the invention have been described herein. It will be recognised that features specified in each embodiment may be combined with other specified features to provide further embodiments.

Chemical Synthesis of Cationic Lipids of the Invention

Route A sets out a general method which can be used to synthesise compounds of the invention. Route CDT illustrates how the cholesterol diglycol tosylate reagent might be prepared.

Route A

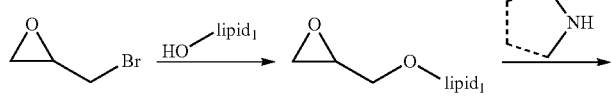 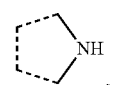

Example 1

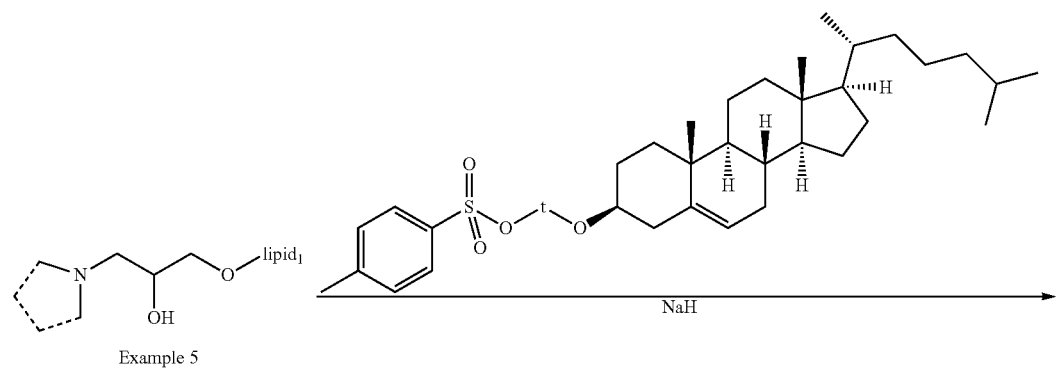
Example 5
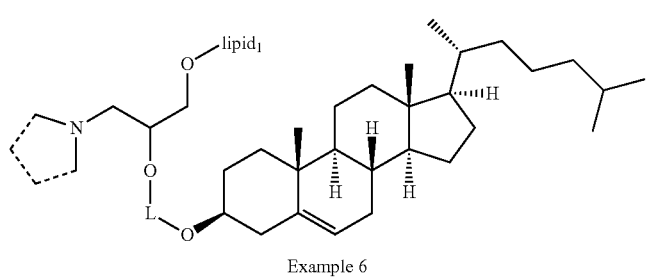
Example 6
Route CDT
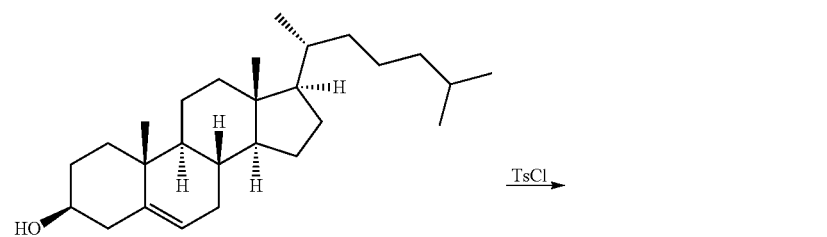
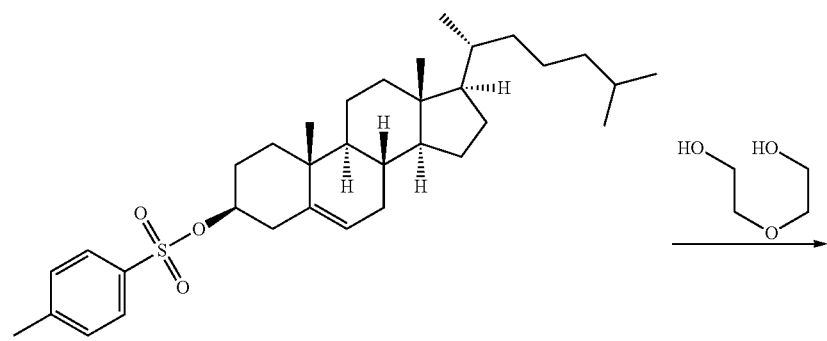
Example 2
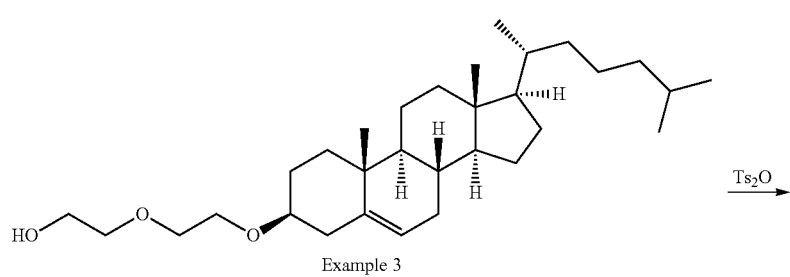
Example 3

-continued

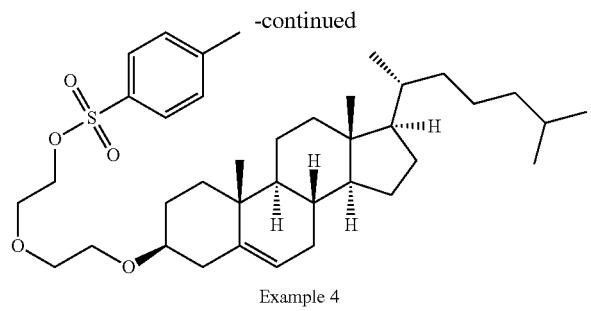

Example 4

Example 1

Epoxide

Linoleyl alcohol (48.7 g, 183 mmol) is added to a round bottom flask and dissolve in THF (400 mL). The resulting solution is cooled using an ice bath and sodium hydride (13.16 g, 329 mmol) is added. The resulting slurry is stirred for 1 h at rt. Epibromohydrin is added in one portion and the reaction is continued at rt. After 4 h stirring, additional sodium hydride (13.16 g, 329 mmol) is added. After an additional h stirring at rt, another aliquot of epibromohydrin (32.5 g, 238 mmol) is added. The reaction is then heated to 50° C. overnight. The reaction is then cooled to rt and quenched with water. EtOAc is added and the resulting organic layer collected, washed with brine and dried over sodium sulfate. The volatiles are removed by rotary evaporation and the resulting residue purified by chromatography on silica in EtOAc/heptanes to yield the desired epoxide.

Example 2

Cholesterol tosylate

Cholesterol (50 g, 129 mmol) is dissolved in DCM (55 mL) and pyridine (150 mL). The resulting solution is cooled to 0° C. and tosyl chloride is added in one portion as a solid. The reaction is allowed to slowly warm to rt overnight. The reaction is concentrated by rotary evaporation and MeOH (500 mL) is added to produce a white solid. Stirring is continued for 30 min and the precipitate collected by filtration, washed with MeOH and dried under vacuum to yield the desired tosylate.

Example 3

Cholesterol diglycol

Cholesterol tosylate (73 g, 128 mmol) is dissolved in 1,4-dioxane (750 mL). Diethylene glycol (294 mL, 3077 mmol) is added and the reaction is heated to a gentle reflux overnight. The resulting solution is cooled to rt and concentrated by rotary evaporation. The resulting gel is taken up in DCM and stirred with water. The resulting organic layer is collected and the aqueous layer extracted once with DCM. The organic layers are combined, dried over sodium sulfate, and concentrated by rotary evaporation. The crude product is purified on silica in EtOAc/heptane to yield the desired cholesterol diglycol.

Example 4

Cholesterol diglycol tosylate

Cholesterol diglycol (51.5 g, 103 mmol) is stirred in DCM (160 mL) and pyridine (60 mL). Tosylanhydride (38.7 g, 119 mmol) is added and the resulting solution is stirred overnight at rt. The reaction is concentrated by rotary evaporation and the resulting residue purified on silica in EtOAc/heptane to yield the desired product.

Example 5

3-piperidinyl-1,2-propanediol 1-linoleylether

The epoxide from Example 1 (1.0 g, 3.1 mmol) is dissolved in EtOH (17 mL). Piperidine (0.45 mL, 4.65 mmol) is added and the mixture is heated in a microwave reactor to 140° C. for 5 min. After cooling to rt, the mixture is concentrated by rotary evaporation and purified on silica in MeOH/DCM to yield the desired amino alcohol.

Example 6

Final Compound 1

The amino alcohol from Example 5 (0.447 mg, 1.09 mmol) is stirred in toluene (15 mL) and NaH (0.102 g, 4.24 mmol) is added in one portion. The resulting mixture is stirred at rt for 30 min and the tosylate from Example 4 is added in one portion. The reaction is heated to reflux overnight. After cooling to room temperature ("rt"), the reaction is quenched by the addition of saturated aqueous sodium bicarbonate. The resulting mixture is stirred for 5 min and then concentrated by rotary evaporation. The resulting residue is purified directly on silica in MeOH/DCM to yield a crude product that is repurified on silica in EtOAc/heptane to yield the desired compound.

The following compounds (the structures of which are set out below) can be manufactured by the Route A methodology.

| | | | | |
|---|---|---|---|---|
| E0011; | E0002; | E0003; | E0013; | E0015; |
| E0006; | E0008; | E0001; | E0022; | E0026; |
| E0030; | E0037; | E0038; | E0039; | E0042; |
| E0050; | E0055; | E0061 | E0062; | E0063; |
| E0064; | E0065; | E0066; | E0068; | E0069; |
| E0070; | E0071; | E0072; | E0073; | E0074; |
| E0075; | E0076; | E0077; | E0078; | E0079; |
| E0080; | E0081; | E0082; | E0083; | E0084; |
| E0085; | E0086; | E0087; | E0088; | E0089; |
| E0090; | E0091; | E0092; | E0093; | E0094; |
| E0095; | E0096; | E0107; | E0109; | E0023; |
| E0024; | E0025; | E0031; | E0033; | E0034; |
| E0043; | E0046; | E0059; | E0067; | E0014; |
| E0119; | E0016; | E0004; | E0005; | E0017; |
| E0018; | E0019; | E0120; | E0007; | E0020; |
| E0010; | E0021; | E0027; | E0028; | E0029; |
| E0032; | E0035; | E0009; | E0040; | E0041; |
| E0044; | E0048; | E0049; | E0052; | E0053; |
| E0057; | E0119; | E0120; | E0121; | E0124; |
| E0126; | E0127; | E0147; | E0149; | E0158; |
| E0051; | E0067; | E0112; | E0113; | E0114; |
| E0118; | E0159; | E0170; and | E0171. | |

Route B also represents a general method which can be used to synthesise compounds of the invention.

Route B

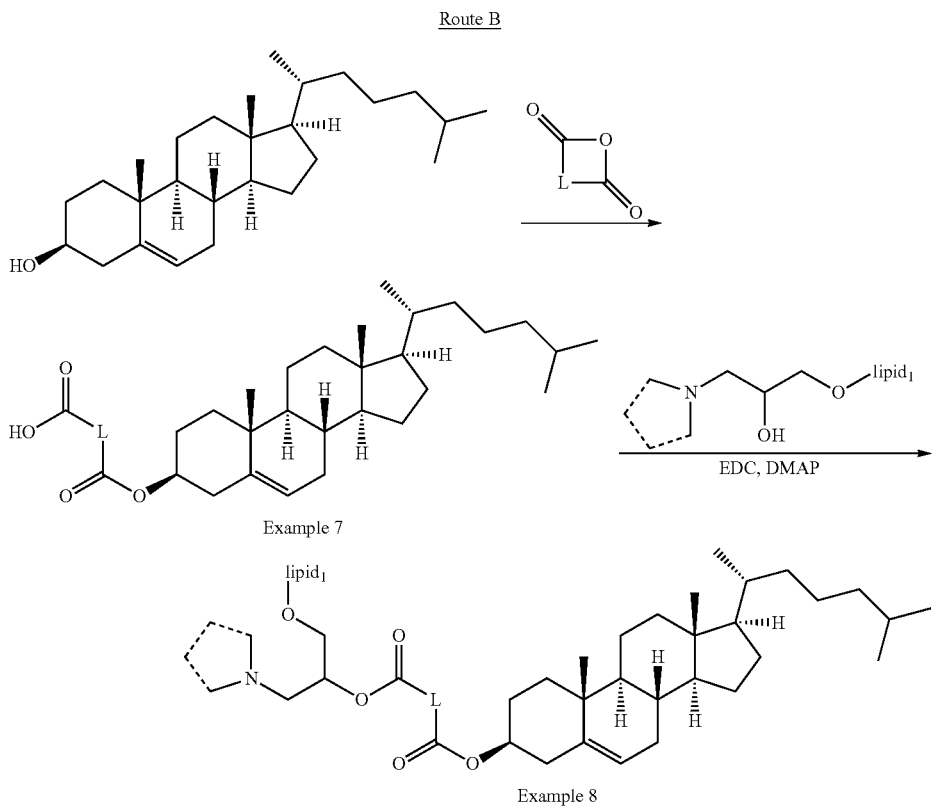

Example 7

Example 8

Example 7

Cholesterol (3.33 g, 8.62 mmol), diglycolic anhydride (1 g, 8.62 mmol), DMAP (0.263 g, 2.154 mmol), CH$_2$Cl$_2$ (35 ml), and a stirbar is added to a round bottomed flask. The reaction is stirred for three days at room temperature.

The reaction mixture is concentrated, and the residue is purified by flash chromatography on an IntelliFlash 280 (AnaLogix) using a SF40-80G column: 0-2 CV, 100% CH$_2$Cl$_2$; 2-10 CV, linear gradient of 100:0 CH$_2$Cl$_2$:(MeOH 10% AcOH) to 90:10 CH$_2$Cl$_2$:(MeOH 10% AcOH); 10-25 CV, linear gradient of 90:10 CH$_2$Cl$_2$:(MeOH 10% AcOH) to 85:15 CH$_2$Cl$_2$:(MeOH 10% AcOH). The product co-elutes with cholesterol. The product-containing fractions are combined and concentrated in vacuo to a white slurry, then diluted with heptanes (cholesterol is soluble in heptanes) and chilled in an ice bath. The white solid is filtered off, washed with heptanes, and placed under vacuum, yielding 1.50 g (35%) of pure product.

Example 8

The amino alcohol from example 5 (105.3 mg, 0.258 mmol), DMAP (22 mg, 0.180 mmol), and the carboxylic acid from example 7 (135.6 mg, 0.270 mmol) are weighed into a small vial. Dichloromethane (2.5 mL) is added, followed by EDC.HCl (67.1 mg, 0.350 mmol). The reaction mixture is stirred at rt overnight.

The crude reaction mixture is purified via flash chromatography on an IntelliFlash 280 (AnaLogix) using a SF15-24G column: 0-3 CV, 100% CH$_2$Cl$_2$; 3-25 CV, linear gradient of 100:0 CH$_2$Cl$_2$:MeOH to 95:5 CH$_2$Cl$_2$:MeOH. The product is still impure. The residue is purified again via flash chromatography on an IntelliFlash 280 (AnaLogix) using a SF15-24G column. 0-3 CV, 100% heptanes; 3-30 CV, linear gradient of 100:0 heptanes:ethyl acetate to 65:35 heptanes:ethyl acetate. The product-containing fractions are identified by TLC, combined, and concentrated in vacuo to yield 38 mg (13%) of pure product as a clear liquid.

The following compounds (the structures of which are set out below) can be manufactured by the Route B methodology: E0036 and E0047.

Route C also represents a general method which can be used to synthesise compounds of the invention.

Route C

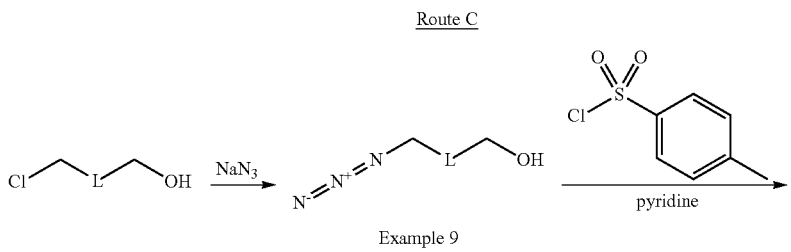

Example 9

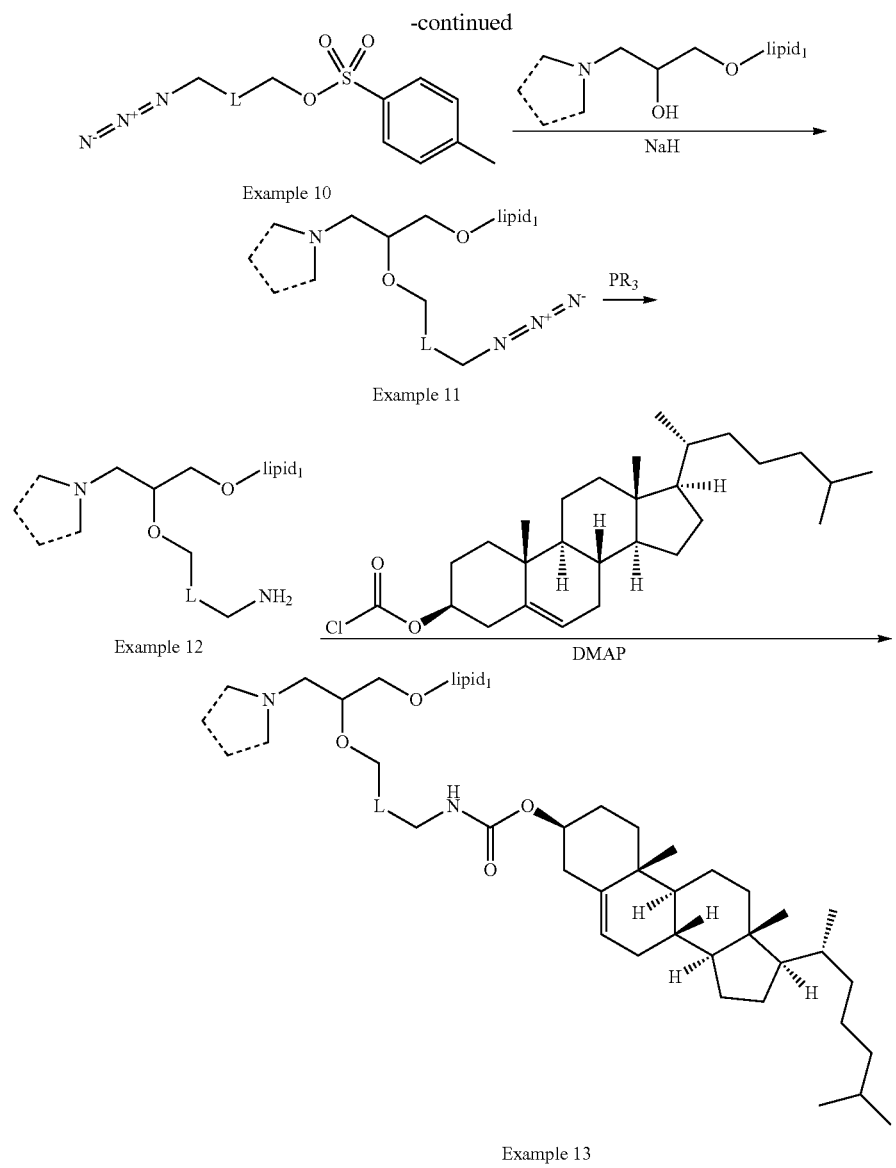

Example 9

2-(2-Chloroethoxyethanol) (5.01 g, 40.2 mmol) is weighed into a round bottomed flask and dissolve in DMF (100 ml). The solution is stirred, $NaN_3$ (2.89 g, 44.5 mmol) is added, and the temperature is increased to 80° C. The solution became cloudy. The reaction is stirred overnight.

The next morning, the reaction is removed from the heat and diluted with 300 mL water. This solution is washed with ethyl acetate to extract the product (4×100 mL). The organic phase is dried with sodium sulfate and concentrated to a liquid. By $^1$H NMR, this liquid contained 44% by weight of DMF. The product—5.19 g (98%)—is taken to the next step without further purification.

Example 10

The azidoalcohol from example 9 (5.25 g, 22.42 mmol) and pyridine (3 mL, 37.1 mmol) are dissolved in $CH_2Cl_2$ (45 ml) in a round bottomed flask and stirred in an ice bath. Once cold, tosyl chloride (4.70 g, 24.66 mmol) is added in one portion. The reaction is stored in a refrigerator overnight.

The next day, the reaction is diluted with $CH_2Cl_2$ (50 mL) and extracted with 1M HCl (2×40 mL) to remove the pyridine. The organic phase is washed once with brine (40 mL) and concentrated. The residue is purified via flash chromatography on IntelliFlash 280 (AnaLogix) using a SF40-115G column: 0-20 CV, linear gradient of 100:0 heptanes:ethyl acetate to 50:50 heptanes:ethyl acetate. The product containing fractions are identified by TLC, combined, and concentrated in vacuo to yield the product with an estimated 90% purity: 0.61 g (10%).

Example 11

Performed as in example 6 but using the amino alcohol from example 5 and the tosylate from example 10.

Example 12

The alkylazide from example 11 (334 mg, 0.641 mmol) is dissolved in THF (4 mL) and water (0.400 mL) in a small vial.

To this solution is added a solution of trimethylphosphine in THF (2.5 mL, 2.500 mmol trimethylphosphine) and the reaction is stirred overnight. The reaction appears complete by TLC the next morning. The solvent is evaporated and the residue is dissolved in 10 mL MeOH. The solution is loaded onto a SCX (10 g) column preequilibrated with MeOH, washed with 50 mL MeOH, then elutes with 4×10 mL 7M $NH_3$ in MeOH. The product elutes in the second, third and fourth fractions; these fractions are pooled and concentrated. Trimethyphosphine is still present by TLC (and by smell), so the residue is taken up in 50 mL EtOAc and washed with 3×15 mL water made slightly basic with $NaHCO_3$. The organic phase is dried with $Na_2SO_4$ and concentrated to a colorless liquid: 232 mg (73%).

Example 13

Dissolve the amine from example 12 (232 mg, 0.469 mmol) in $CH_2Cl_2$ (5 mL) in a round bottomed flask. To this solution is added cholesterol chloroformate (316 mg, 0.703 mmol) and DMAP (86 mg, 0.703 mmol). The solution is stirred at rt overnight.

The crude reaction mixture is purified directly via flash chromatography on an IntelliFlash 280 (AnaLogix) using a SF15-24G column: 0-5 CV, 100% $CH_2Cl_2$; 5-15 CV, linear gradient of 100:0 $CH_2Cl_2$:MeOH to 95:5 $CH_2Cl_2$:MeOH; 15-30, 95:5 $CH_2Cl_2$:MeOH. The product containing fractions are identified by TLC, combined, and concentrated to a pale yellow oil: 339 mg (80%).

The following compounds (the structures of which are set out below) can be manufactured by the Route C methodology:

| | | | | |
|---|---|---|---|---|
| E0054; | E0097; | E0099; | E0103; | E0148; |
| E0169; | E0175; and | E0176. | | |

Route D also represents a general method which can be used to synthesize compounds of the invention Route D

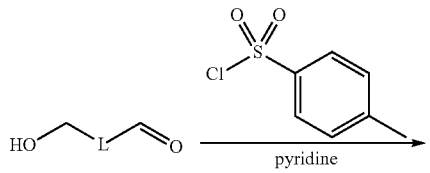

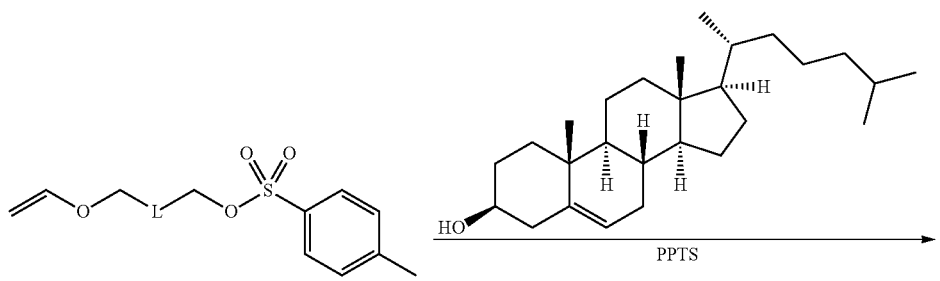

Example 14

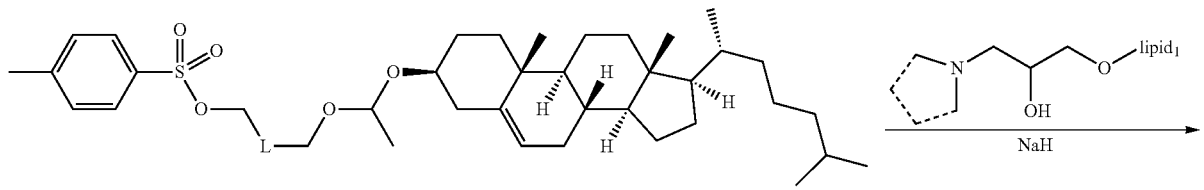

Example 15

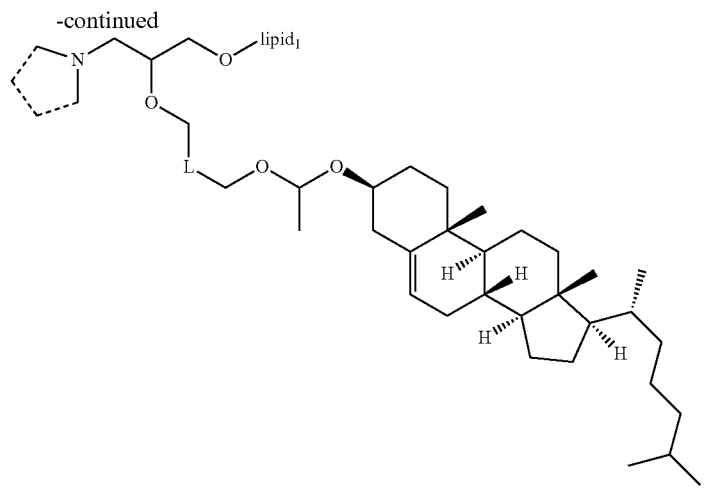

Example 16

Example 14

To a solution of diethylene glycol vinyl ether (3.96 g, 30 mmol) in CH$_2$Cl$_2$ at 0° C., pyridine (4.85 mL) is added, followed by tosyl chloride (6.86 g, 36 mmol). After 10 min at 0° C., the reaction is warmed to rt and stirred overnight.

The reaction is extracted between a saturated aqueous solution of NaHCO$_3$ and ethyl acetate. The organic extracts are combined, dried and concentrated. The residue is purified via flash chromatography eluting with 30% ethyl acetate/70% heptane: 5.45 g (63%).

Example 15

To a solution of the vinyl ether from example 14 (1.0 g, 3.49 mmol) in CH$_2$Cl$_2$ at rt, cholesterol (0.675 g, 1.746 mmol) is added, followed by PPTS (0.878 g, 3.49 mmol). The reaction is stirred at rt for 5 hrs. By TLC, the product elutes very close to cholesterol and is slightly UV-active. The reaction is extracted between a saturated aqueous solution of NaHCO$_3$ and ethyl acetate. The organic extracts are combined, dried and concentrated. The crude residue is purified via flash chromatography with 30% ethyl acetate/70% heptane: 700 mg (60%).

Example 16

Performed as in example 6 but using the amino alcohol from example 5 and the tosylate from example 15.

The following compounds (the structures of which are set out below) can be manufactured by the Route D methodology: E0058.

Route E also represents a general method which can be used to synthesise compounds of the invention.

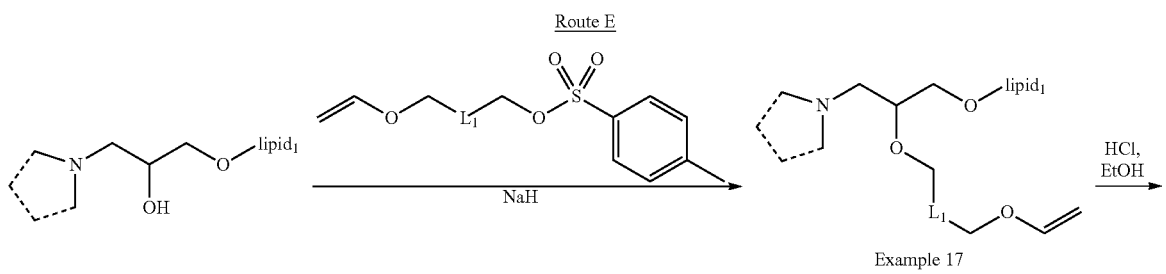

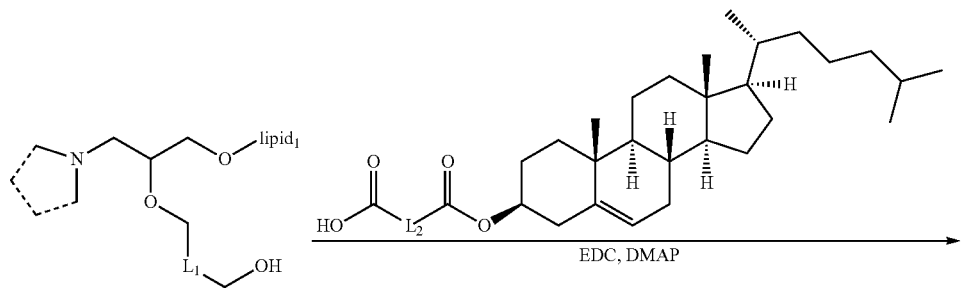

Example 18

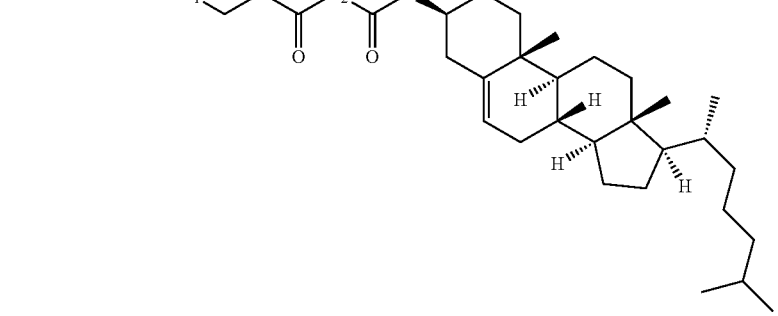

Example 19

Example 17

Performed as in example 6 but using the amino alcohol from example 5 and the tosylate from example 14.

Example 18

A 1N solution of aqueous HCl (0.38 mL, 0.38 mmol) is added dropwise to a solution of the vinyl ether from example 17 (100 mg, 0.19 mmol) in 4 mL of 1:1 ethanol/THF at rt. After 1 h, the reaction is extracted between a saturated aqueous solution of NaHCO$_3$ and ethyl acetate. The organic extracts are combined, dried and concentrated to an oil that is used in the next step without further purification: 85 mg (90%).

Example 19

Performed as in example 8 but using the amino alcohol from example 18 and cholesterol hemisuccinate as the carboxylic acid.

The following compounds (the structures of which are set out below) can be manufactured by the Route E methodology:

| | | | | | |
|---|---|---|---|---|---|
| E0060; | E0104; | E0129; | E0130; | E0143; | E0150; |
| E0151; | E0152; | E0161; | E0162; | E0163; | E0164; |
| E0165; | E0177; | E0178; and | E0179. | | |

Route F also represents a general method which can be used to synthesise compounds of the invention.

Route F

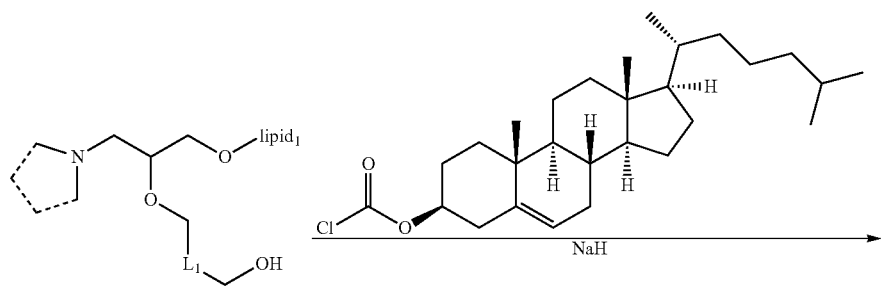

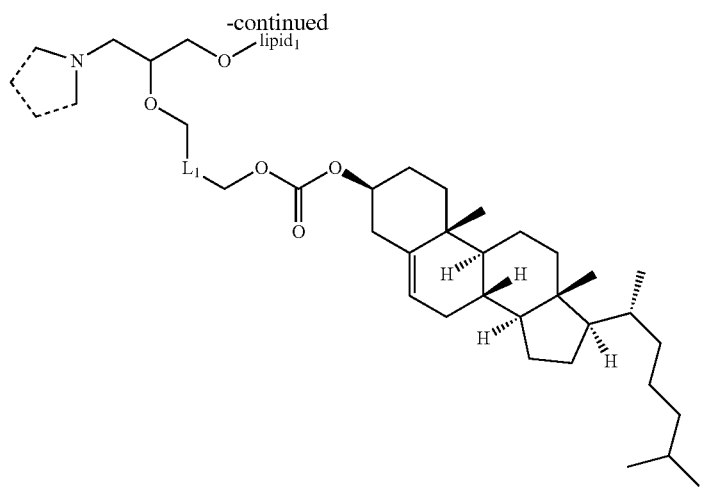

Example 20

Example 20

To a solution of the amino alcohol from example 18 (600 mg, 1.21 mmol) in toluene (12 mL) at rt, 60% NaH (97 mg, 2.42 mmol) is added (reaction became yellow). After 10 min, cholesterol chloroformate (815 mg, 1.815 mmol) is added. The reaction is then heated to 80° C. (reaction became orange) and stirred overnight.

The reaction mixture is cooled and extracted between brine and ethyl acetate. The organic extracts are combined, dried with $Na_2SO_4$, and concentrated to an oil. The crude oil is purified via flash chromatography with 5% MeOH/95% $CH_2Cl_2$: 720 mg (66%).

The following compounds (the structures of which are set out below) can be manufactured by the Route F methodology.

E0056; E0122; E0123; E0138; and E0139.

Route G also represents a general method which can be used to synthesise compounds of the invention.

Route G

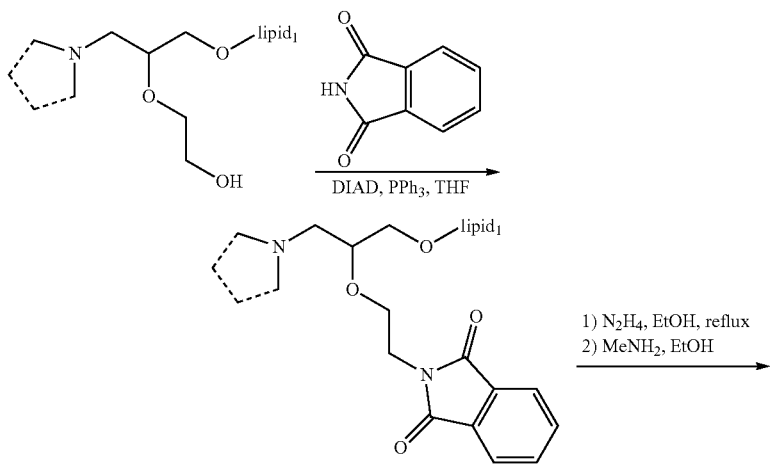

Example 21

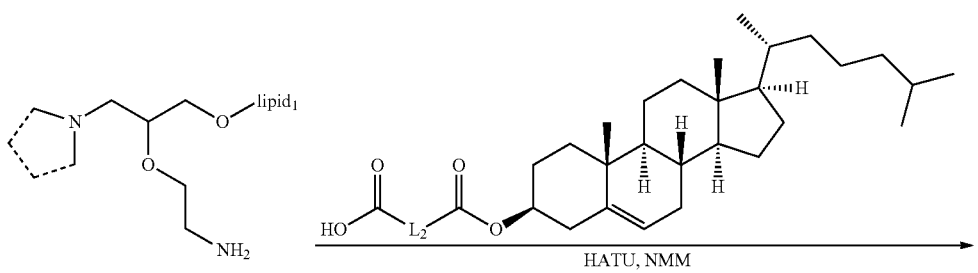

Example 22

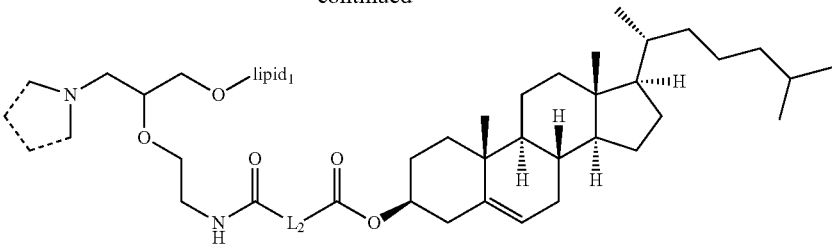

Example 23

Example 21

A solution of the amino alcohol from example 5 (12.4 mmol) in THF (10 mL) and a solution of DIAD (3 mL) in THF (10 mL) are added simultaneously to a solution of PPh₃ (2.5 g) and phthalimide (2.5 g) in THF (50 mL). The resulting mixture is stirred overnight at rt. The reaction is concentrated to dryness and used directly in the next step.

Example 22

The material from example 21 is stirred in ethanol (25 mL) and a solution of methylamine in THF is added. The reaction is stirred at rt for 16 h and then concentrated to dryness. The crude material is purified by chromatography on silica.

Example 23

The amine from example 22 (0.22 mmol) is stirred in DMF (5 mL) along with the cholesterol hemisuccinate (0.25 mmol), HATU (0.26 mmol). N-methylmorpholine (0.55 mmol) is added and the reaction is stirred overnight at rt. The resulting solution is concentrated under vacuum and diluted with EtOAc. The resulting organic layer is washed with water then brine and concentrated to a yellow liquid. The resulting residue is purified on neutral alumina to yield a pale yellow liquid.

The following compounds can be manufactured by the Route G methodology:
E0098; E0100; E0101; E0105; E0106; and E0108.

Route H also represents a general method which can be used to synthesise compounds of the invention.

Route H

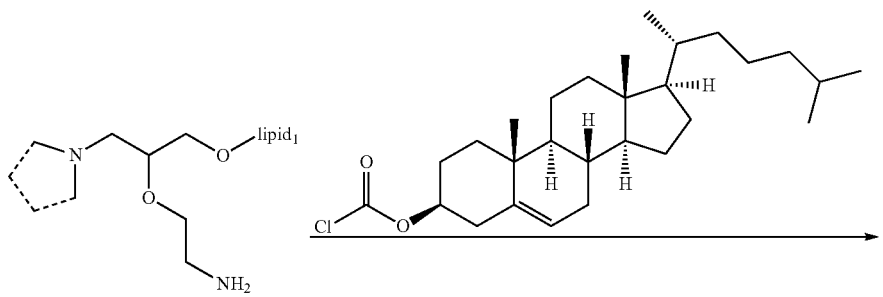

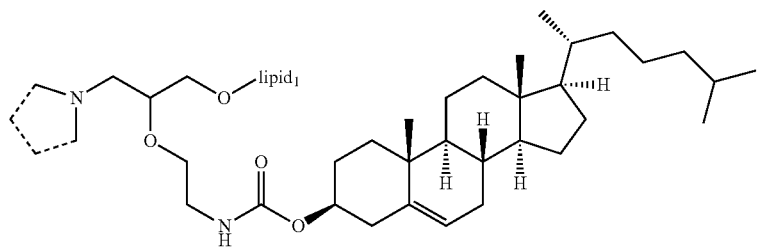

Example 24

Example 24

To a solution of the amine from example 22 (3.55 mmol) in DCM (10 mL) is added DIEA (5.7 mmol) and cholesterol chloroformate (6.0 mmol). The resulting reaction is stirred at rt overnight. The reaction is diluted with EtOAc (50 mL) and washed with water then brine. The resulting organic layer is concentrated to a residue and purified by chromatography on silica to yield a pale yellow liquid.

E0102 can be prepared using the Route H methodology.

Route I also represents a general method which can be used to synthesise compounds of the invention.

Example 26

The material from the previous step is stirred in DCM (15 mL) and TFA (5 mL) is added. The resulting solution is stirred overnight at rt. The resulting mixture is concentrated to dryness and 1.5N HCl (20 mL) is added. The solution is washed with EtOAc and then reduced to pH>7 with solid NaHCO$_3$. The resulting mixture is extracted with DCM and the resulting organic layer dried over sodium sulfate and concentrated to a crude solid that is used without further purification.

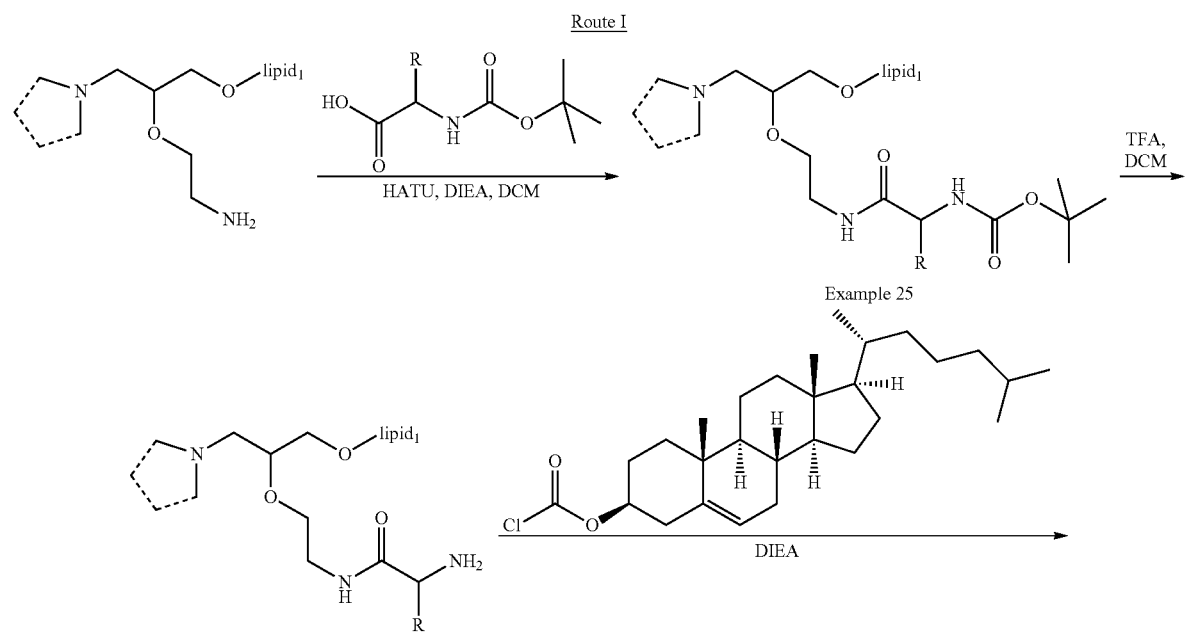

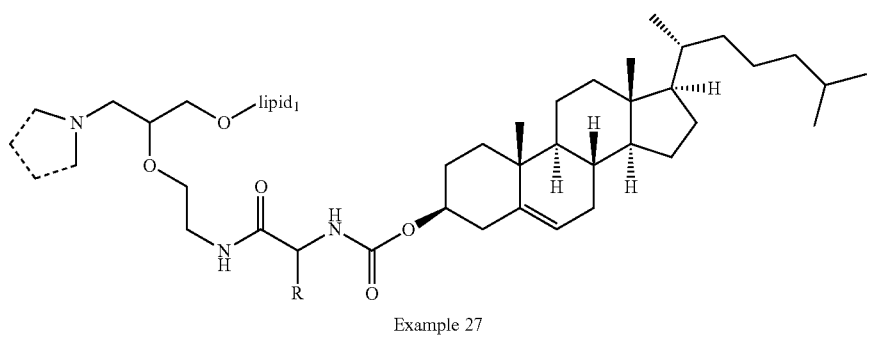

Example 25

To a solution of amine from example 22 (0.33 mmol) in DCM (25 mL) is added to BOC glycine (0.36 mmol), HATU (0.36 mmol) and DIEA (0.66 mmol). The resulting mixture is stirred at rt overnight. The resulting reaction mixture is washed with saturated aqueous NH$_4$Cl, dried over sodium sulfate and concentrated to a crude solid that is used without further purification.

Example 27

The material from the previous step is stirred in DCM (20 mL) and DIEA (0.53 mmol) is added. To this solution is added cholesterol chloroformate (0.53 mmol) and the reaction is stirred overnight at rt. The reaction is then diluted with EtOAc (50 mL) and the resulting solution washed with 1.5 N HCl, 10% aq. NaHCO$_3$, and brine. The resulting organic layer is dried over sodium sulfate and concentrated to solid.

E0110 and E0111 can be prepared using the Route I methodology.

Examples 28 to 32 also represent routes which can be used to synthesise compounds of the invention.

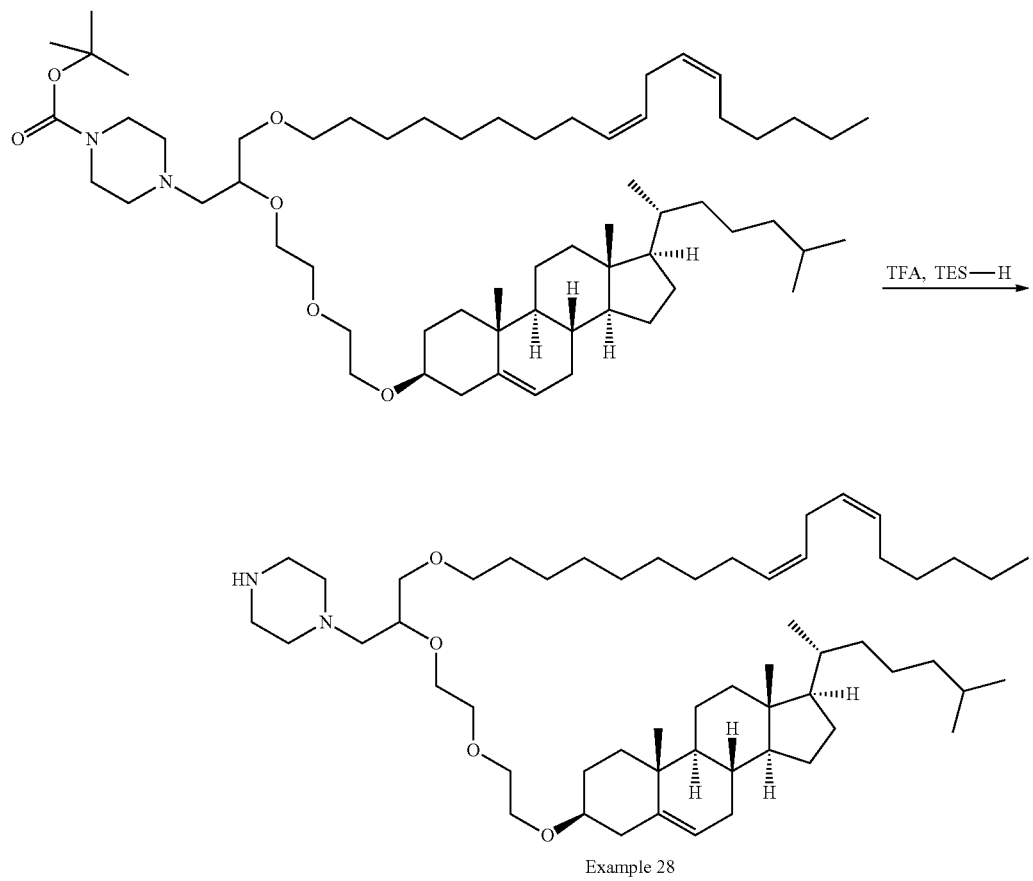
Example 28
BOC protected cationic lipid prepared using Route A methodology (150 mg) is stirred with triethylsilane (0.5 mL) and TFA (10 mL) is added in one portion. After 2 h, the reaction is concentrated to dryness. The resulting residue is purified on silica on 0 to 15% MeOH in DCM and concentrated to a glassy oil.
E0012 can be made using this process.
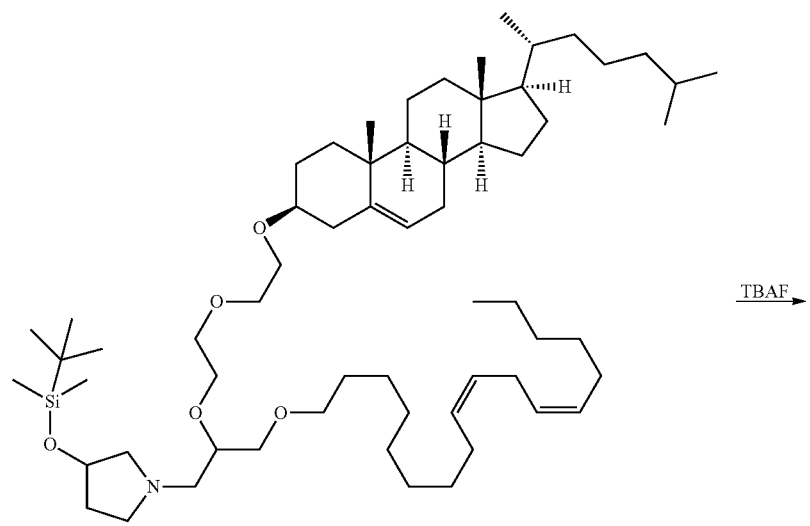

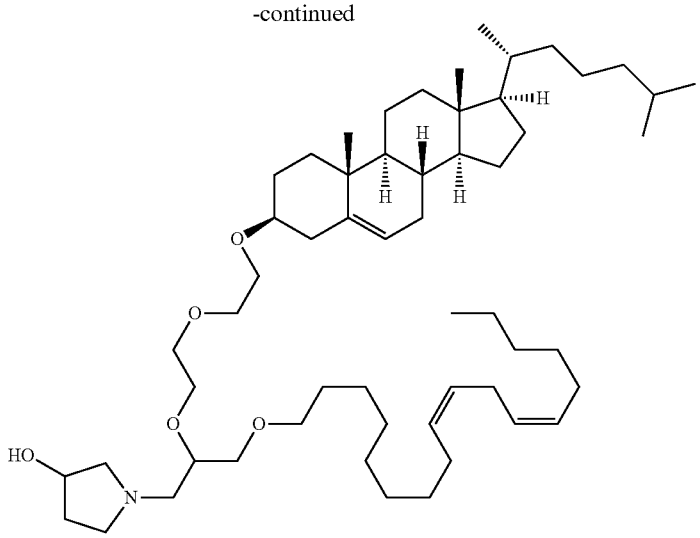

Example 29

Example 29

TBDMS protected cationic lipid prepared using Route A methodology (135 mg, 0.138 mmol) is stirred in THF (2 mL) and a solution of TBAF (0.28 mL, 1.0 M in THF, 0.28 mmol) is added. The reaction is stirred at rt overnight. The reaction is purified directly on silica in 0 to 20% MeOH in DCM to yield a clear oil.

E0045 can be made using this process.

Examples 30 to 31 also represent routes which can be used to synthesise compounds of the invention.

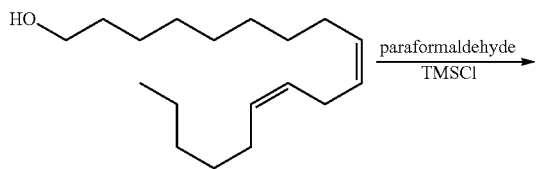

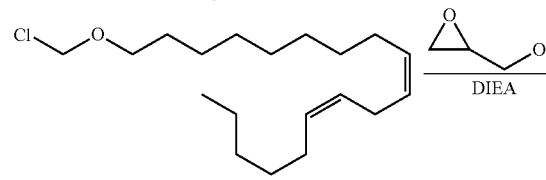

Example 30

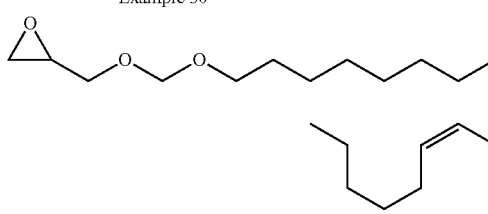

Example 31

Example 30

To a stirred suspension of paraformaldehyde (536 mg) in TMSCl (9.4 mL) is added linoleyl alcohol (5.0 g) dropwise over 15 min. Once the reaction turns clear it is concentrated under reduced pressure and used immediately in the next step.

Example 31

To a stirred solution of glycidol (1.5 mL) in THF (50 mL) is added the compound from Example 30 (5.8 g), DIEA (9.5 mL), tetrabutylammonium iodide (6.8 g). The reaction is stirred at rt for 5 h. The solids are removed by filtration and washed with diethyl ether. The filtrate is collected and washed with water and brine. The resulting organic layer is dried over sodium sulfate and concentrated under reduced pressure to a crude oil. The crude material is purified by chromatography on silica that had been pretreated with 3% triethylamine containing mobile phase. The material is elutes using EtOAc in heptanes to yield 1.65 g pure product as a clear liquid.

The starting material for making E0115, E0116, E0117, and E0160 can be made using steps from Example 30 and this Example 31.

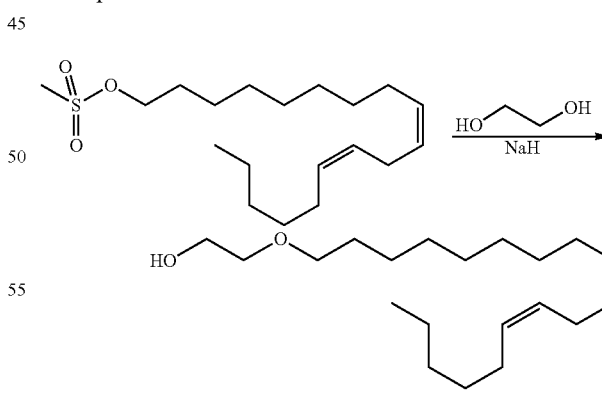

Example 32

Example 32

Ethylene glycol (0.30 g) is stirred in THF (20 mL) and 60 wt % sodium hydride is added (0.19 g). The resulting mixture is stirred for 20 min. Linoleyl mesylate (1.64 g) is added and the reaction is heated to 50° C. for 2 h and then to reflux overnight. The reaction is cooled to rt and stirred for an additional 24 h. To the reaction is added saturated aqueous ammonium chloride and the resulting mixture is extracted with DCM. The resulting organic layer is dried over sodium sulfate and concentrated to a crude oil. The crude material is purified on silica using EtOAc in heptanes to yield 640 mg of the desired product.

The methods of examples 30 to 32 may be used in the synthesis of lipids (e.g. E0055) having a spacer between the linoleyl chains and the core of the molecule.

Route J also represents a general method which can be used to synthesise compounds of the invention.

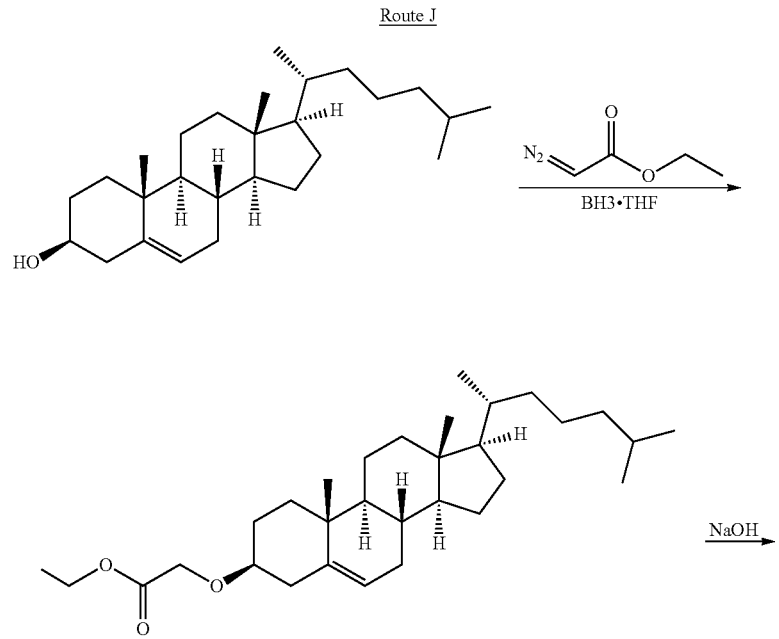

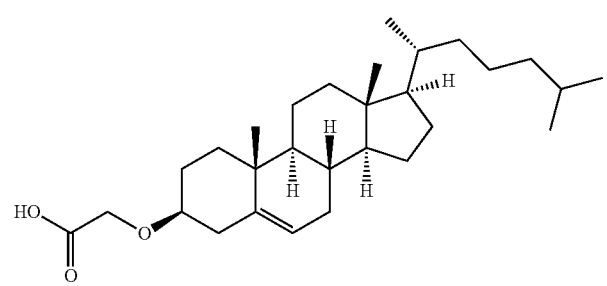

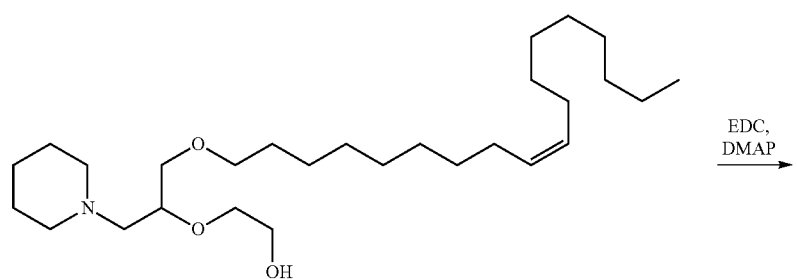

-continued

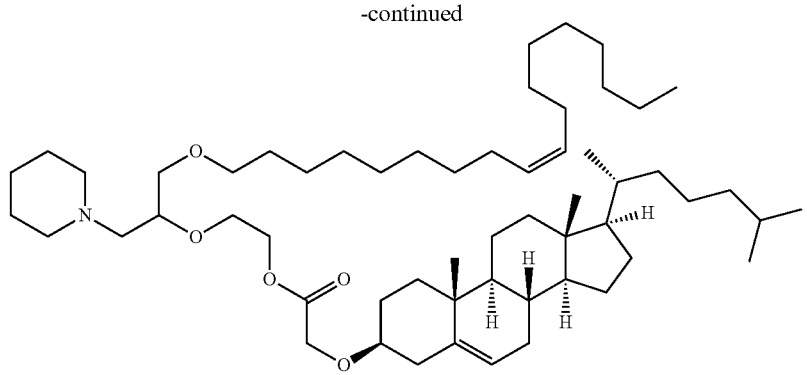

Example 35

Example 33

To a solution of cholesterol (10 g, 26 mmol) and borane-THF (5 drops) in DCM (30 mL) is added ethyldiazoacetate (3.5 mL, 52 mmol). After stirring for 5 min the reaction mixture is concentrated and purified by chromatography on silica in hexane/EtOAc to yield 9 g of the desired product.

Example 34

To a solution of the compound from Example 33 (9 g, 19 mmol) in EtOH (110 mL) is added NaOH (3 g, 76 mmol). The resulting mixture is heated to 70° C. for 3 h. The reaction is cooled to rt and concentrated. The residue is taken up in water and acidified with 2 N HCl and extracted with DCM (2×). The resulting organic layers are combined and concentrated to yield 8 g of the desired product.

Example 35

EDC (1.8 g, 9.8 mmol) and DMAP (80 mg, 0.66 mmol) is added to a solution of the compound from Example 34 (2.2 g, 4.9 mmol) in DCM (5 mL). The reaction is stirred for 10 min and then the alcohol (1.5 g) is added and the reaction is allowed to stir overnight at rt. The reaction is diluted with DCM and washed with water. The resulting organic layer is concentrated to a residue and purified on silica in chloroform/MeOH to yield the desired product as an oil.

The following compounds can be manufactured by the Route J methodology:

E0125; E0128; E0131; E0140; and E0144.

Route K also represents a general method which can be used to synthesise compounds of the invention.

Route K

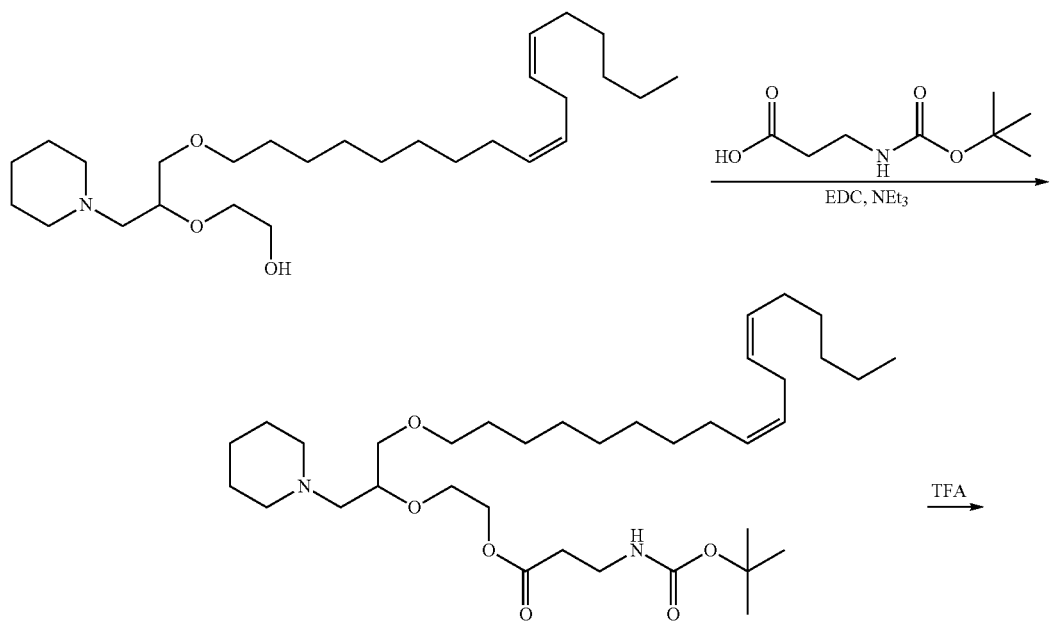

Example 36

-continued

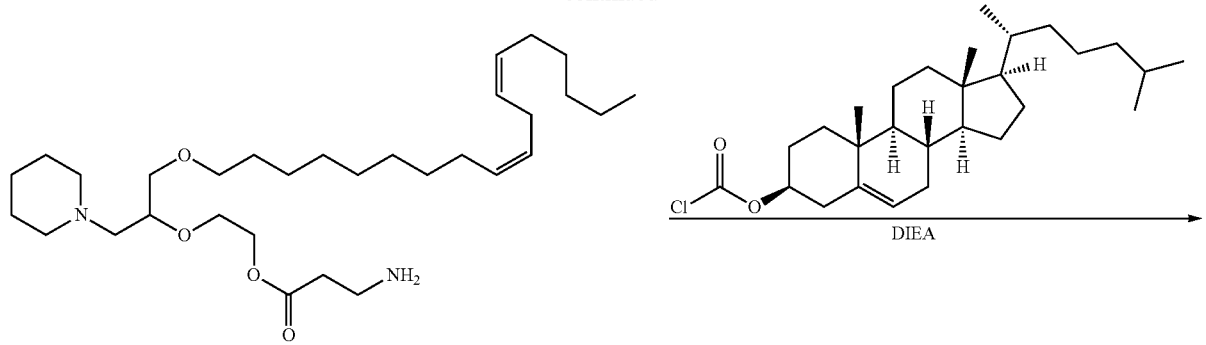

Example 37

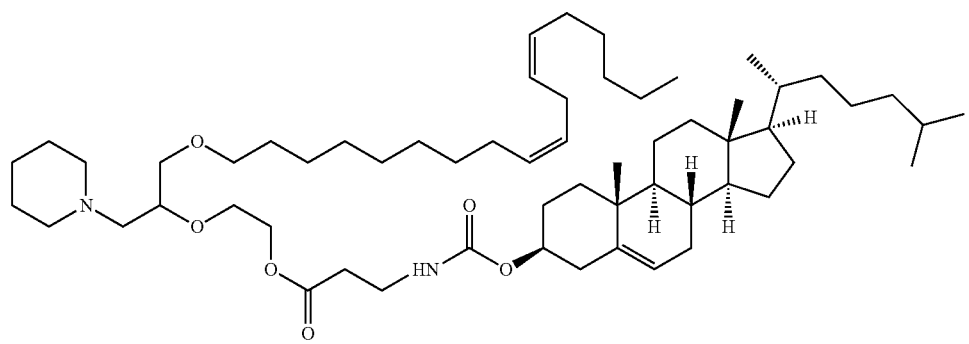

Example 38

Example 36

To a solution of N-Boc-betaalanine (1.25 g, 6.61 mmol) in DCM (6 mL) is added EDC (2.5 g, 13 mmol) HOBt (0.3 g, 2 mmol) and TEA (2 mL, 13 mmol). The resulting mixture is stirred for 30 minutes. A solution of the amino alcohol (2 g) in DCM (4 mL) is added and the reaction stirred for 10 h. The reaction is diluted with DCM and washed with saturated sodium bicarbonate and brine. The resulting organic layer is dried over sodium sulfate and concentrated to an oil that is purified on silica in MeOH/DCM. The product is concentrated to 2.65 g of an oil.

Example 37

The compound from Example 36 (2.6 g) is stirred in DCM (10 mL) and TFA (10 mL) is added. After 3 h, the reaction is concentrated to dryness and used directly in the next step.

Example 38

To a olution of the compound from Example 37 (2 g) in DCM (20 mL) is added DIEA (2.7 mL, 15.7 mmol) and DMAP (80 mg, 0.6 mmol) followed by cholesterol chloroformate (2.1 g, 4.7 mmol). The reaction is stirred for 3 h at rt. The reaction is diluted with DCM and washed with water. The resulting organic layer is concentrated and purified on silica in MeOH/chloroform to yield 2.1 g of the desired product.

The following compounds can be manufactured by the Route K methodology:

| E0133; | E0134; | E0135; | E0136;      | E0137; | E0141; |
| E0132; | E0142; | E0145; | E0166; and  | E0168. |        |

Route L also represents a general method which can be used to synthesise compounds of the invention.

Route L

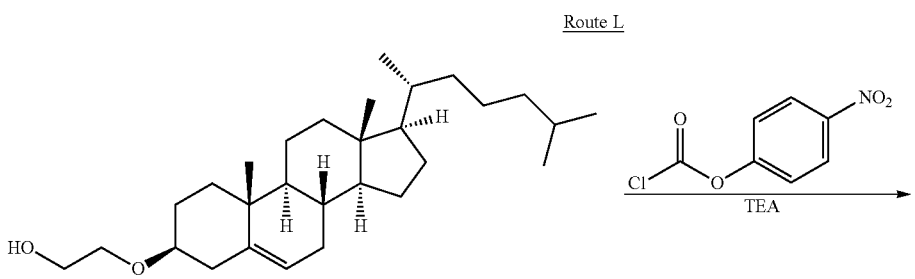

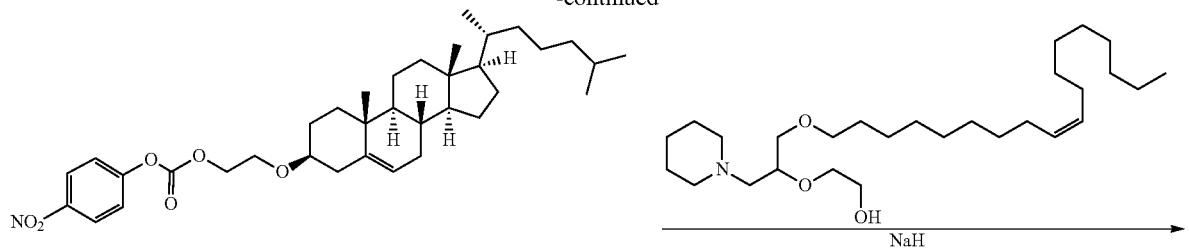

Example 39

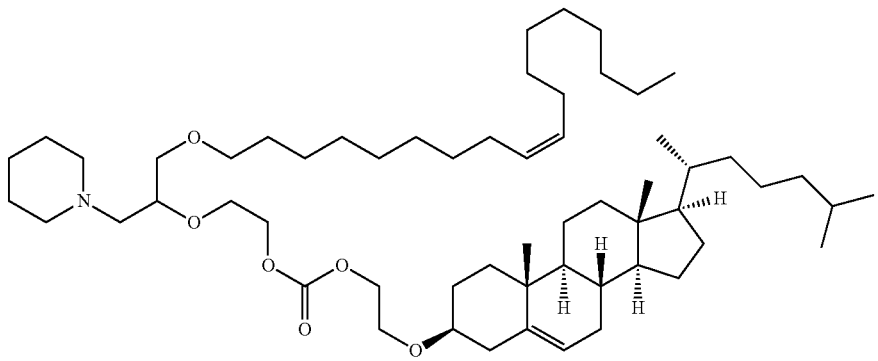

Example 40

Example 39

To a solution of the alcohol (2.5 g, 5.8 mmol) in DCM (10 mL) is added p-nitrochloroformate and TEA. The reaction is stirred at rt overnight. The reaction is diluted with DCM and washed with water. The resulting organic layer is dried over sodium sulfate and concentrated to an oil and purified on silica in EtOAc/hexane to yield the desired product.

Example 40

The alcohol (1.3 g, 2.9 mmol) is stirred in MePh (10 mL). NaH is added (0.46 g, 11.4 mmol) and the reaction is stirred at rt for 30 min. The compound from Example 39 (1.7 g, 1.2 mmol) is added and the reaction is stirred for 16 h at rt. The reaction is cooled in an ice bath and quenched with water. The resulting mixture is extracted with EtOAc. The organic layers are combined, washed with brine, dried over sodium sulfate and concentrated to a crude oil. The material is purified on silica in EtOAc/hexane to yield 1 g of the desired product.

E0146 can be made using Route L technology.

EXAMPLES 41, 42 AND 43

Examples 41, 42 and 43 are reserved and are purposefully left blank.

Route X also represents a general method that can be used to synthesise compounds of the invention.

Route X

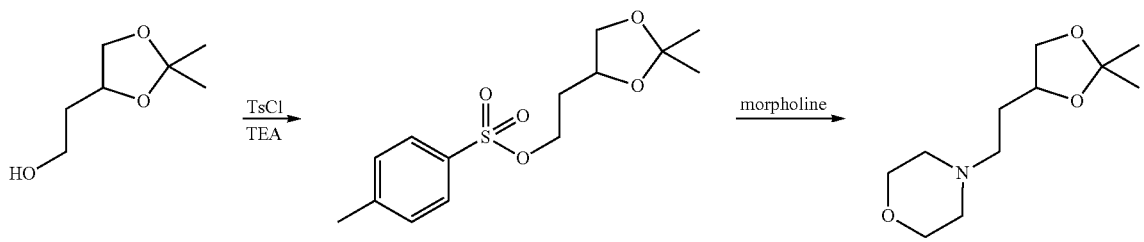

Example 44     Example 45

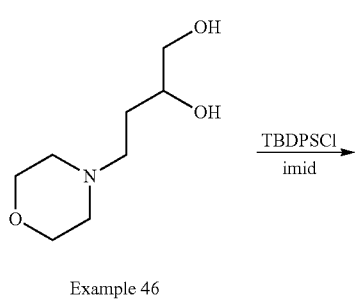

Example 46

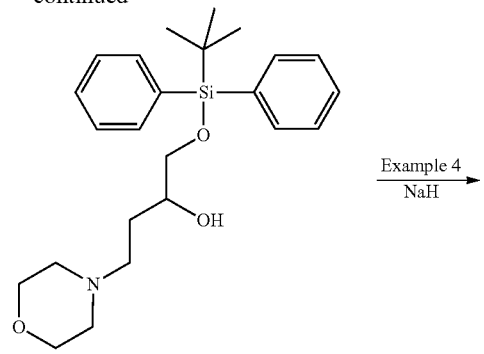

Example 47

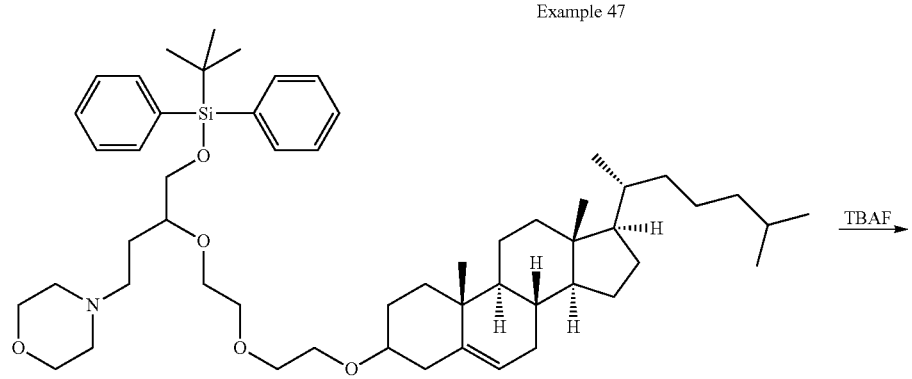

Example 48

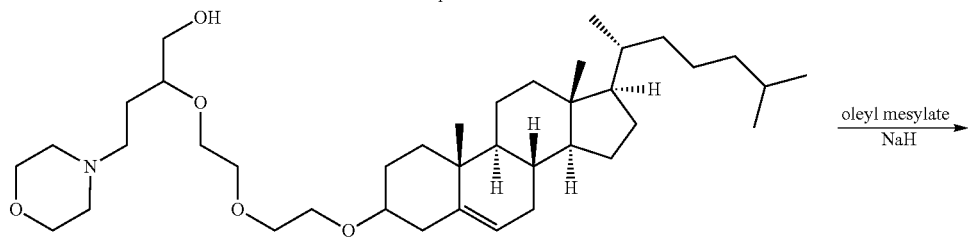

Example 49

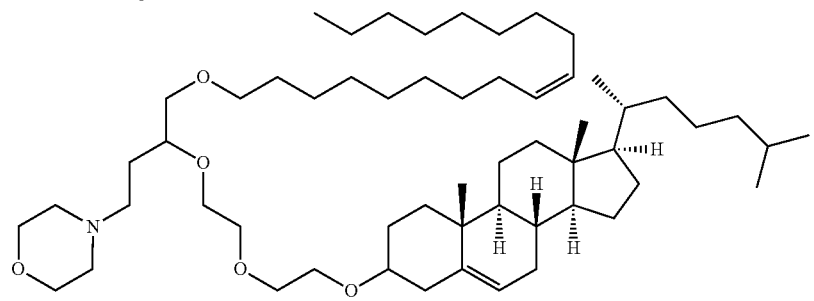

Example 50

Example 44

To a solution of 2-(2,2-dimethyl-1,3-dioxolan-4-yl)ethanol (800 mg, 5.47 mmol), triethylamine (0.915 mL, 6.57 mmol) and N,N-dimethylaminopyridine (134 mg, 1.10 mmol) in dichloromethane (25 mL) at rt is added to tosyl chloride (1.10 g, 5.75 mmol). The reaction is stirred at rt for 3 h. The reaction is diluted with saturated aqueous $NaHCO_3$, and extracted with ethyl acetate. The organic phase is dried, concentrated and the crude product is purified by flash chromatography on silica with an ethyl acetate/heptane gradient: 1.24 g, 75%.

Example 45

The tosylate from example 44 (1.03 g, 3.43 mmol) and morpholine (2.97 mL, 34.3 mmol) are combined in a flask. The flask is sealed and heated at 60° C. overnight. The reaction mixture is diluted with ethylacetate and washed with saturated aqueous $NaHCO_3$. The organic phase is dried, concentrated and the crude product is purified by flash chromatography on silica with a dichloromethane/methanol gradient: 670 mg, 91%.

Example 46

The amine from example 45 (530 mg, 2.46 mmol) is dissolved in dioxane (15 mL) at 0° C. To the cooled solution is added concentrated HCl (aqueous, 7.39 mmol). The reaction is stirred at rt overnight. Excess solid $K_2CO_3$ is added to neutralize the acid. The solids are removed by filtration and washed with acetone. The filtrate is concentrated and the crude product is purified by flash chromatography on silica with a dichloromethane/methanol gradient: 320 mg, 74%.

Example 47

The diol from the previous step in Example 46 (320 mg, 1.8 mmol) is stirred in DCM (12 mL) with imidazole (249 mg, 3.65 mmol). To this solution is added TBDPSCl (0.475 mL), 1.8 mmol). The resulting mixture is stirred at rt overnight. The reaction is diluted with DCM and ished with satureated sodium bicarbonate. The resulting organic layer is dried over sodium sulfate, concentrated to an oil and purified on silica in DCM/MeOH to yield 650 mg of the desired product.

Example 48

To the material from the previous step (640 mg, 1.5 mmol) in toluene (15 mL) is added sodium hydride (124 mg, 60 wt% in oil, 3.1 mmol). After 20 min, the cholesterol reagent (1.17 g, 1.86 mmol) is added and the reaction heated to reflux overnight. After cooling to rt, the reaction is quenched with brine and extracted with ethyl acetate. The resulting organic layer is dried, concentreated, and purified on silica in EtOAc/heptanes to yield 560 mg of the desired product.

Example 49

To the material from the previous step (660 mg, 0.76 mmol) in THF (6 mL) is added a 1 M solution of TBAF in THF (1.5 mL0, 1.5 mmol). The reaction is stirred at rt for 2 h and then diluted with EtOAc. The resulting organic layer is ished with brine, dried, and concentrated to a crude product that is purified on silica in MeOH/DCM.

Example 50

The amino alcohol from example 49 (280 mg, 0.443 mmol) is dissolved in toluene (4 mL) at rt, and then 60% NaH is added (44 mg, 1.1 mmol). After 20 minutes, oleyl tosylate (prepared from oleyl alcohol in a method analagous to that described in example 10) (187 mg, 0.443 mmol) is added. The reaction is refluxed for 3 h. The reaction is cooled to rt diluted with ethyl acetate, and ished with brine. The organic phase is dried, concentrated and the crude product is purified by flash chromatography on silica with an ethyl acetate/heptane gradient: 183 mg, 47%.

E0180 can be manufactured by the Route X methodology

Route Y also represents a general method that can be used to synthesise compounds of the invention.

Route Y

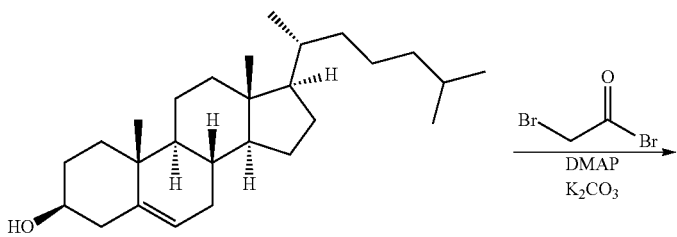

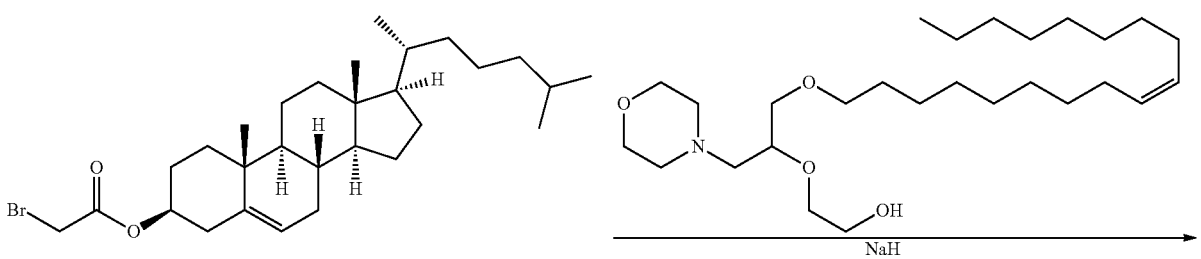

Example 51

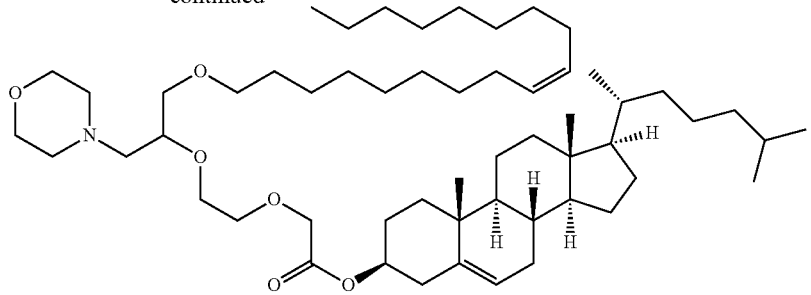

Example 52

Example 51

To a solution of cholesterol (700 mg, 1.8 mmol) in DCM (20 mL) is added potassium carbonate (750 g, 5.4 mmol) and DMAP (22 mg, 0.18 mmol) bromoacetyl bromide (0.19 mL, 2.2 mmol) is added dropwise. After stirring for 90 min in an ice bath the reaction is filtered, concentrated and purified on silica in DCM/heptane to yield 850 mg of the desired product.

Example 52

To a solution of the amino alcohol (1.08 g, 2.37 mmol) in MePh (20 mL) is added NaH (190 mg, 60 wt % in oil, 4.74 mmol). The mixture is heated at reflux for 10 min and then the bromoacetyl cholesterol (1.20 g, 2.37 mmol) is added. The reaction is stirred for 2 h at reflux and the cooled to rt. To the reaction is added water and EtOAc and brine. The resulting organic layer is collected, dried, and concentrated to a crude material that is purified on silica in EtOAc/heptane after the column is equilibrated with 1% acetic acid in DCM. After purification, the fractions containing product are combined and washed with saturated aqueous sodium bicarbonate before concentrating to 700 mg of the desired product.

E0167 can be manufactured using route Y methodology.

Example 53

Stealth Lipid Structures and Syntheses

The structures of the stealth lipids S001 through S026 are provided in Table 3. The following examples 54 to 67 illustrate the synthesis of stealth lipids.

TABLE 3

Stealth lipid structures

| Stealth Lipid | Lipid |
|---|---|
| S001 | 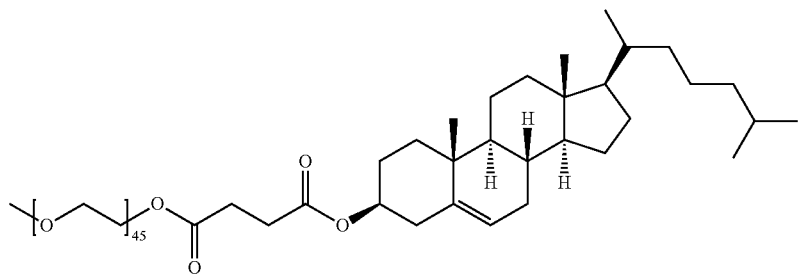 |
| S002 | 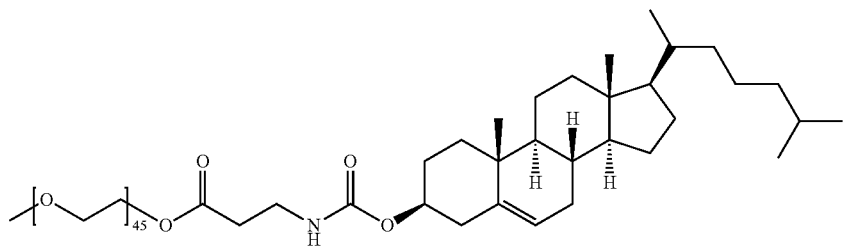 |

TABLE 3-continued

Stealth lipid structures

| Stealth Lipid | Lipid |
|---|---|

S003

S004

S005

S006

S007

S008

S009

S010

S011

TABLE 3-continued

Stealth lipid structures

| Stealth Lipid | Lipid |
|---|---|
| S012 | |
| S013 | |
| S014 | |
| S015 | |
| S016 | |
| S017 | |
| S018 | |
| S019 | |
| S020 | |

TABLE 3-continued
Stealth lipid structures
| Stealth Lipid | Lipid |
|---|---|
| S021 | |
| S022 | |
| S023 | |
| S024 | |
| S025 | |
| S026 | |
Example 54
S001
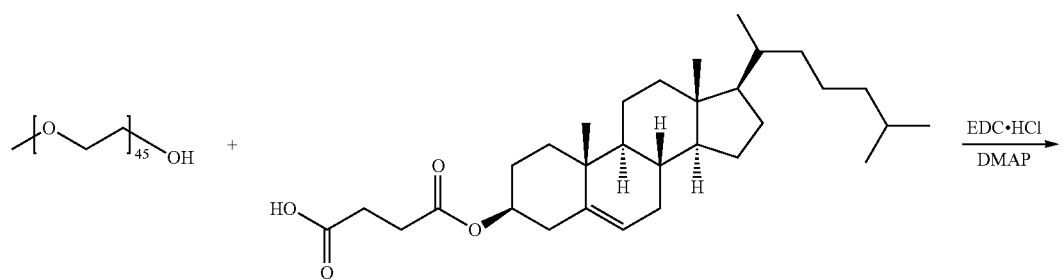

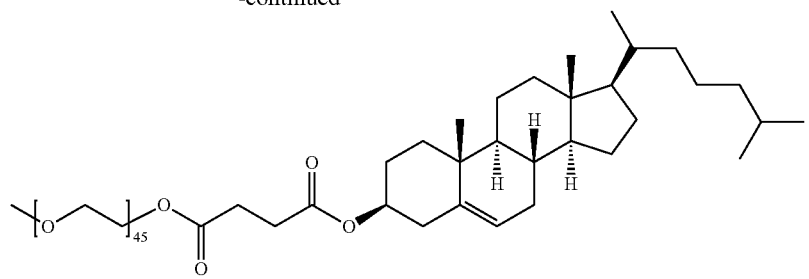

Cholesterol hemisuccinate (608 mg, 1.25 mmol) and N-(3-dimethylaminopropyl)-N'-ethylcarbodiimide hydrochloride (240 mg, 1.25 mmol, EDC.HCl) are dissolved in anhydrous dichloromethane (4 mL), and then N,N-dimethylaminopyridine (305 mg, 2.50 mmol) and poly(ethylene glycol) methyl ether (500 mg, 0.250 mmol, $M_n$~2,000 g/mol, Sigma-Aldrich) are added. The reaction mixture is stirred at rt. After 72 h, the entire reaction mixture is loaded onto a 10 g Bond Elut SCX column (from Varian; pre-equilibrated with 50:50 dichloromethane:methanol) and elutes with 50:50 dichloromethane:methanol. The product containing fractions are identified by TLC, combined, and concentrated. The crude product is further purified by flash chromatography on silica with a dichloromethane/methanol gradient. The product containing fractions are identified by TLC, combined and concentrated to a white solid: 304 mg, 48.6%.

Size exclusion chromatography in tetrahydrofuran shows a single narrow peak. The peaks and integral values observed in the $^1$H NMR spectrum are consistent with the expected product.

Example 55

S002

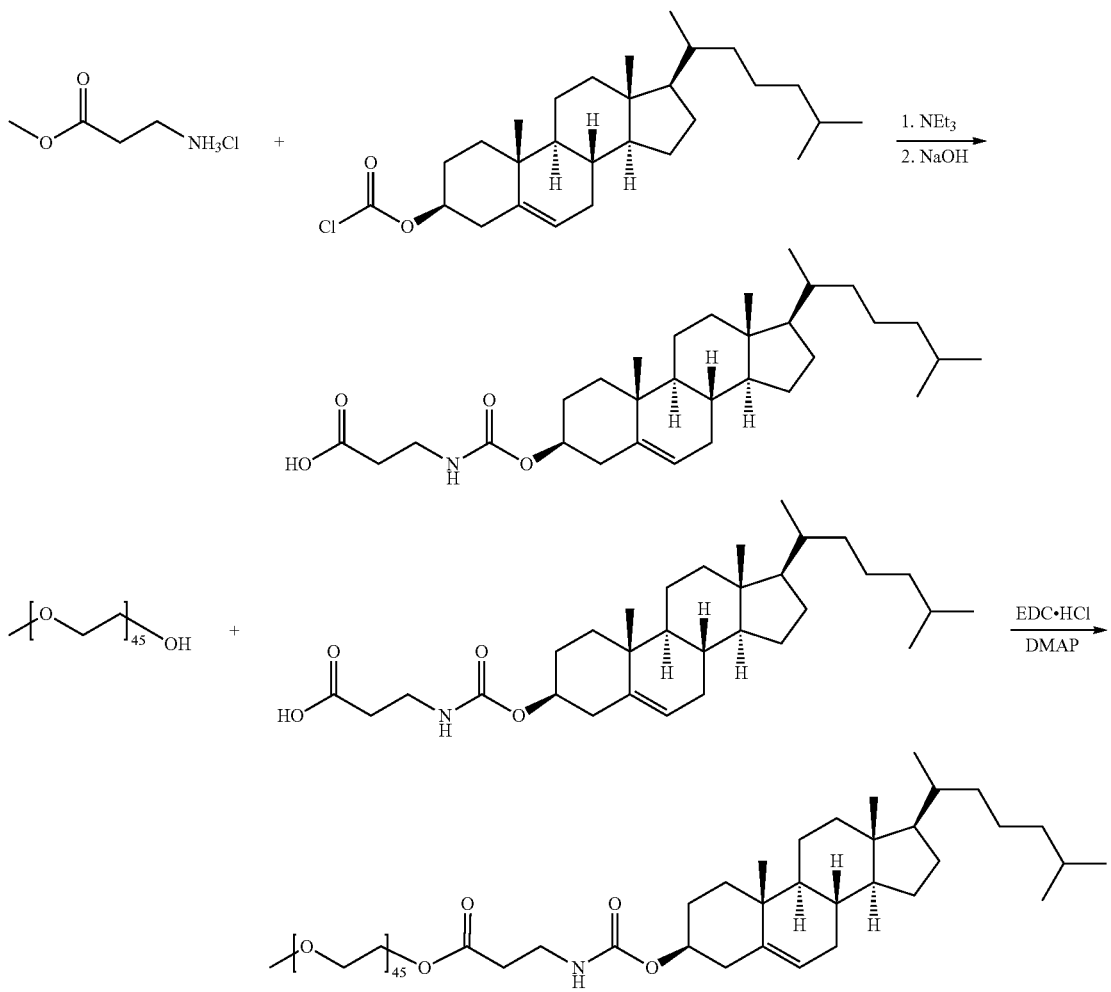

Step 1

β-alanine hydrochloride (1.00 g, 7.16 mmol), cholesterol chloroformate (3.06 g, 6.81 mmol) and triethylamine (2.0 ml, 14 mmol) are dissolved in anhydrous chloroform (25 ml). The solution is stirred at rt overnight. The next morning, the solvent is evaporated and the residue is dissolved in ethyl acetate (100 mL) and washed with 1 M HCl, brine, and dried with $Na_2SO_4$. The product is concentrated to a white solid and used in the next step without further purification: 3.31 g, 90.0%.

Step 2

The product (methyl ester) from the previous step (298 mg, 0.578 mmol) is dissolved in tetrahydrofuran (2 mL) and 1 M NaOH (2.0 mL, 2.0 mmol) is added, resulting in a biphasic solution. The solution is stirred at rt, forming an emulsion. After 2 h, the reaction mixture is diluted with 10 mL water and acidified with 1 M HCl. The product is extracted into ethyl acetate (100 mL). The organic phase is washed with brine, dried with $Na_2SO_4$, and concentrated to a white solid. $^1H$ NMR indicated the presence of a small amount of methyl ester starting material (~5 mol %) but is deemed pure enough for use in the next step without further purification: 252 mg, 83.0%.

Step 3

N-(3-dimethylaminopropyl)-N'-ethylcarbodiimide hydrochloride (96 mg, 0.50 mmol), the product (carboxylic acid) from the previous step (252 mg, 0.477 mmol), N,N-dimethylaminopyridine (122 mg, 1.00 mmol) and poly(ethylene glycol) methyl ether (200 mg, 0.100 mmol, $M_n$~2,000 g/mol, Sigma-Aldrich) are dissolved in anhydrous dichloromethane (5.0 mL) and stirred at rt. After 24 h the reaction mixture is loaded onto a 10 g Bond Elut SCX column (from Varian; pre-equilibrated with 50:50 dichloromethane:methanol) and elutes with 50:50 dichloromethane:methanol. The product containing fractions are identified by TLC, combined, and concentrated. The crude product is further purified by flash chromatography on silica with a dichloromethane/methanol gradient. The product containing fractions are identified by TLC, combined and concentrated to a white solid: 151 mg, 60.3%.

Size exclusion chromatography in tetrahydrofuran shows a single narrow peak. The peaks and integral values observed in the $^1H$ NMR spectrum are consistent with the expected product.

Example 56

S003

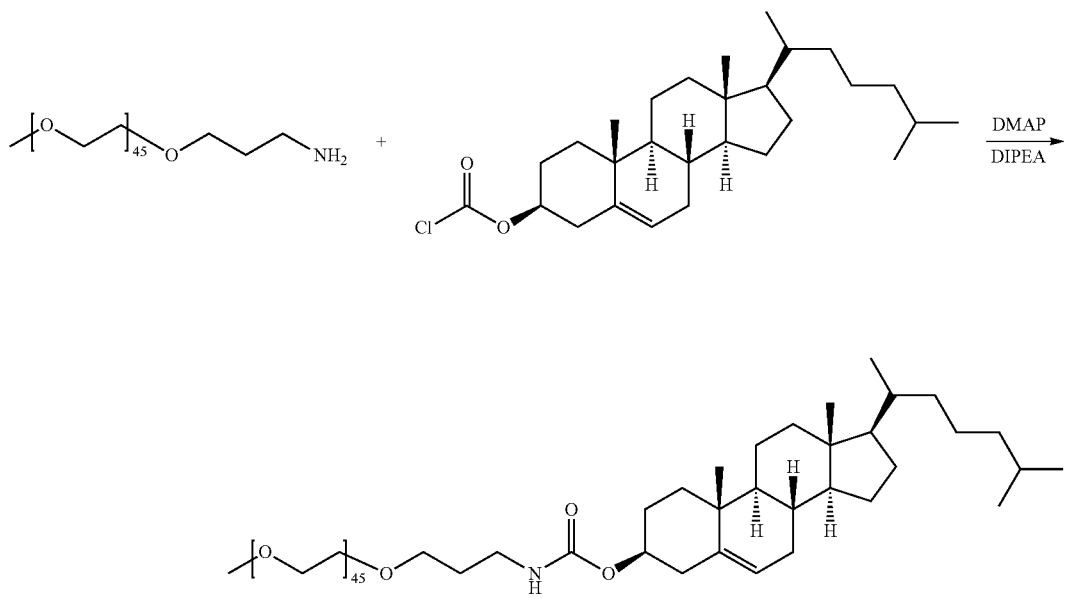

PEG-NH$_2$ (500 mg, 0.250 mmol, $M_n$~2000 g/mol, "Sunbright MEPA-20H", NOF Corp.), cholesterol chloroformate (449 mg, 1.00 mmol), N,N-dimethylaminopyridine (122 mg, 1.00 mmol), and N,N-diisopropylethylamine (148 mg, 1.15 mmol) are dissolved in 5 mL of 1:1 toluene:dichloromethane and stirred at rt. After 72 h, N,N-dimethylethylenediamine (0.2 mL) is added to quench excess cholesterol chloroformate. After stirring 30 min, the reaction mixture is loaded onto a 10 g Bond Elut SCX column (from Varian; pre-equilibrated with 50:50 dichloromethane:methanol) and elutes with 50:50 dichloromethane:methanol. The product containing fractions are identified by TLC, combined, and concentrated. The crude product is further purified by flash chromatography on silica with a dichloromethane/methanol gradient. The product containing fractions are identified by TLC, combined and concentrated to a white solid: 376 mg, 57.8%.

Size exclusion chromatography in tetrahydrofuran shows a single narrow peak. The peaks and integral values observed in the $^1H$ NMR spectrum are consistent with the expected product.

Example 57

S004

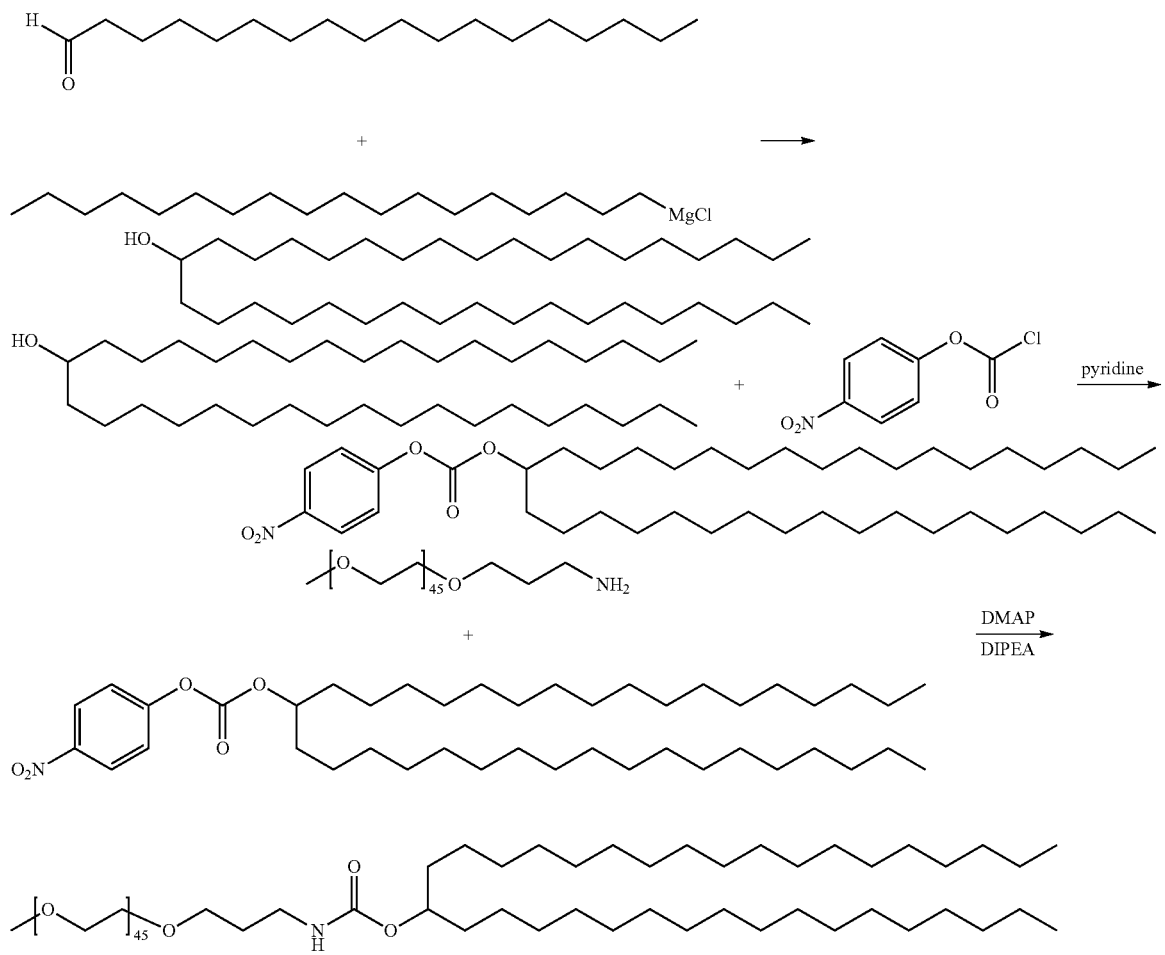

Step 1

To a heatgun-dried round bottomed flask and under nitrogen is added octadecyl aldehyde (500 mg, 1.86 mmol) and tetrahydrofuran (10 mL). A solution of 0.5 M octadecyl magnesium chloride in tetrahydrofuran (7.5 mL, 3.8 mmol) is added via syringe and the reaction is warmed to 40° C. When the addition is complete, the reaction is stirred for 1 h. The reaction is removed from the heat and quenched with 1 mL of acetic acid. After reaching rt, the solution is diluted with dichloromethane and washed with water, 0.1 M NaOH, 1 M HCl, and brine. The organic phase is dried with sodium sulfate and filtered. The crude material is crystallized twice from hot heptane, yielding the product as a white powder: 195 mg, 20.0%.

Step 2

The product (alcohol) from the previous step (194 mg, 0.371 mmol) is dissolved in dichloromethane (4 ml) at 40° C. and then pyridine (100 µl, 1.24 mmol) and 4-nitrophenylchloroformate (93 mg, 0.46 mmol) are added. The reaction is stirred at 40° C. overnight and then cooled to rt. The crude product is purified by flash chromatography on silica with a heptane/dichloromethane gradient. The product containing fractions are identified by TLC, combined and concentrated to a white solid: 219 mg, 86.0%.

Step 3

The product (4-nitrophenyl carbonate) from the previous step is dissolved in toluene (5 ml) at rt. PEG-NH$_2$ (800 mg, 0.400 mmol, $M_n$~2000 g/mol, "Sunbright MEPA-20H", NOF Corp.), N,N-dimethylaminopyridine (50 mg, 0.409 mmol), and N,N-diisopropylethylamine (200 µl, 1.145 mmol) are added and the solution is stirred at rt. After 72 h the reaction is loaded onto a 10 g Bond Elut SCX column (from Varian; pre-equilibrated with 50:50 dichloromethane:methanol) and elutes with 50:50 dichloromethane:methanol. The product containing fractions are identified by TLC, combined, and concentrated. The crude product is further purified by flash chromatography on silica with a dichloromethane/methanol gradient. The product containing fractions are identified by TLC, combined and concentrated. To remove 4-nitrophenol impurities, the product is dissolved in dichloromethane (10 mL) and Si-Amine scavenging resin from Silicycle (2.0 g, catalog number R52030B) is added. The solution is agitated at rt for 1 h, filtered to remove the resin, and concentrated to a pale yellow solid: 806 mg, 97.0%.

Size exclusion chromatography in N,N-dimethylformamide shows a single narrow peak. The peaks and integral values observed in the $^1$H NMR spectrum are consistent with the expected product.

Example 58

S005

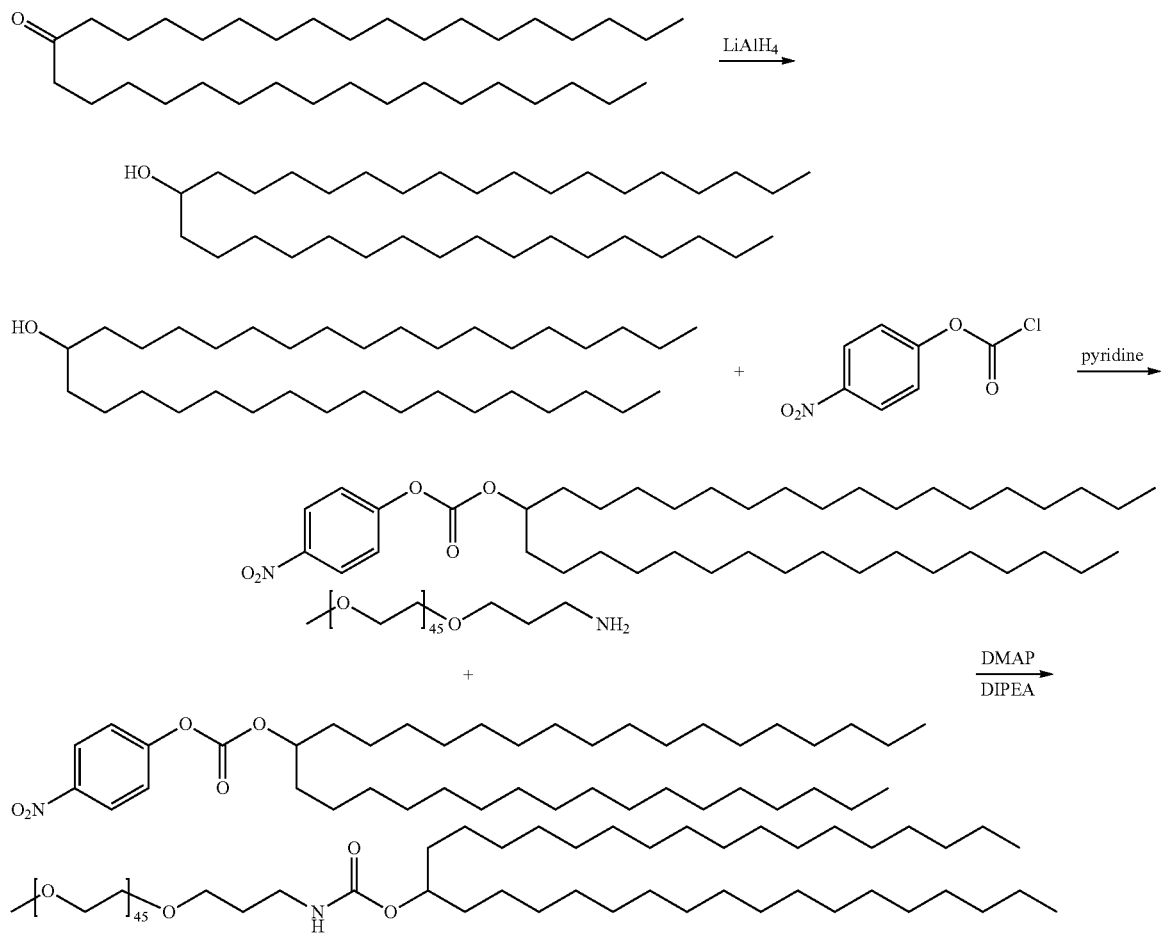

Step 1
In a round bottomed flask, pentatriacontan-18-one (750 mg, 1.48 mmol) is dissolved in tetrahydrofuran (40 mL) with gentle heating. After the ketone-containing solution cooled to rt, a 4 M solution of lithium aluminum hydride in diethyl ether (0.74 mL, 2.96 mmol) is added dropwise. The reaction is stirred for 30 min at rt. Solid sodium sulfate decahydrate is added and the slurry is stirred for 20 min to quench excess lithium aluminum hydride. The solids are filtered off, and the filtrate is diluted with heptane and washed with 1 M HCl. The organic phase is dried with sodium sulfate and concentrated to a white solid. The crude product is pure enough to use in the next step without further purification: 650 mg, 86.0%.

Step 2
To a solution of the product (alcohol) from the previous step (200 mg, 0.393 mmol) and pyridine (78 mg, 0.98 mmol) in dichloromethane (10 mL) at rt is added 4-nitrophenyl chloroformate (99 mg, 0.49 mmol). The reaction mixture is heated at 35° C. for 4 h. The reaction mixture is then diluted with heptane, extracted with 1 M HCl, and then saturated sodium bicarbonate. The organic phase is dried with sodium sulfate, concentrated, and purified by flash chromatography on silica with a heptane:ethyl acetate gradient. The product containing fractions are identified by TLC, combined, and concentrated to a white solid: 200 mg, 76%.

Step 3
The product (4-nitrophenyl carbonate) from the previous step (260 mg, 0.386 mmol) is dissolved in toluene (4 mL), followed by PEG2k (620 mg, 0.310 mmol, $M_n$~2000 g/mol, "Sunbright MEPA-20H", NOF Corp.), N,N-dimethylaminopyridine (40 mg, 0.33 mmol), and N,N-diisopropylethylamine (200 µl, 1.15 mmol). The solution is stirred at rt overnight. The reaction mixture is loaded onto a 10 g Bond Elut SCX column (from Varian; pre-equilibrated with 50:50 dichloromethane:methanol) and elutes with 50:50 dichloromethane:methanol. The product containing fractions are identified by TLC, combined, and concentrated. The crude product is further purified by flash chromatography on silica with a dichloromethane/methanol gradient. The product containing fractions are identified by TLC, combined and concentrated. To remove 4-nitrophenol impurities, the crude product is dissolved in 1:1 dichloromethane:methanol and elutes through a 10 g Bond Elut NH2 column (from Varian; pre-equilibrated with 50:50 dichloromethane:methanol). The product containing fractions are identified by TLC, combined, and concentrated to a pale yellow solid: 631 mg, 78.0%.

Size exclusion chromatography in N,N-dimethylformamide shows a single narrow peak. The peaks and integral values observed in the $^1$H NMR spectrum are consistent with the expected product.

Example 59

S007

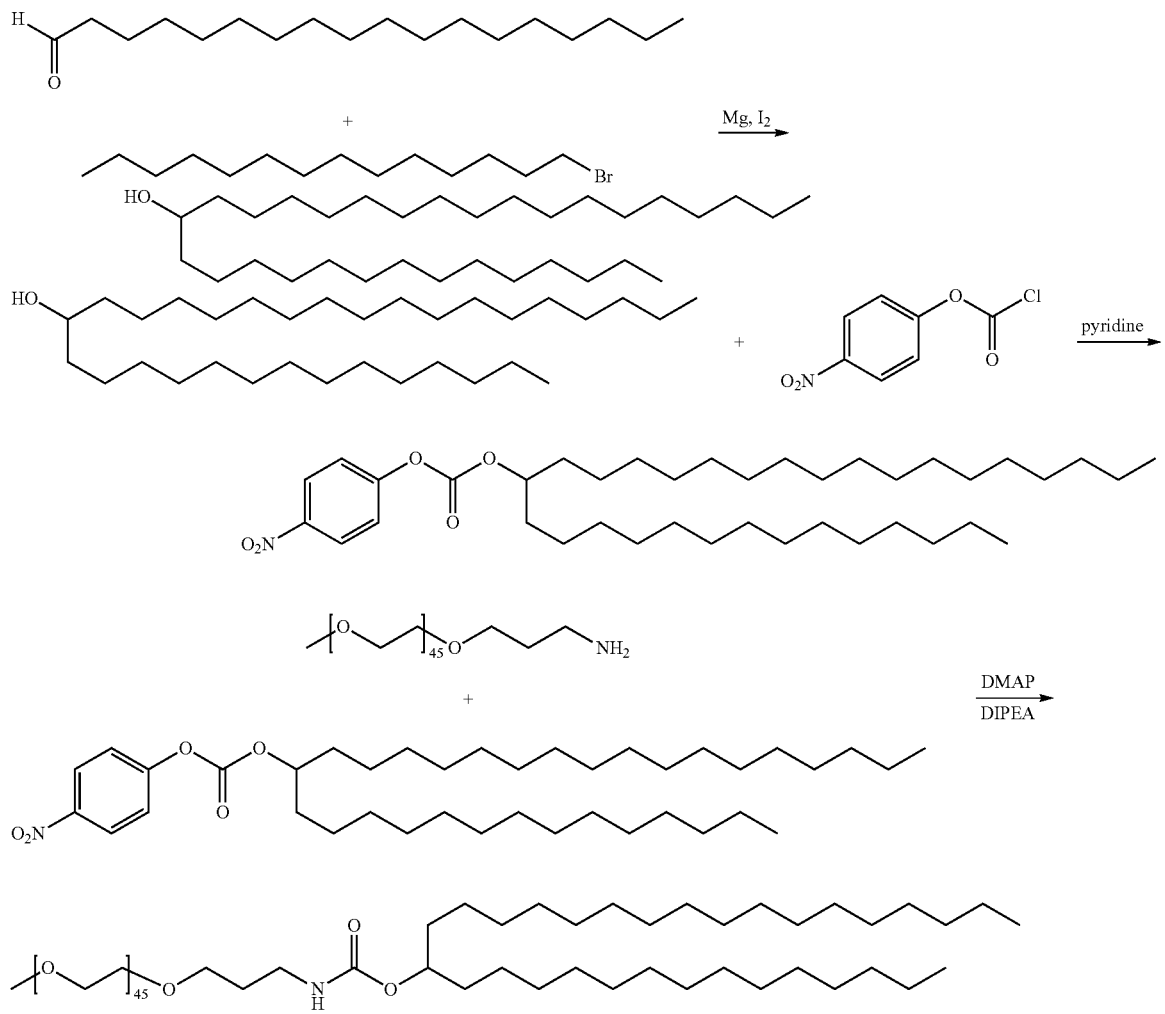

Step 1

To a round bottomed flask is added magnesium metal (0.201 g, 8.27 mmol) and a catalytic amount of iodine, followed by tetrahydrofuran (30 mL) and 1-bromotetradecane (2.17 g, 7.82 mmol). The mixture is refluxed for 2 h and then cooled to rt. A solution of octadecyl aldehyde (0.600 g, 2.24 mmol) in tetrahydrofuran (5 mL) is added, and the reaction mixture is stirred for 30 min at rt. The reaction is diluted with ethyl acetate, washed with 1 M HCl, dried with sodium sulfate and concentrated. The crude product is further purified by flash chromatography on silica with a heptane/ethyl acetate gradient. The product containing fractions are identified by TLC, combined and concentrated: 310 mg, 29.7%.

Step 2

The product (alcohol) from the previous step (310 mg, 0.664 mmol) is dissolved in dichloromethane (15 mL). Pyridine (0.134 mL, 1.66 mmol) is then added, followed by 4-nitrophenyl chloroformate (167 mg, 0.830 mmol). The reaction is stirred overnight at rt. The reaction is diluted with ethyl acetate, washed with a saturated aqueous solution of NaHCO$_3$, dried with sodium sulfate, and concentrated. The crude product is further purified by flash chromatography on silica with a heptane/ethyl acetate gradient. The product containing fractions are identified by TLC, combined and concentrated: 315 mg, 75.0%.

Step 3

To a solution of the product (4-nitrophenyl carbonate) from the previous step (315 mg, 0.498 mmol) in toluene (10 mL) at rt are added N,N-dimethylaminopyridine (48.7 mg, 0.399 mmol), and N,N-diisopropylethylamine (0.174 ml, 0.997 mmol), followed by PEG-NH$_2$ (798 mg, 0.399 mmol, M$_n$~2000 g/mol, "Sunbright MEPA-20H", NOF Corp.). The yellow solution is stirred at rt overnight. The reaction mixture is loaded onto a 10 g Bond Elut SCX column (from Varian; pre-equilibrated with 50:50 dichloromethane:methanol) and elutes with 50:50 dichloromethane:methanol. The product containing fractions are identified by TLC, combined, and concentrated. The crude product is further purified by flash chromatography on silica with a dichloromethane/methanol gradient. The product containing fractions are identified by TLC, combined and concentrated: 540 mg, 54.3%.

The peaks and integral values observed in the $^1$H NMR spectrum are consistent with the expected product.

Example 60

S008

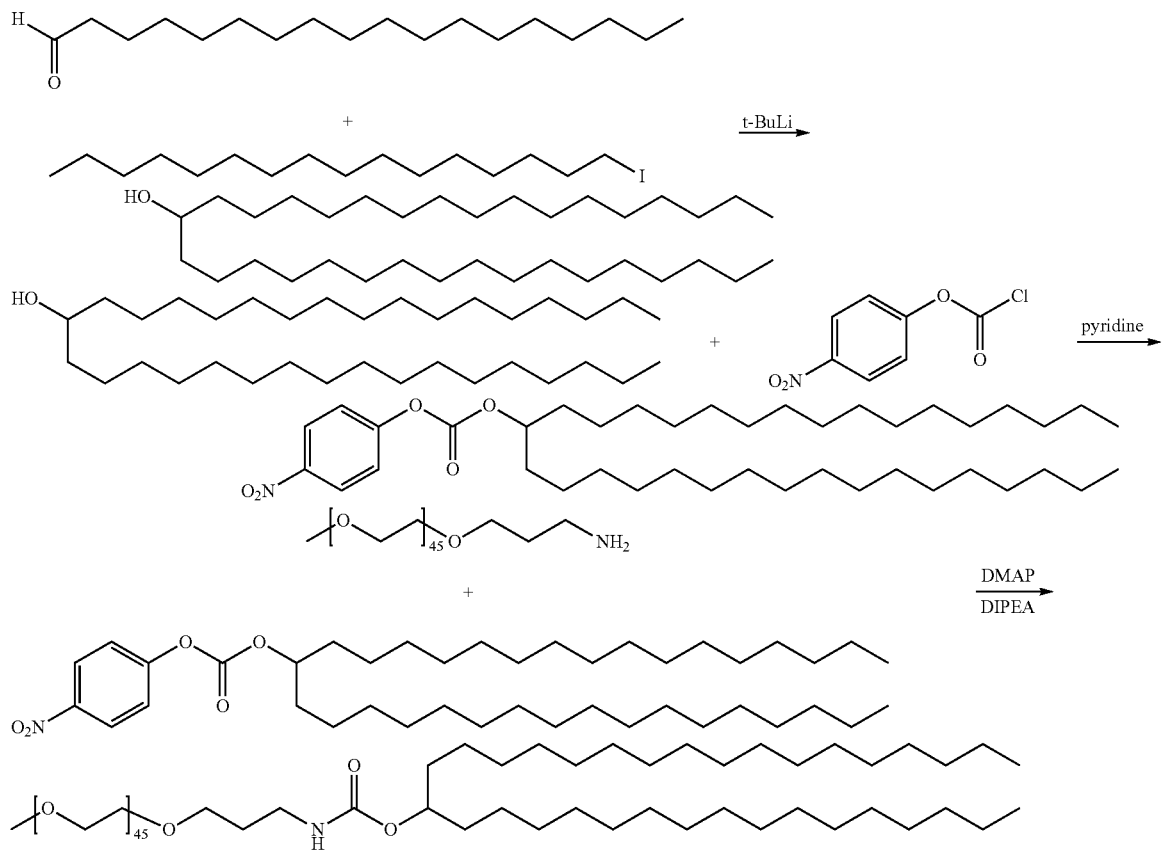

Step 1

To a dried round bottomed flask under nitrogen is added 1-iodohexadecane (0.705 g, 2.00 mmol) and diethyl ether (15 mL). The solution is cooled to −78° C. (solution becomes a white slurry) and a 1.7 M solution of t-butyl lithium in heptane (2.59 mL, 4.40 mmol) is added drop-wise. After stirring for 20 min, the reaction mixture is warmed to rt and stirred for an additional 2 h. To the reaction mixture is added a solution of octadecyl aldehyde (0.268 g, 1.00 mmol) in diethyl ether (3 mL) drop-wise (exothermic). The reaction is quenched with ice cold 1 M HCl, extracted with dichloromethane, dried with sodium sulfate, and concentrated. The crude product is further purified by flash chromatography on silica with a heptane/dichloromethane gradient. The product containing fractions are identified by TLC, combined and concentrated: 150 mg, 30.3%.

Step 2

The product (alcohol) from the previous step (200 mg, 0.404 mmol) is dissolved in dichloromethane (6 mL). Pyridine (0.082 mL, 1.01 mmol) is then added, followed by 4-nitrophenyl chloroformate (102 mg, 0.505 mmol). The reaction is stirred overnight at rt. The reaction is diluted with ethyl acetate, washed with a saturated aqueous solution of NaHCO$_3$, dried with sodium sulfate, and concentrated. The crude product is further purified by flash chromatography on silica with a heptane/ethyl acetate gradient. The product containing fractions are identified by TLC, combined and concentrated: 220 mg, 82.0%.

Step 3

To a solution of the product (4-nitrophenyl carbonate) from the previous step (230 mg, 0.348 mmol) in toluene (6 mL) at rt are added N,N-dimethylaminopyridine (42.6 mg, 0.348 mmol), and N,N-diisopropylethylamine (0.152 ml, 0.871 mmol), followed by PEG-NH$_2$ (697 mg, 0.348 mmol, M$_n$~2000 g/mol, "Sunbright MEPA-20H", NOF Corp.). The yellow solution is stirred at rt overnight. The reaction mixture is loaded onto a 10 g Bond Elut SCX column (from Varian; pre-equilibrated with 50:50 dichloromethane:methanol) and elutes with 50:50 dichloromethane:methanol. The product containing fractions are identified by TLC, combined, and concentrated. The crude product is further purified by flash chromatography on silica with a dichloromethane/methanol gradient. The product containing fractions are identified by TLC, combined and concentrated: 600 mg, 68.3%.

The peaks and integral values observed in the $^1$H NMR spectrum are consistent with the expected product.

S009 may be prepared in a manner analogous to that described for S008.

Example 61

S010 and S011

S010 and S011 may be prepared, e.g., as provided in PCT publication WO2009086558 compounds IVa and IVc, respectively. These compounds may be synthesized as provided in Example 19 of WO2009086558.

129
Example 62
S012
S012 may be prepared in a manner analogous to that described for S001, utilizing PEG-NH$_2$ ("Sunbright MEPA-20H", NOF Corp.) instead of poly(ethylene glycol) methyl ether.
130
Example 63
S006 and S013 through S024
S006, S013, S014, S015, S016, S017, S018, S019, S020, S021, S022, S023, and S024 may be prepared in a manner analogous to that described for S004.
Example 64
S025
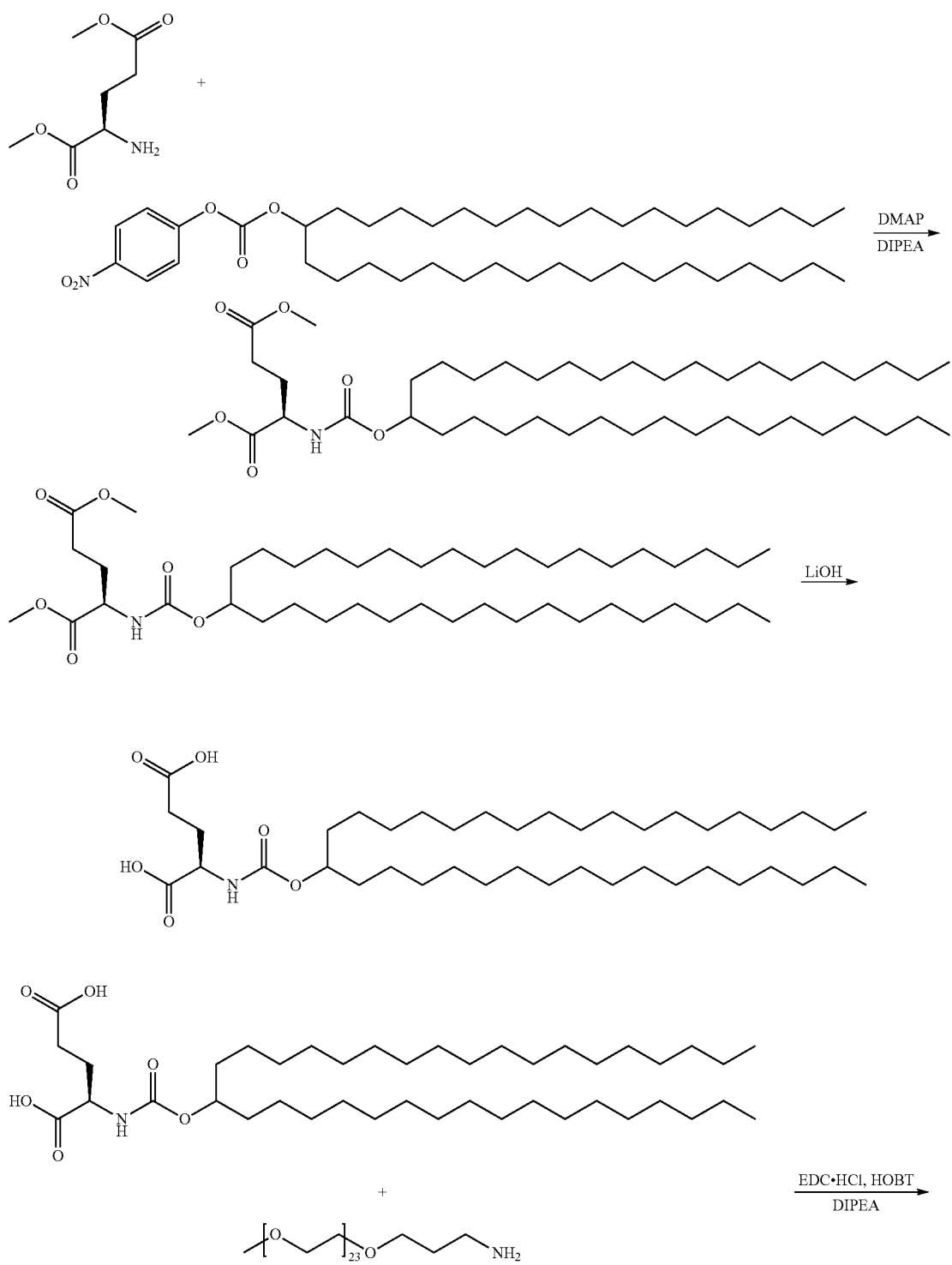

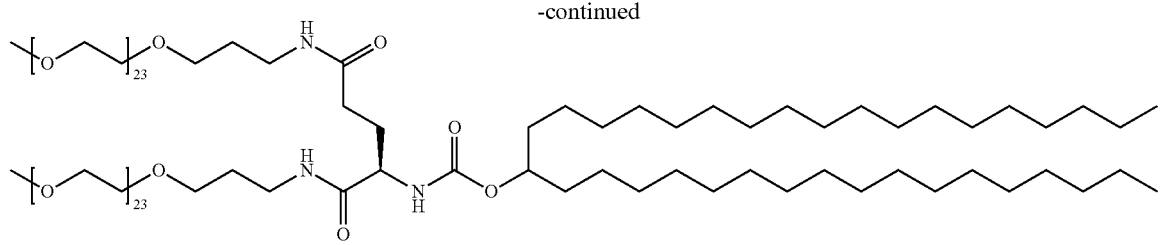

Step 1

The product of Step 2 in the synthesis of compound S004 described herein (4-nitrophenyl carbonate) (285 mg, 0.414 mmol) is suspended in N,N-dimethylformamide (5 mL), followed by D-glutamic acid dimethyl ester (145 mg, 0.828 mmol), N,N-diisopropylethylamine (0.145 ml, 0.828 mmol), and N,N-dimethylaminopyridine (101 mg, 0.828 mmol). The solution is heated at 60° C. overnight. The reaction mixture is loaded onto a 10 g Bond Elut SCX column (from Varian; pre-equilibrated with 50:50 dichloromethane:methanol) and elutes with 50:50 dichloromethane:methanol. The product containing fractions are identified by TLC, combined, and concentrated. The crude product is further purified by flash chromatography on silica with an ethyl acetate/heptane gradient. The product containing fractions are identified by TLC, combined and concentrated to a white solid: 131 mg, 44%.

Step 2

The product from the previous step (di-methyl ester) (0.160 g, 0.221 mmol) is dissolved in tetrahydrofuran (5 mL), and a solution of LiOH (52.9 mg, 2.21 mmol) in water (5 mL) is added. The reaction is stirred at rt for 72 h. The solution is diluted with chloroform and washed with 1N HCl (aqueous) and then brine. The organic phase is dried with sodium sulfate and filtered. The filtrate is concentrated to a white solid: 130 mg, 85%.

Step 3

The product from the previous step (di-acid) (130 mg, 0.187 mmol) is suspended in dichloromethane (9 mL) and heptane (1.5 mL) at rt. N-(3-dimethylaminopropyl)-N'-ethylcarbodiimide hydrochloride (107 mg, 0.560 mmol) is added to the suspension, followed by hydroxybenzotriazole (86 mg, 0.56 mmol). After 30 min., PEG-NH2 (411 mg, 0.411 mmol, Mn~1000 g/mol, "mPEG-Amine, 1k", Creative PEG-Works) and N,N-diisopropylethylamine (65 µL, 0.374 mmol) are added. The reaction is stirred overnight at rt. The reaction mixture is loaded onto a 10 g Bond Elut SCX column (from Varian; pre-equilibrated with 50:50 dichloromethane:methanol) and elutes with 50:50 dichloromethane:methanol. The product containing fractions are identified by TLC, combined, and concentrated. The crude product is further purified by flash chromatography on silica with a dichloromethane/methanol gradient. The product containing fractions are identified by TLC, combined and concentrated to a white solid: 376 mg, 57.8%.

Example 65

S026

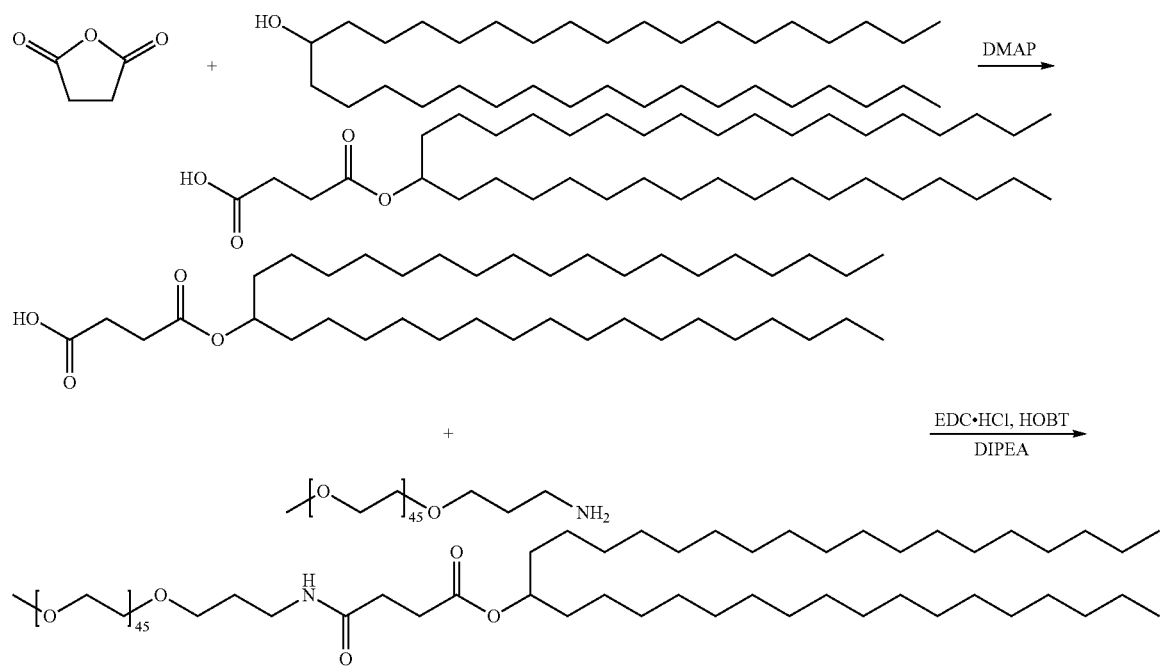

Step 1

The product of Step 1 in the synthesis of compound S004 described herein (alcohol) (200 mg, 0.382 mmol), succinic anhydride (38 mg, 0.38 mmol), and N,N-dimethylaminopyridine (12 mg, 0.096 mmol) are weighed into a flask and suspended in chloroform (3.5 mL). The reaction mixture is stirred at 70° C. overnight. The reaction mixture is loaded onto a 1 g Bond Elut SCX column (from Varian; pre-equilibrated with dichloromethane) and elutes with dichloromethane. The product containing fractions are identified by TLC, combined, and concentrated. The crude product is further purified by flash chromatography on silica with an ethyl acetate/heptane gradient. The product containing fractions are identified by TLC, combined and concentrated to a white solid: 134 mg, 56%.

Step 2

The product from the previous step (carboxylic acid) (75 mg, 0.12 mmol), N-(3-dimethylaminopropyl)-N'-ethylcarbodiimide hydrochloride (35 mg, 0.18 mmol) and hydroxybenzotriazole (28 mg, 0.18 mmol) is dissolved in anhydrous chloroform (1 mL) and stirred for 0.5 h at rt. Then PEG-NH2 (265 mg, 0.132 mmol, Mn~2000 g/mol, "Sunbright MEPA-20H", NOF Corp.) and N,N-diisopropylethylamine (32 µL, 0.18 mmol) is added and the solution is stirred overnight at rt. The reaction mixture is loaded onto a 2 g Bond Elut SCX column (from Varian; pre-equilibrated with 50:50 dichloromethane:methanol) and elutes with dichloromethane. The product containing fractions are identified by TLC, combined, and concentrated to a white solid: 240 mg, 76%.

Characterisation data for these stealth lipids is as follows in Tables 4 and 5.

TABLE 4

$^1$H NMR for Stealth Lipids S001 through S026

| | |
|---|---|
| S001 | 0.68 (s, 3H), 0.78-1.63 (m, 33H), 1.76-1.91 (m, 3H), 1.91-2.07 (m, 2H), 2.32 (d, 2H), 2.56-2.70 (m, 4H), 3.39 (s, 3H), 3.43-3.89 (m, 210H), 4.25 (t, 2H), 4.64 (m, 1H), 5.33-5.41 (m, 1H) |
| S002 | 0.67 (s, 3H), 0.77-1.66 (m, 33H), 1.72-2.10 (m, 7H), 2.17-2.44 (m, 2H), 2.57 (t, 2H), 3.38 (s, 3H), 3.41-3.94 (m, 196H), 4.26 (t, 2H), 4.38-4.61 (m, 1H), 5.19-5.30 (m, 1H), 5.34-5.43 (m, 1H) |
| S003 | 0.68 (s, 3H), 0.78-1.67 (m, 33H), 1.68-1.92 (m, 5), 1.92-2.07 (m, 2H), 2.15-2.46 (m, 2H), 3.22-3.34 (m, 2H), 3.38 (s, 3H), 3.41-3.90 (m, 200H), 4.40-4.57 (m, 1H), 5.14 (br, 1H), 5.33-5.43 (m, 1H) |
| S004 | 0.88 (t, 6H), 1.25 (m, 62H), 1.48 (m, 4H), 1.77 (m, 2H), 3.18-3.34 (m, 2H), 3.38 (s, 3H), 3.42-3.88 (m, 205H), 4.71 (m, 1H), 5.06 (m, 1H) |
| S005 | 0.89 (t, 6H), 1.26 (m, 60H), 1.48 (m, 4H), 1.78 (m, 2H), 3.17-3.33 (m, 2H), 3.39 (s, 3H), 3.42-3.88 (m, 203H), 4.71 (m, 1H), 5.07 (m, 1H) |
| S006 | 0.88 (t, 6H), 1.25 (m, 46H), 1.48 (m, 4H), 1.77 (m, 2H), 3.14-3.34 (m, 2H), 3.38 (s, 3H), 3.41-3.91 (m, 209H), 4.71 (m, 1H), 5.06 (m, 1H) |
| S007 | 0.87 (m, 6H), 1.25 (m, 54H), 1.48 (m, 4H), 1.76 (m, 2H), 3.15-3.32 (m, 2H), 3.37 (s, 3H), 3.41-3.89 (m, 206H), 4.70 (m, 1H), 5.06 (m, 1H) |
| S008 | 0.84 (t, 6H), 1.21 (m, 58H), 1.43 (m, 4H), 1.74 (m, 2H), 2.99-3.29 (m, 2H), 3.34 (s, 3H), 3.37-4.08 (m, 187H), 4.66 (m, 1H), 5.08 (m, 1H) |
| S009 | 0.88 (t, 6H), 1.25 (m, 54H), 1.47 (m, 4H), 1.77 (m, 2H), 3.16-3.34 (m, 2H), 3.38 (s, 3H), 3.41-3.87 (m, 207H), 4.70 (m, 1H), 5.06 (m, 1H) |
| S010 | 0.88 (t, 6H), 1.25 (m, 44H), 1.55 (m, 4H), 1.78 (m, 2H), 3.15-3.33 (m, 2H), 3.38 (s, 3H), 3.40-3.95 (m, 207H), 3.97-4.30 (m, 2H), 4.96-5.27 (br m, 1H) |
| S011 | 0.89 (t, 6H), 1.26 (m, 60H), 1.56 (m, 4H), 1.78 (m, 2H), 3.20-3.34 (m, 2H), 3.39 (s, 3H), 3.40-3.89 (m, 219H), 4.02-4.26 (m, 2H), 5.09-5.23 (m, 1H) |
| S013 | 0.89 (t, 6H), 1.26 (m, 54H), 1.48 (m, 4H), 1.77 (m, 2H), 3.16-3.34 (m, 2H), 3.38 (s, 3H), 3.41-3.87 (m, 187H), 4.71 (m, 1H), 5.05 (m, 1H) |
| S014 | 0.89 (t, 6H), 1.26 (m, 54H), 1.49 (m, 4H), 1.78 (m, 2H), 3.16-3.34 (m, 2H), 3.39 (s, 3H), 3.41-3.87 (m, 210H), 4.72 (m, 1H), 5.05 (m, 1H) |
| S015 | 0.89 (t, 6H), 1.26 (m, 50H), 1.48 (m, 4H), 1.78 (m, 2H), 3.16-3.34 (m, 2H), 3.39 (s, 3H), 3.41-3.87 (m, 209H), 4.71 (m, 1H), 5.06 (m, 1H) |
| S016 | 0.88 (t, 6H), 1.26 (m, 50H), 1.47 (m, 4H), 1.77 (m, 2H), 3.16-3.34 (m, 2H), 3.38 (s, 3H), 3.41-3.87 (m, 202H), 4.71 (m, 1H), 5.06 (m, 1H) |
| S017 | 0.89 (t, 6H), 1.26 (m, 46H), 1.49 (m, 4H), 1.78 (m, 2H), 3.16-3.34 (m, 2H), 3.39 (s, 3H), 3.41-3.87 (m, 203H), 4.71 (m, 1H), 5.06 (m, 1H) |
| S018 | 0.88 (t, 6H), 1.25 (m, 48H), 1.48 (m, 4H), 1.77 (m, 2H), 2.05 (m, 4H), 2.77 (m, 2H), 3.16-3.34 (m, 2H), 3.39 (s, 3H), 3.41-3.87 (m, 180H), 4.71 (m, 1H), 5.05 (m, 1H), 5.25-5.50 (m, 4H) |
| S019 | 0.88 (t, 6H), 1.26 (m, 54H), 1.48 (m, 4H), 1.77 (m, 2H), 2.01 (m, 4H), 3.16-3.34 (m, 2H), 3.38 (s, 3H), 3.41-3.87 (m, 200H), 4.71 (m, 1H), 5.05 (m, 1H), 5.31-5.49 (m, 2H) |
| S020 | 0.88 (t, 6H), 1.26 (m, 62H), 1.49 (m, 4H), 3.38 (s, 3H), 3.4-3.9 (m, 299H), 4.72 (m, 1H), 5.11 (m, 1H) |
| S021 | 0.89 (t, 6H), 1.26 (m, 36H), 1.48 (m, 4H), 1.78 (m, 2H), 3.20-3.35 (m, 2H), 3.39 (s, 3H), 3.41-3.87 (m, 196H), 4.71 (m, 1H), 5.07 (m, 1H) |
| S022 | 0.89 (t, 6H), 1.26 (m, 62H), 1.49 (m, 4H), 3.36 (s, 3H), 3.41-3.87 (m, 161H), 4.72 (m, 1H), 5.14 (m, 1H) |
| S023 | 0.88 (t, 6H), 1.26 (m, 64H), 1.47 (m, 4H), 1.77 (m, 2H), 3.20-3.35 (m, 2H), 3.39 (s, 3H), 3.42-3.88 (m, 194H), 4.71 (m, 1H), 5.06 (m, 1H) |
| S024 | 0.88 (t, 6H), 1.25 (m, 48H), 1.47 (m, 4H), 1.77 (m, 2H), 3.20-3.35 (m, 2H), 3.39 (s, 3H), 3.42-3.88 (m, 194H), 4.70 (m, 1H), 5.08 (m, 1H) |
| S025 | 0.87 (t, 6H), 1.24 (m, 62H), 1.47 (m, 4H), 2.01 (m, 2H), 2.2-2.4 (m, 2H), 3.36 (s, 3H), 3.41-3.87 (m, 229H), 4.13 (m, 1H), 4.65 (m, 1H), 5.78 (m, 1H), 6.65 (m, 1H), 7.07 (m, 1H) |

TABLE 4-continued

¹H NMR for Stealth Lipids S001 through S026

| | |
|---|---|
| S026 | 0.87 (t, 6H), 1.25 (m, 62H), 1.49 (m, 4H), 1.76 (m, 2H), 2.44 (t, J = 8 Hz, 2H), 2.63 (t, J = 8 Hz, 2H), 3.37 (s, 3H), 3.41-3.87 (m, 213H), 4.84 (m, 1H), 6.32 (m, 1H) |

TABLE 5

Other characteristics for Stealth Lipids S001 through S026

| | SEC | MALDI | TLC | TLC conditions | TLC solvent |
|---|---|---|---|---|---|
| S001 | single peak (THF) | ~2550 | | | |
| S002 | single peak (THF) | ~2550 | | | |
| S003 | single peak (THF) | ~2600 | | | |
| S004 | single peak (DMF) | | | | |
| S005 | single peak (DMF) | | | | |
| S006 | single peak (DMF) | | | | |
| S007 | | | 0.39 | 1:9 | MeOH:CH$_2$Cl$_2$ |
| S008 | | | 1.39 | 1:9 | MeOH:CH$_2$Cl$_2$ |
| S010 | single peak (THF) | ~2800 | | | |
| S011 | single peak (DMF) | | | | |
| S013 | single peak (THF) | ~2650 | | | |
| S014 | single peak (THF) | ~2750 | | | |
| S015 | single peak (THF) | ~2750 | | | |
| S016 | single peak (THF) | ~2700 | | | |
| S017 | single peak (THF) | ~2650 | | | |
| S018 | single peak (THF) | ~2750 | | | |
| S019 | single peak (THF) | ~2750 | | | |
| S020 | single peak (THF) | ~3600 | | | |
| S021 | single peak (DMF) | ~2700 | | | |
| S022 | single peak (DMF) | 2364.1 (exact) | | | |
| S023 | | ~2900 | | | |
| S024 | | ~2700 | | | |
| S025 | single peak (THF) | ~3000 | | | |
| S026 | single peak (THF) | ~3050 | | | |

Example 66

Summary Table of Results

The synthesised compounds are represented in the following tables. For the avoidance of doubt, some of the substituent groups have been drawn in such a way that they are overlapping, but the true structure of the compound is nonetheless perfectly clear. For example, the notation

does not represent a chemically-impossible 3-membered hydrogen-containing ring but instead represents the following.

Table 6 provides the structures of the cationic lipids of the invention.

TABLE 6

Characterization and structures for Cationic Lipids

| Lipid | Structure | $R^1$—N—$R^2$ | $Y^1$ | L |
|---|---|---|---|---|
| E0001 | 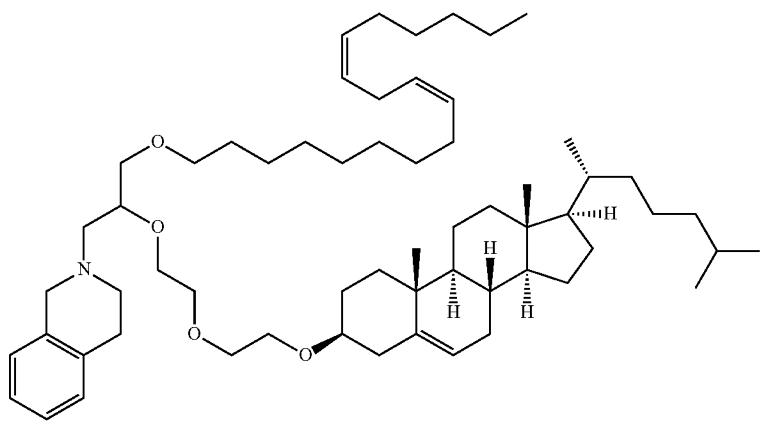 | $H^{15}$ | $Y^{1-i}$ | $L^{c-i}$ |

TABLE 6-continued
Characterization and structures for Cationic Lipids
| Lipid | Structure | $R^1$—N—$R^2$ | $Y^1$ | $Y^{1-i}$ | $L^{c-i}$ | L |
|---|---|---|---|---|---|---|
| E0002 | Chiral | $H^2$ | | | | |
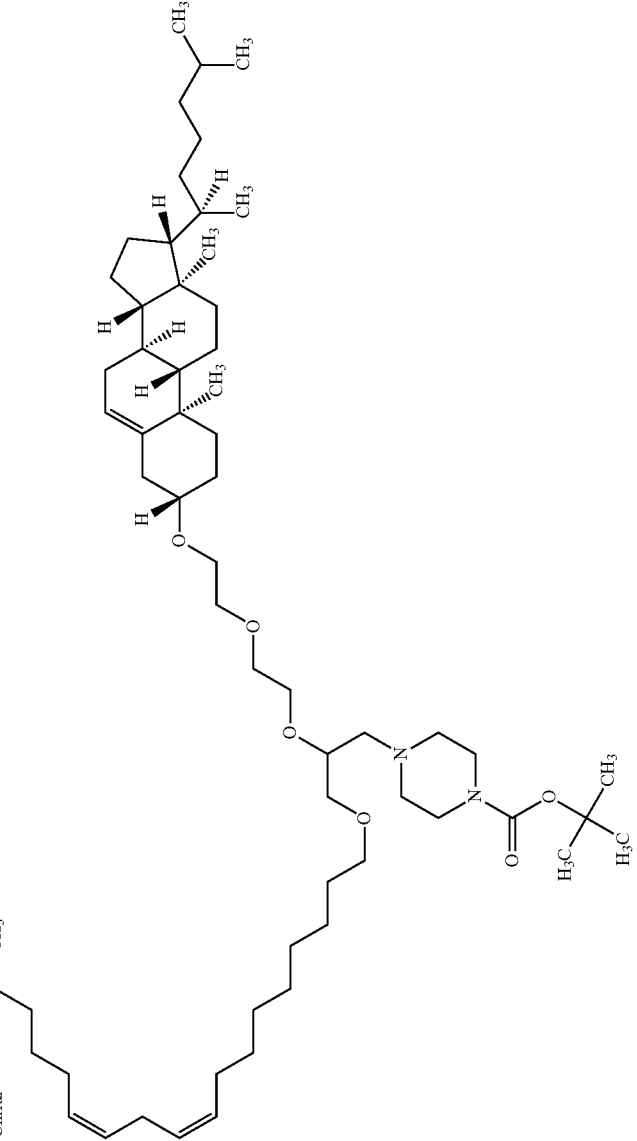

TABLE 6-continued
Characterization and structures for Cationic Lipids
| Lipid | Structure | $R^1-N-R^2$ | $Y^1$ | $Y^{1-ii}$ | $L^{c-i}$ | L |
|---|---|---|---|---|---|---|
| E0003 | 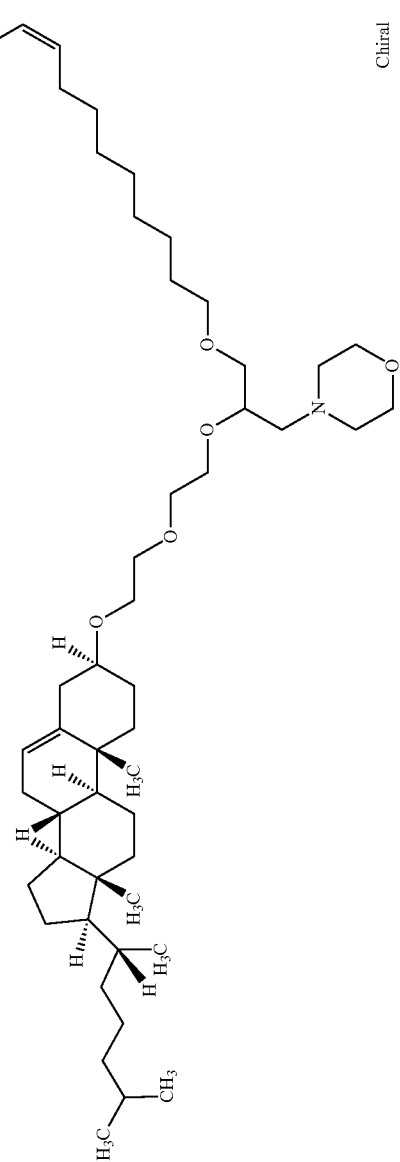 Chiral | $H^1$ | | | | |

TABLE 6-continued
Characterization and structures for Cationic Lipids
| Lipid | Structure | $R^1$—N—$R^2$ | $Y^1$ | $Y^{1-i}$ | L | $L^{c-i}$ |
|---|---|---|---|---|---|---|
| E0004 Chiral | 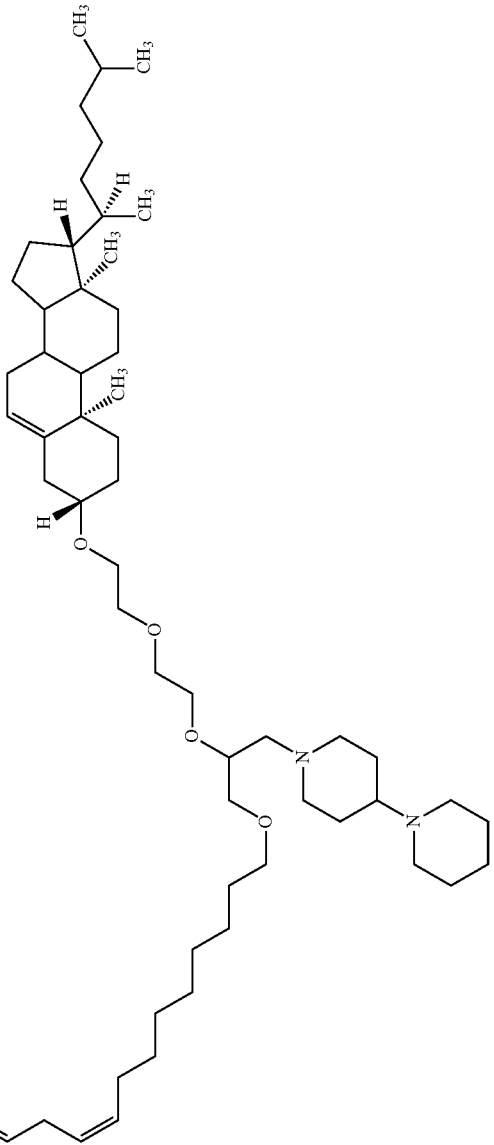 | $H^{10}$ | | | | |

TABLE 6-continued

Characterization and structures for Cationic Lipids

| Lipid | Structure | R¹—N—R² | Y¹ | Y¹⁻ʲ | L | Lᶜ⁻ʲ |
|---|---|---|---|---|---|---|
| E0005 | Chiral | H¹¹ | | | | |

TABLE 6-continued

Characterization and structures for Cationic Lipids

| Lipid | Structure | $R^1-N-R^2$ | $Y^1$ | $Y^{1-i}$ | $L^{c-i}$ | L |
|---|---|---|---|---|---|---|
| E0006 | Chiral [structure] | $H^{13}$ | | | | |

TABLE 6-continued

Characterization and structures for Cationic Lipids

| Lipid | Structure | $R^1\text{—N—}R^2$ | $Y^1$ | $Y^{1-i}$ | L | $L^{c-i}$ |
|---|---|---|---|---|---|---|
| E0007 | Chiral | $H^{19}$ | | | | |

TABLE 6-continued

Characterization and structures for Cationic Lipids

| Lipid | Structure | $R^1$—N—$R^2$ | $Y^1$ | $Y^{1-i}$ | $L^{c-i}$ | L |
|---|---|---|---|---|---|---|
| E0008 Chiral | | $H^{43}$ | | | | |

TABLE 6-continued

Characterization and structures for Cationic Lipids

| Lipid | Structure | $R^1$—N—$R^2$ | $Y^1$ | $Y^{1-i}$ | L | $L^{c-i}$ |
|---|---|---|---|---|---|---|
| E0009 Chiral | | $H^{34}$ | | | | |

TABLE 6-continued

Characterization and structures for Cationic Lipids

| Lipid | Structure | $R^1$—N—$R^2$ | $Y^1$ | $Y^{1-i}$ | L | $L^{c-i}$ |
|---|---|---|---|---|---|---|
| E0010 | Chiral | $H^{22}$ | | | | |

TABLE 6-continued

Characterization and structures for Cationic Lipids

| Lipid | | Structure | $R^1$—N—$R^2$ | $Y^1$ | L | $L^{c-i}$ |
|---|---|---|---|---|---|---|
| E0011 | Chiral | 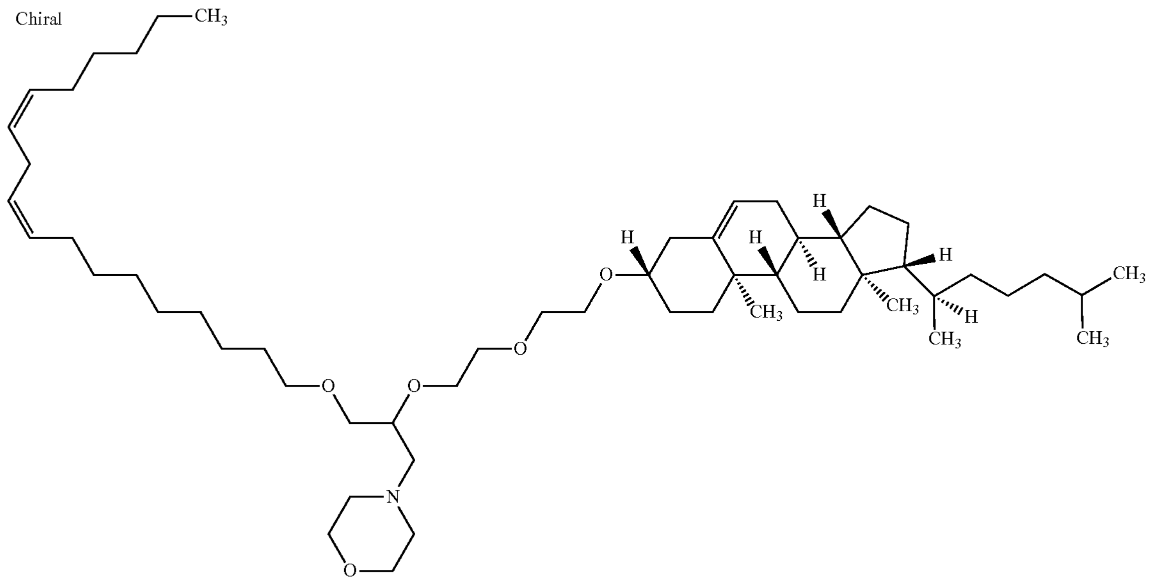 | $H^1$ | $Y^{1-i}$ | | |

TABLE 6-continued

Characterization and structures for Cationic Lipids

| Lipid | Structure | $R^1$—N—$R^2$ | $Y^1$ | $L$ |
|---|---|---|---|---|
| E0012 | Chiral | $H^3$ | $Y^{1\text{-}i}$ | $L^{c\text{-}i}$ |

TABLE 6-continued

Characterization and structures for Cationic Lipids

| Lipid | Structure | $R^1$—N—$R^2$ | $Y^1$ | $Y^{1-i}$ | $L$ | $L^{c-i}$ |
|---|---|---|---|---|---|---|
| E0013 | CHiral | $H^4$ | | | | |

TABLE 6-continued
Characterization and structures for Cationic Lipids
| Lipid | Structure | $R^1$—N—$R^2$ | $Y^1$ | $Y^{1-i}$ | L | $L^{c-i}$ |
|---|---|---|---|---|---|---|
| E0014 | Chiral 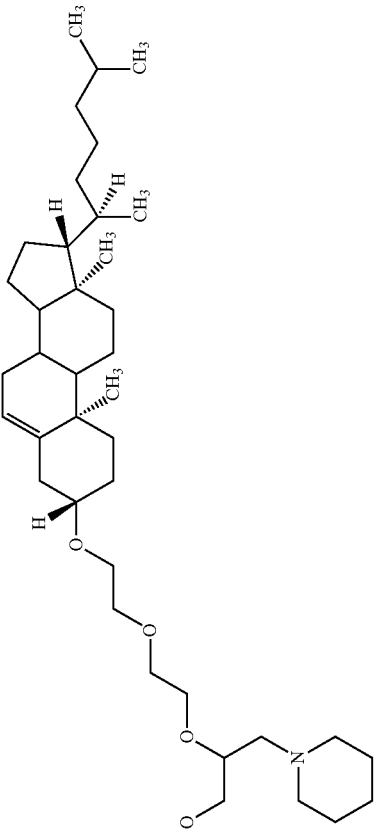 | $H^5$ | | | | |

TABLE 6-continued

Characterization and structures for Cationic Lipids

| Lipid | Structure | $R^1$—N—$R^2$ | $Y^1$ | $Y^{1-i}$ | $L^{c-i}$ | L |
|---|---|---|---|---|---|---|
| E0015 | Chiral | $H^7$ | | | | |

TABLE 6-continued

Characterization and structures for Cationic Lipids

| Lipid | Structure | $R^1$—N—$R^2$ | $Y^1$ | $Y^{1-i}$ | L | $L^{c-i}$ |
|---|---|---|---|---|---|---|
| E0016 | Chiral | $H^8$ | | | | |

TABLE 6-continued

Characterization and structures for Cationic Lipids

| Lipid | Structure | R¹—N—R² | Y¹ | Y¹⁻ʲ | L | Lᶜ⁻ʲ |
|---|---|---|---|---|---|---|
| E0017 Chiral | | H¹⁴ | | | | |

TABLE 6-continued
Characterization and structures for Cationic Lipids
| Lipid | Structure | $R^1$—N—$R^2$ | $Y^1$ | $Y^{1-i}$ | L | $L^{c-i}$ |
|---|---|---|---|---|---|---|
| E0018 Chiral | 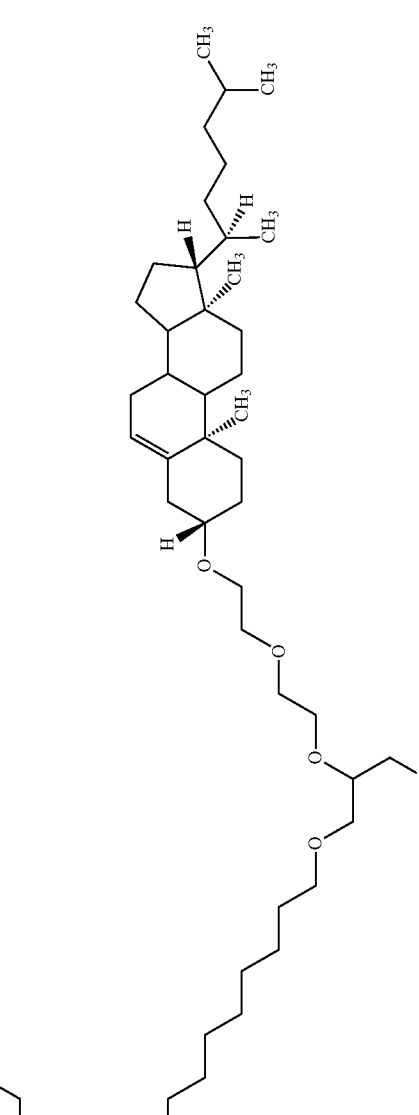 | $H^{16}$ | | | | |

TABLE 6-continued

Characterization and structures for Cationic Lipids

| Lipid | Structure | $R^1$—N—$R^2$ | $Y^1$ | $Y^{1-i}$ | L | $L^{c-i}$ |
|---|---|---|---|---|---|---|
| E0019 | Chiral | $H^{17}$ | | | | |

TABLE 6-continued

Characterization and structures for Cationic Lipids

| Lipid | Structure | $R^1$—N—$R^2$ | $Y^1$ | $Y^{i,i}$ | L | $L^{c-i}$ |
|---|---|---|---|---|---|---|
| E0020 | Chiral | $H^{21}$ | | | | |

TABLE 6-continued

Characterization and structures for Cationic Lipids

| Lipid | | Structure | $R^1$—N—$R^2$ | $Y^1$ | $Y^{L-i}$ | L | $L^{c-i}$ |
|---|---|---|---|---|---|---|---|
| E0021 | Chiral | 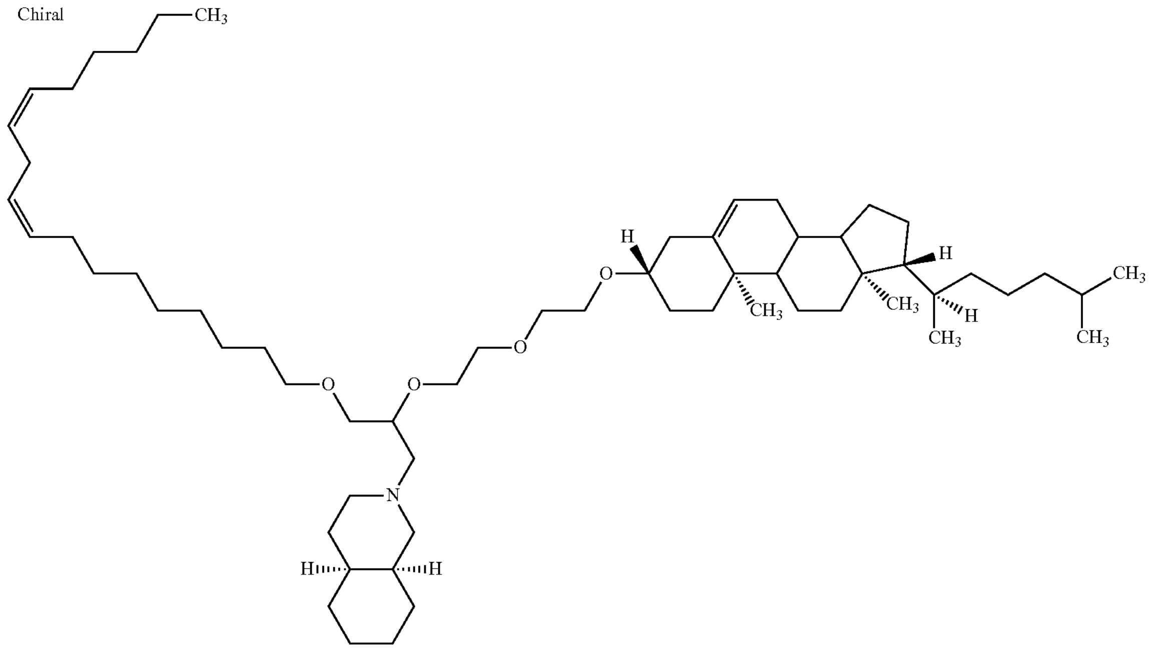 [SMILES: CCCCC/C=C\C/C=C\CCCCCCCCOCC(CN1CC[C@@H]2CCCC[C@@H]2C1)OCCOCCO[C@H]1CC[C@@]2(C)C(=CCC3C2CC[C@@]2(C)C3CC[C@@H]2[C@H](C)CCCC(C)C)C1] | $H^{23}$ | | | | |

TABLE 6-continued

Characterization and structures for Cationic Lipids

| Lipid | Structure | $R^1$—N—$R^2$ | $Y^1$ | $Y^{1-i}$ | L | $L^{c-i}$ |
|---|---|---|---|---|---|---|
| E0022 | Chiral | $H^{24}$ | | | | |

TABLE 6-continued

Characterization and structures for Cationic Lipids

| Lipid | Structure | $R^1$—N—$R^2$ | $Y^1$ | $Y^{1-i}$ | L | $L^{c-i}$ |
|---|---|---|---|---|---|---|
| E0023 | Chiral | $H^{25}$ | | | | |

TABLE 6-continued

Characterization and structures for Cationic Lipids

| Lipid | Structure | $R^1$—N—$R^2$ | $Y^1$ | $Y^{1-i}$ | L | $L^{c-i}$ |
|---|---|---|---|---|---|---|
| E0024 | Chiral | $H^{35}$ | | | | |

TABLE 6-continued

Characterization and structures for Cationic Lipids

| Lipid | Structure | $R^1$—N—$R^2$ | $Y^1$ | $L^{c-i}$ | L |
|---|---|---|---|---|---|
| E0025 | Chiral | $H^{27}$ | | | |

TABLE 6-continued
Characterization and structures for Cationic Lipids
| Lipid | Structure | $R^1$—N—$R^2$ | $Y^1$ | $Y^{1-i}$ | $L^{c-i}$ | L |
|---|---|---|---|---|---|---|
| E0026 | Chiral 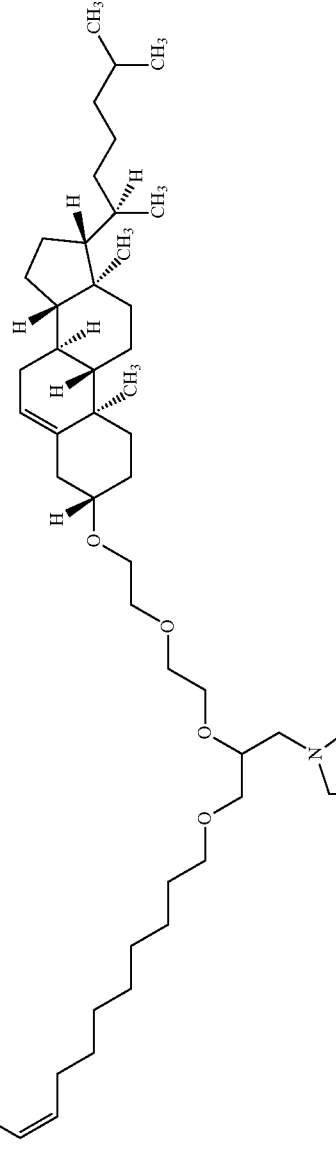 | $H^{28}$ | | | | |

TABLE 6-continued
Characterization and structures for Cationic Lipids
| Lipid | Structure | $R^1-N-R^2$ | $Y^1$ | $Y^{1-i}$ | $L$ | $L^{c-ii}$ |
|---|---|---|---|---|---|---|
| E0027 | Chiral 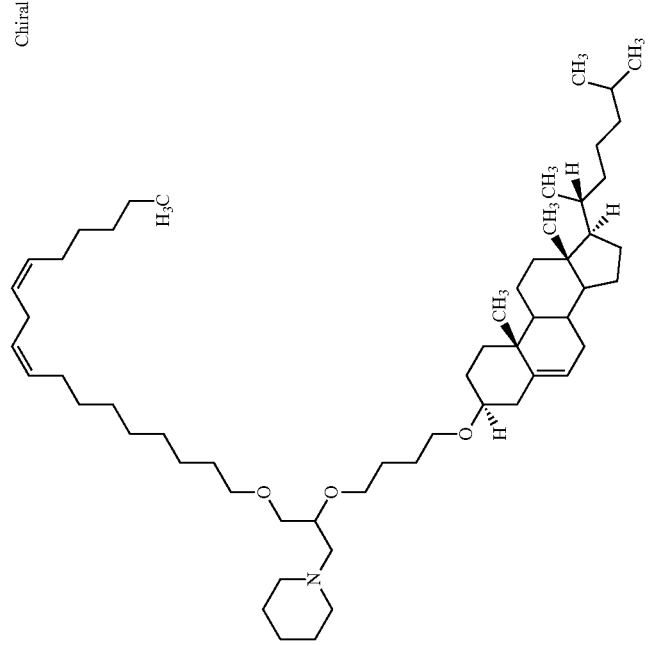 | $H^5$ | | | | |

TABLE 6-continued
Characterization and structures for Cationic Lipids
| Lipid | Structure | $R^1$—N—$R^2$ | $Y^1$ | L |
|---|---|---|---|---|
| E0028 | Chiral 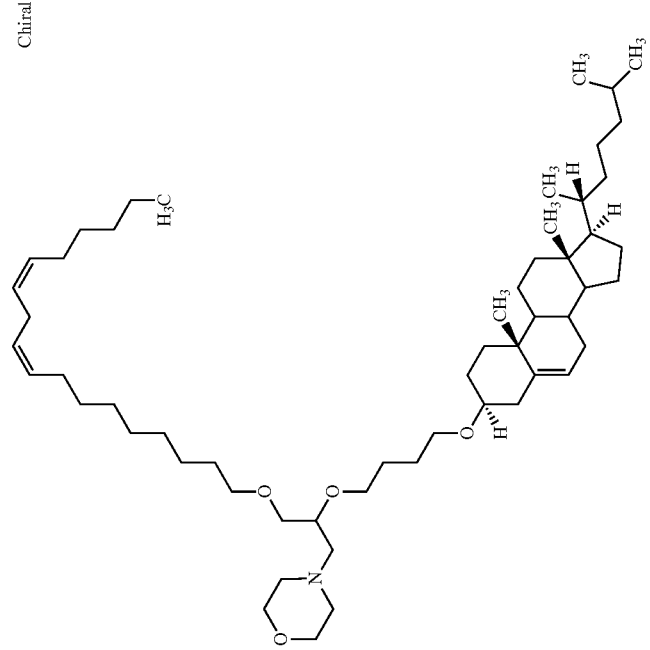 | $H^1$ | $Y^{1-i}$ | $L^{c-ii}$ |

TABLE 6-continued
Characterization and structures for Cationic Lipids
| Lipid | Structure | $R^1$—N—$R^2$ | $Y^1$ | $Y^{1-i}$ | L | $L^{c-i}$ |
|---|---|---|---|---|---|---|
| E0029 | 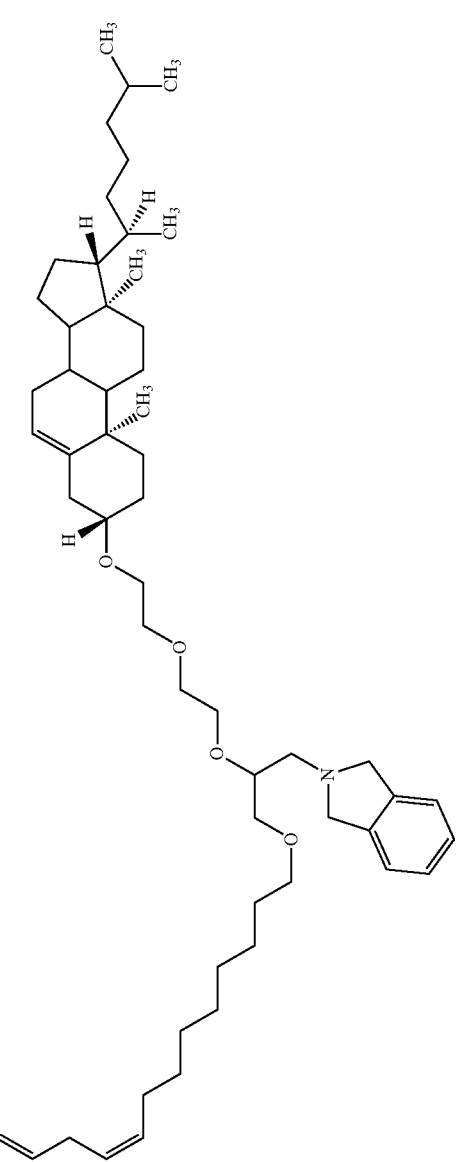 Chiral | $H^{29}$ | | | | |

TABLE 6-continued
Characterization and structures for Cationic Lipids
| Lipid | Structure | $R^1$—N—$R^2$ | $Y^1$ | L |
|---|---|---|---|---|
| | | | $Y^{1\text{-}i}$ | $L^{c\text{-}i}$ |
| E0030 | 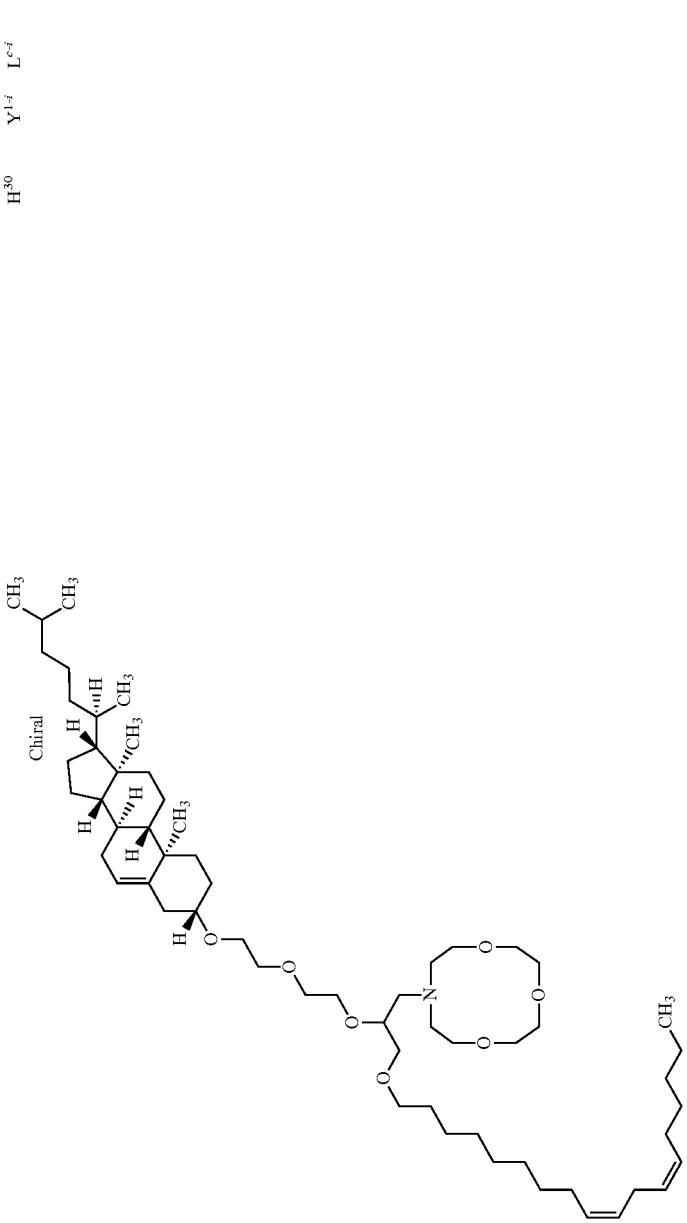 | $H^{30}$ | | |

TABLE 6-continued
Characterization and structures for Cationic Lipids
| Lipid | Structure | $R^1$—N—$R^2$ | $Y^1$ | $L$ |
|---|---|---|---|---|
| E0031 | 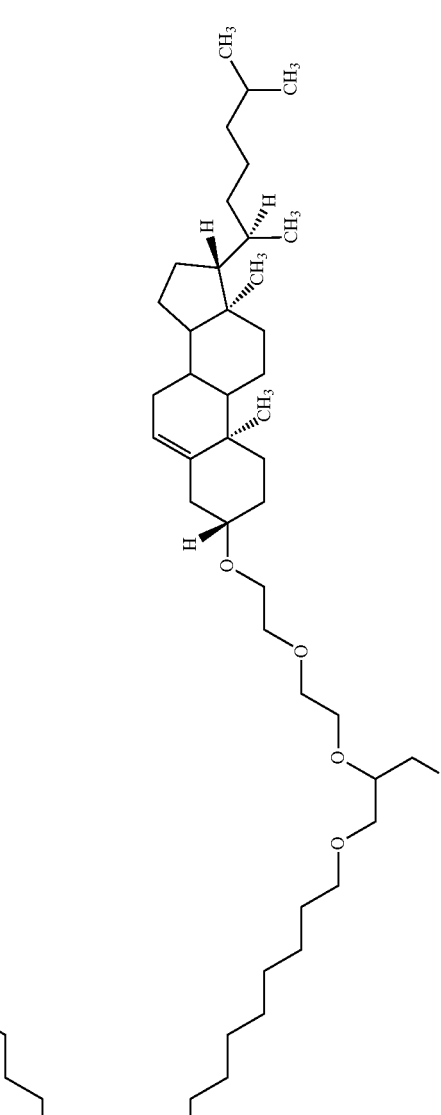 Chiral | $H^{31}$ | $Y^{1\text{-}i}$ | $L^{c\text{-}i}$ |

TABLE 6-continued

Characterization and structures for Cationic Lipids

| Lipid | Structure | $R^1$—N—$R^2$ | $Y^1$ | $Y^{1-i}$ | L | $L^{c-i}$ |
|---|---|---|---|---|---|---|
| E0032 Chiral | | $H^{20}$ | | | | |

TABLE 6-continued

Characterization and structures for Cationic Lipids

| Lipid | Structure | $R^1$—N—$R^2$ | $Y^1$ | $Y^{1-i}$ | $L^{c-i}$ | L |
|---|---|---|---|---|---|---|
| E0033 | Chiral | $H^{33}$ | | | | |

TABLE 6-continued
Characterization and structures for Cationic Lipids
| Lipid | Structure | $R^1$—N—$R^2$ | $Y^1$ | $Y^{1\text{-}i}$ | L | $L^{c\text{-}i}$ |
|---|---|---|---|---|---|---|
| E0034 | 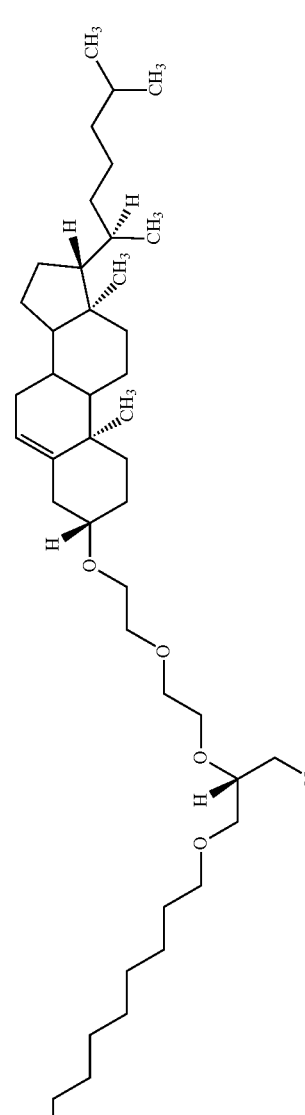 | $H^5$ | | | | |

TABLE 6-continued
Characterization and structures for Cationic Lipids
| Lipid | Structure | $R^1$—N—$R^2$ | $Y^1$ | L |
|---|---|---|---|---|
| E0035 | Chiral 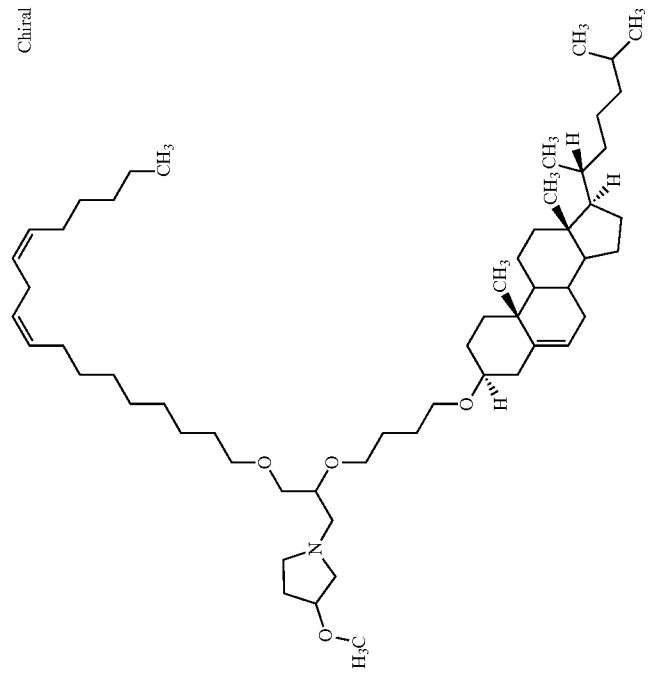 | $H^{35}$ | $Y^{1-i}$ | $L^{c-ii}$ |

TABLE 6-continued
Characterization and structures for Cationic Lipids
| Lipid | Structure | $R^1$—N—$R^2$ | $Y^1$ | L |
|---|---|---|---|---|
| E0036 | Chiral 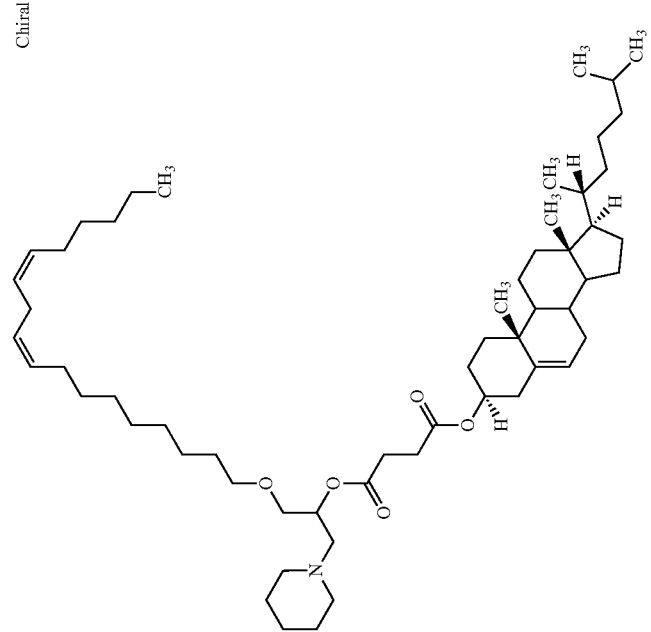 | $H^5$ | $Y^{1-i}$ | $L^{c-iii}$ |

TABLE 6-continued

Characterization and structures for Cationic Lipids

| Lipid | Structure | $R^1$—N—$R^2$ | $Y^1$ | $Y^{1-i}$ | L | $L^{c-i}$ |
|---|---|---|---|---|---|---|
| E0037 | Chiral | $H^{44}$ | | | | |

TABLE 6-continued

Characterization and structures for Cationic Lipids

| Lipid | Structure | R¹—N—R² | Y¹ | Y¹⁻ⁱ | L | L^{c-i} |
|-------|-----------|---------|----|----|---|---------|
| E0038 | 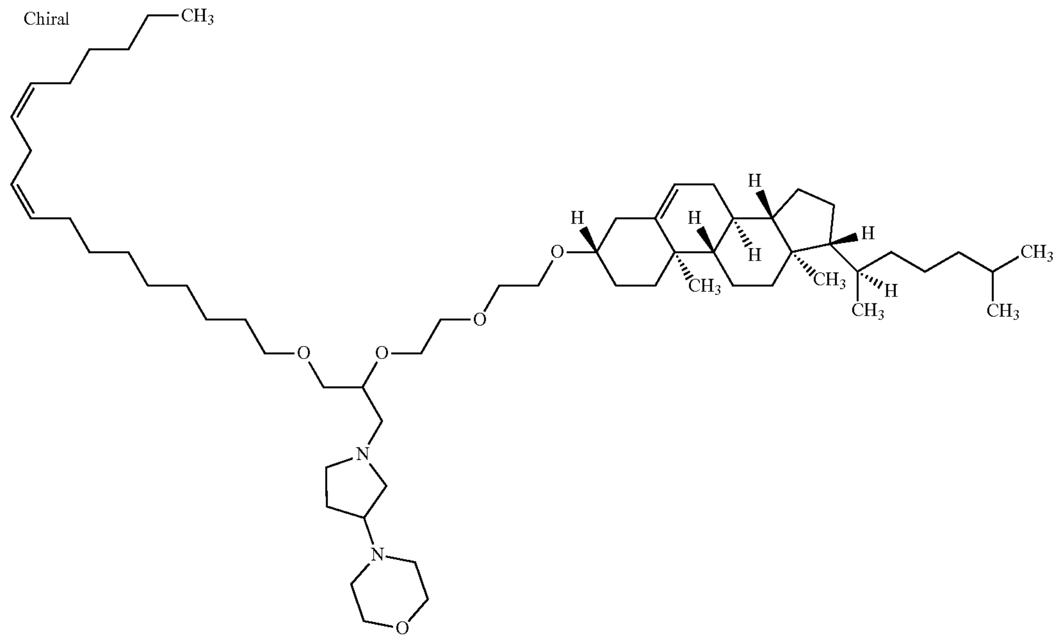 | H³⁶ | | | | |

TABLE 6-continued

Characterization and structures for Cationic Lipids

| Lipid | Structure | $R^1$—N—$R^2$ | $Y^1$ | L |
|---|---|---|---|---|
| E0039 Chiral | | $H^{37}$ | $Y^{1-i}$ | $L^{c-i}$ |
| E0040 | Mixture of the isomers E0053 and E0052 | $H^{12/26}$ | $Y^{1-i}$ | $L^{c-i}$ |

TABLE 6-continued
Characterization and structures for Cationic Lipids
| Lipid | Structure | $R^1$—N—$R^2$ | $Y^1$ | $Y^{1\text{-}i}$ | L | $L^{c\text{-}i}$ |
|---|---|---|---|---|---|---|
| E0041 | Chiral 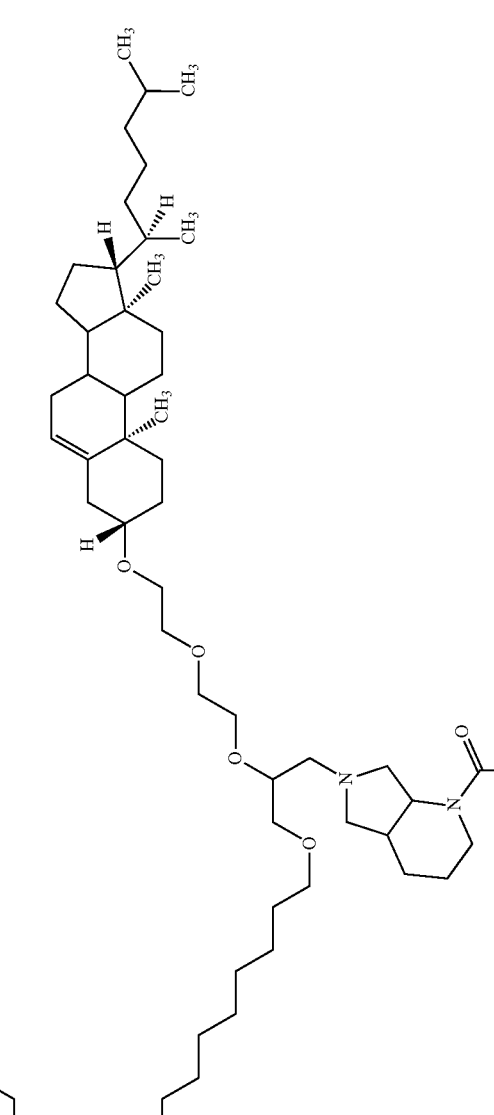 | $H^{32}$ | | | | |

TABLE 6-continued
Characterization and structures for Cationic Lipids
| Lipid | Structure | $R^1$—N—$R^2$ | $Y^1$ | $Y^{1-i}$ | $L$ | $L^{c-i}$ |
|---|---|---|---|---|---|---|
| E0042 | 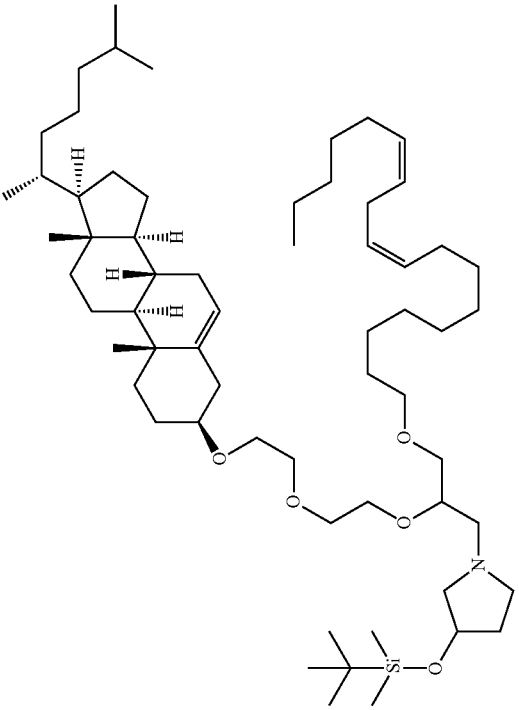 | $H^{39}$ | | | | |

TABLE 6-continued
Characterization and structures for Cationic Lipids
| Lipid | Structure | $R^1$—N—$R^2$ | $Y^1$ | $Y^{1-i}$ | L | $L^{c-i}$ |
|---|---|---|---|---|---|---|
| E0043 | 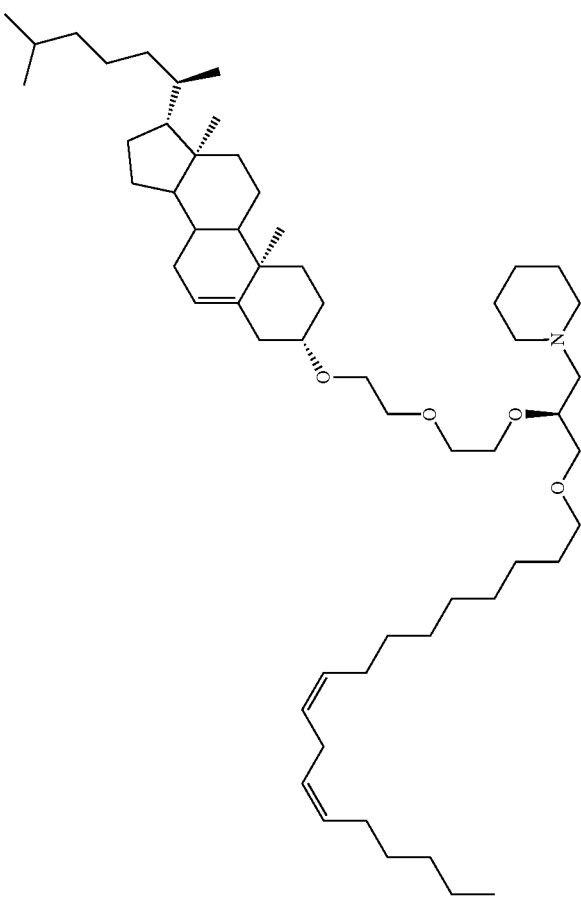 | $H^5$ | | | | |

TABLE 6-continued

Characterization and structures for Cationic Lipids

| Lipid | Structure | $R^1$—N—$R^2$ | $Y^1$ | $Y^{1-i}$ | L | $L^{c-i}$ |
|---|---|---|---|---|---|---|
| E0044 | 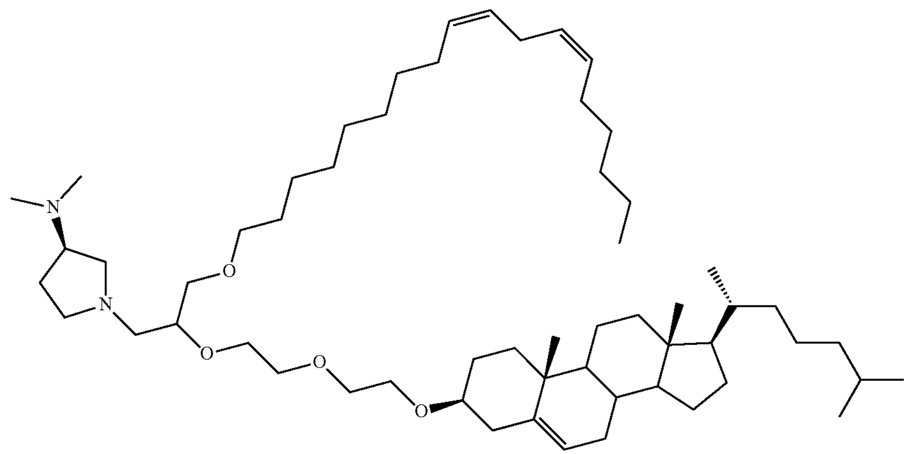 [SMILES: CCCCC/C=C\C/C=C\CCCCCCCCOCC(CN1CC[C@@H](N(C)C)C1)OCCOCCO[C@H]1CC[C@@]2(C)C(=CCC3C2CC[C@@]2(C)C3CC[C@@H]2[C@H](C)CCCC(C)C)C1] | $H^{48}$ | | | | |

TABLE 6-continued

Characterization and structures for Cationic Lipids

| Lipid | Structure | $R^1$—N—$R^2$ | $Y^1$ | $Y^{1\text{-}i}$ | L | $L^{c\text{-}i}$ |
|---|---|---|---|---|---|---|
| E0045 | Chiral | $H^{41}$ | | | | |

TABLE 6-continued

Characterization and structures for Cationic Lipids

| Lipid | Structure | $R^1$—N—$R^2$ | $Y^1$ | $Y^{1-i}$ | L | $L^{c-i}$ |
|---|---|---|---|---|---|---|
| E0046 | Chiral | $H^{42}$ | | | | |

TABLE 6-continued
Characterization and structures for Cationic Lipids
| Lipid | Structure | $R^1$—N—$R^2$ | $Y^1$ | $Y^{1-i}$ | L | $L^{c-v}$ |
|---|---|---|---|---|---|---|
| E0047 | 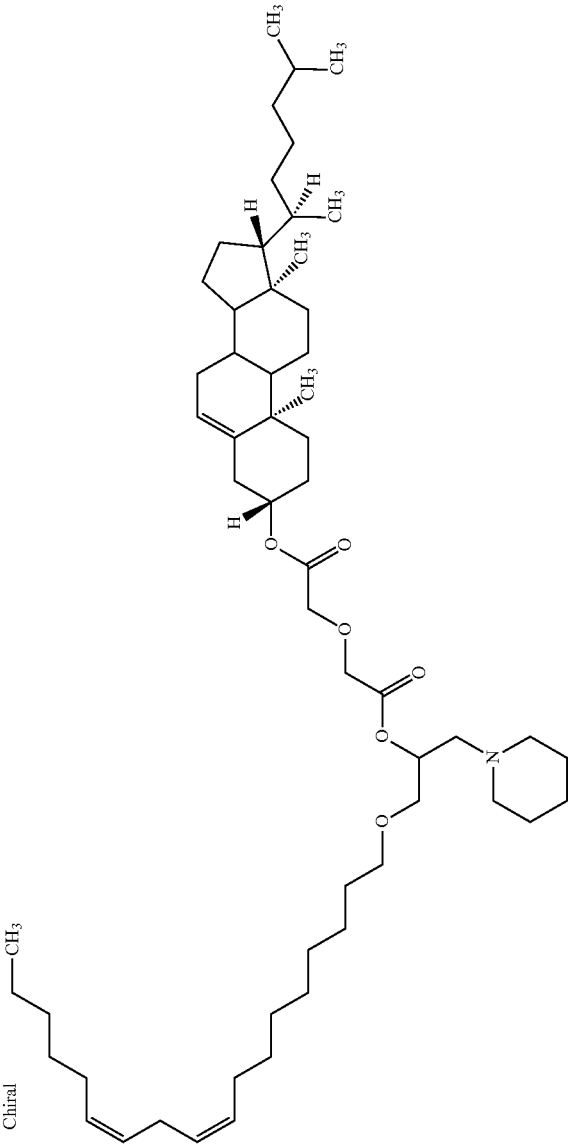 Chiral | $H^5$ | | | | |

TABLE 6-continued
Characterization and structures for Cationic Lipids
| Lipid | Structure | $R^1$—N—$R^2$ | $Y^1$ | $Y^{1-i}$ | L | $L^{c-i}$ |
|---|---|---|---|---|---|---|
| E0048 | Chiral 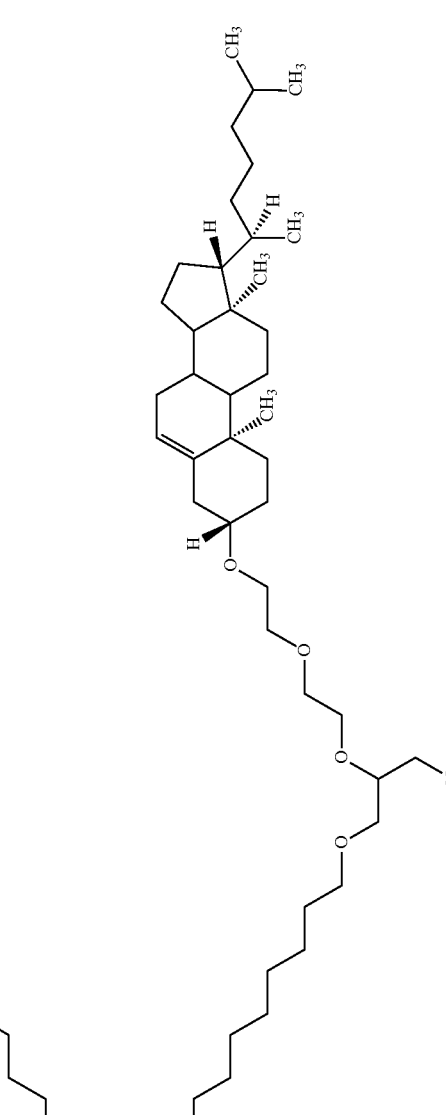 | $H^{26}$ | | | | |

TABLE 6-continued

Characterization and structures for Cationic Lipids

| Lipid | Structure | $R^1$—N—$R^2$ | $Y^1$ | $Y^{1-i}$ | L | $L^{c-i}$ |
|---|---|---|---|---|---|---|
| E0049 | Chiral | $H^{12}$ | | | | |

TABLE 6-continued

Characterization and structures for Cationic Lipids

| Lipid | Structure | $R^1$—N—$R^2$ | $Y^1$ | $Y^{1-i}$ | L | $L^{c-i}$ |
|---|---|---|---|---|---|---|
| E0050 Chiral | | $H^9$ | | | | |

TABLE 6-continued
Characterization and structures for Cationic Lipids
| Lipid | Structure | $R^1$—N—$R^2$ | $Y^1$ | $Y^{1-i}$ | L | $L^{c-i}$ |
|---|---|---|---|---|---|---|
| E0051 | Chiral 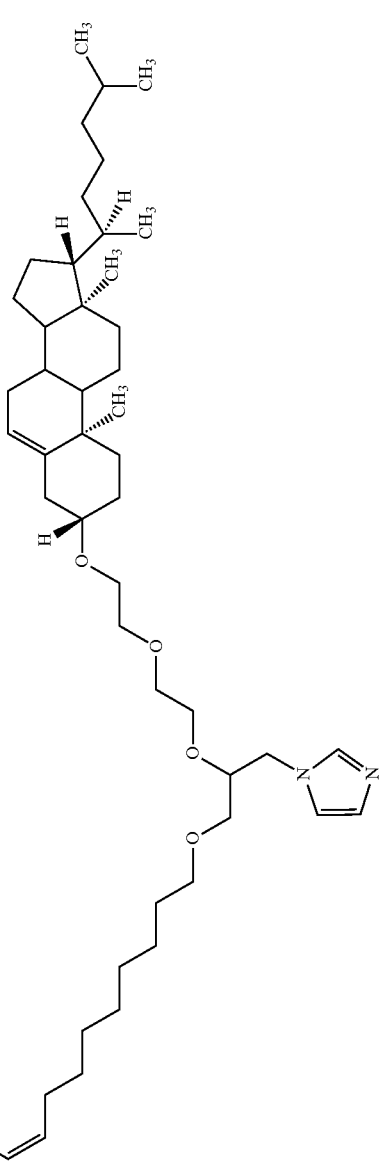 | $H^{40}$ | | | | |

TABLE 6-continued

Characterization and structures for Cationic Lipids

| Lipid | | Structure | $R^1$—N—$R^2$ | $Y^1$ | $Y^{1-i}$ | L | $L^{c-i}$ |
|---|---|---|---|---|---|---|---|
| E0052 | Chiral | 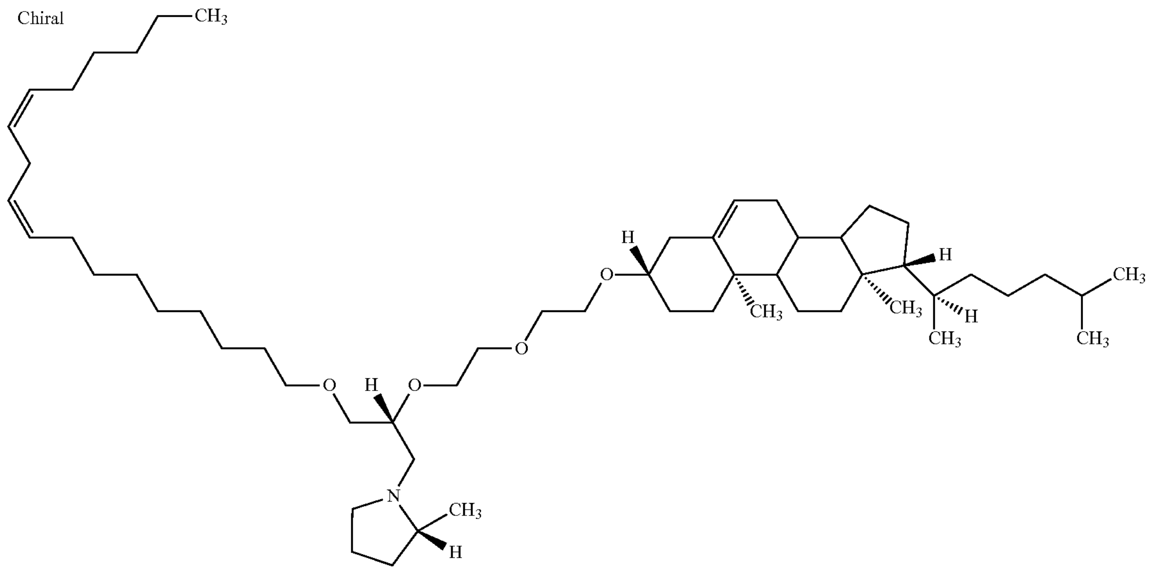 [SMILES: CCCCC/C=C\C/C=C\CCCCCCCCOC[C@@H](CN1CCC[C@H]1C)OCCOCCO[C@H]1CC[C@@]2(C)C(=CCC3C2CC[C@@]2(C)C3CC[C@@H]2[C@H](C)CCCC(C)C)C1] | $H^{12}$ | | | | |

TABLE 6-continued

Characterization and structures for Cationic Lipids

| Lipid | Structure | $R^1$—N—$R^2$ | $Y^1$ | $Y^{1-i}$ | L | $L^{c-i}$ |
|---|---|---|---|---|---|---|
| E0053 | Chiral | $H^{26}$ | | | | |

TABLE 6-continued

Characterization and structures for Cationic Lipids

| Lipid | Structure | $R^1$—N—$R^2$ | $Y^1$ | $Y^{1-i}$ | L | $L^{c-vi}$ |
|---|---|---|---|---|---|---|
| E0054 | Chiral | $H^5$ | | | | |

TABLE 6-continued
Characterization and structures for Cationic Lipids
| Lipid | Structure | $R^1$—N—$R^2$ | $Y^1$ | L |
|---|---|---|---|---|
| E0055 | 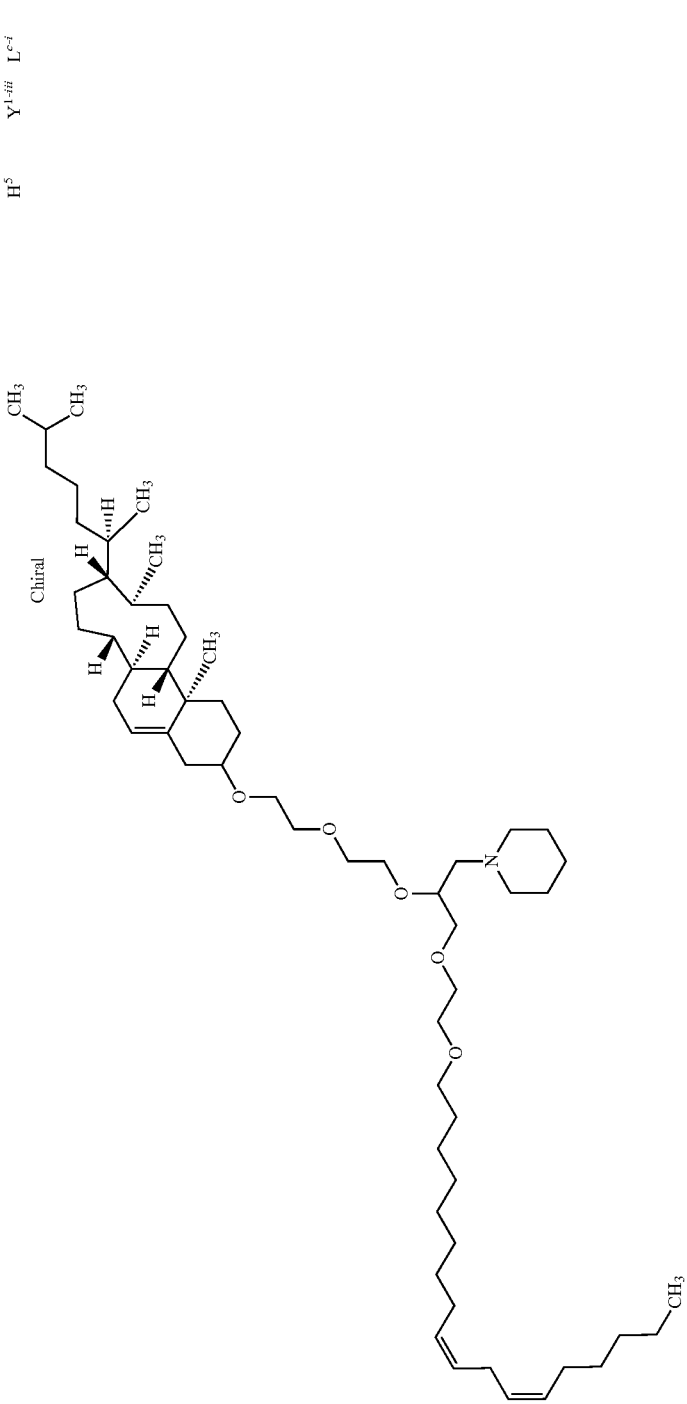 | $H^5$ | $Y^{1-iii}$ | $L^{c-i}$ |

TABLE 6-continued
Characterization and structures for Cationic Lipids
| Lipid | Structure | $R^1$—N—$R^2$ | $Y^1$ | L |
|---|---|---|---|---|
| E0056 | 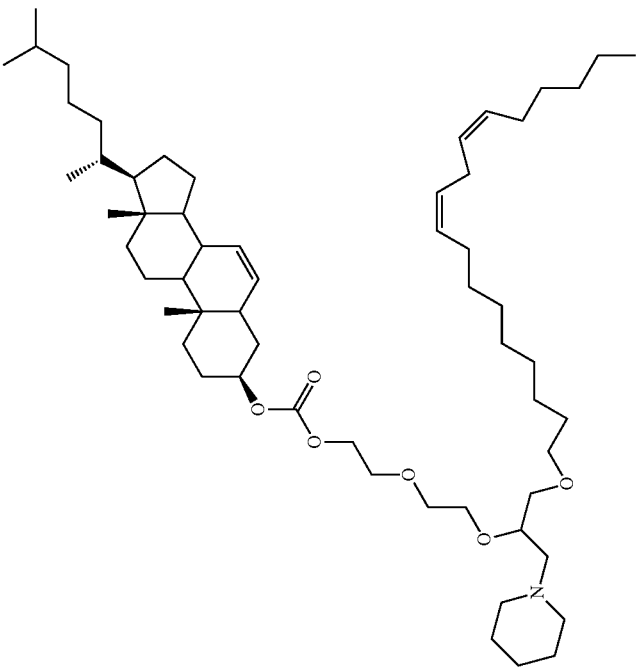 | $H^5$ | $Y^{1-i}$ | $L^{c-xviii}$ |

TABLE 6-continued
Characterization and structures for Cationic Lipids
| Lipid | Structure | $R^1$—N—$R^2$ | $Y^1$ | $Y^{1-i}$ | L | $L^{c-i}$ |
|---|---|---|---|---|---|---|
| E0057 | 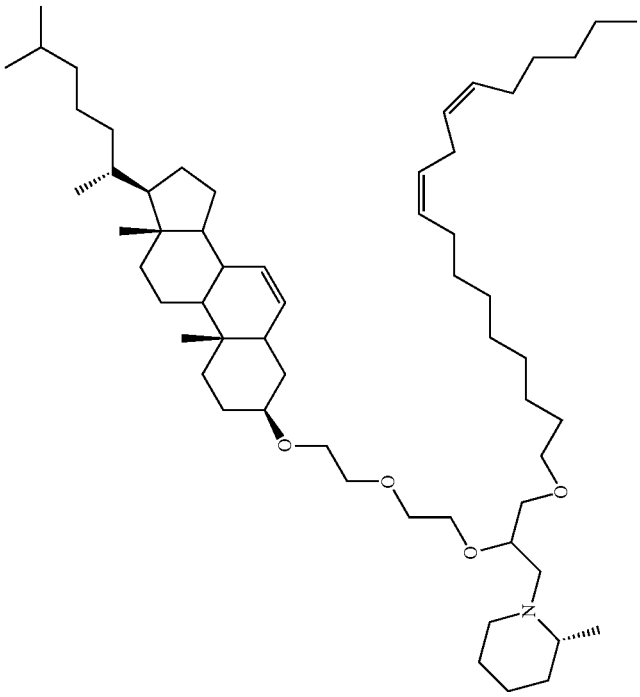 | $H^{47}$ | | | | |

TABLE 6-continued

Characterization and structures for Cationic Lipids

| Lipid | Structure | $R^1$—N—$R^2$ | $Y^1$ | L |
|---|---|---|---|---|
| E0058 | 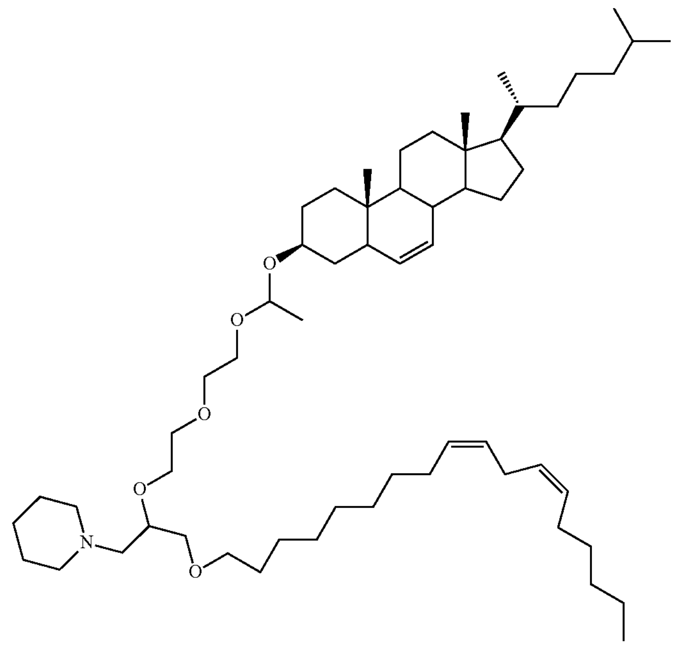 [SMILES: CCCCC/C=C\C/C=C\CCCCCCCCOCC(CN1CCCCC1)OCCOCCOC(C)O[C@H]1CC[C@@]2(C)C(C=CC3C2CC[C@@]2(C)C3CC[C@@H]2[C@H](C)CCCC(C)C)C1] | $H^5$ | $Y^{1-i}$ | $L^{c-xv}$ |

TABLE 6-continued

Characterization and structures for Cationic Lipids

| Lipid | Structure | $R^1$—N—$R^2$ | $Y^1$ | $Y^{1-i}$ | L | $L^{c-i}$ |
|---|---|---|---|---|---|---|
| E0059 | 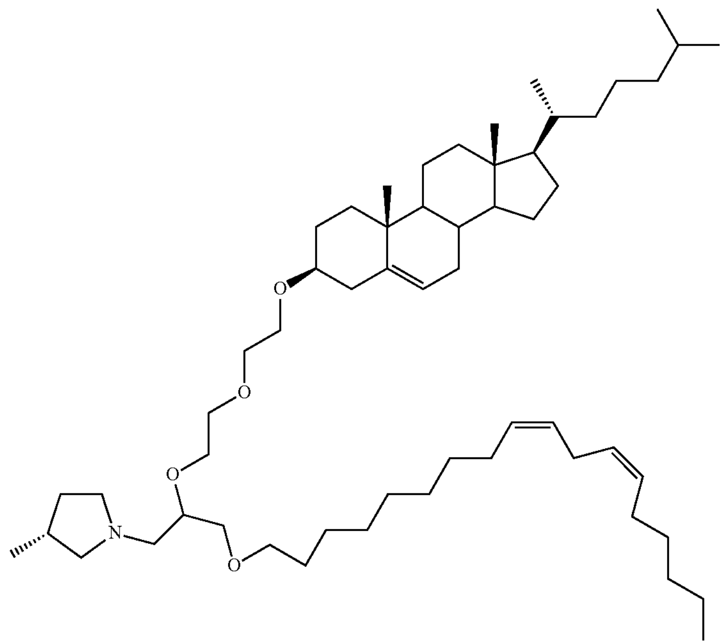 [SMILES: CCCCC/C=C\C/C=C\CCCCCCCCOCC(CN1CC[C@@H](C)C1)OCCOCCO[C@H]1CC[C@@]2(C)C(=CCC3C2CC[C@@]2(C)C3CC[C@@H]2[C@H](C)CCCC(C)C)C1] | $H^{45}$ | | | | |

TABLE 6-continued
Characterization and structures for Cationic Lipids
| Lipid | Structure | $R^1$—N—$R^2$ | $Y^1$ | L |
|---|---|---|---|---|
| E0060 | 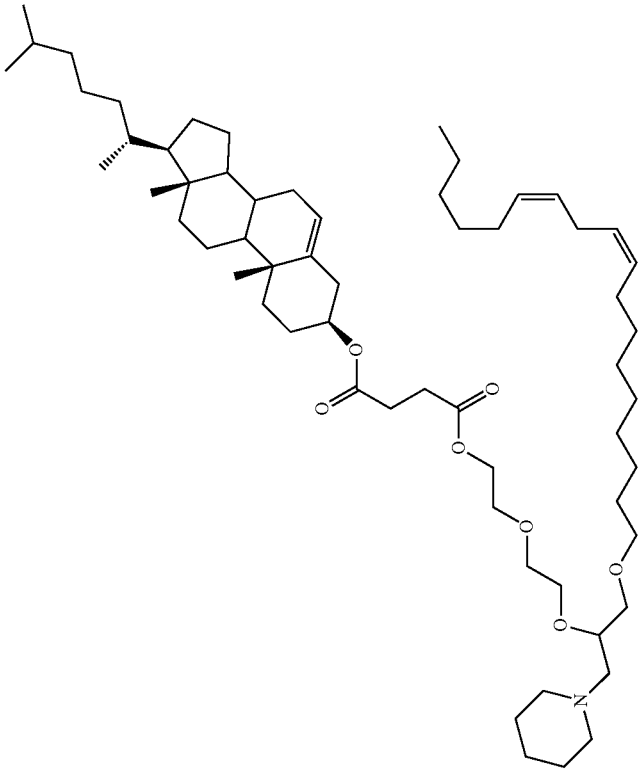 | $H^5$ | $Y^{1-i}$ | $L^{c-xvi}$ |

TABLE 6-continued

Characterization and structures for Cationic Lipids

| Lipid | Structure | $R^1$—N—$R^2$ | $Y^1$ | L |
|---|---|---|---|---|
| E0061 | 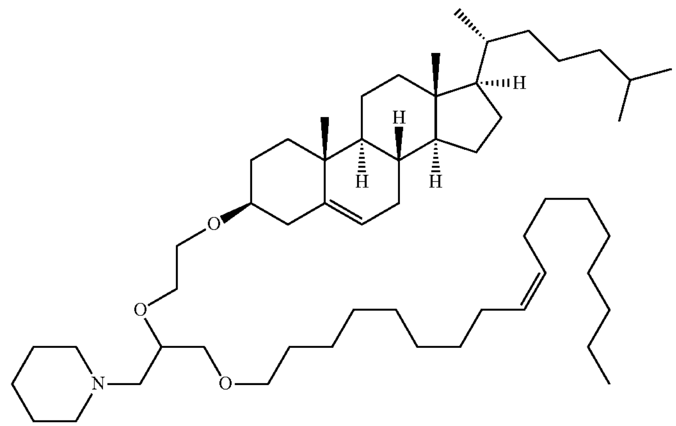 | $H^5$ | $Y^{1-iv}$ | $L^{c-viii}$ |
| E0062 | 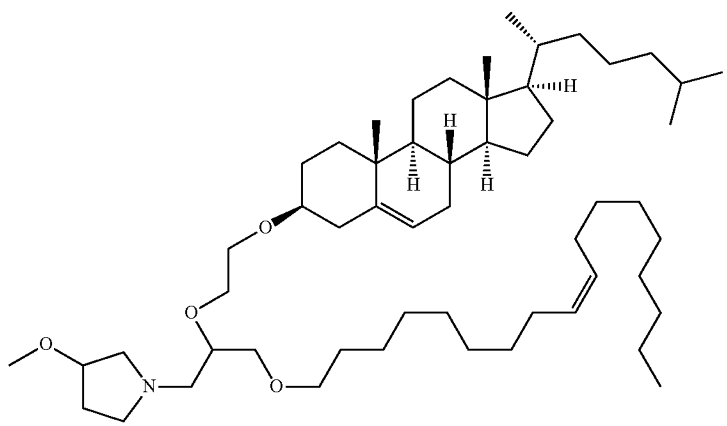 | $H^{35}$ | $Y^{1-iv}$ | $L^{c-viii}$ |

TABLE 6-continued

Characterization and structures for Cationic Lipids

| Lipid | Structure | $R^1$—N—$R^2$ | $Y^1$ | $Y^{1-iv}$ | L | $L^{c-i}$ |
|---|---|---|---|---|---|---|
| E0063 | Chiral [structure] | $H^5$ | | | | |

TABLE 6-continued

Characterization and structures for Cationic Lipids

| Lipid | Structure | $R^1$—N—$R^2$ | $Y^1$ | $Y^{1-iv}$ | L | $L^{c-i}$ |
|---|---|---|---|---|---|---|
| E0064 | 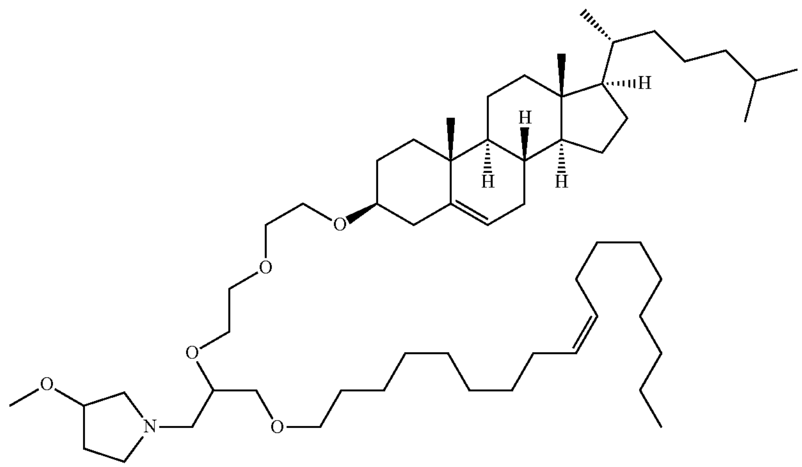 | $H^{35}$ | | | | $L^{c-i}$ |

TABLE 6-continued
Characterization and structures for Cationic Lipids
| Lipid | Structure | $R^1$—N—$R^2$ | $Y^1$ | L |
|---|---|---|---|---|
| E0065 | 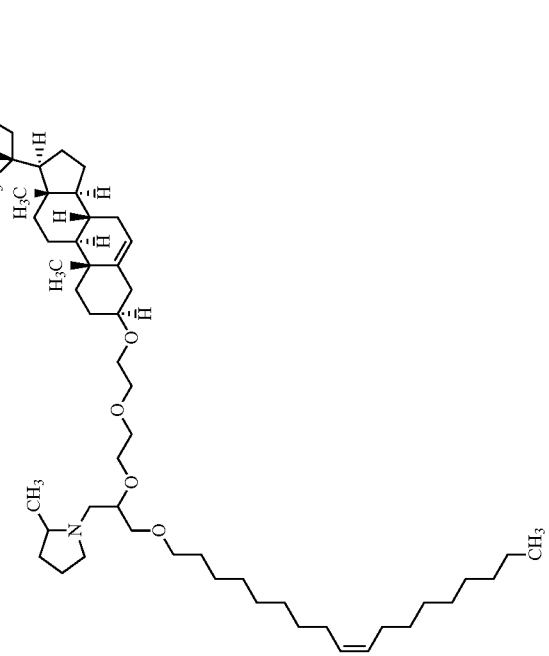 Chiral | $H^{12/26}$ | $Y^{i\text{-}iv}$ | $L^{c\text{-}i}$ |

TABLE 6-continued

Characterization and structures for Cationic Lipids

| Lipid | Structure | $R^1\text{—}N\text{—}R^2$ | $Y^1$ | L |
|---|---|---|---|---|
| E0066 | 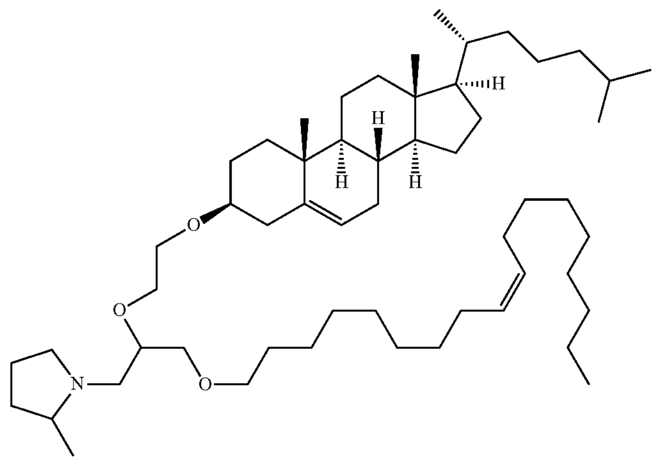 | $H^{12/26}$ | $Y^{i\text{-}iv}$ | $L^{c\text{-}viii}$ |

TABLE 6-continued

Characterization and structures for Cationic Lipids

| Lipid | Structure | $R^1$—N—$R^2$ | $Y^1$ | L |
|---|---|---|---|---|
| E0067 | 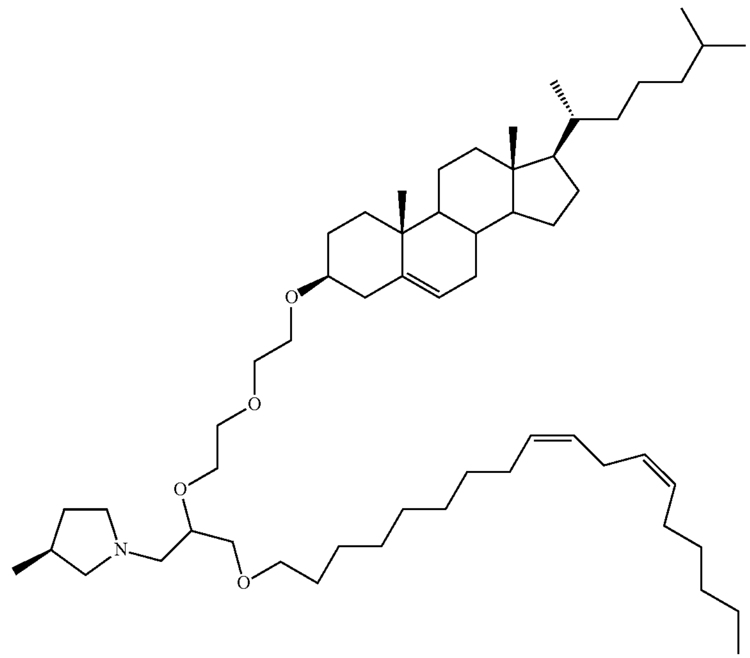 [SMILES: CCCCC/C=C\C/C=C\CCCCCCCCOCC(CN1CC[C@H](C)C1)OCCOCCO[C@H]1CC[C@@]2(C)C(=CCC3C2CC[C@@]2(C)C3CC[C@@H]2[C@H](C)CCCC(C)C)C1] | $H^{46}$ | $Y^{1-i}$ | $L^{c-i}$ |
| E0068 | 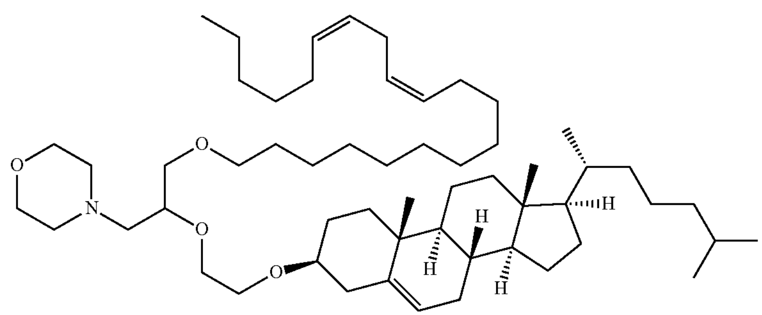 | $H^1$ | $Y^{1-v}$ | $L^{c-viii}$ |

TABLE 6-continued
Characterization and structures for Cationic Lipids
| Lipid | Structure | $R^1$—N—$R^2$ | $Y^1$ | L |
|---|---|---|---|---|
| E0069 | 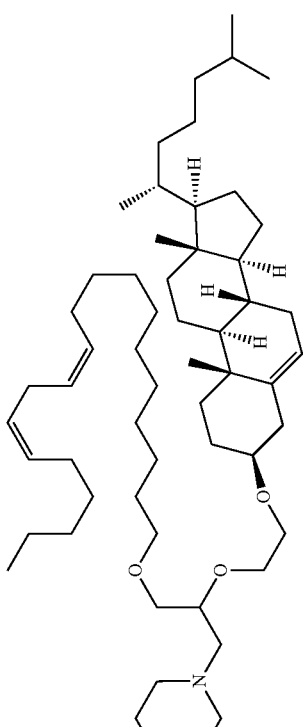 | $H^5$ | $Y^{1-v}$ | $L^{c-viii}$ |
| E0070 | 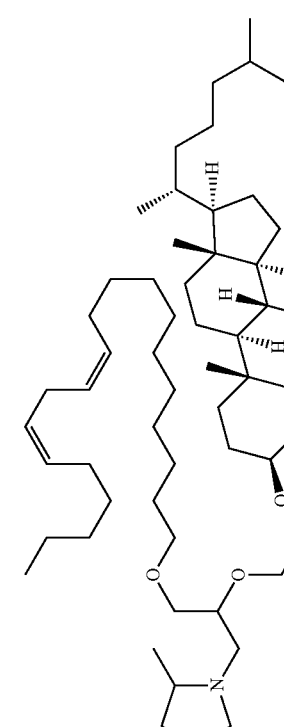 | $H^{12/26}$ | $Y^{1-v}$ | $L^{c-viii}$ |

TABLE 6-continued

Characterization and structures for Cationic Lipids

| Lipid | Structure | $R^1$—N—$R^2$ | $Y^1$ | L |
|---|---|---|---|---|
| E0071 | 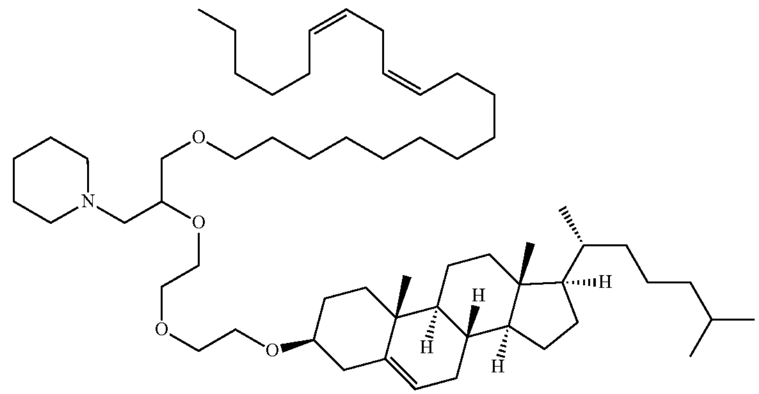 | $H^5$ | $Y^{1-v}$ | $L^{c-i}$ |
| E0072 | 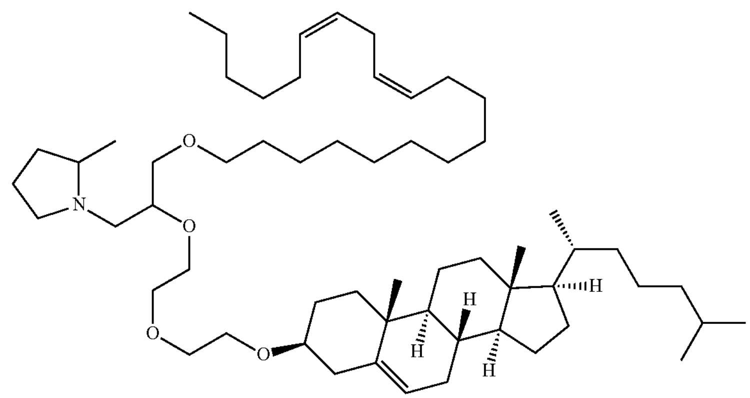 | $H^{12/26}$ | $Y^{1-v}$ | $L^{c-i}$ |

TABLE 6-continued

Characterization and structures for Cationic Lipids

| Lipid | Structure | $R^1-N-R^2$ | $Y^1$ | L |
|---|---|---|---|---|
| E0073 | 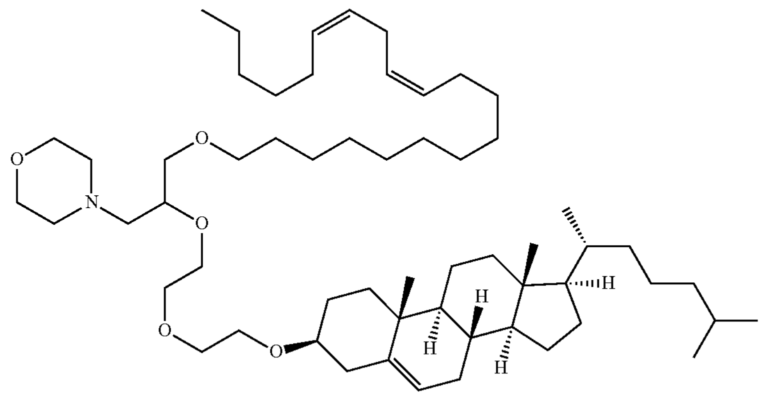 | $H^1$ | $Y^{1-v}$ | $L^{c-i}$ |
| E0074 | 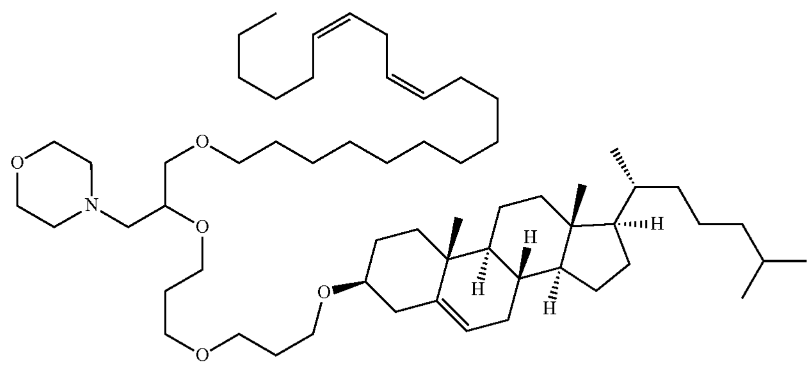 | $H^1$ | $Y^{1-v}$ | $L^{c-vii}$ |

TABLE 6-continued

Characterization and structures for Cationic Lipids

| Lipid | Structure | $R^1$—N—$R^2$ | $Y^1$ | L |
|---|---|---|---|---|
| E0075 | Chiral | $H^{12/26}$ | $Y^{1-i}$ | $L^{c-vii}$ |

TABLE 6-continued

Characterization and structures for Cationic Lipids

| Lipid | Structure | $R^1$—N—$R^2$ | $Y^1$ | L |
|---|---|---|---|---|
| E0076 | Chiral | $H^5$ | $Y^{1-i}$ | $L^{c\text{-}viii}$ |

TABLE 6-continued
Characterization and structures for Cationic Lipids
| Lipid | Structure | $R^1$—N—$R^2$ | $Y^1$ | L |
|---|---|---|---|---|
| E0077 | 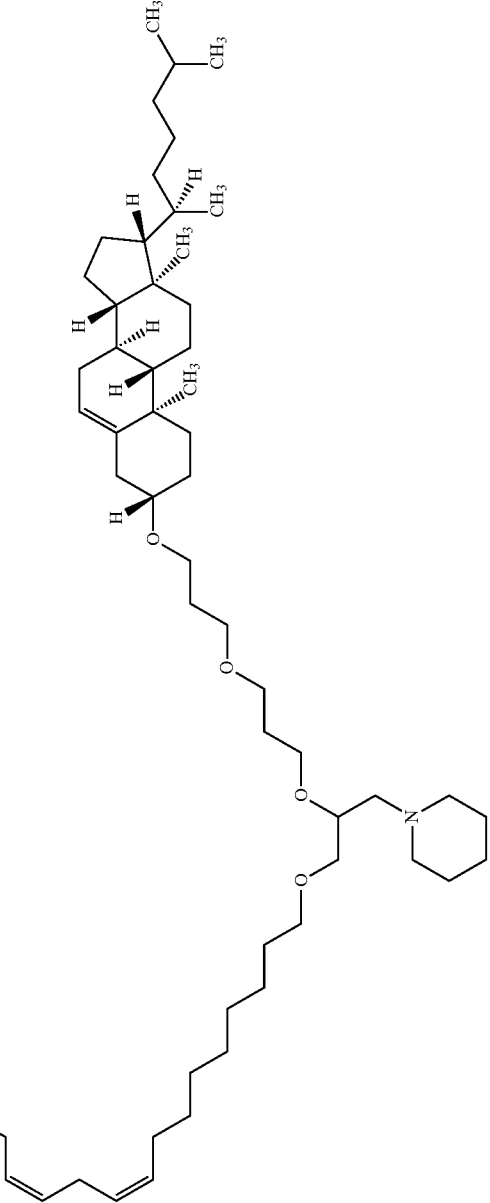 Chiral | $H^5$ | $Y^{1-i}$ | $L^{c-vii}$ |
| E0078 | 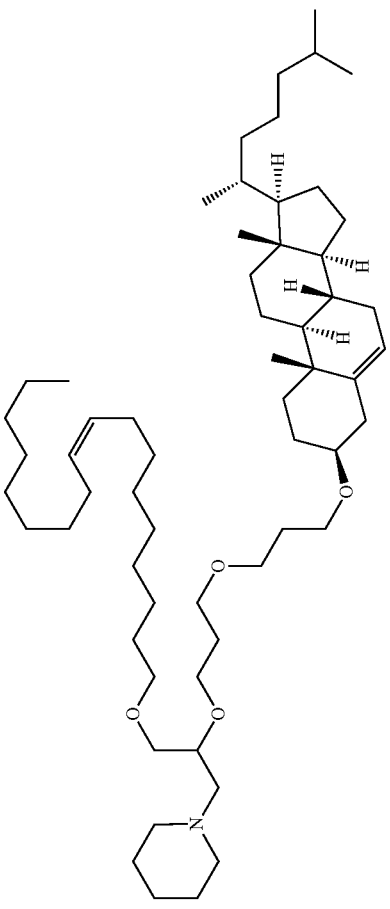 | $H^5$ | $Y^{1-iv}$ | $L^{c-vii}$ |

TABLE 6-continued

Characterization and structures for Cationic Lipids

| Lipid | Structure | $R^1\text{—N—}R^2$ | $Y^1$ | L |
|---|---|---|---|---|
| E0079 Chiral | | $H^5$ | $Y^{1-i}$ | $L^{c-ix}$ |
| E0080 | 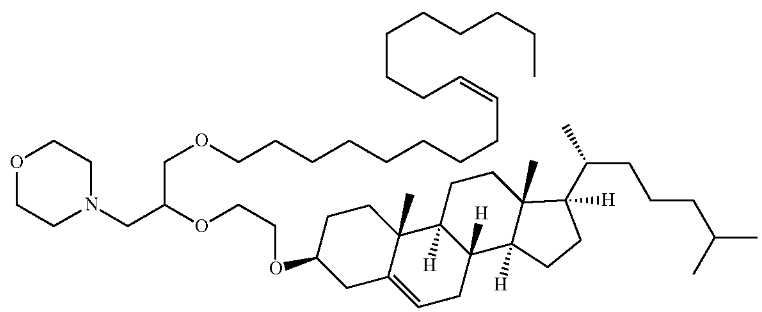 | $H^1$ | $Y^{1-iv}$ | $L^{c-viii}$ |

TABLE 6-continued
Characterization and structures for Cationic Lipids
| Lipid | Structure | $R^1$—N—$R^2$ | $Y^1$ | L |
|---|---|---|---|---|
| E0081 | 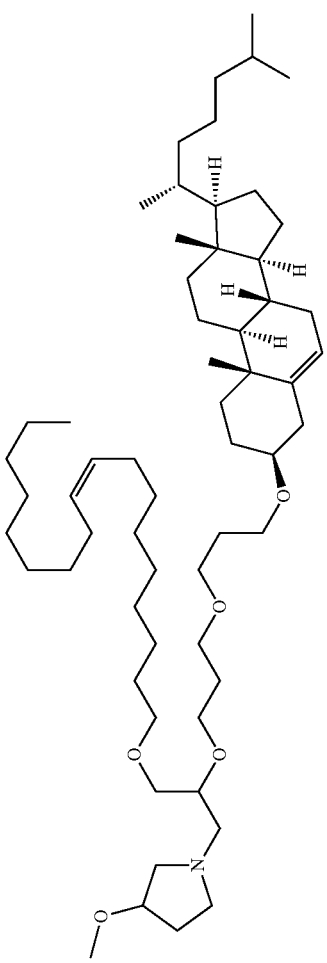 | $H^{35}$ | $Y^{1-iv}$ | $L^{c-vii}$ |
| E0082 | 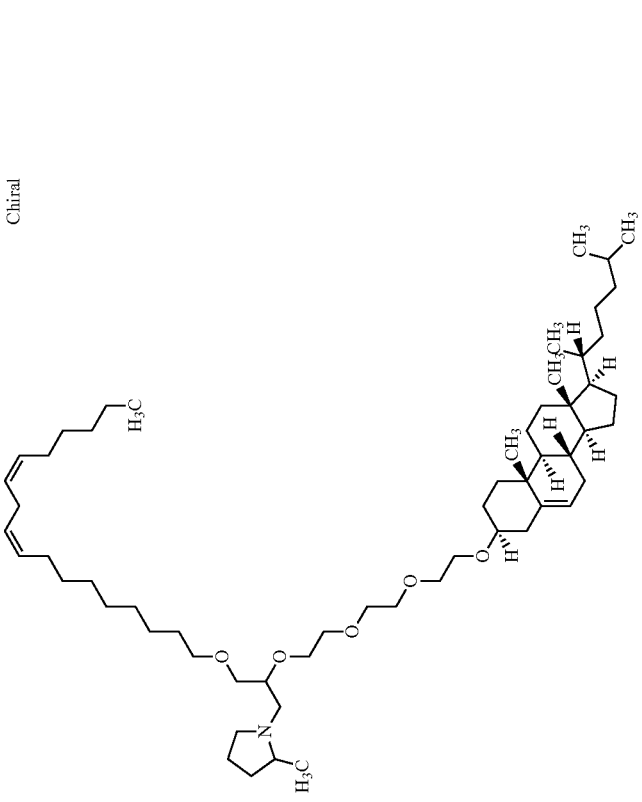 | $H^{12/26}$ | $Y^{1-i}$ | $L^{c-x}$ |

TABLE 6-continued

Characterization and structures for Cationic Lipids

| Lipid | Structure | $R^1$—N—$R^2$ | $Y^1$ | L |
|---|---|---|---|---|
| E0083 Chiral | | $H^{12/26}$ | $Y^{1-i}$ | $L^{c-i}$ |
| E0084 | 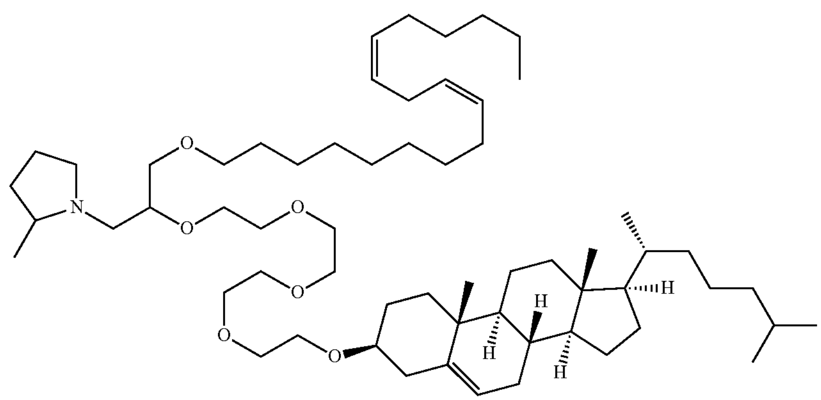 | $H^{12/26}$ | $Y^{1-i}$ | $L^{c-ix}$ |

TABLE 6-continued

Characterization and structures for Cationic Lipids

| Lipid | Structure | $R^1-N-R^2$ | $Y^1$ | L |
|---|---|---|---|---|
| E0085 | 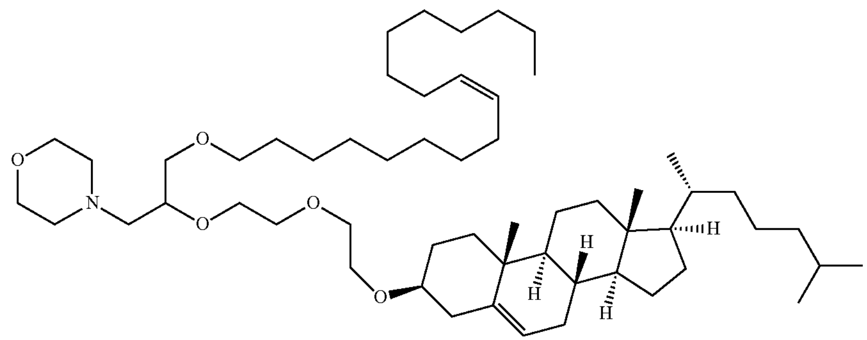 | $H^1$ | $Y^{1-iv}$ | $L^{c-i}$ |
| E0086 | 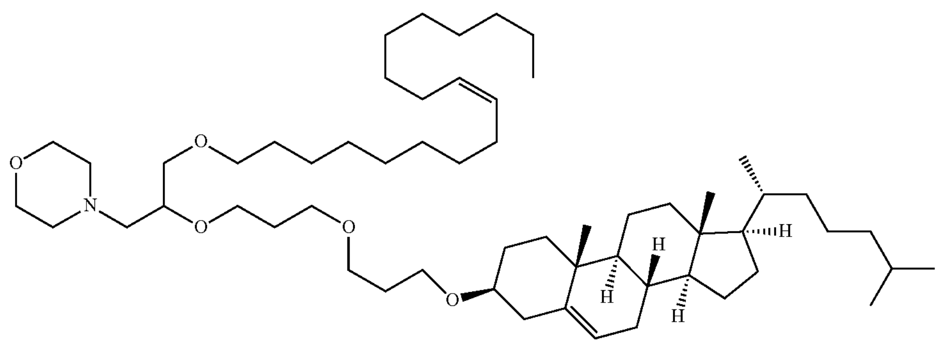 | $H^1$ | $Y^{1-iv}$ | $L^{c-vii}$ |
| E0087 | 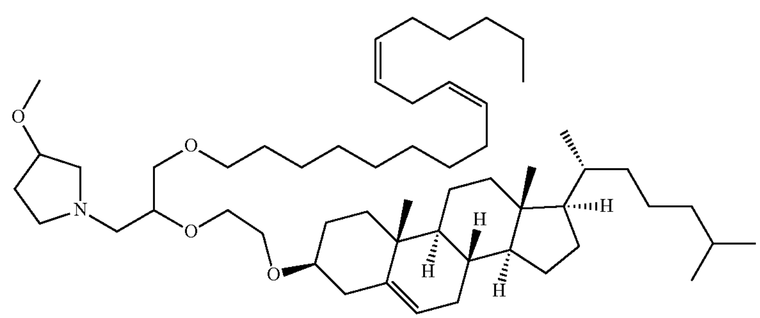 | $H^{35}$ | $Y^{1-i}$ | $L^{c-viii}$ |

TABLE 6-continued

Characterization and structures for Cationic Lipids

| Lipid | Structure | $R^1$—N—$R^2$ | $Y^1$ | L |
|---|---|---|---|---|
| E0088 | 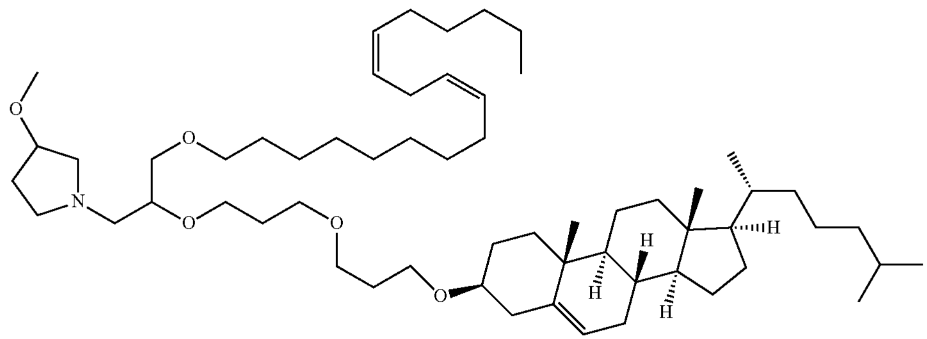 | $H^{35}$ | $Y^{1-i}$ | $L^{c-viii}$ |
| E0089 | 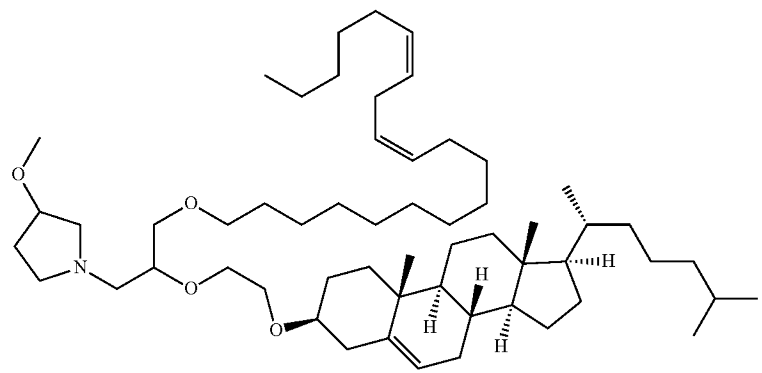 | $H^{35}$ | $Y^{1-v}$ | $L^{c-viii}$ |

TABLE 6-continued
Characterization and structures for Cationic Lipids
| Lipid | Structure | $R^1$—N—$R^2$ | $Y^1$ | L |
|---|---|---|---|---|
| E0090 | 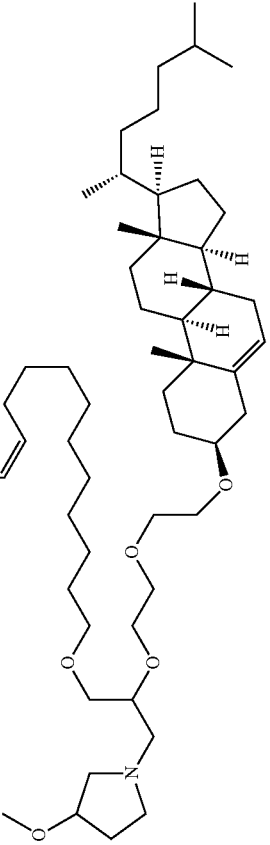 | $H^{35}$ | $Y^{1-v}$ | $L^{c-i}$ |
| E0091 | 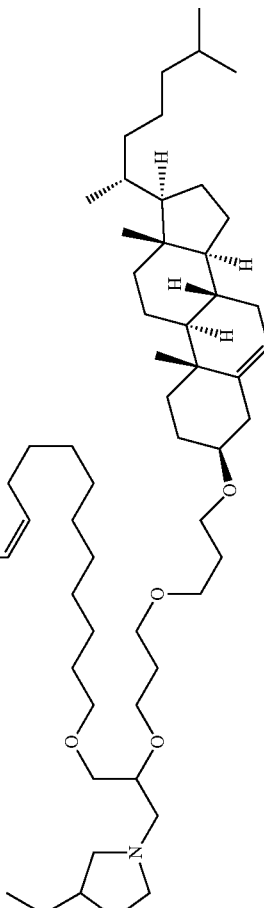 | $H^{35}$ | $Y^{1-v}$ | $L^{c-vii}$ |

TABLE 6-continued

Characterization and structures for Cationic Lipids

| Lipid | Structure | $R^1$—N—$R^2$ | $Y^1$ | L |
|---|---|---|---|---|
| E0092 | 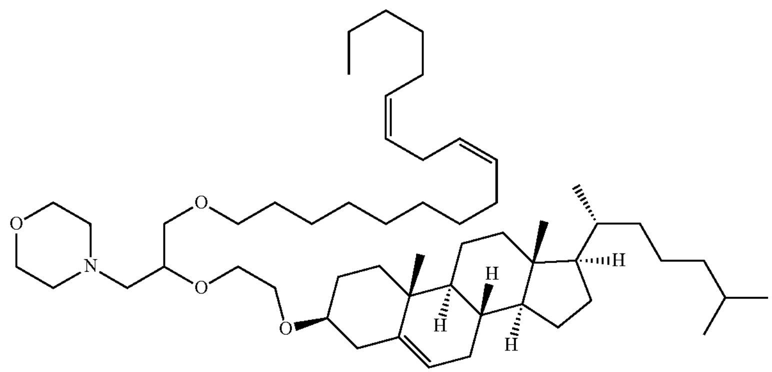 | $H^1$ | $Y^{1-i}$ | $L^{c-viii}$ |
| E0093 | 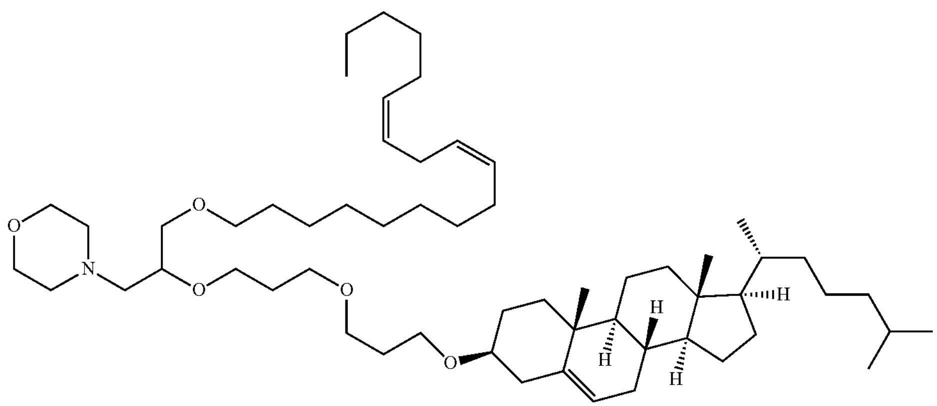 | $H^1$ | $Y^{1-i}$ | $L^{c-viii}$ |

TABLE 6-continued

Characterization and structures for Cationic Lipids

| Lipid | Structure | $R^1$—N—$R^2$ | $Y^1$ | L |
|---|---|---|---|---|
| E0094 | 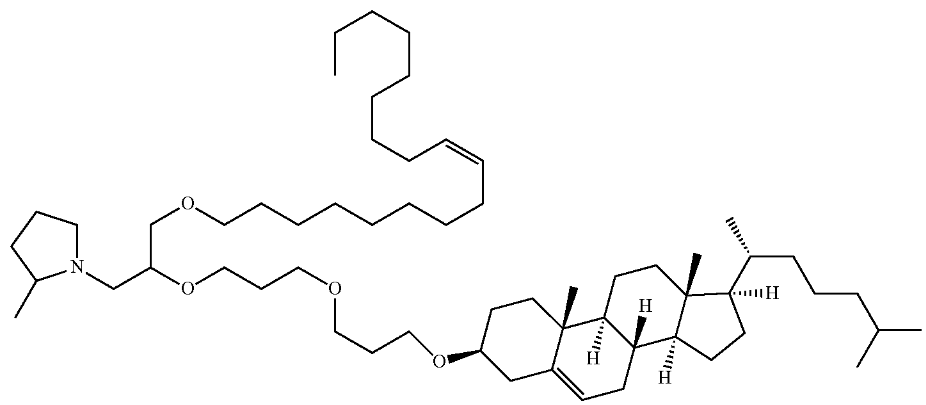 | $H^{12/26}$ | $Y^{1\text{-}iv}$ | $L^{c\text{-}vii}$ |
| E0095 | 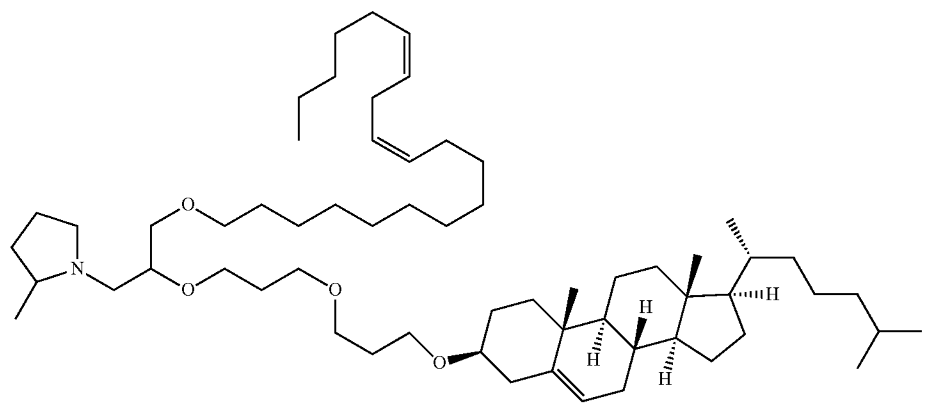 | $H^{12/26}$ | $Y^{1\text{-}v}$ | $L^{c\text{-}vii}$ |

TABLE 6-continued

Characterization and structures for Cationic Lipids

| Lipid | Structure | $R^1$—N—$R^2$ | $Y^1$ | L |
|---|---|---|---|---|
| E0096 | 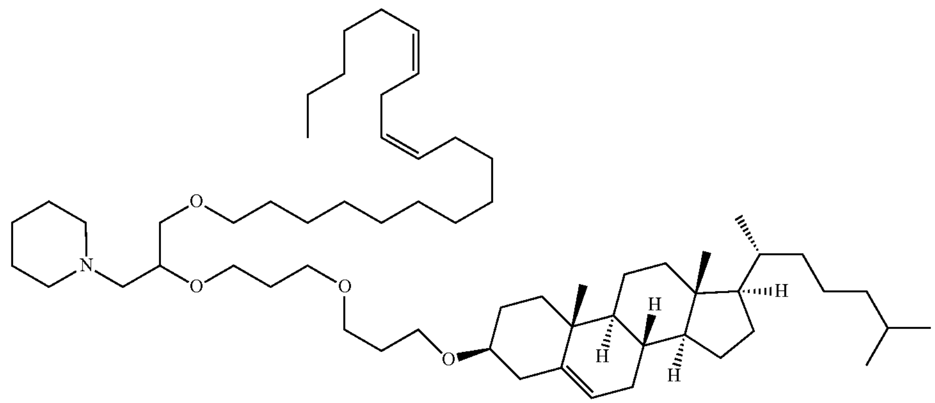 | $H^5$ | $Y^{1-v}$ | $L^{c-vii}$ |
| E0097 | 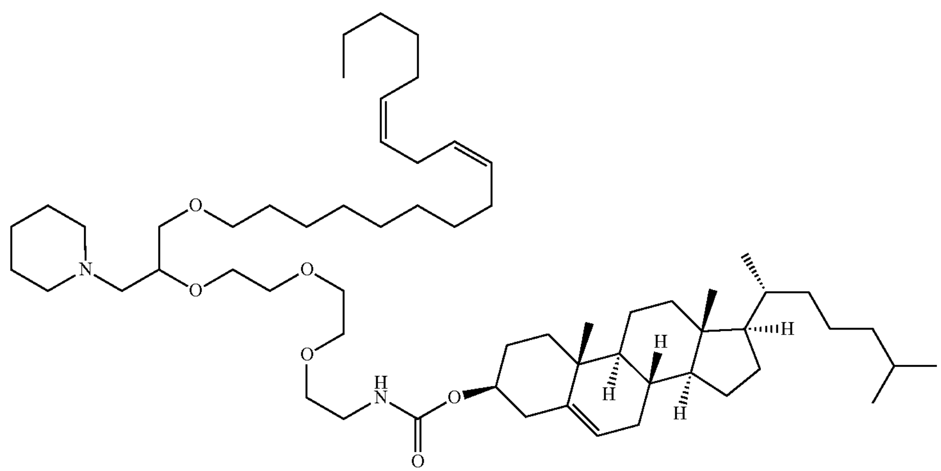 | $H^5$ | $Y^{1-i}$ | $L^{c-xiv}$ |

TABLE 6-continued

Characterization and structures for Cationic Lipids

| Lipid | Structure | $R^1$—N—$R^2$ | $Y^1$ | L |
|---|---|---|---|---|
| E0098 | 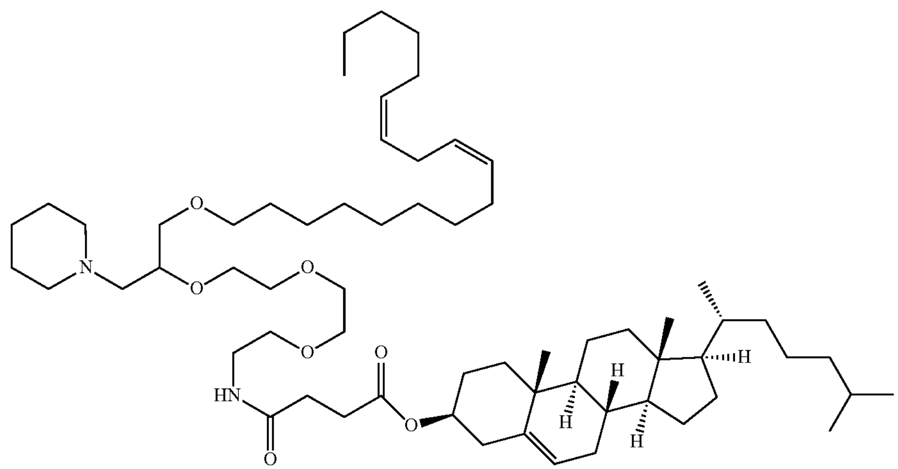 | $H^5$ | $Y^{1\text{-}i}$ | $L^{c\text{-}xi}$ |
| E0099 | 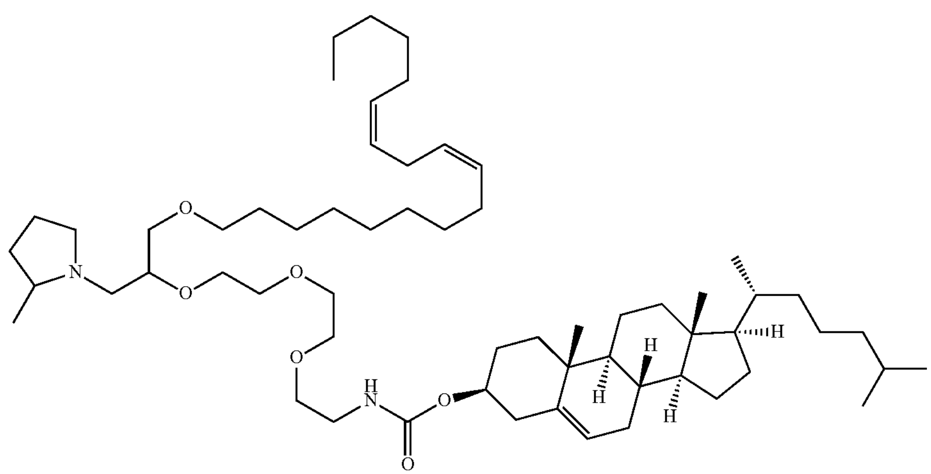 | $H^{12/26}$ | $Y^{1\text{-}i}$ | $L^{c\text{-}xiv}$ |

TABLE 6-continued

Characterization and structures for Cationic Lipids

| Lipid | Structure | R¹—N—R² | Y¹ | L |
|---|---|---|---|---|
| E0100 | 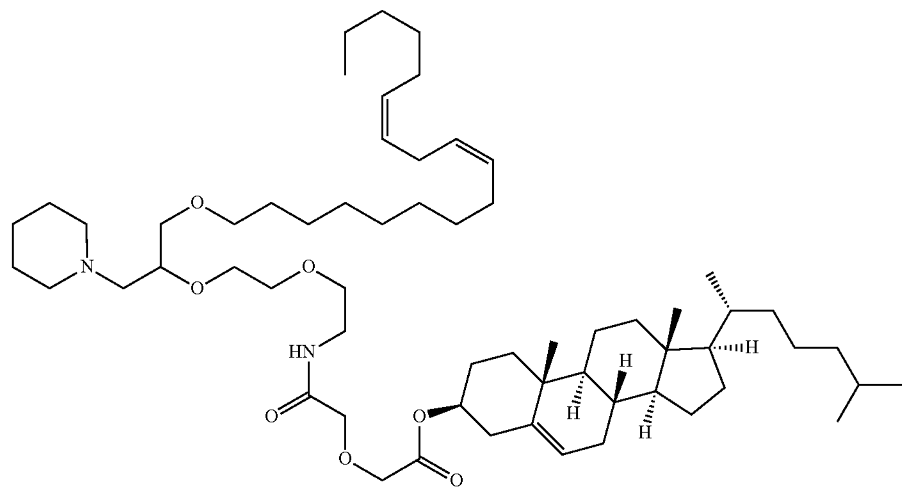 | H⁵ | Y¹⁻ⁱ | L^c-xiii |
| E0101 | 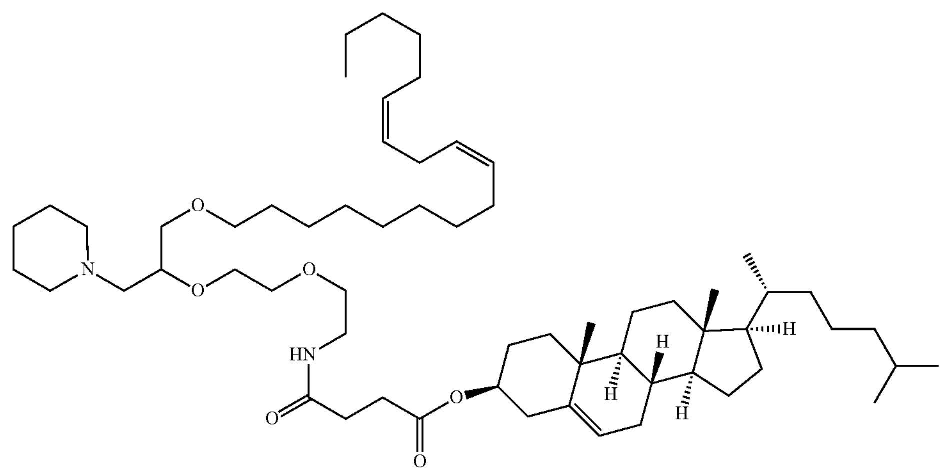 | H⁵ | Y¹⁻ⁱ | L^c-xiii |

TABLE 6-continued

Characterization and structures for Cationic Lipids

| Lipid | Structure | $R^1$—N—$R^2$ | $Y^1$ | L |
|---|---|---|---|---|
| E0102 | 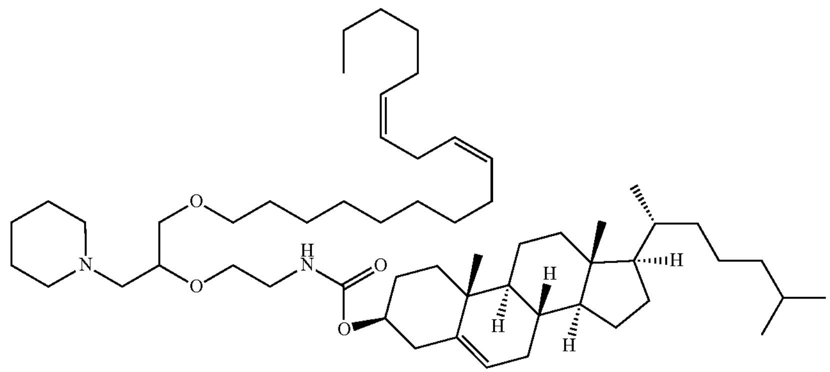 | $H^5$ | $Y^{1-i}$ | $L^{c-xxi}$ |
| E0103 | 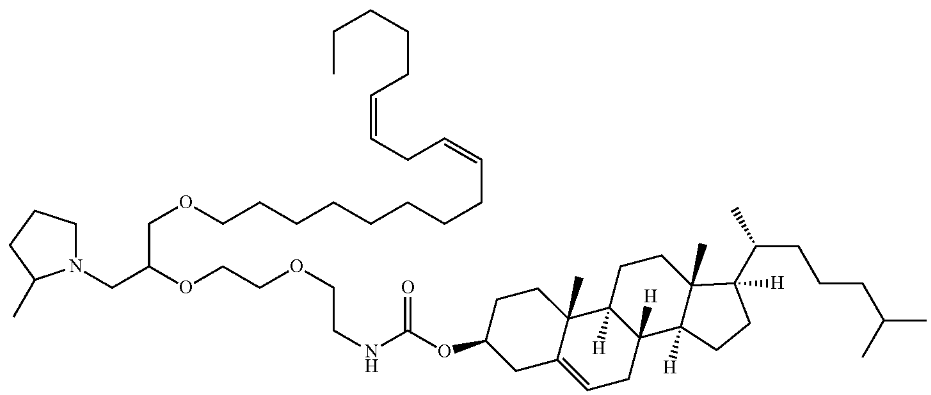 | $H^{12/26}$ | $Y^{1-i}$ | $L^{c-vi}$ |

TABLE 6-continued

Characterization and structures for Cationic Lipids

| Lipid | Structure | $R^1-N-R^2$ | $Y^1$ | L |
|-------|-----------|-------------|-------|---|
| E0104 | 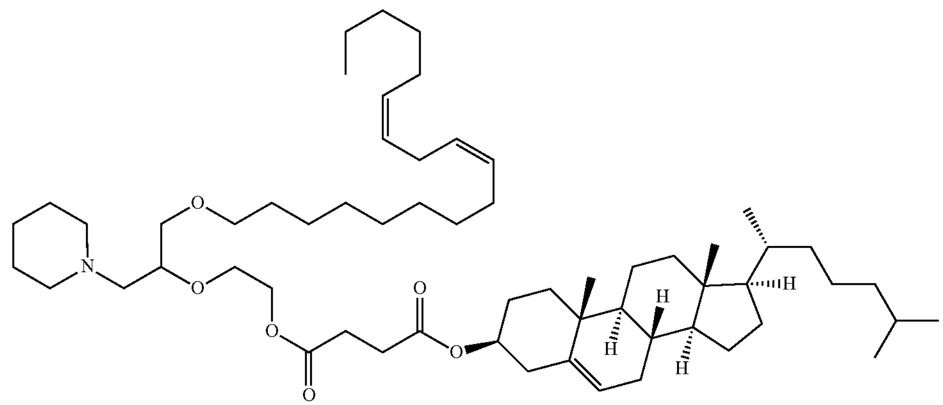 | $H^5$ | $Y^{1-i}$ | $L^{c\text{-}xvii}$ |
| E0105 | 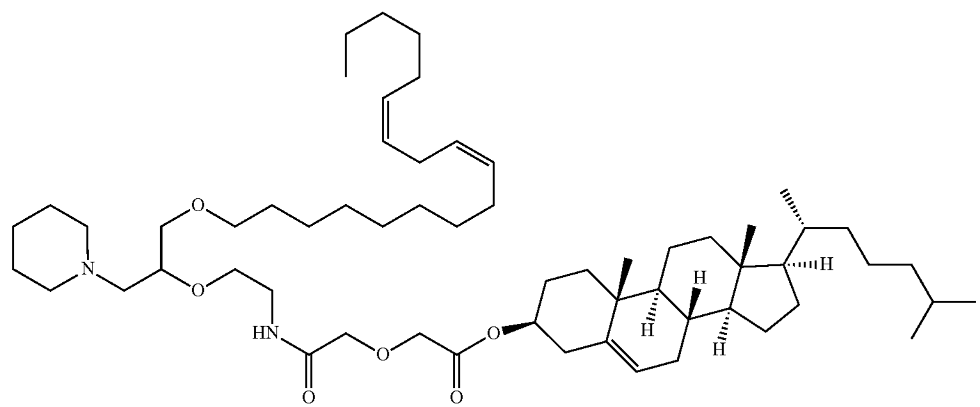 | $H^5$ | $Y^{1-i}$ | $L^{c\text{-}xix}$ |

TABLE 6-continued

Characterization and structures for Cationic Lipids

| Lipid | Structure | $R^1$—N—$R^2$ | $Y^1$ | L |
|---|---|---|---|---|
| E0106 | 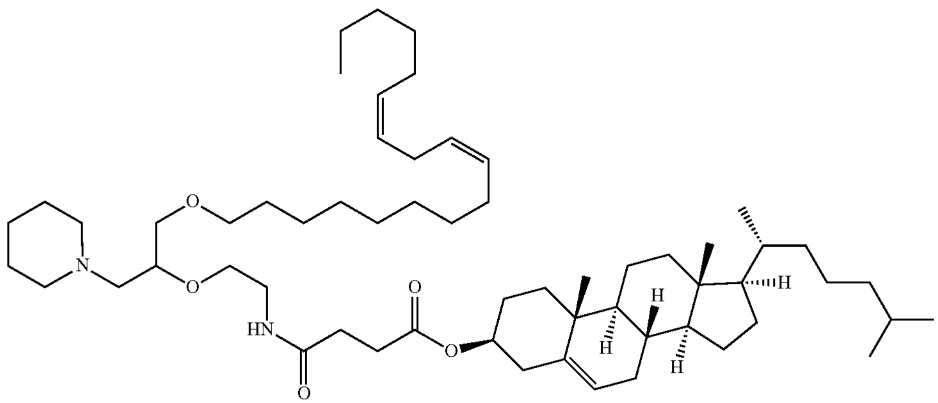 | $H^5$ | $Y^{1-i}$ | $L^{c-xx}$ |
| E0107 | 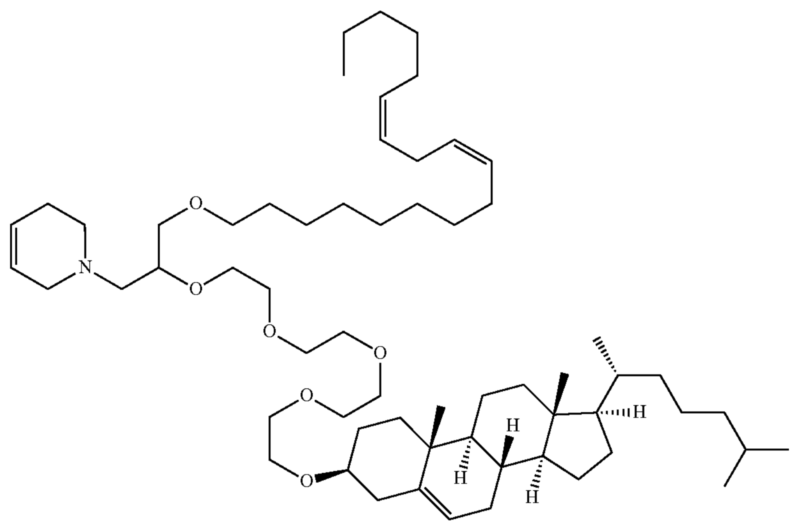 | $H^{16}$ | $Y^{1-i}$ | $L^{c-ix}$ |

TABLE 6-continued

Characterization and structures for Cationic Lipids

| Lipid | Structure | $R^1$—N—$R^2$ | $Y^1$ | L |
|---|---|---|---|---|
| E0108 | 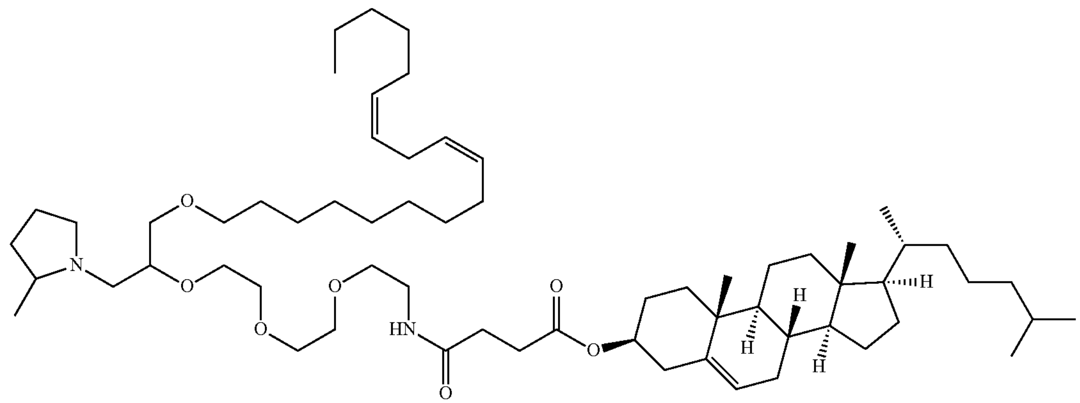 | $H^{12/26}$ | $Y^{1-i}$ | $L^{c-xi}$ |
| E0109 | 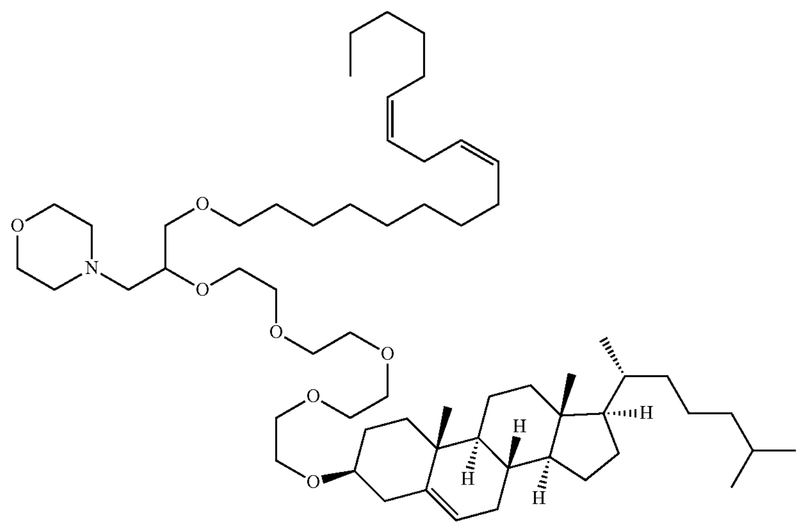 | $H^1$ | $Y^{1-i}$ | $L^{c-ix}$ |

TABLE 6-continued

Characterization and structures for Cationic Lipids

| Lipid | Structure | R¹—N—R² | Y¹ | L |
|---|---|---|---|---|
| E0110 | 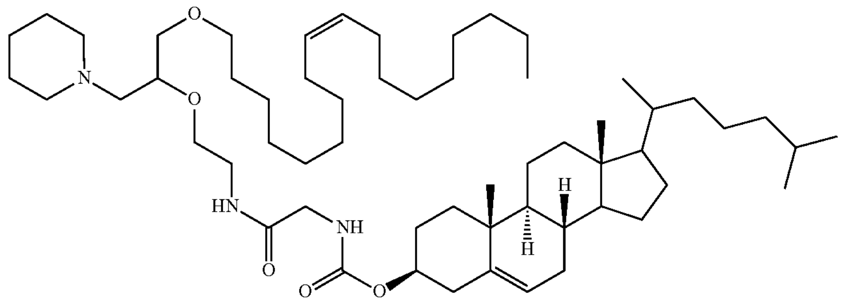 | H⁵ | Y$^{1-i}$ | L$^{c-xxii}$ |
| E0111 | 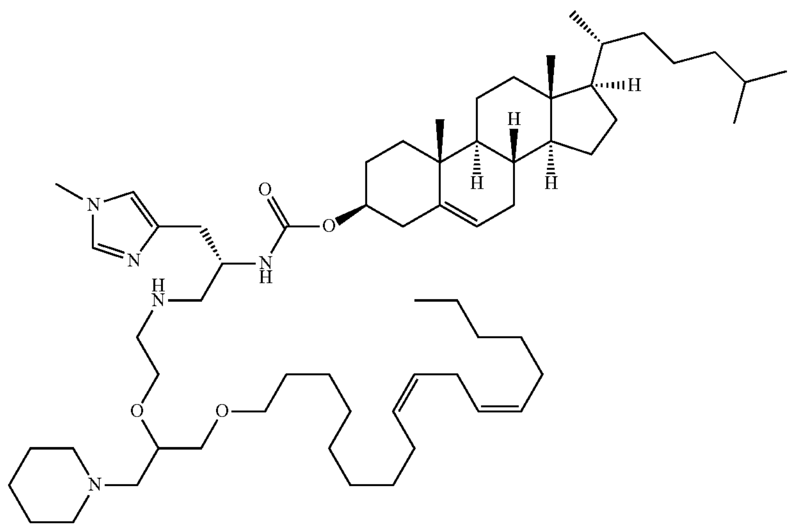 | H⁵ | Y$^{1-i}$ | L$^{c-xxiii}$ |

TABLE 6-continued

Characterization and structures for Cationic Lipids

| Lipid | Structure | $R^1$—N—$R^2$ | $Y^1$ | $Y^{1-i}$ | L | $L^{c-x}$ |
|---|---|---|---|---|---|---|
| E0112 | 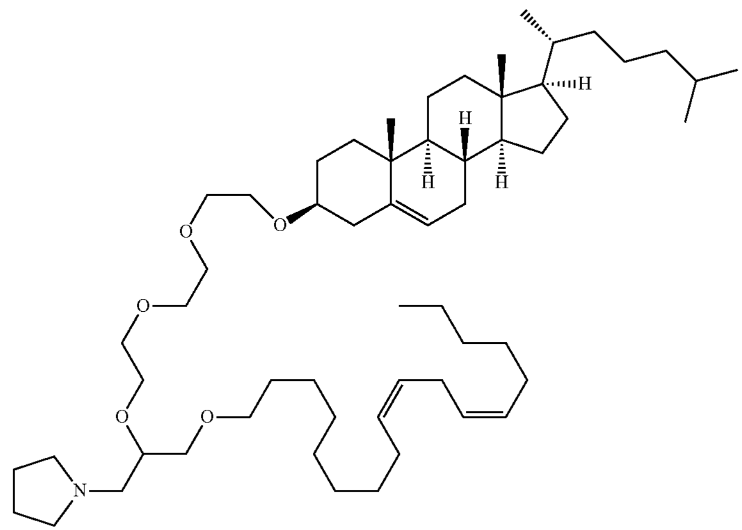 | $H^7$ | | | | |

TABLE 6-continued
Characterization and structures for Cationic Lipids
| Lipid | Structure | $R^1$—N—$R^2$ | $Y^1$ | $Y^{1-i}$ | L | $L^{c-ix}$ |
|---|---|---|---|---|---|---|
| E0113 | 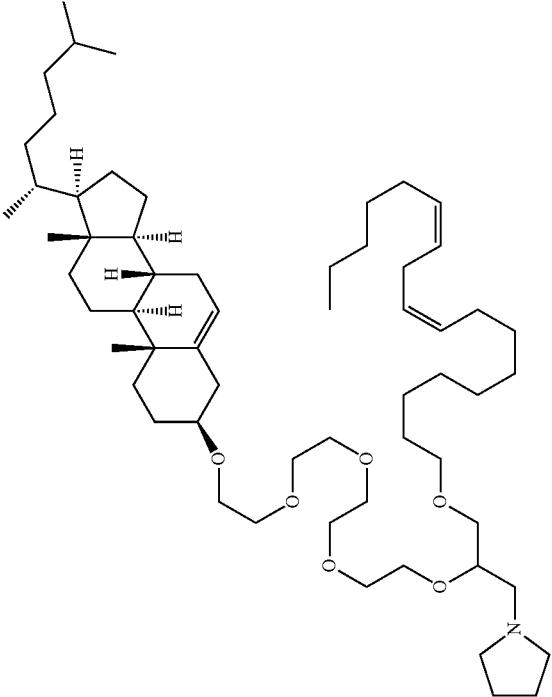 | $H^7$ | | | | |

TABLE 6-continued

Characterization and structures for Cationic Lipids

| Lipid | Structure | R¹—N—R² | Y¹ | L |
|---|---|---|---|---|
| E0114 | 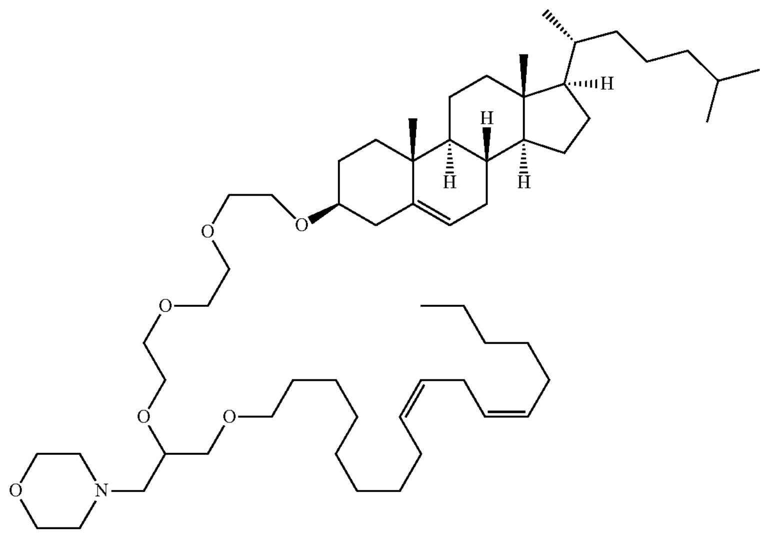 | H¹ | Y$^{1-i}$ | L$^{c-x}$ |
| E0115 | 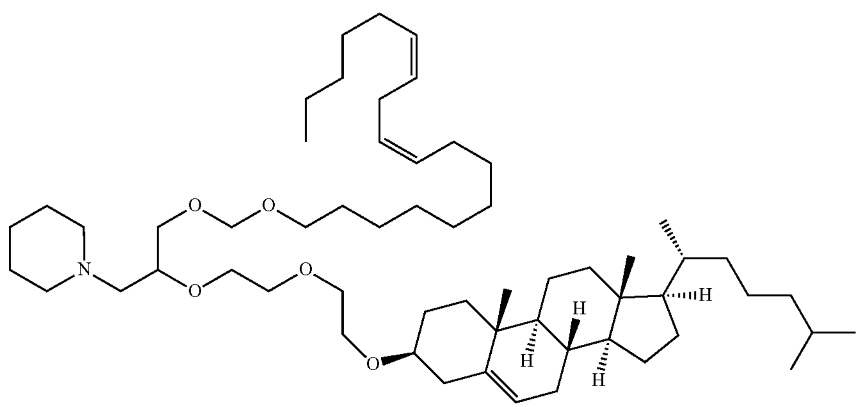 | H⁵ | Y$^{1-vi}$ | L$^{c-i}$ |

TABLE 6-continued

Characterization and structures for Cationic Lipids

| Lipid | Structure | $R^1$—N—$R^2$ | $Y^1$ | L |
|---|---|---|---|---|
| E0116 | 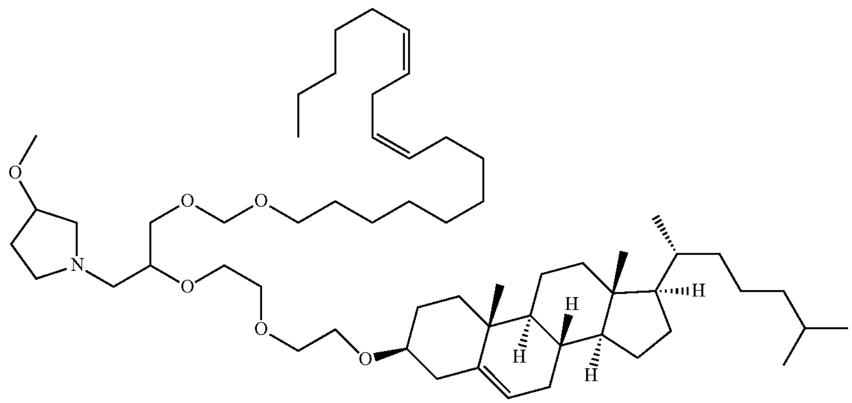 | $H^{35}$ | $Y^{1-vi}$ | $L^{c-i}$ |
| E0117 | 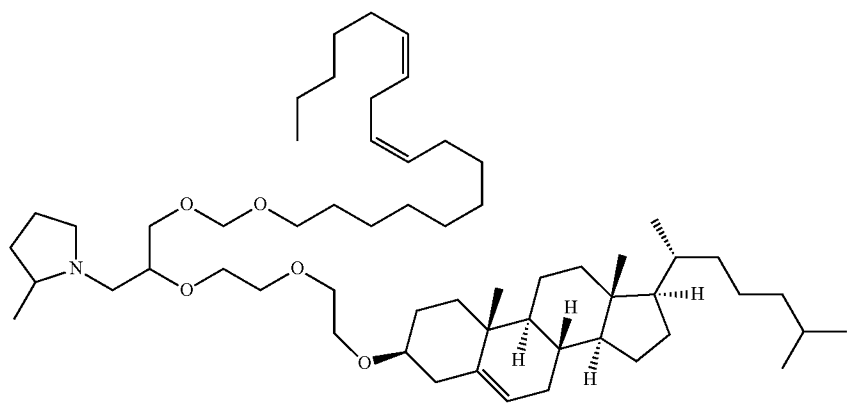 | $H^{12/26}$ | $Y^{1-vi}$ | $L^{c-i}$ |
| E0118 | Another mixture of the isomers E0053 and E0052 | $H^{12/26}$ | $Y^{1-i}$ | $L^{c-i}$ |

TABLE 6-continued

Characterization and structures for Cationic Lipids

| Lipid | Structure | $R^1$—N—$R^2$ | $Y^1$ | L |
|---|---|---|---|---|
| E0119 | 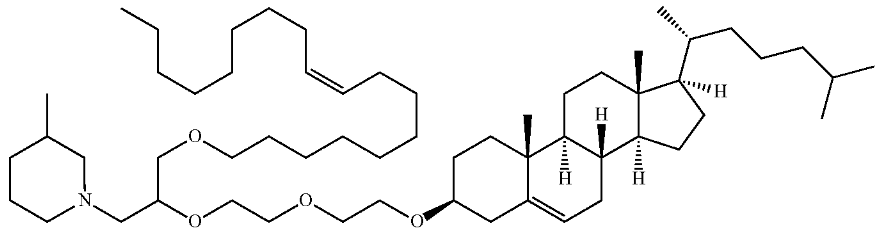 | $H^{25}$ | $Y^{1-iv}$ | $L^{c-i}$ |
| E0120 | 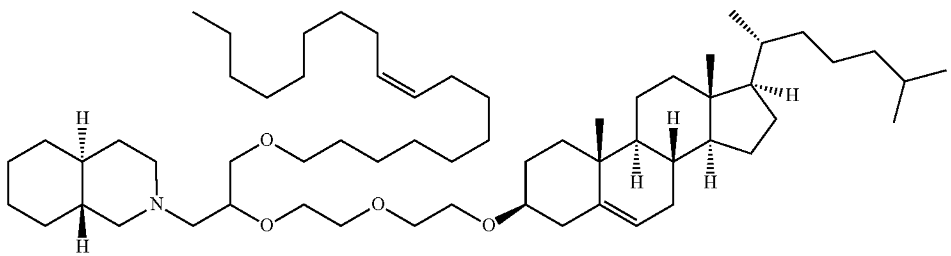 | $H^{21}$ | $Y^{1-iv}$ | $L^{c-i}$ |
| E0121 | 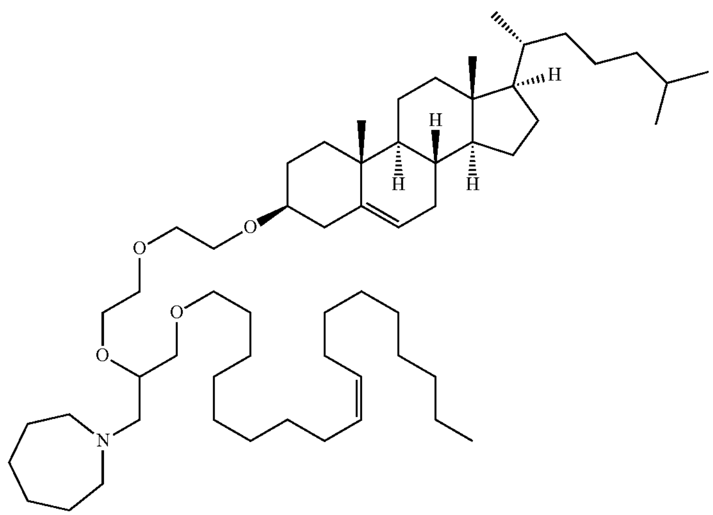 | $H^{14}$ | $Y^{1-iv}$ | $L^{c-i}$ |

TABLE 6-continued

Characterization and structures for Cationic Lipids

| Lipid | Structure | $R^1$—N—$R^2$ | $Y^1$ | L |
|---|---|---|---|---|
| E0122 | 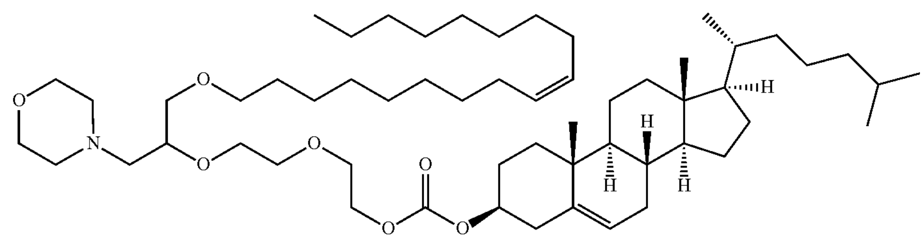 | $H^1$ | $Y^{1-iv}$ | $L^{c-xviii}$ |
| E0123 | 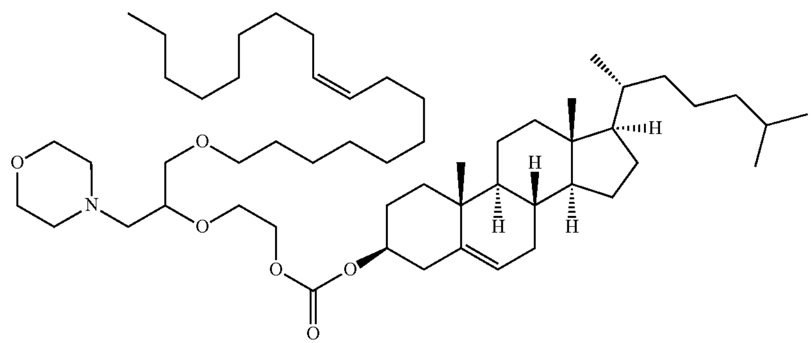 | $H^1$ | $Y^{1-iv}$ | $L^{c-xxiv}$ |

TABLE 6-continued

Characterization and structures for Cationic Lipids

| Lipid | Structure | $R^1$—N—$R^2$ | $Y^1$ | L |
|---|---|---|---|---|
| E0124 | 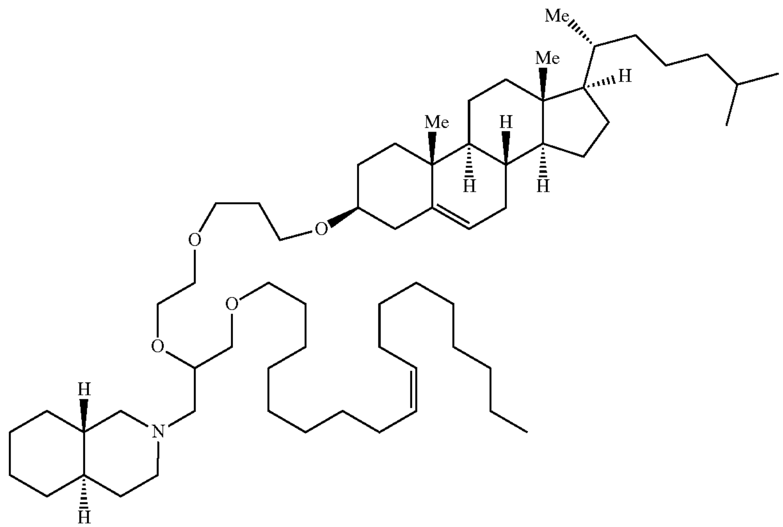 | $H^{21}$ | $Y^{1-iv}$ | $L^{c-vii}$ |
| E0125 | 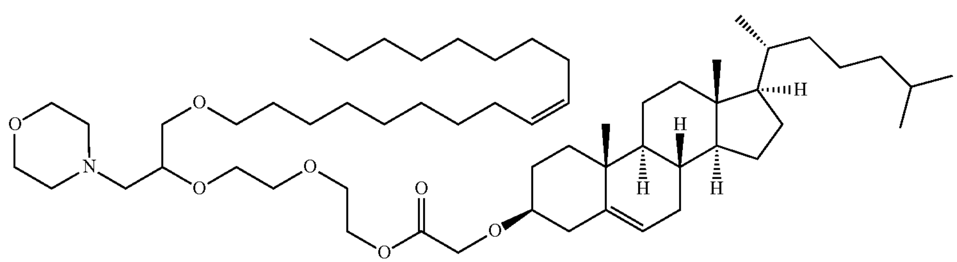 | $H^1$ | $Y^{1-iv}$ | $L^{c-xxv}$ |

TABLE 6-continued

Characterization and structures for Cationic Lipids

| Lipid | Structure | $R^1$—N—$R^2$ | $Y^1$ | L |
|---|---|---|---|---|
| E0126 | 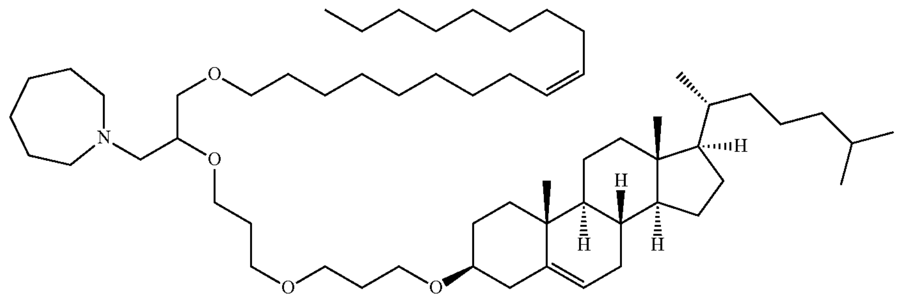 | $H^{14}$ | $Y^{1-iv}$ | $L^{c-vii}$ |
| E0127 | 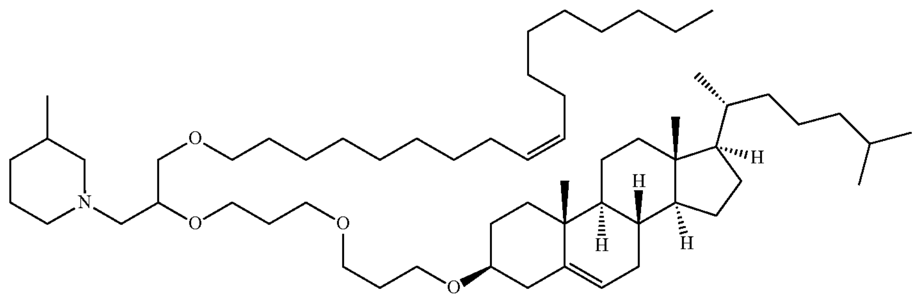 | $H^{25}$ | $Y^{1-iv}$ | $L^{c-vii}$ |

TABLE 6-continued
Characterization and structures for Cationic Lipids
| Lipid | Structure | R¹—N—R² | Y¹ | L |
|---|---|---|---|---|
| E0128 | 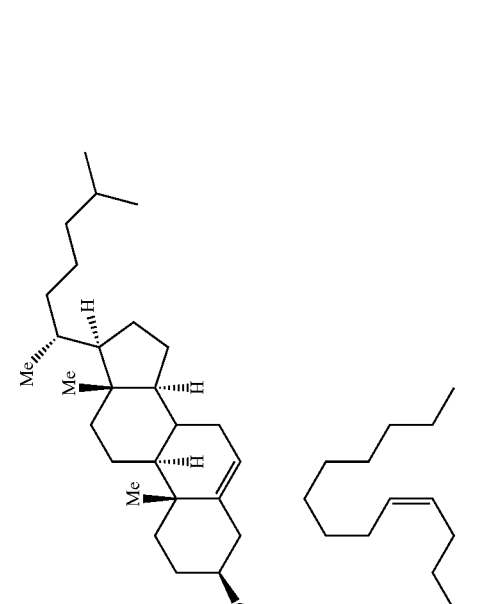 | H¹ | Y$^{1\text{-}iv}$ | L$^{c\text{-}xxvi}$ |
| E0129 | 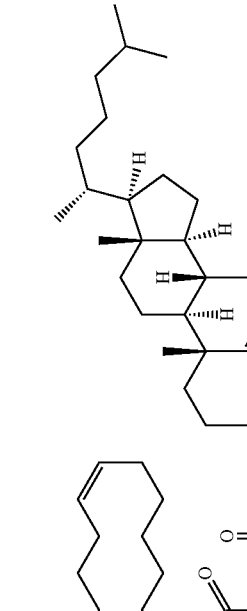 | H⁴⁹ | Y$^{1\text{-}iv}$ | L$^{c\text{-}xxvii}$ |

TABLE 6-continued

Characterization and structures for Cationic Lipids

| Lipid | Structure | R¹—N—R² | Y¹ | L |
|---|---|---|---|---|
| E0130 | 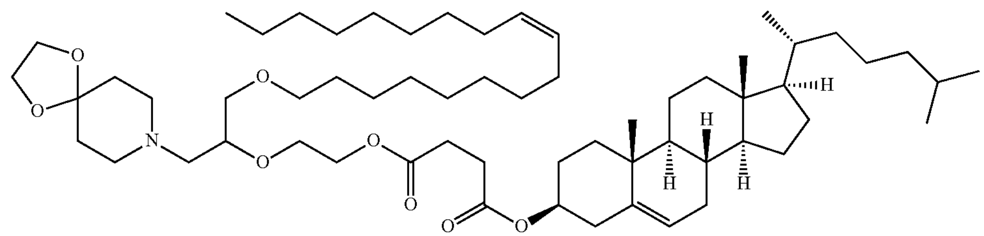 | H⁸ | Y^{1-iv} | L^{c-xvii} |
| E0131 | 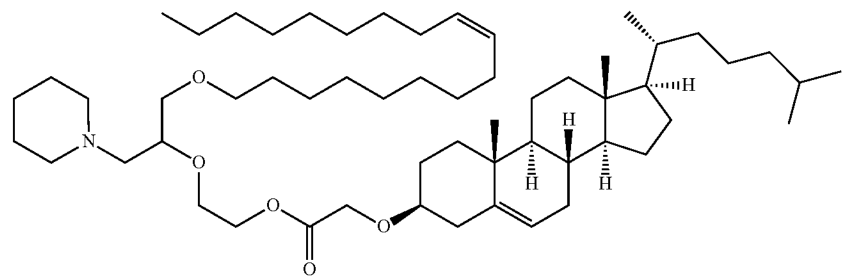 | H⁵ | Y^{1-iv} | L^{c-xxvi} |
| E0132 | 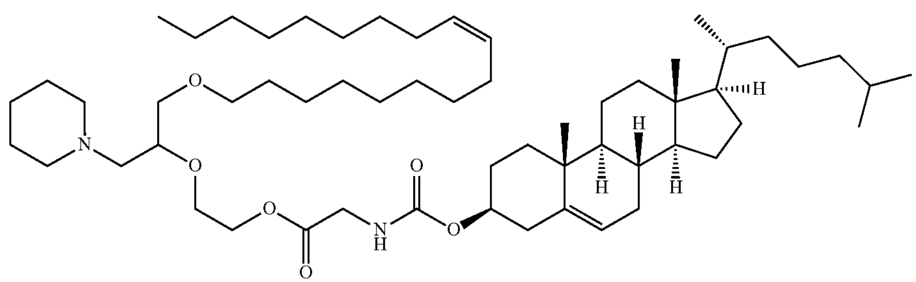 | H⁵ | Y^{1-iv} | L^{c-xxvii} |

TABLE 6-continued

Characterization and structures for Cationic Lipids

| Lipid | Structure | $R^1$—N—$R^2$ | $Y^1$ | L |
|---|---|---|---|---|
| E0133 | 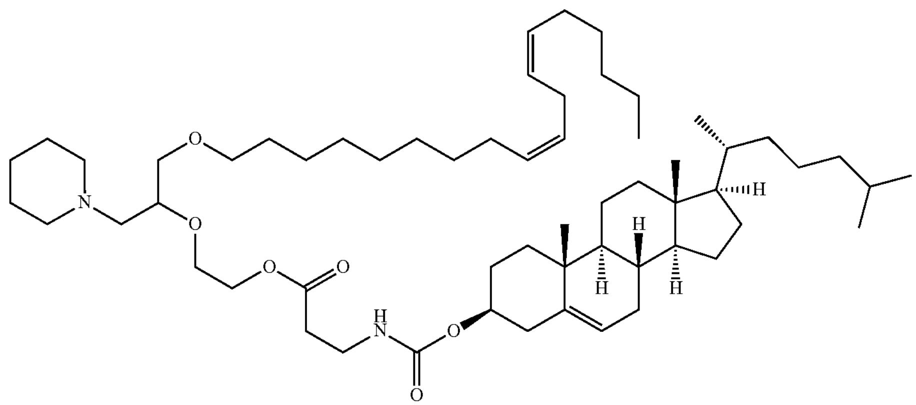 | $H^5$ | $Y^{1-i}$ | $L^{c-xxviii}$ |
| E0134 | 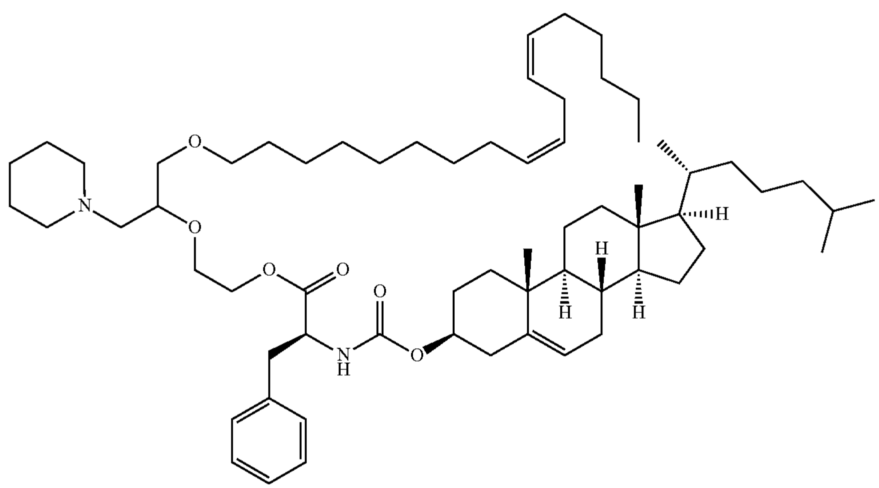 | $H^5$ | $Y^{1-i}$ | $L^{c-xxix}$ |

TABLE 6-continued

Characterization and structures for Cationic Lipids

| Lipid | Structure | $R^1$—N—$R^2$ | $Y^1$ | L |
|---|---|---|---|---|
| E0135 | 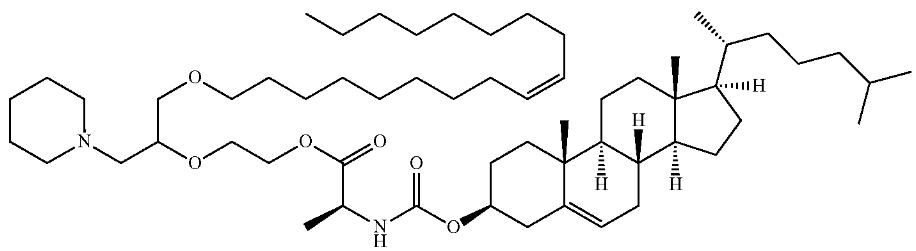 | $H^5$ | $Y^{1-iv}$ | $L^{c-xxx}$ |
| E0136 | 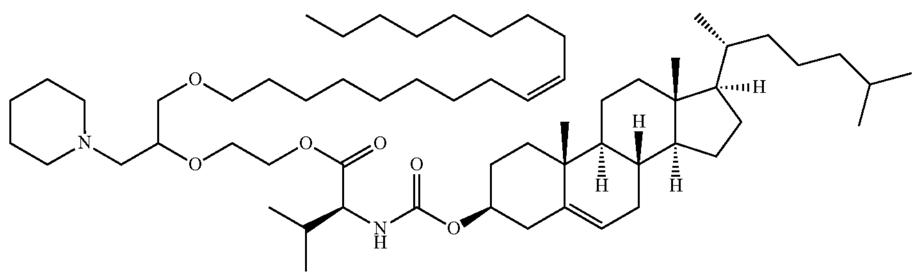 | $H^5$ | $Y^{1-iv}$ | $L^{c-xxxi}$ |
| E0137 | 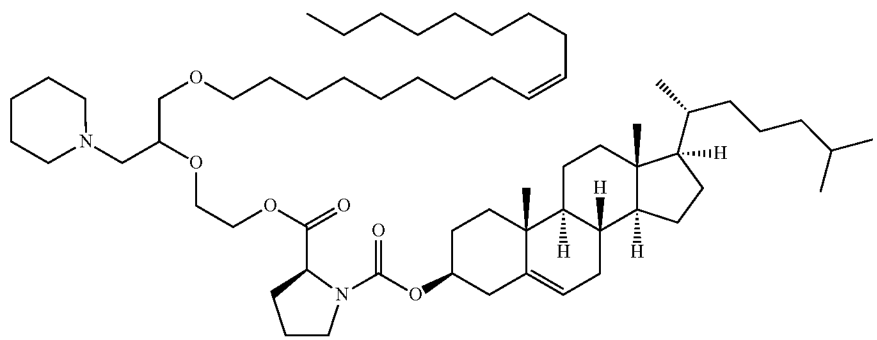 | $H^5$ | $Y^{1-iv}$ | $L^{c-xxxii}$ |

TABLE 6-continued

Characterization and structures for Cationic Lipids

| Lipid | Structure | R$^1$—N—R$^2$ | Y$^1$ | L |
|---|---|---|---|---|
| E0138 | 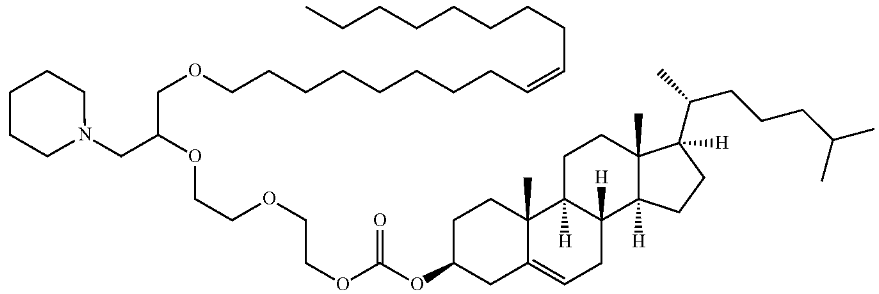 | H$^5$ | Y$^{1-iv}$ | L$^{c-xviii}$ |
| E0139 | 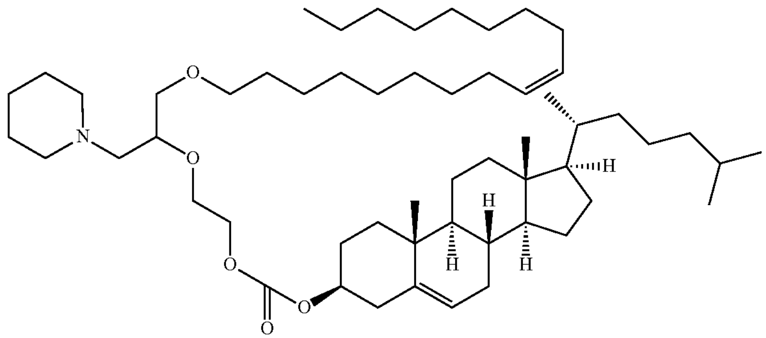 | H$^5$ | Y$^{1-iv}$ | L$^{c-xxiv}$ |
| E0140 | 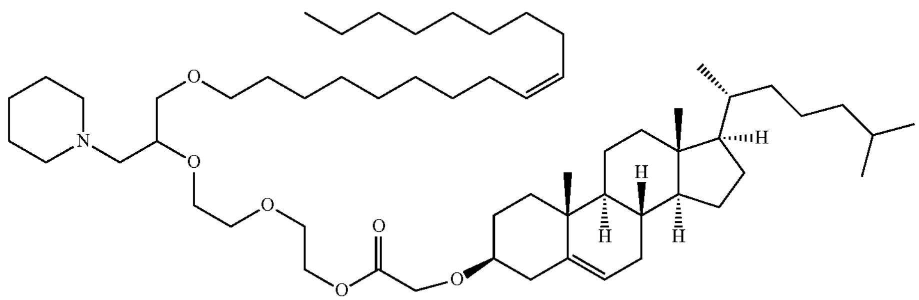 | H$^5$ | Y$^{1-iv}$ | L$^{c-xxv}$ |

TABLE 6-continued

Characterization and structures for Cationic Lipids

| Lipid | Structure | R¹—N—R² | Y¹ | L |
|---|---|---|---|---|
| E0141 | 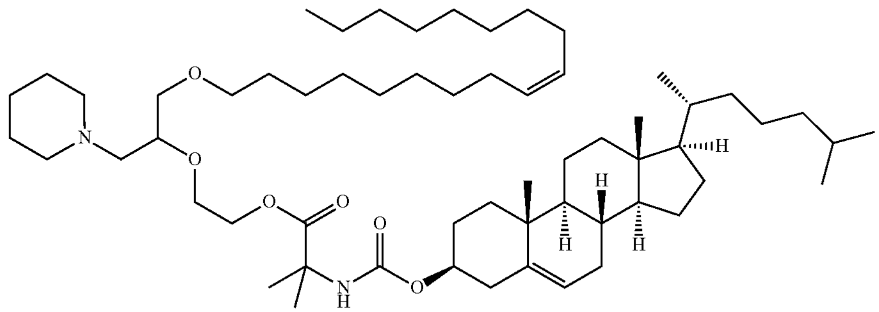 | H⁵ | Y$^{1-iv}$ | L$^{c-xxxiii}$ |
| E0142 | 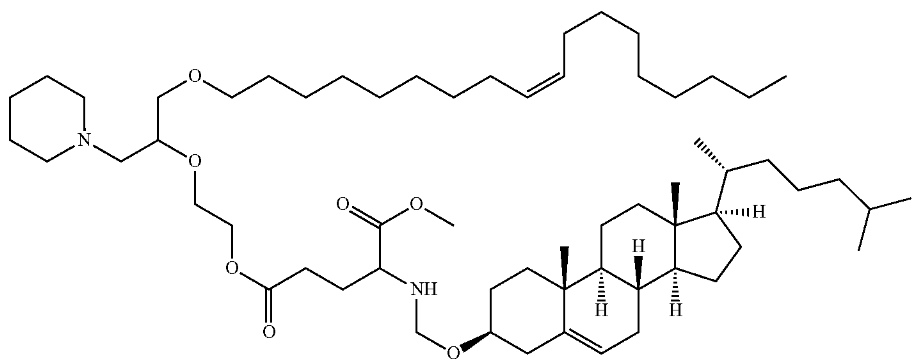 | H⁵ | Y$^{1-iv}$ | L$^{c-xxxiv}$ |

TABLE 6-continued

Characterization and structures for Cationic Lipids

| Lipid | Structure | $R^1$—N—$R^2$ | $Y^1$ | L |
|---|---|---|---|---|
| E0143 | 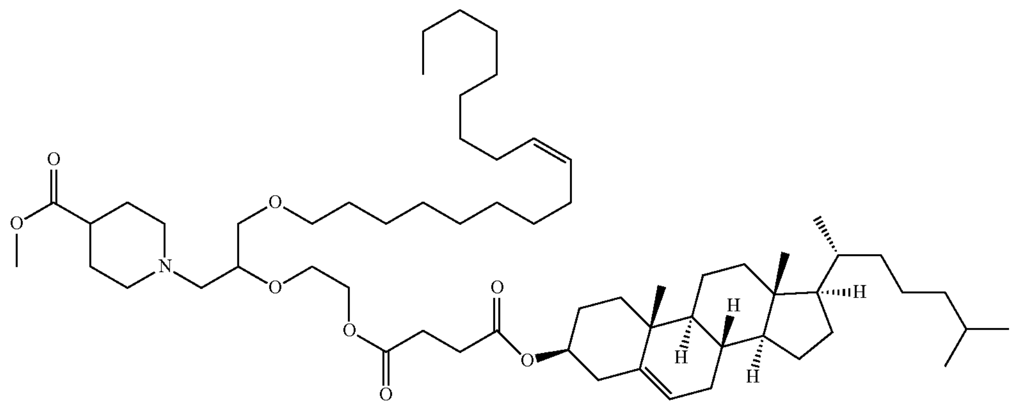 | $H^{50}$ | $Y^{1-iv}$ | $L^{c-xvii}$ |
| E0144 | 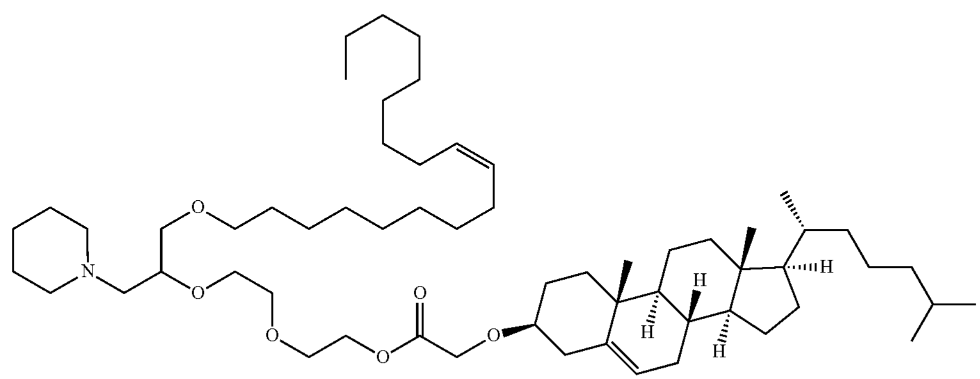 | $H^5$ | $Y^{1-iv}$ | $L^{c-xxv}$ |

TABLE 6-continued

Characterization and structures for Cationic Lipids

| Lipid | Structure | $R^1$—N—$R^2$ | $Y^1$ | L |
|---|---|---|---|---|
| E0145 | 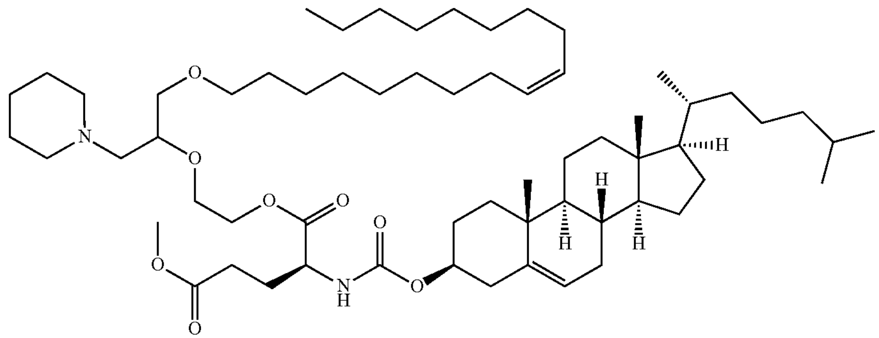 | $H^5$ | $Y^{1-iv}$ | $L^{c-xxxv}$ |
| E0146 | 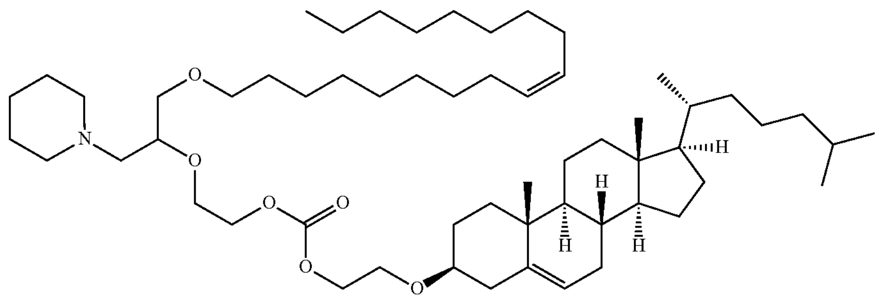 | $H^5$ | $Y^{1-iv}$ | $L^{c-xxxvi}$ |
| E0147 | 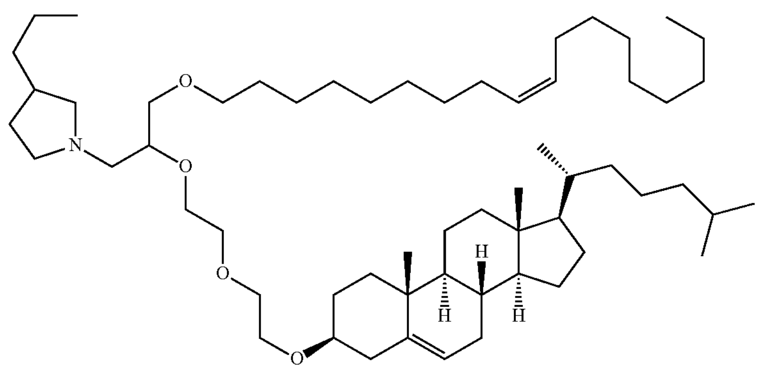 | $H^{27}$ | $Y^{1-iv}$ | $L^{c-i}$ |

TABLE 6-continued

Characterization and structures for Cationic Lipids

| Lipid | Structure | $R^1$—N—$R^2$ | $Y^1$ | L |
|---|---|---|---|---|
| E0148 | 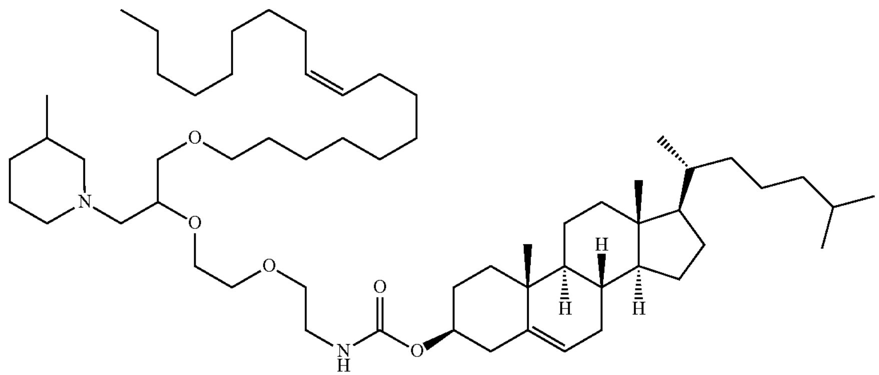 | $H^{25}$ | $Y^{1-iv}$ | $L^{c-vi}$ |
| E0149 | 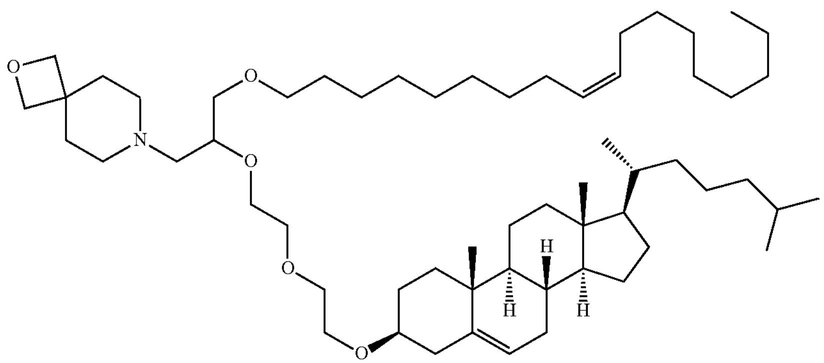 | $H^{51}$ | $Y^{1-iv}$ | $L^{c-i}$ |

TABLE 6-continued

Characterization and structures for Cationic Lipids

| Lipid | Structure | $R^1-N-R^2$ | $Y^1$ | L |
|---|---|---|---|---|
| E0150 | 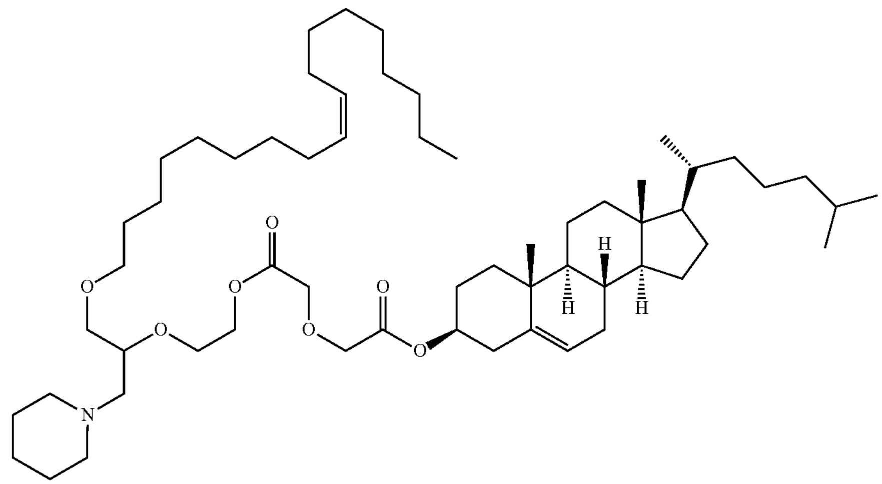 | $H^5$ | $Y^{1-iv}$ | $L^{c\text{-}xxxvii}$ |
| E0151 | 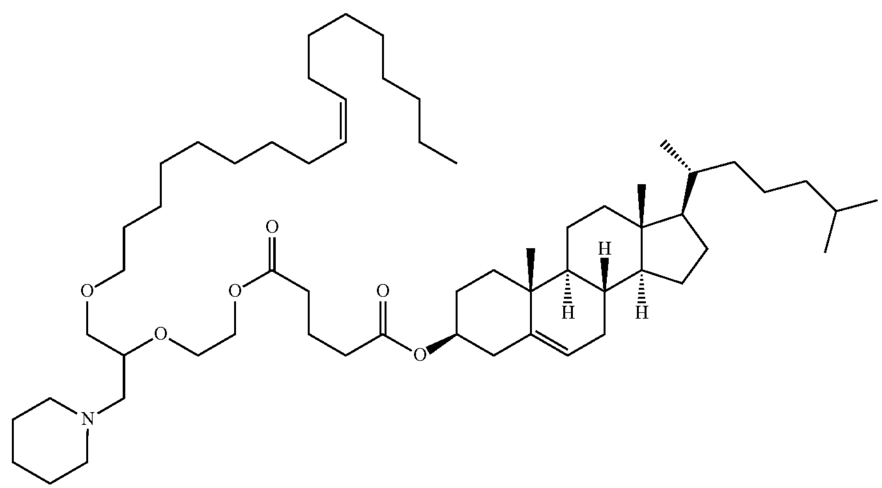 | $H^5$ | $Y^{1-iv}$ | $L^{c\text{-}xxxviii}$ |

TABLE 6-continued

Characterization and structures for Cationic Lipids

| Lipid | Structure | $R^1$—N—$R^2$ | $Y^1$ | L |
|---|---|---|---|---|
| E0152 | 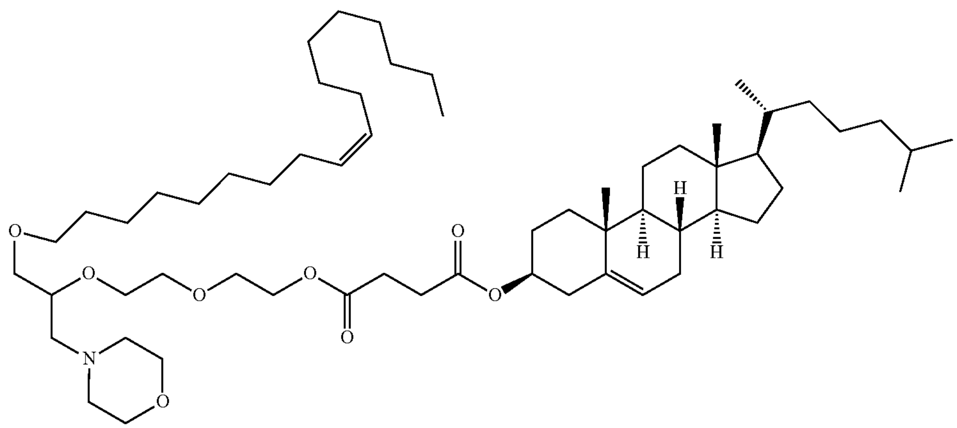 | $H^1$ | $Y^{1-iv}$ | $L^{c-xvi}$ |
| E0158 | 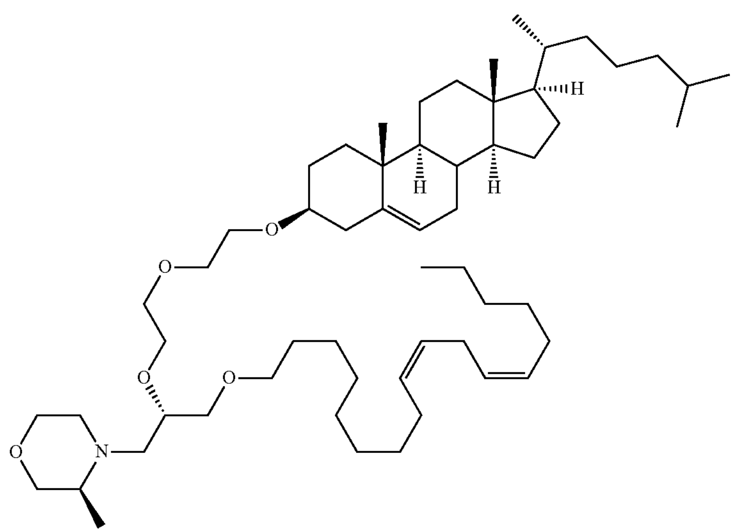 | $H^{52}$ | $Y^{1-i}$ | $L^{c-i}$ |

TABLE 6-continued

Characterization and structures for Cationic Lipids

| Lipid | Structure | $R^1$—N—$R^2$ | $Y^1$ | L |
|---|---|---|---|---|
| E0159 | 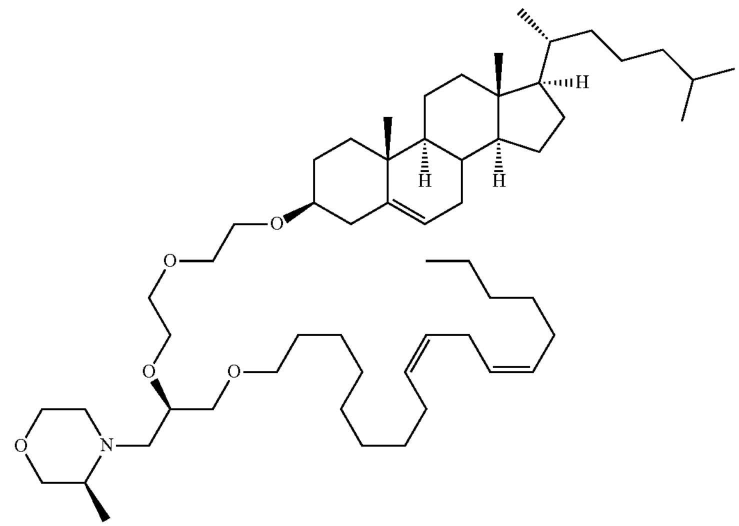 | $H^{52}$ | $Y^{I\text{-}i}$ | $L^{c\text{-}i}$ |
| E0160 | 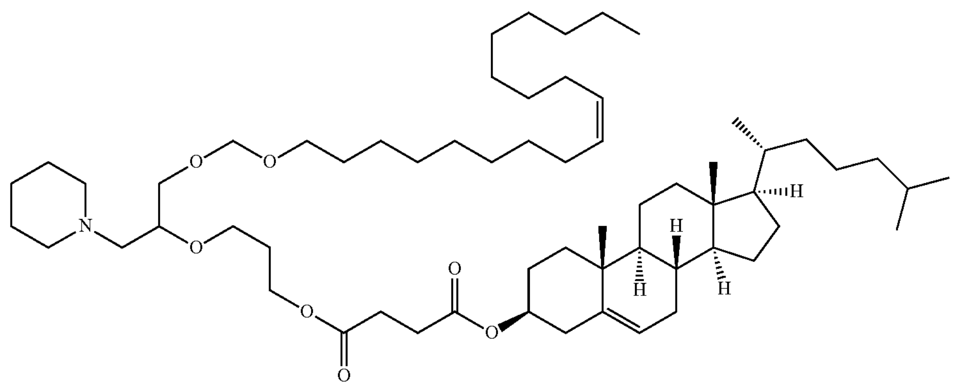 | $H^5$ | $Y^{I\text{-}vii}$ | $L^{c\text{-}xxxix}$ |

TABLE 6-continued

Characterization and structures for Cationic Lipids

| Lipid | Structure | $R^1$—N—$R^2$ | $Y^1$ | L |
|---|---|---|---|---|
| E0161 | 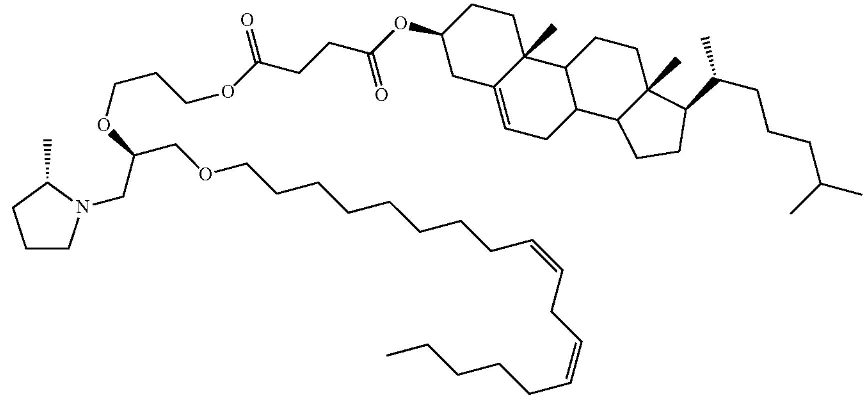 [SMILES: CCCCC/C=C\C/C=C\CCCCCCCCOC[C@@H](CN1CCC[C@@H]1C)OCCCOC(=O)CCC(=O)O[C@H]1CC[C@@]2(C)C(=CCC3C2CC[C@@]2(C)C3CC[C@@H]2[C@H](C)CCCC(C)C)C1] | $H^{26}$ | $Y^{J\text{-}i}$ | $L^{c\text{-}xxxix}$ |
| E0162 | 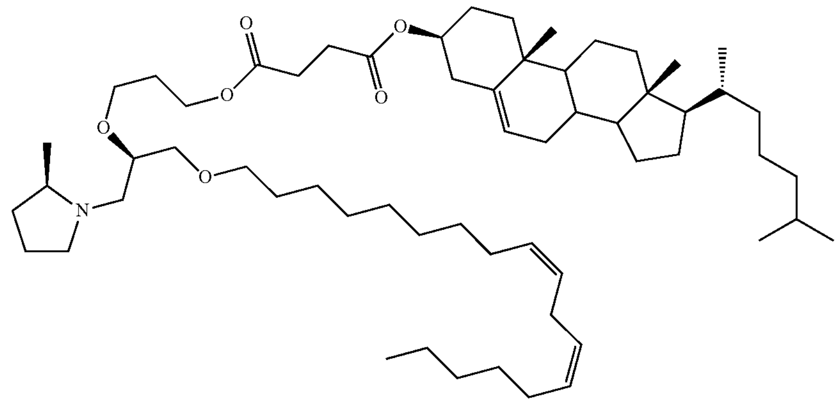 [SMILES: CCCCC/C=C\C/C=C\CCCCCCCCOC[C@@H](CN1CCC[C@H]1C)OCCCOC(=O)CCC(=O)O[C@H]1CC[C@@]2(C)C(=CCC3C2CC[C@@]2(C)C3CC[C@@H]2[C@H](C)CCCC(C)C)C1] | $H^{12}$ | $Y^{J\text{-}i}$ | $L^{c\text{-}xxxix}$ |

TABLE 6-continued

Characterization and structures for Cationic Lipids

| Lipid | Structure | $R^1$—N—$R^2$ | $Y^1$ | L |
|---|---|---|---|---|
| E0163 | 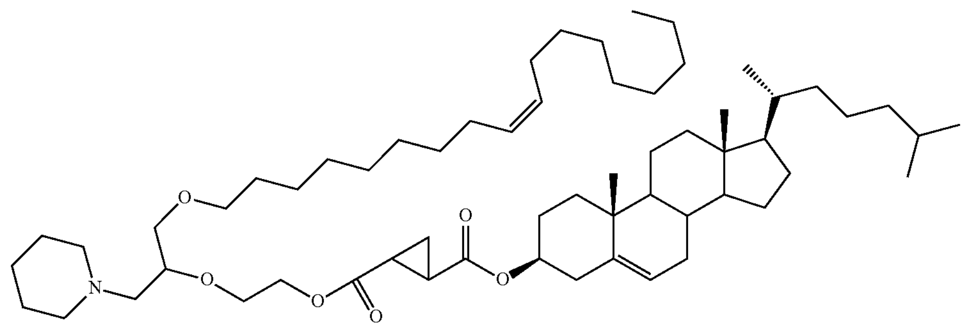 [SMILES: CCCCCCCC/C=C\CCCCCCCCOCC(CN1CCCCC1)OCCOC(=O)C1CC1C(=O)O[C@H]1CC[C@@]2(C)C(=CCC3C2CC[C@@]2(C)C3CC[C@@H]2[C@H](C)CCCC(C)C)C1] | $H^5$ | $Y^{1\text{-}iv}$ | $L^{c\text{-}xxxx}$ |
| E0164 | 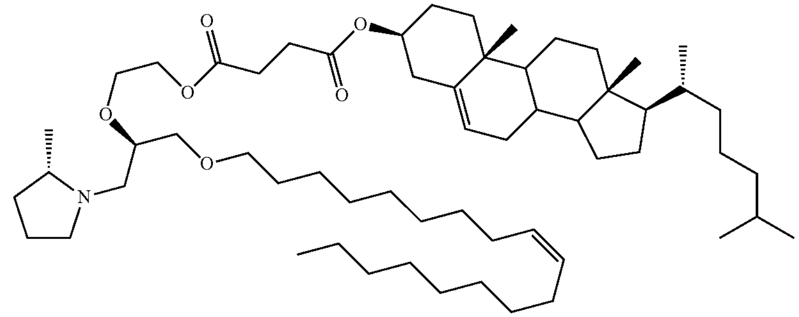 [SMILES: CCCCCCCC/C=C\CCCCCCCCOC[C@@H](CN1CCC[C@@H]1C)OCCOC(=O)CCC(=O)O[C@H]1CC[C@@]2(C)C(=CCC3C2CC[C@@]2(C)C3CC[C@@H]2[C@H](C)CCCC(C)C)C1] | $H^{26}$ | $Y^{1\text{-}iv}$ | $L^{c\text{-}xvii}$ |
| E0165 | 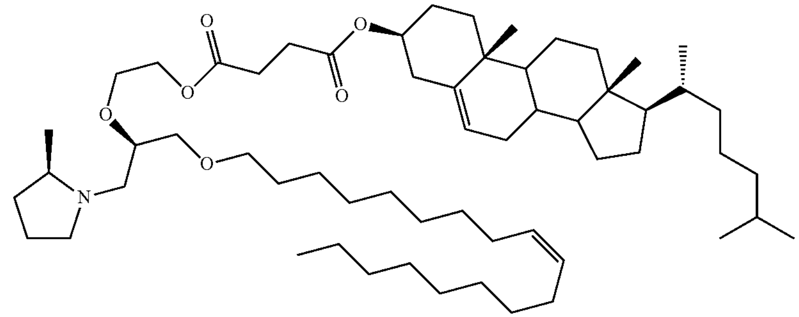 [SMILES: CCCCCCCC/C=C\CCCCCCCCOC[C@@H](CN1CCC[C@H]1C)OCCOC(=O)CCC(=O)O[C@H]1CC[C@@]2(C)C(=CCC3C2CC[C@@]2(C)C3CC[C@@H]2[C@H](C)CCCC(C)C)C1] | $H^{12}$ | $Y^{1\text{-}iv}$ | $L^{c\text{-}xvii}$ |

TABLE 6-continued

Characterization and structures for Cationic Lipids

| Lipid | Structure | $R^1$—N—$R^2$ | $Y^1$ | L |
|---|---|---|---|---|
| E0166 | 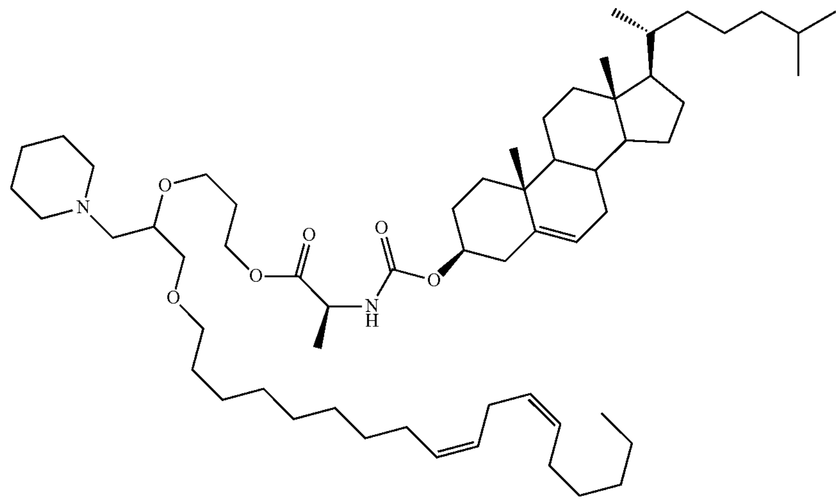 [SMILES: CCCCC/C=C\C/C=C\CCCCCCCCOCC(CN1CCCCC1)OCCCOC(=O)[C@H](C)NC(=O)O[C@H]1CC[C@@]2(C)C(=CCC3C2CC[C@@]2(C)C3CC[C@@H]2[C@H](C)CCCC(C)C)C1] | $H^5$ | $Y^{l\text{-}i}$ | $L^{c\text{-}xxxxi}$ |
| E0167 | 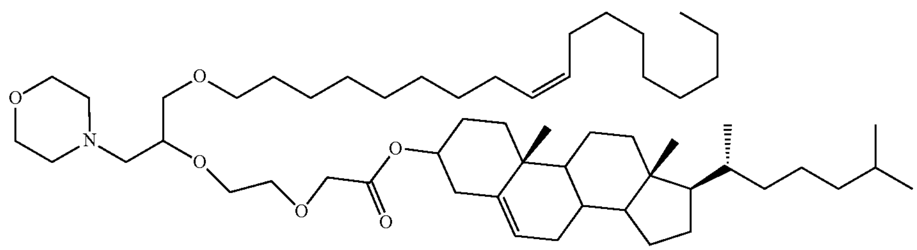 [SMILES: CCCCCCCC/C=C\CCCCCCCCOCC(CN1CCOCC1)OCCOCC(=O)OC1CC[C@@]2(C)C(=CCC3C2CC[C@@]2(C)C3CC[C@@H]2[C@H](C)CCCC(C)C)C1] | $H^1$ | $Y^{l\text{-}iv}$ | $L^{c\text{-}xxxxii}$ |

TABLE 6-continued

Characterization and structures for Cationic Lipids

| Lipid | Structure | $R^1$—N—$R^2$ | $Y^1$ | L |
|---|---|---|---|---|
| E0168 | 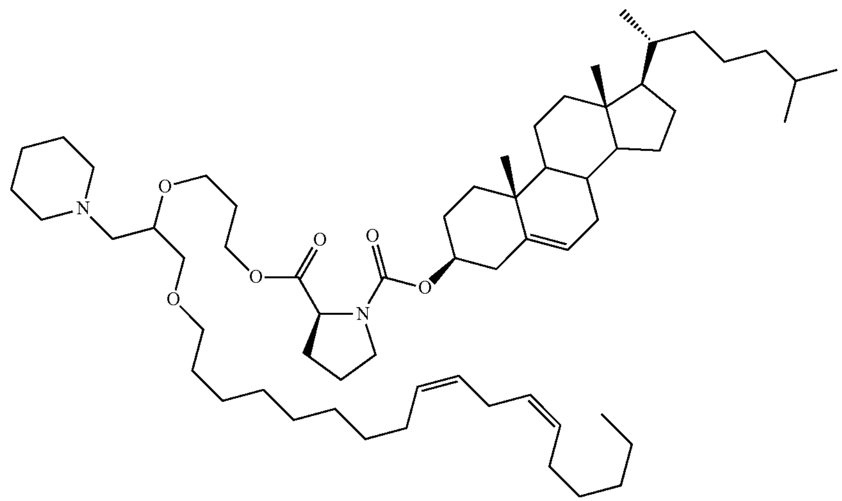 [SMILES: CCCCC/C=C\C/C=C\CCCCCCCCOCC(CN1CCCCC1)OCCCOC(=O)[C@@H]1CCCN1C(=O)O[C@H]1CC[C@@]2(C)C(=CCC3C2CC[C@@]2(C)C3CC[C@@H]2[C@H](C)CCCC(C)C)C1] | $H^5$ | $Y^{i\text{-}i}$ | $L^{c\text{-}xxxxiii}$ |

TABLE 6-continued
Characterization and structures for Cationic Lipids
| Lipid | Structure | $R^1$—N—$R^2$ | $Y^1$ | L |
|---|---|---|---|---|
| E0169 | 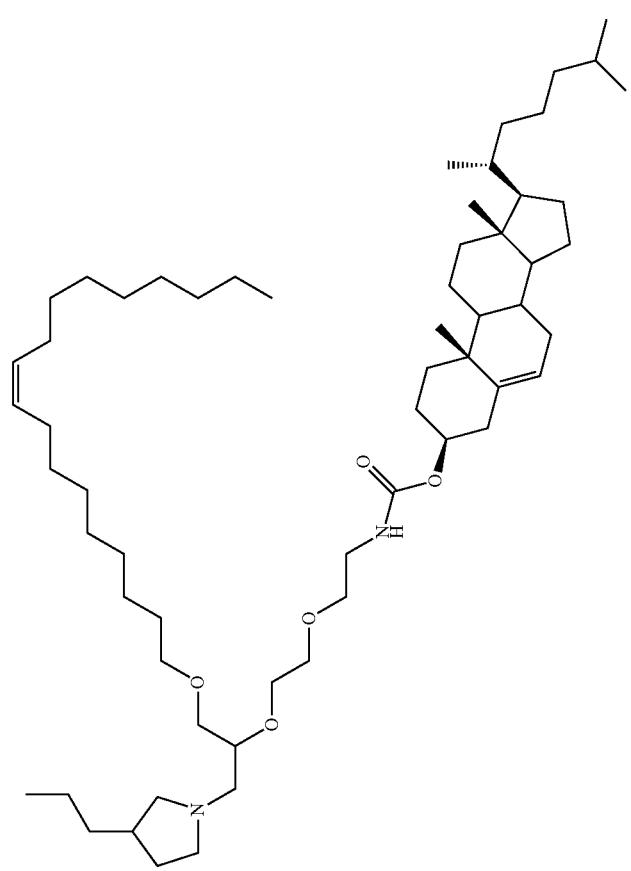 | $H^{27}$ | $Y^{i\text{-}iv}$ | $L^{c\text{-}vi}$ |

TABLE 6-continued

Characterization and structures for Cationic Lipids

| Lipid | Structure | $R^1$—N—$R^2$ | $Y^1$ | $Y^{1-i}$ | L | $L^{c-i}$ |
|---|---|---|---|---|---|---|
| E0170 | Chiral | $H^6$ | | | | |

TABLE 6-continued

Characterization and structures for Cationic Lipids

| Lipid | Structure | $R^1$—N—$R^2$ | $Y^1$ | L |
|---|---|---|---|---|
| | | $H^{18}$ | $Y^{i\text{-}i}$ | $L^{c\text{-}i}$ |
| E0171 | Chiral | | | |

TABLE 6-continued

Characterization and structures for Cationic Lipids

| Lipid | | Structure | $R^1$—N—$R^2$ | $Y^1$ | L |
|---|---|---|---|---|---|
| | | | | $Y^{f\text{-}i}$ | $L^{c\text{-}i}$ |
| E0172 (comparative) | Chiral | 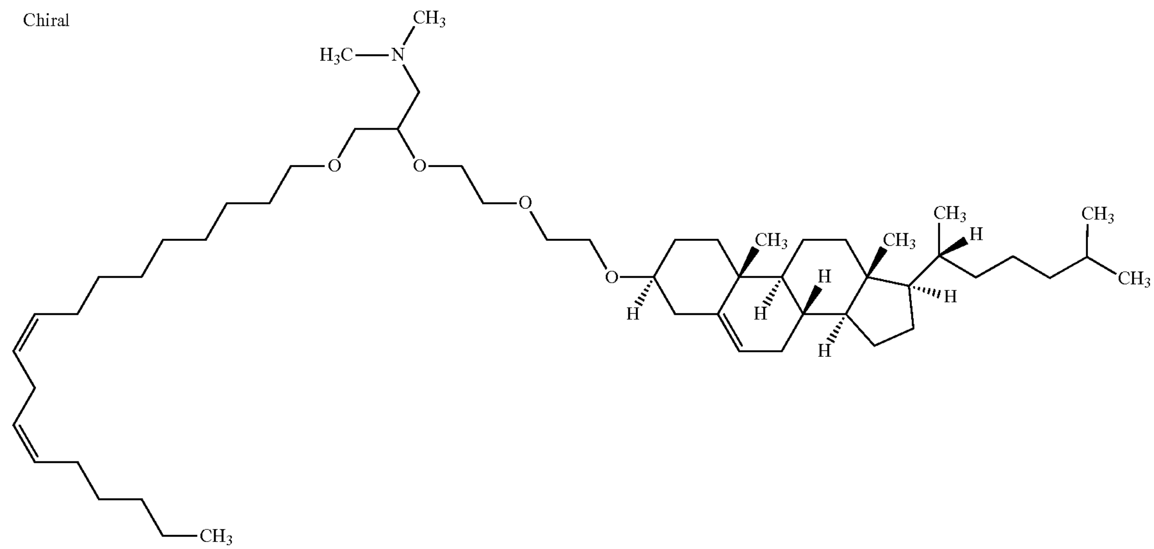 | | | |

TABLE 6-continued
Characterization and structures for Cationic Lipids
| Lipid | Structure | $R^1$—N—$R^2$ | $Y^1$ | L |
|---|---|---|---|---|
| E0173 (comparative) | Chiral 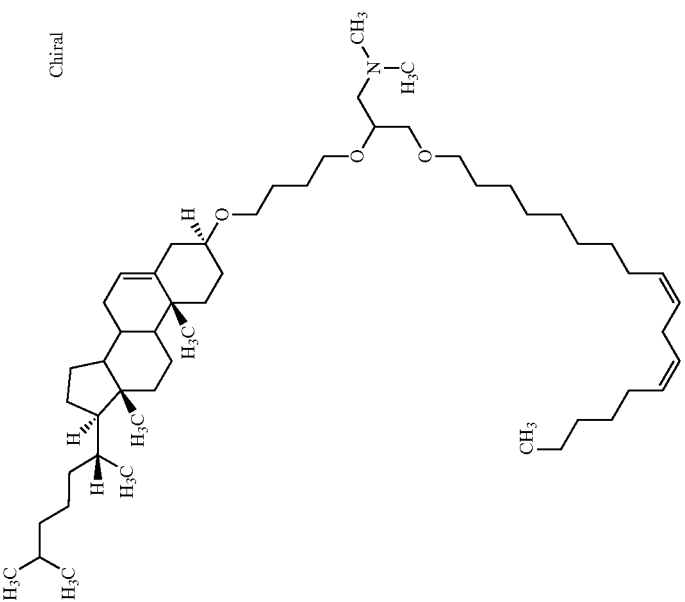 | | $Y^{I\text{-}i}$ | $L^{c\text{-}ii}$ |

TABLE 6-continued

Characterization and structures for Cationic Lipids

| Lipid | Structure | $R^1$—N—$R^2$ | $Y^1$ | L |
|---|---|---|---|---|
| E0174 (comparative) | Chiral | | $Y^{1-i}$ | $L^{c-iii}$ |
| E0175 | 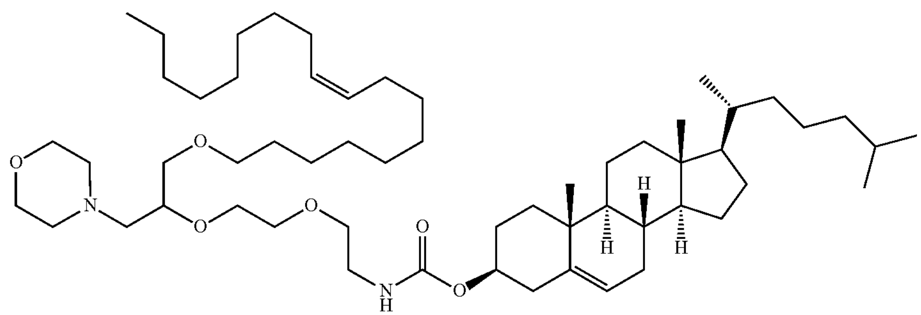 | $H^1$ | $Y^{1-iv}$ | $L^{c-vi}$ |

TABLE 6-continued

Characterization and structures for Cationic Lipids

| Lipid | Structure | $R^1$—N—$R^2$ | $Y^1$ | L |
|---|---|---|---|---|
| E0176 | 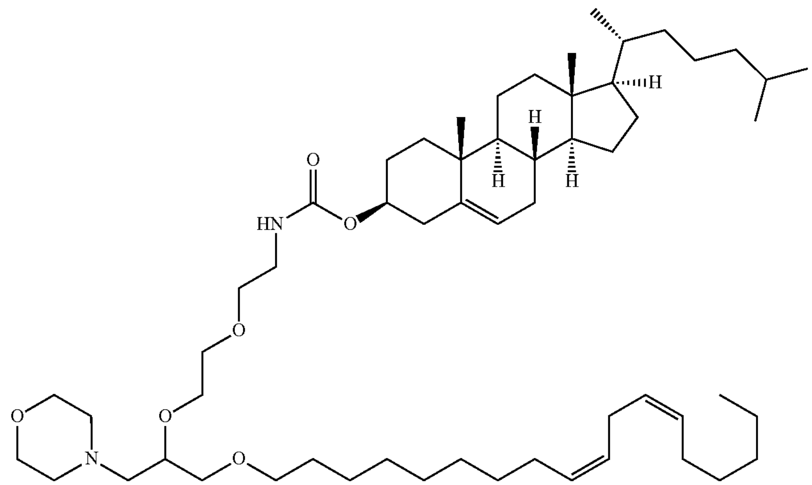 | $H^1$ | $Y^{l-i}$ | $L^{c-vi}$ |
| E0177 | 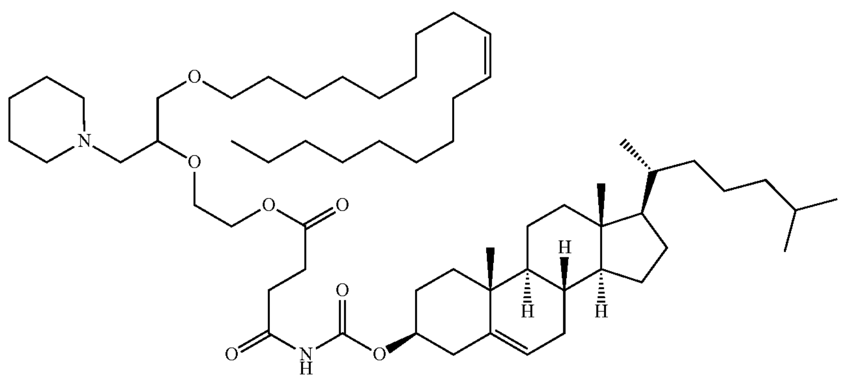 | $H^5$ | $Y^{l-iv}$ | $L^{c-xvii}$ |

TABLE 6-continued
Characterization and structures for Cationic Lipids
| Lipid | Structure | $R^1\text{—}N\text{—}R^2$ | $Y^1$ | L |
|---|---|---|---|---|
| E0178 | 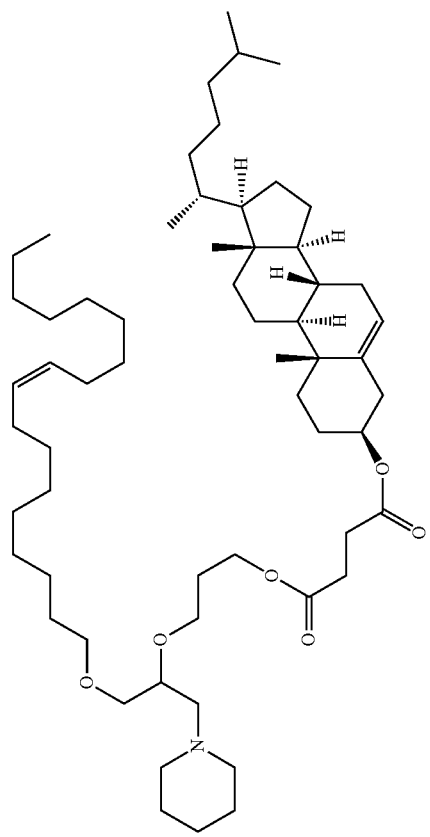 | $H^5$ | $Y^{1-iv}$ | $L^{c-xxxix}$ |
| E0179 | 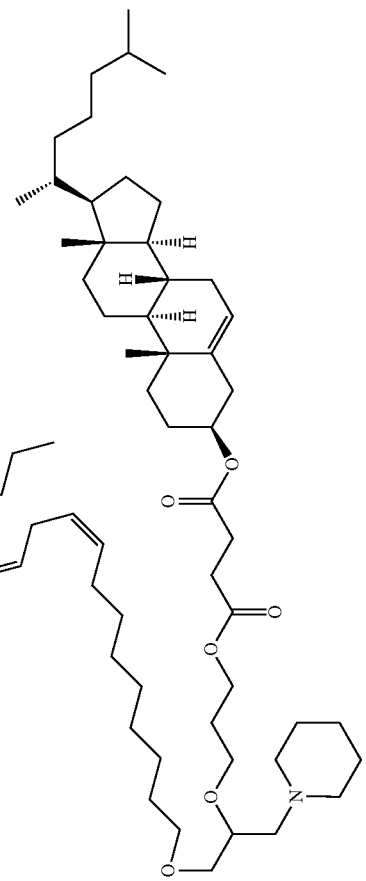 | $H^5$ | $Y^{1-i}$ | $L^{c-xxxiv}$ |

TABLE 6-continued

Characterization and structures for Cationic Lipids

| Lipid | Structure | $R^1$—N—$R^2$ | $Y^1$ | $Y^{i\text{-}iv}$ | L | $L^{c\text{-}i}$ |
|---|---|---|---|---|---|---|
| E0180 | 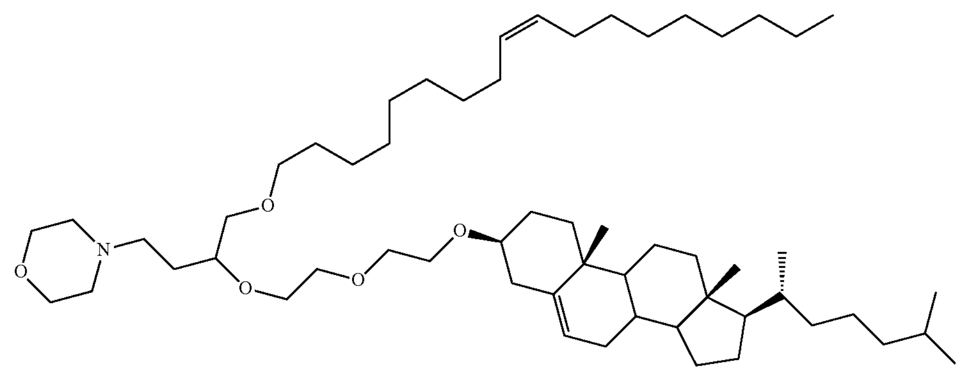 [SMILES: CCCCCCCC/C=C\CCCCCCCCOCC(CCN1CCOCC1)OCCOCCO[C@H]1CC[C@@]2(C)C(=CCC3C2CC[C@@]2(C)C3CC[C@@H]2[C@H](C)CCCC(C)C)C1] | $H^1$ | | | $L^{c\text{-}i}$ | |

For each of the above compounds except E0180, $Y^2$ is cholesterol linked to L via an oxygen atom on the 3-position of the A steroid ring (the hydrogen atom on said hydroxy group being absent); $X^1$ and $X^2$ are O; a=methylene; b=methylene and c is absent; whereas for E0180, a=ethylene.

In addition to the characterisation data below, $^1$H NMR is taken of all lipids to assess purity and any olefin isomerization that may have occurred in the synthesis. Specifically, the integrals for the cholesterol derived singlet, usually at or close to 0.68 ppm, is compared to the olefin derived signals in the 5.2 to 5.5 ppm range. The olefin integral for the desired cis, unconjugated olefins and the cholesterol olefinic hydrogen is compared to any new signals above 5.5 ppm which corresponded to isomerized products. In all cases, the degree of isomerization is less than 10% as determined by comparing the integrated signals in the $^1$H NMR.

Example 67

NMR characterization of the various lipids is provided below.

E0008
$^1$H NMR (400 MHz, CDCl$_3$) δ 5.25-5.48 (m, 5H), 3.69-3.86 (m, 2H), 3.55-3.69 (m, 7H), 3.34-3.55 (m, 4H), 3.07-3.25 (m, 1H), 2.70-3.01 (m, 4H), 2.30-2.53 (m, 3H), 2.15-2.30 (m, 1H), 1.78-2.14 (m, 11H), 1.42-1.66 (m, 12H), 0.97-1.42 (m, 34H), 0.81-0.97 (m, 16H), 0.68 (s, 3H) ppm.

E0006
$^1$H NMR (400 MHz, CDCl$_3$) δ 5.25-5.47 (m, 5H), 3.56-3.85 (m, 11H), 3.48-3.56 (m, 1H), 3.36-3.48 (m, 3H), 3.11-3.27 (m, 1H), 2.66-2.83 (m, 4H), 2.41-2.49 (m, 2H), 2.30-2.41 (m, 1H), 2.15-2.28 (m, 1H), 1.72-2.12 (m, 11H), 0.96-1.70 (m, 60H), 0.68 (s, 3H) ppm.
$^{13}$C NMR (400 MHz, CDCl$_3$) δ 140.9, 130.2, 130.1, 128.0, 127.9, 121.6, 79.5, 72.0, 71.7, 71.6, 70.9, 69.4, 67.3, 60.2, 60.1, 59.7, 56.8, 56.1, 50.2, 42.3, 39.8, 39.5, 39.0, 37.2, 36.8, 36.2, 35.8, 31.9, 31.9, 31.5, 29.7, 29.5, 29.5, 29.3, 29.3, 29.0, 28.3, 28.2, 28.0, 27.2, 27.2, 26.2, 25.6, 24.3, 23.8, 22.8, 22.7, 22.6, 22.6, 21.0, 19.4, 18.7, 14.1, 11.8 ppm.

E0003
$^1$H NMR (400 MHz, CDCl$_3$) δ 5.22-5.46 (m, 7H), 3.66-3.93 (m, 5H), 3.54-3.66 (m, 6H), 3.35-3.54 (m, 4H), 3.07-3.23 (m, 1H), 2.73-2.89 (m, 4H), 2.39-2.73 (m, 4H), 2.28-2.39 (m, 1H), 2.28-2.39 (m, 1H), 1.70-2.12 (m, 10H), 1.20-1.65 (m, 24H), 0.94-1.19 (m, 13H), 0.77-0.94 (m, 14H), 0.66 (s, 3H) ppm.
$^{13}$C NMR (400 MHz, CDCl$_3$) δ 140.9, 130.4, 130.0, 128.3, 128.1, 127.8, 127.6, 121.6, 79.5, 71.6, 70.8, 70.7, 69.2, 67.3, 60.1, 56.7, 56.1, 54.2, 50.1, 42.3, 39.7, 39.5, 39.0, 37.2, 36.8, 36.2, 35.8, 31.9, 31.8, 31.5, 29.5, 29.4, 29.3, 28.3, 28.2, 28.0, 27.2, 27.2, 25.8, 25.6, 24.3, 23.8, 22.8, 22.6, 22.5, 21.0, 19.4, 18.7, 14.1, 11.8 ppm.

E0002
$^1$H NMR (400 MHz, CDCl$_3$) δ 5.26-5.44 (m, 5H), 3.68-3.84 (m, 3H), 5.54-3.68 (m, 7H), 3.32-3.54 (m, 6H), 3.09-3.24 (m, 1H), 2.68-2.80 (m, 2H), 2.27-2.58 (m, 3H), 2.12-2.27 (m, 1H), 1.69-2.12 (m, 9H), 1.41-1.69 (m, 20H), 1.19-1.40 (m, 20H), 0.95-1.19 (m, 11H), 0.78-0.95 (m, 12 H), 0.66 (s, 3H) ppm.

E0001
$^1$H NMR (400 MHz, CDCl$_3$) δ 7.10-7.24 (m, 3H), 6.96-7.10 (m, 1H), 5.21-5.48 (m, 5H), 3.73-3.90 (m, 3H), 3.37-3.72 (m, 11H), 3.10-3.25 (m, 1H), 2.72-2.86 (m, 2H), 2.28-2.42 (m, 1H), 2.14-2.28 (m, 1H), 1.92-2.14 (m, 6H), 1.78-1.92 (m, 4H), 1.22-1.78 (m, 34H), 0.95-1.22 (m, 13H), 0.84-0.95 (m, 13H), 0.68 (s, 3H) ppm.

E0004
$^1$H NMR (400 MHz, CDCl$_3$) δ 5.24-5.44 (m, 5H), 3.66-3.83 (m, 2H), 3.54-3.65 (m, 7H), 3.34-3.51 (m, 4H), 3.11-3.23 (m, 1H), 2.94-3.10 (m, 2H), 2.56-2.87 (m, 6.5H), 2.41-2.50 (d, J=5.02 Hz, 2H), 2.29-2.40 (m, 2.5H), 1.96-2.26 (m, 8H), 1.62-1.96 (m, 8H), 1.62-1.96 (m, 11H), 1.40-1.61 (m, 11H), 1.22-1.40 (m, 20H), 0.81-1.21 (m, 26H), 0.66 (s, 3H) ppm.
$^{13}$C NMR CDCl$_3$, 400 MHz) δ 142.5, 140.9, 139.7, 130.1, 130.1, 128.7, 127.9, 127.9, 125.8, 121.5, 79.4, 77.2, 71.8, 71.6, 70.8, 70.8, 69.3, 67.3, 63.1, 59.3, 56.7, 56.1, 53.6, 53.3, 50.1, 49.9, 42.2, 39.7, 39.4, 39.0, 37.2, 36.8, 36.1, 35.7, 31.9, 31.8, 31.5, 29.6, 29.5, 29.4, 29.3, 29.3, 28.3, 28.2, 27.9, 27.2, 27.1, 27.0, 26.9, 26.1, 25.6, 24.8, 24.2, 23.8, 22.8, 22.5, 21.3, 21.0, 19.3, 18.6, 14.0, 11.8 ppm.

E0005
$^1$H NMR (400 MHz, CDCl$_3$) δ 5.28-5.44, (m, 3H), 3.69-3.82 (m, 2H), 3.57-3.67 (m, 7H), 3.48-3.64 (m, 1H), 3.39-3.48 (m, 3H), 3.33 (s, 3H), 3.12-3.24 (m, 2H), 2.70-2.86 (m, 4H), 2.42-2.47 (d, J=6.02 Hz, 2H), 2.33-2.42 (m, 3H), 1.97-2.10 (m, 5H), 1.76-1.97 (m, 7H), 1.42-1.64 (m, 12H), 1.23-1.42 (m, 20H), 0.97-1.23 (m, 12H), 0.81-0.97 (m, 13H), 0.68 (s, 3H) ppm.
$^{13}$C NMR (400 MHz, CDCl$_3$) δ 140.9, 130.2, 130.1, 127.9, 127.9, 121.5, 79.5, 77.5, 72.5, 72.1, 70.9, 70.8, 69.3, 67.3, 63.1, 59.3, 56.7, 56.1, 55.5, 52.0, 51.7, 50.1, 42.3, 39.8, 39.5, 39.0, 37.2, 36.8, 36.2, 35.8, 31.9, 31.9, 31.5, 31.0, 29.7, 29.5, 29.5, 29.3, 29.3, 28.3, 28.2, 28.0, 27.2, 27.2, 26.1, 25.6, 24.3, 23.8, 22.8, 22.6, 21.0, 19.4, 18.7, 14.1, 11.8 ppm.

E0007
$^1$H NMR (400 MHz, CDCl$_3$) δ 5.26-5.44 (m, 5H), 3.84-3.94 (t, J=5.56 Hz, 4H), 3.68-3.87 (m, 2H), 3.56-3.67 (m, 7H), 3.47-3.54 (m, 1H), 3.38-3.47 (m, 3H), 3.11-3.23 (m, 1H), 2.73-2.82 (t, J=6.44 Hz, 2H), 2.42-2.57 (m, 5H), 2.32-2.41 (m, 1H), 2.11-2.27 (m, 2H), 1.97-2.10 (m, 6H), 1.76-1.96 (m, 7H), 1.66-1.75 (m, 2H), 1.41-1.62 (m, 9H), 1.22-1.41 (m, 20H), 0.81-1.22 (m, 25H), 0.67 (s, 3H) ppm.
$^1$H NMR (400 MHz, CDCl$_3$) δ 141.0, 130.1, 130.1, 127.9, 127.9, 121.5, 96.2, 79.5, 77.6, 72.2, 71.6, 70.9, 70.8, 69.4, 67.3, 63.1, 59.3, 59.1, 56.8, 56.1, 50.5, 50.2, 42.3, 39.8, 39.5, 39.1, 37.2, 36.8, 36.2, 35.7, 32.8, 31.9, 31.9, 31.5, 29.7, 29.5, 29.4, 29.3, 29.3, 28.3, 28.2, 28.0, 27.2, 27.2, 26.1, 25.6, 25.6, 24.3, 23.8, 22.8, 22.5, 21.0, 19.3, 18.7, 14.0, 11.8 ppm.

E0009
$^1$H NMR (400 MHz, CDCl$_3$) δ 5.27-5.44 (m, 5H), 4.07-4.22 (m, 2H), 3.67-3.83 (m, 2H), 3.55-3.67 (m, 6H), 3.37-3.52 (m, 4H), 3.12-3.25 (m, 1H), 2.81-2.90 (m, 1H), 2.73-2.81 (t, J=6.53 Hz, 2H), 2.42-2.64 (m, 3H), 2.15-2.41 (m, 4H), 1.76-2.11 (m, 11H), 1.64-1.72 (m, 4H), 1.42-1.63 (m, 12H), 1.21-1.41 (m, 22H), 0.81-1.22 (m, 26H), 0.68 (s, 3H) ppm.
$^{13}$C NMR (400 MHz, CDCl$_3$) δ 140.9, 130.2, 130.1, 127.9, 127.9, 121.5, 79.5, 77.2, 72.7, 72.0, 71.6, 71.5, 70.8, 69.4, 67.3, 61.9, 59.5, 56.7, 56.5, 56.1, 50.1, 49.3, 49.3, 42.3, 39.7, 39.5, 39.0, 37.2, 36.8, 36.2, 35.8, 31.9, 31.9, 31.5, 29.7, 29.5, 29.5, 29.3, 29.3, 28.4, 28.3, 28.2, 28.0, 27.4, 27.4, 27.2, 27.2, 26.5, 26.1, 25.6, 24.3, 23.8, 22.8, 22.6, 22.6, 21.0, 19.4, 18.7, 14.1, 11.8 ppm.

E0170
$^1$H NMR (400 MHz, CDCl$_3$) δ 5.26-5.45 (m, 5H), 3.68-3.82 (m, 2H), 3.56-3.68 (m, 7H), 3.38-3.53 m, 4H), 3.11-3.24 (m, 1H), 2.73-2.82 (t, J=6.53 Hz, 2H), 2.56-2.69 (m, 4H), 2.50-2.56 (m, 2H), 2.32-2.41 (m, 1H), 2.09-2.27 (m, 2H), 1.77-2.09 (m, 13H), 1.42-1.63 (m, 9H), 1.21-1.42 (m, 20H), 0.83-1.21 (m, 25H), 0.68 (s, 3H) ppm.
$^{13}$C NMR (400 MHz, CDCl$_3$) δ 140.9, 130.2, 130.1, 128.0, 127.9, 124.4, 122.0, 121.5, 119.6, 79.5, 77.6, 77.2, 71.8, 71.6, 70.9, 70.8, 69.4, 67.3, 58.7, 56.7, 56.1, 50.7, 50.1, 42.3, 39.7, 39.5, 39.0, 37.2, 36.8, 36.1, 35.8, 34.0, 31.9, 31.8, 31.5, 29.6, 29.5, 29.4, 29.3, 28.3, 28.2, 28.0, 27.2, 27.2, 26.1, 25.6, 24.3, 23.8, 22.8, 22.6, 21.0, 19.3, 18.7, 14.1, 11.8 ppm.

E0171

$^1$H NMR (400 MHz, CDCl$_3$) δ 5.27-5.46 (m, 5H), 3.58-3.82 (m, 9H), 3.38-3.54 (m, 4H), 3.13-3.26 (m, 1H), 2.74-2.82 (m, 2H), 2.31-2.50 (m, 6H), 2.16-2.2 (m, 1H), 1.70-2.10 (m, 12H), 1.24-1.65 (m, 33H), 0.97-1.23 (m, 13H), 0.82-0.97 (m, 19H), 0.68 (s, 3H) ppm.

$^{13}$C NMR (400 MHz, CDCl$_3$) δ 141.0, 130.2, 130.1, 127.9, 127.9, 121.5, 79.5, 77.2, 73.2, 72.5, 72.3, 71.6, 70.9, 70.8, 69.3, 67.3, 66.0, 61.9, 60.9, 60.2, 56.7, 56.1, 50.7, 50.1, 42.3, 39.8, 39.5, 39.0, 38.7, 37.2, 36.8, 36.2, 35.8, 31.9, 31.9, 31.5, 29.7, 29.5, 29.5, 29.3, 29.3, 28.3, 28.2, 28.0, 27.2, 27.2, 26.1, 25.6, 24.3, 23.8, 22.8, 22.6, 21.0, 19.4, 18.7, 14.1, 11.8 ppm.

E0010

$^1$H NMR (400 MHz, CDCl$_3$) δ 5.26-5.45 (m, 5H), 3.53-3.84 (m, 9H), 3.37-3.53 (m, 4H), 3.13-3.24 (m, 1H), 2.91-3.00 (m, 1H), 2.74-2.86 (m, 2H), 2.28-2.43 (m, 2H), 2.10-2.28 (m, 2H), 1.42-2.10 (m, 32H), 0.82-1.41 (m, 50H), 0.68 (s, 3H) ppm.

$^{13}$C NMR (400 MHz, CDCl$_3$) δ 141.0, 130.2, 130.1, 127.9, 127.9, 121.5, 79.5, 77.2, 71.9, 71.6, 70.9, 70.8, 69.1, 67.3, 66.7, 56.8, 56.1, 55.5, 54.6, 54.0, 50.1, 42.3, 42.1, 42.0, 39.8, 39.5, 39.0, 37.2, 36.8, 36.2, 35.8, 33.2, 32.6, 31.9, 31.9, 31.5, 30.7, 29.7, 29.5, 29.5, 29.3, 29.3, 28.3, 28.2, 28.0, 27.2, 27.2, 26.2, 26.1, 25.8, 25.6, 24.3, 23.8, 22.8, 22.6, 21.0, 19.4, 18.7, 14.1, 11.8 ppm.

Other characterisation data for the compounds is set out in the following Table 7.

TABLE 7

Cationic Lipid Characterization Data

| Lipid | Expected MW | Observed MW (M + H) | TLC Rf | TLC Ratio | TLC Solvents | HPLC RT (min) | HPLC % purity | Method |
|---|---|---|---|---|---|---|---|---|
| E0001 | | | 0.77 | 4:6 | EtOAc:Heptane | | | |
| E0002 | | | 0.67 | 1:0 | EtOAc:Heptane | | | |
| E0003 | | | 0.45 | 1:0 | EtOAc:Heptane | | | |
| E0004 | | | 0.23 | 1:9 | MeOH:DCM | | | |
| E0005 | | | 0.52 | 1:9 | MeOH:DCM | | | |
| E0006 | | | 0.64 | 1:0 | EtOAc:Heptane | | | |
| E0007 | | | 0.80 | 1:9 | MeOH:DCM | | | |
| E0008 | 877.8 | 879.3 | | | | | | |
| E0009 | 935.8 | 937.3 | | | | | | |
| E0010 | 917.8 | 919.3 | 0.59 | 1:9 | MeOH:DCM | | | |
| E0011 | 865.8 | 867.2 | 0.51 | 1:19 | MeOH:DCM | | | |
| E0012 | 864.8 | 865.9 | 0.10 | 1:9 | MeOH:DCM | | | |
| E0013 | 878.8 | 880.0 | 0.40 | 1:9 | MeOH:DCM | | | |
| E0014 | 863.8 | 864.5 | | | | 19.3 | 98.9 | *1 |
| E0015 | 849.8 | 850.9 | 0.62 | 1:9 | MeOH:DCM | | | |
| E0016 | 921.8 | 923.0 | 0.49 | 1:9 | MeOH:DCM | | | |
| E0017 | 877.8 | 879.0 | 0.51 | 1:9 | MeOH:DCM | | | |
| E0018 | 861.8 | 863.3 | 0.54 | 1:9 | MeOH:DCM | | | |
| E0019 | 877.8 | 879.0 | 0.54 | 1:9 | MeOH:DCM | | | |
| E0020 | 917.8 | 919.3 | 0.15 | 2:1 | heptane:EtOAc | | | |
| E0021 | 917.8 | 919.3 | 0.46 | 1:9 | MeOH:DCM | | | |
| E0022 | 889.8 | 891.3 | 0.54 | 1:9 | MeOH:DCM | | | |
| E0023 | 878.4 | 879.2 | 0.44 | 1:10 | MeOH:EtOAc | | | |
| E0024 | 879.8 | 880.7 | 0.62 | 1:9 | MeOH:DCM | 15.3 | 99.4 | *1 |
| E0025 | 892.5 | 893.2 | 0.31 | 1:10 | MeOH:EtOAc | | | |
| E0026 | 877.8 | 879.3 | 0.51 | 1:9 | MeOH:DCM | | | |
| E0027 | 847.8 | 849.3 | 0.48 | 1:9 | MeOH:DCM | | | |
| E0028 | 849.8 | 851.0 | 0.75 | 1:9 | MeOH:DCM | | | |
| E0029 | 897.8 | 899.2 | 0.78 | 1:9 | MeOH:DCM | | | |
| E0030 | 953.8 | 955.3 | 0.65 | 1:9 | MeOH:DCM | | | |
| E0031 | 882.5 | 882.7 | 0.31 | 1:3 | EtOAc:Heptane | | | |
| E0032 | 847.7 | 849.2 | 0.43 | 1:9 | MeOH:DCM | | | |
| E0033 | 922.5 | 923.2 | 0.53 | 1:10 | MeOH:DCM | | | |
| E0034 | 864.4 | 865.1 | 0.30 | 1:10 | MeOH:EtOAc | | | |
| E0035 | 863.8 | 865.2 | 0.64 | 1:9 | MeOH:DCM | | | |
| E0036 | 876.4 | 877.0 | 0.54 | 1:10 | MeOH:DCM | | | |
| E0037 | 893.8 | 895.2 | 0.55 | 1:9 | MeOH:DCM | | | |
| E0038 | 934.8 | 936.3 | 0.41 | 1:9 | MeOH:DCM | | | |
| E0039 | 892.8 | 894.2 | 0.37 | 1:9 | MeOH:DCM | | | |
| E0040 | 863.8 | 865.2 | 0.50 | 1:9 | MeOH:DCM | | | |
| E0041 | 1004.8 | 1006.3 | 0.79 | 1:9 | MeOH:DCM | | | |
| E0042 | 979.8 | 981.1 | 0.59 | 1:9 | MeOH:DCM | | | |
| E0043 | 864.4 | 865.2 | 0.40 | 1:9 | MeOH:DCM | | | |
| E0044 | 892.8 | 894.1 | 0.22 | 1:9 | MeOH:DCM | | | |
| E0045 | 865.8 | 867.1 | 0.37 | 1:9 | MeOH:DCM | | | |
| E0046 | 878.4 | 879.1 | 0.42 | 1:9 | MeOH:DCM | | | |
| E0047 | 892.4 | 893.0 | 0.60 | 1:10 | MeOH:DCM | | | |
| E0048 | 863.8 | 865.2 | 0.45 | 1:9 | MeOH:DCM | | | |
| E0049 | 863.8 | 865.1 | 0.45 | 1:9 | MeOH:DCM | | | |
| E0050 | 925.8 | 927.0 | 0.33, 0.40 $^a$ | 1:19 | MeOH:DCM | | | |
| E0051 | 847.4 | 847.9 | 0.39 | 1:3:6 | MeOH:EtOAc:Heptane | | | |
| E0052 | 863.8 | 865.1 | 0.47 | 1:9 | MeOH:DCM | | | |

TABLE 7-continued

Cationic Lipid Characterization Data

| Lipid | Expected MW | Observed MW (M + H) | TLC Rf | TLC Ratio | TLC Solvents | HPLC RT (min) | HPLC % purity | Method |
|---|---|---|---|---|---|---|---|---|
| E0053 | 863.8 | 865.1 | 0.34 | 1:9 | MeOH:DCM | | | |
| E0054 | 907.4 | 908.0 | 0.38 | 1:10 | MeOH:DCM | | | |
| E0055 | 907.8 | 909.0 | 0.35 | 1:9 | MeOH:DCM | | | |
| E0056 | 908.4 | 909.1 | 0.37 | 1:19 | MeOH:DCM | | | |
| E0057 | 878.4 | 880.0 | 0.37 | 1:10 | MeOH:DCM | | | |
| E0058 | 908.5 | 909.0 | 0.37 | 1:19 | MeOH:DCM | | | |
| E0059 | 864.4 | 864.9 | 0.37 | 1:19 | MeOH:DCM | | | |
| E0060 | 964.5 | 965.0 | 0.56 | 4:96 | MeOH:DCM | 15.3 | 99.7 | *1 |
| E0061 | 821.8 | 822.8 | | | | 5.3 | 97.3 | *2 |
| E0062 | 837.8 | 838.6 | | | | 5.8 | 99.8 | *2 |
| E0063 | 865.8 | 866.7 | | | | 14.2 | 97.4 | *1 |
| E0064 | 881.8 | 882.6 | | | | 6.8 | 99.7 | *3 |
| E0065 | 865.7 | 866.7 | | | | 15.2 | 97.8 | *1 |
| E0066 | 821.8 | 822.9 | | | | 15.2 | 98.9 | *1 |
| E0067 | 864.4 | 866.0 | 0.37 | 1:19 | MeOH:DCM | | | |
| E0068 | 849.8 | 850.5 | | | | 15.7 | 99.5 | *1 |
| E0069 | 847.8 | 848.5 | | | | 15.9 | 100.0 | *1 |
| E0070 | 847.8 | 848.5 | | | | 15.9 | 99.7 | *1 |
| E0071 | 891.8 | 892.5 | | | | 15.7 | 97.8 | *1 |
| E0072 | 891.8 | 892.5 | | | | 15.7 | 99.6 | *1 |
| E0073 | 891.8 | 892.5 | | | | 15.7 | 97.8 | *1 |
| E0074 | 921.8 | 922.7 | | | | 20.7 | 92.2 | *1 |
| E0075 | 891.8 | 892.5 | | | | 20.2 | 99.9 | *1 |
| E0076 | 819.7 | 820.5 | | | | 14.9 | 99.7 | *1 |
| E0077 | 891.8 | 892.5 | | | | 15.5 | 99.7 | *1 |
| E0078 | 893.8 | 894.7 | | | | 20.4 | 97.7 | *1 |
| E0079 | 951.8 | 952.4 | | | | 20.1 | 99.4 | *1 |
| E0080 | 823.7 | 824.7 | | | | 15.2 | 99.8 | *1 |
| E0081 | 909.8 | 911.5 | | | | 20.4 | 97.6 | *1 |
| E0082 | 907.7 | 909.3 | | | | 15.5 | 99.9 | *1 |
| E0083 | 863.8 | 864.5 | | | | 15.5 | 99.8 | *1 |
| E0084 | 951.8 | 953.5 | | | | 15.3 | 97.4 | *1 |
| E0085 | 867.8 | 868.4 | | | | 15.2 | 99.6 | *1 |
| E0086 | 895.8 | 897.5 | | | | 15.7 | 99.3 | *1 |
| E0087 | 835.7 | 836.5 | | | | 15.2 | 99.4 | *1 |
| E0088 | 907.8 | 908.7 | | | | 18.0 | 99.7 | *1 |
| E0089 | 863.8 | 864.5 | | | | 15.6 | 98.2 | *1 |
| E0090 | 907.8 | 908.7 | | | | 15.3 | 99.5 | *1 |
| E0091 | 935.8 | 936.7 | | | | 15.7 | 99.3 | *1 |
| E0092 | 821.7 | 822.5 | | | | 17.5 | 99.8 | *1 |
| E0093 | 893.8 | 894.7 | | | | 17.9 | 99.8 | *1 |
| E0094 | 893.8 | 894.7 | | | | 18.0 | 99.9 | *1 |
| E0095 | 919.8 | 920.5 | | | | 21.1 | 99.8 | *1 |
| E0096 | 919.8 | 920.5 | | | | 20.6 | 96.8 | *1 |
| E0097 | 950.8 | 951.7 | | | | 15.4 | 95.4 | *1 |
| E0098 | 1006.8 | 1008.6 | | | | 15.1 | 97.8 | *1 |
| E0099 | 950.8 | 951.5 | | | | 14.7 | 98.8 | *1 |
| E0100 | 978.8 | 980.8 | | | | 14.8 | 97.7 | *1 |
| E0101 | 962.8 | 963.6 | | | | 14.7 | 98.3 | *1 |
| E0102 | 862.7 | 863.7 | | | | 15.1 | 99.5 | *1 |
| E0103 | 906.8 | 907.8 | | | | 14.8 | 97.6 | *1 |
| E0104 | 919.8 | 920.5 | | | | 15.3 | 99.8 | *1 |
| E0105 | 934.8 | 935.5 | | | | 15.0 | 98.6 | *1 |
| E0106 | 918.8 | 919.7 | | | | 15.3 | 98.5 | *1 |
| E0107 | 949.8 | 950.8 | | | | 14.9 | 99.9 | *1 |
| E0108 | 1006.8 | 1008.5 | | | | 15.0 | 97.9 | *1 |
| E0109 | 953.8 | 954.7 | | | | 15.1 | 99.8 | *1 |
| E0110 | 919.8 | 920.7 | | | | 15.0 | 98.7 | *1 |
| E0111 | 1013.8 | 1015.6 | | | | 16.9 | 95.8 | *4 |
| E0112 | 893.8 | 894.8 | | | | 15.2 | 99.8 | *1 |
| E0113 | 937.8 | 938.5 | | | | 15.2 | 99.6 | *1 |
| E0114 | 909.8 | 910.5 | | | | 14.5 | 99.0 | *1 |
| E0115 | 893.8 | 894.7 | | | | 15.4 | 98.9 | *1 |
| E0116 | 909.8 | 910.6 | | | | 15.5 | 99.2 | *1 |
| E0117 | 893.7 | 894.5 | | | | 15.5 | 99.4 | *1 |
| E0118 | 863.8 | 865.2 | 0.47 | 1:9 | MeOH:DCM | | | |
| E0119 | 880.5 | 880.6 | 0.84 | 85:5 | Chloroform:MeOH | | | |
| E0120 | 920.5 | 920.7 | 0.85 | 9:1 | Chloroform:MeOH | | | |
| E0121 | 880.5 | 880.1 | 0.83 | 95:5 | Chloroform:MeOH | | | |
| E0122 | 912.4 | 912.6 | 0.66 | 95:5 | DCM:MeOH | | | |
| E0123 | 867.9 | 868.0 | 0.36 | 95:5 | DCM:MeOH | | | |
| E0124 | 947.8 | 948.5 | 0.84 | 9:1 | Chloroform:MeOH | | | |
| E0125 | 925.8 | 926.3 | 0.60 | 95:5 | DCM:MeOH | | | |
| E0126 | 907.8 | 908.5 | 0.83 | 95:5 | DCM:MeOH | | | |

TABLE 7-continued

Cationic Lipid Characterization Data

| Lipid | Expected MW | Observed MW (M + H) | TLC Rf | TLC Ratio | TLC Solvents | HPLC RT (min) | HPLC % purity | Method |
|---|---|---|---|---|---|---|---|---|
| E0127 | 907.8 | 908.1 | 0.83 | 85:15 | Chloroform:MeOH | | | |
| E0128 | 881.8 | 882.5 | 0.61 | 95:5 | DCM:MeOH | | | |
| E0129 | 993.8 | 994.4 | 0.29 | 95:5 | DCM:MeOH | | | |
| E0130 | 979.8 | 980.1 | 0.60 | 9:1 | Chloroform:MeOH | 17.0 | 99.5 | *5 |
| E0131 | 879.8 | 880.3 | 0.43 | 9:1 | Chloroform:MeOH | | | |
| E0132 | 922.8 | 923.0 | 0.43 | 9:1 | Chloroform:MeOH | | | |
| E0133 | 934.8 | 935.5 | 0.44 | 9:1 | Chloroform:MeOH | | | |
| E0134 | 1010.8 | 1012.2 | 0.40 | 95:5 | DCM:MeOH | | | |
| E0135 | 936.7 | 937.4 | 0.45 | 9:1 | Chloroform:MeOH | 16.0 | 98.4 | *6 |
| E0136 | 964.8 | 965.5 | 0.46 | 9:1 | DCM:MeOH | 16.3 | 98.8 | *6 |
| E0137 | 962.8 | 963.8 | 0.43 | 9:1 | Chloroform:MeOH | 16.8 | 97.3 | *6 |
| E0138 | 909.8 | 910.4 | 0.43 | 95:5 | DCM:MeOH | 16.7 | 99.2 | *6 |
| E0139 | 865.7 | 866.4 | 0.43 | 95:5 | DCM:MeOH | 11.8 | 99.1 | *7 |
| E0140 | 923.8 | 924.5 | 0.42 | 95:5 | DCM:MeOH | 16.2 | 96.2 | *6 |
| E0141 | 950.8 | 951.0 | 0.38 | 95:5 | DCM:MeOH | 10.8 | 99.5 | *7 |
| E0142 | 1008.8 | 1009.7 | 0.38 | 95:5 | DCM:MeOH | | | |
| E0143 | 979.8 | 980.9 | 0.46 | 95:5 | DCM:MeOH | 10.9 | 95.5 | *7 |
| E0144 | 923.8 | 925.0 | 0.47 | 95:5 | DCM:MeOH | 10.9 | 96.1 | *7 |
| E0145 | 1008.8 | 1010.2 | 0.38 | 95:5 | DCM:MeOH | 10.5 | 92.1 | *7 |
| E0146 | 909.8 | 910.8 | 0.18 | 50:50 | EtOAc:hexane | | | |
| E0147 | 893.8 | 895.0 | 0.68 | 9:1 | DCM:MeOH | | | |
| E0148 | 922.8 | 923.7 | 0.50 | 9:1 | DCM:MeOH | | | |
| E0149 | 907.8 | 908.9 | 0.47 | 9:1 | DCM:MeOH | | | |
| E0150 | 937.8 | 939.0 | 0.61 | 9:1 | DCM:MeOH | | | |
| E0151 | 935.8 | 937.0 | 0.65 | 9:1 | DCM:MeOH | | | |
| E0152 | 967.8 | 968.3 | 0.43 | 95:5 | DCM:MeOH | | | |
| E0158 | 879.8 | 881.1 | 0.47 | 8:2 | EtOAc:heptane | | | |
| E0159 | 879.8 | 881.0 | 0.41 | 8:2 | EtOAc:heptane | | | |
| E0160 | 965.8 | 967.0 | | | | 6.9 | 100.0 | *8 |
| E0161 | 933.8 | 935.0 | 0.43 | 9:1 | DCM:MeOH | | | |
| E0162 | 933.8 | 935.0 | 0.60 | 9:1 | DCM:MeOH | | | |
| E0163 | 933.8 | 934.9 | | | | 4.2 | 100.0 | *8 |
| E0164 | 921.8 | 923.0 | 0.41 | 9:1 | DCM:MeOH | | | |
| E0165 | 921.8 | 923.0 | 0.48 | 9:1 | DCM:MeOH | | | |
| E0166 | 948.8 | 949.5 | 0.58 | 9:1 | DCM:MeOH | | | |
| E0167 | 881.7 | 882.9 | | | | 4.3 | 100.0 | *8 |
| E0168 | 974.8 | 975.4 | 0.58 | 9:1 | DCM:MeOH | | | |
| E0169 | 936.8 | 938.0 | 0.46 | 9:1 | DCM:MeOH | | | |
| E0170 | | | | | | | | |
| E0171 | | | | | | | | |
| E0175 | 910.8 | 911.5 | 0.50 | 9:1 | DCM:MeOH | | | |
| E0176 | 908.8 | 909.5 | 0.28 | 95:5 | DCM:MeOH | | | |
| E0177 | 921.8 | 922.9 | 0.48 | 9:1 | DCM:MeOH | | | |
| E0178 | 935.8 | 937.0 | 0.54 | 9:1 | DCM:MeOH | | | |
| E0179 | 933.8 | 935.1 | 0.35 | 95:5 | DCM:MeOH | | | |
| E0180 | 881.8 | 882.9 | 0.49 | 95:5 | DCM:MeOH | | | |

$^a$ E0050 is a mixture of diastereomers whose two diastereomeric components have different Rf values on silica.
Method used is as follows where indicated:
*1—Zorbax 300SB C3 150 × 4.6, 1 mL/min, water:MeCN w/0.1% TFA, 40 to 100% over 15 min, 100% for 5 min, ELSD detection.
*2—Zorbax RX-SIL 250 × 4.6, 0.7 mL/min, hexane:EtOH 4:6, ELSD detection.
*3—Zorbax NH2 250 × 4.6, 1 mL/min, hexane:IPA, 30 to 60% over 10 min, 60% for 5 min, ELSD detector.
*4—Xbridge C8, 150 × 4.6 mm, 1 mL/min, water:MeCN w/0.1% TFA, 30 to 100% over 15 min, 100% for 5 min, ELSD detection.
*5—Zorbax Eclipse XDB-C18 250 × 4.6, 1 mL/min, water:MeCN w/0.1% TFA, 50% for 5 min, then 50 to 100% over 5 min, then hold at 100% for 12 min, ELSD detector
*6—Zorbax Eclipse XDB-C18 250 × 4.6, 1 mL/min, water:MeOH w/0.1% TFA, 50% for 5 min, then 50 to 100% over 5 min, then hold at 100% for 5 min, ELSD detector.
*7—Zorbax Eclipse XDB-C18 250 × 4.6, 1 mL/min, water:MeOH w/0.1% TFA, 50 to 70% over 2 min, 70 to 100% over 3 min, then hold at 100% for 5 min, ELSD detector.
*8—Acquity BEH Shield RP 18 50 × 2.1, 0.5 mL/min, 65° C., water:IPA w/0.0125% TFA, 30 to 50% over 1.5 min, 50 to 75% over 10.5 min, 75 to 90% over 0.6 min, then hold at 90% for 0.4 min, CAD detector.

Example 68

Preparation of the Compositions

It is preferred that the compounds of the invention are administered in the form of lipid nanoparticles. Thus it is preferred that the compositions of the invention comprise lipid nanoparticles which comprise the compounds of the invention and optionally one or more other lipid components.

To achieve size reduction and/or to increase the homogeneity of size in the particles, the skilled person may use the method steps set out below, experimenting with different combinations. Additionally, the skilled person could employ sonication, filtration or other sizing techniques which are used in liposomal formulations.

The process for making a composition of the invention typically comprises providing an aqueous solution comprising a biologically active agent in a first reservoir, providing a second reservoir comprising an organic solution of the lipid(s) and then mixing the aqueous solution with the organic lipid solution. The first reservoir is optionally in fluid communication with the second reservoir. The mixing step is optionally followed by an incubation step, a filtration step, and a dilution and/or concentration step.

In one embodiment, the biologically active agent(s) and/or the lipid(s) is/are in a suitable buffer. In one embodiment, the biologically active agent(s) is in an aqueous buffer such as a citrate buffer. In one embodiment, the lipid(s) is in an organic alcohol such as ethanol.

In one embodiment, the incubation step comprises allowing the solution from the mixing step to stand in a vessel for about 0 to about 100 hours (preferably about 0 to about 24 hours) at about rt and optionally protected from light.

In one embodiment, a dilution step follows the incubation step. The dilution step may involve dilution with aqueous buffer (e.g. citrate buffer) e.g., using a pumping apparatus (e.g. a peristaltic pump).

In one embodiment, the filtration step is ultrafiltration. In one embodiment, the ultrafiltration comprises concentration of the diluted solution followed by diafiltration, e.g., using a suitable pumping system (e.g. pumping apparatus such as a peristaltic pump or equivalent thereof) in conjunction with a suitable ultrafiltration membrane (e.g. GE Hollow fiber cartridges or equivalent).

The process should result in the formation of lipid nanoparticles. In one embodiment, the lipid nanoparticles comprise the biologically active agent.

In one embodiment, the mixing step provides a clear single phase.

In one embodiment, after the mixing step, the organic solvent is removed to provide a suspension of particles, wherein the biologically active agent is encapsulated by the lipid(s), e.g. in a lipid bilayer.

The selection of an organic solvent will typically involve consideration of solvent polarity and the ease with which the solvent can be removed at the later stages of particle formation.

The organic solvent, which is also used as a solubilizing agent, is preferably in an amount sufficient to provide a clear single phase mixture of biologically active agents and lipids.

The organic solvent may be selected from one or more (e.g. two) of chloroform, dichloromethane, diethylether, cyclohexane, cyclopentane, benzene, toluene, methanol, and other aliphatic alcohols (e.g. $C_1$ to $C_8$) such as ethanol, propanol, isopropanol, butanol, tert-butanol, iso-butanol, pentanol and hexanol.

The mixing step can take place by any number of methods, e.g., by mechanical means such as a vortex mixer.

The methods used to remove the organic solvent will typically involve diafiltration or evaporation at reduced pressures or blowing a stream of inert gas (e.g. nitrogen or argon) across the mixture.

In other embodiments, the method further comprises adding nonlipid polycations which are useful to effect the transformation of cells using the present compositions. Examples of suitable nonlipid polycations include, but are limited to, hexadimethrine bromide (sold under the brandname POLYBRENE®, from Aldrich Chemical Co., Milwaukee, Wis., USA) or other salts of hexadimethrine. Other suitable polycations include, e.g., salts of poly-L-ornithine, poly-L-arginine, poly-L-lysine, poly-D-lysine, polyallylamine and polyethyleneimine.

In certain embodiments, the formation of the lipid nanoparticles can be carried out either in a mono-phase system (e.g. a Bligh and Dyer monophase or similar mixture of aqueous and organic solvents) or in a two-phase system with suitable mixing.

The lipid nanoparticle may be formed in a mono- or a bi-phase system. In a mono-phase system, the cationic lipid(s) and biologically active agent are each dissolved in a volume of the mono-phase mixture. Combining the two solutions provides a single mixture in which the complexes form. In a bi-phase system, the cationic lipids bind to the biologically active agent (which is present in the aqueous phase), and "pull" it into the organic phase.

In one embodiment, the lipid nanoparticles are prepared by a method which comprises: (a) contacting the biologically active agent with a solution comprising noncationic lipids and a detergent to form a compound-lipid mixture; (b) contacting cationic lipids with the compound-lipid mixture to neutralize a portion of the negative charge of the biologically active agent and form a charge-neutralized mixture of biologically active agent and lipids; and (c) removing the detergent from the charge-neutralized mixture.

In one group of embodiments, the solution of neutral lipids and detergent is an aqueous solution. Contacting the biologically active agent with the solution of neutral lipids and detergent is typically accomplished by mixing together a first solution of the biologically active agent and a second solution of the lipids and detergent. Preferably, the biologically active agent solution is also a detergent solution. The amount of neutral lipid which is used in the present method is typically determined based on the amount of cationic lipid used, and is typically of from about 0.2 to 5 times the amount of cationic lipid, preferably from about 0.5 to about 2 times the amount of cationic lipid used.

The biologically active agent-lipid mixture thus formed is contacted with cationic lipids to neutralize a portion of the negative charge which is associated with the molecule of interest (or other polyanionic materials) present. The amount of cationic lipids used is typically the amount sufficient to neutralize at least 50% of the negative charge of the biologically active agent. Preferably, the negative charge will be at least 70% neutralized, more preferably at least 90% neutralized.

The methods used to remove the detergent typically involve dialysis. When organic solvents are present, removal is typically accomplished by diafilitration or evaporation at reduced pressures or by blowing a stream of inert gas (e.g. nitrogen or argon) across the mixture.

There is herein disclosed an apparatus for making a composition of the present invention. The apparatus typically includes a first reservoir for holding an aqueous solution comprising a biologically active agent and a second reservoir for holding an organic lipid solution. The apparatus also typically includes a pump mechanism configured to pump the aqueous and the organic lipid solutions into a mixing region or mixing chamber at substantially equal flow rates. In one embodiment, the mixing region or mixing chamber comprises a T coupling or equivalent thereof, which allows the aqueous and organic fluid streams to combine as input into the T connector and the resulting combined aqueous and organic solutions to exit out of the T connector into a collection reservoir or equivalent thereof.

Example 69

Example Method of Making Compositions

The lipid nanoparticles (LNPs) are formed by mixing equal volumes of lipids dissolved in alcohol with siRNA dissolved in a citrate buffer by an impinging jet process. The lipid solution contains a cationic lipid compound of the invention or a comparative lipid, a helper lipid (cholesterol), an optional neutral lipid (DSPC) and a PEG (PEG) lipid at a concentration of 8-16 mg/mL with a target of 12 mg/mL in an alcohol. The relative molar ratios of each lipid component in the formulations of this invention are reported in Tables 8 through 11. Where a LNP formulation contains four lipid components, the molar ratios correspond to the type of lipid as it appears in the first four columns of the table, in the order that they appear. Where a LNP formulation contains three lipid components, there is no neutral lipid.

The ratio of the lipids ranges from 20 to 70 mole percent for the cationic lipid with a target of 40-60, the mole percent of helper lipid ranges from 20 to 70 with a target of 30 to 50, the mole percent of neutral lipid ranges from 0-30, the mole percent of PEG lipid has a range from 1 to 6 with a target of 2 to 5. The concentration of siRNA solution ranges from 0.7 to 1.0 mg/mL with a target of 0.8 to 0.9 mg/mL in a sodium citrate:sodium chloride buffer pH 4. The LNPs are formed by mixing equal volumes of lipid solution in ethanol with siRNA dissolved in a citrate buffer by an impinging jet process through tubings with ID ranging from 0.25 to 2.0 mm at a total flow rate from 10 to 120 mL/min. The mixed LNP solution is held at rt for 0-48 hrs prior to a dilution step. The solution is then concentrated and diafiltered with suitable buffer by ultrafiltration process using membranes with a MW cutoff from 30 to 100 KD. The final product is sterile filtered and stored at 4° C.

Example 70

Transfection in Vivo in a Mouse Model

Female CD-1 mice are received from Charles River Labs and maintained on standard lab chow and water ad libitum. The animals weigh approximately 25 grams at time of dosing. Formulated siRNA is administered as a single dose at various dose levels intravenously via the lateral tail vein calculated on a (mg siRNAs/kg) basis according to individual animal weights (10 ml/kg injection volume).

Formulated siRNAs are made up of double stranded siRNA sequences specific to a target mRNA sequence, and are in the form of lipid nucleotid particles (LNPs) containing cationic lipids, stealth lipids and neutral lipids, as provided in the Examples below. The siRNA construct for use in targeting the liver is specific to Factor VII. The siRNA construct for use in targeting tumors is specific to PLK1-424, which is published by Judge et al., See, J Clin Invest. 2009 March; 119(3):661-73; doi: 10.1172/JCI37515).

1. FVII siRNA duplex sequence

```
                                       (SEQ ID NO: 1)
    5' UUu AAU UGA AAC cAA GAc Auu 3'

(SEQ ID NO: 2)
    5' uGu cuu GGu uuc AAu uAA Auu 3'
```

2. PLK1-424 siRNA duplex sequence

```
                                       (SEQ ID NO: 3)
    5' UAU UUA AgG AGG GUG AuC Uuu 3'

(SEQ ID NO: 4)
    5' AGA Uca cCC Ucc uuA AAU auu 3'
```

The following abbreviations are used in these sequences:
A=adenosine
U=uridine
G=guanosine
C=cytosine
a=2'-O-methyl-adenosine
u=2'-O-methyl-uridine
g=2'-O-methyl-guanosine
c=2'-O-methyl-cytosine Example 71

Factor VII Activity Assay

Formulated Factor VII siRNA is administered as a single dose at various dose levels intravenously via the lateral tail vein calculated on a mg siRNAs/kg basis according to individual animal weights (10 ml/kg injection volume). Approximately 48 h after injection, the mice are euthanized by $CO_2$ inhalation followed by exsanguinations through the vena cava. The blood is collected in tubes containing 0.105M sodium citrate anticoagulant for plasma Factor VII activity analysis. In some cases, small pieces (~50 mg) of liver are collected and snap frozen in liquid nitrogen for follow up mRNA quantitation.

Plasma collected from injected mice is assayed for Factor VII activity using the Biophen FVII kit from Hyphen Biomedical (catalog number 221304). An assay standard curve is prepared using pooled plasma aliquots from the vehicle control animals. All samples are diluted to fall within the linear range of the standard curve and a relative Factor VII activity is reported.

In some cases, total liver RNA is prepared using Qiagen's RNeasy isolation kit (catalog number 74106) according to the manufacture's protocol. Factor VII mRNA is analyzed by quantitative PCR and normalized to GAPDH. Applied Biosystems Factor VII gene expression assay Mm00487333_m1 and mouse GAPDH endogenous control cat number 4352339E are used for mRNA detection.

The results for the FVII assay are set out in the following Table 8.

TABLE 8

Factor VII assay—In vivo liver results

| Lipid | Neutral lipid[1] | Helper lipid | Stealth lipid[2,3] | Lipid ratio (molar ratio)[4] | N/P ratio | Final size (nm) | PDI | pKa | dose (mg/kg) | FVII inhib % |
|---|---|---|---|---|---|---|---|---|---|---|
| E0001 | DSPC | CHOL | AVANTI | 50/28/18/4 | 3.43 | 71 | 0.101 | 4.84 | 3 | 27.6 |
| E0001 |  | CHOL | AVANTI | 50/0/46/4 | 3.43 | 77 | 0.16 | 4.84 | 3 | 20.1 |
| E0002 | DSPC | CHOL | AVANTI | 50/28/18/4 | 3.43 | 109 | 0.221 |  | 3 | 10.4 |
| E0002 | DSPC | CHOL | AVANTI | 50/28/18/4 | 3.43 | 109 | 0.221 |  | 1 | −0.3 |
| E0003 | DSPC | CHOL | AVANTI | 50/28/18/4 | 3.43 | 106 | 0.224 |  | 3 | 2.9 |
| E0004 |  | CHOL | AVANTI | 50/0/46/4 | 3.43 | 186 | 0.201 | 7.48 | 3 | 41 |
| E0004 | DSPC | CHOL | AVANTI | 50/28/18/4 | 3.43 | 142 | 0.113 | 7.48 | 3 | 23.4 |
| E0005 |  | CHOL | AVANTI | 50/0/46/4 | 3.43 | 146 | 0.07 |  | 1.5 | 59.9 |
| E0005 | DSPC | CHOL | AVANTI | 50/28/18/4 | 3.43 | 168 | 0.069 |  | 3 | 12.2 |
| E0006 |  | CHOL | AVANTI | 50/0/46/4 | 3.43 | 95 | 0.142 | 4.88 | 3 | 21.2 |
| E0006 | DSPC | CHOL | AVANTI | 50/28/18/4 | 3.43 | 146 | 0.04 | 4.88 | 3 | 15.7 |
| E0007 |  | CHOL | AVANTI | 50/0/46/4 | 3.43 | 138 | 0.148 | 5.84 | 3 | 76.8 |
| E0007 | DSPC | CHOL | AVANTI | 50/28/18/4 | 3.43 | 92 | 0.178 | 5.84 | 3 | 72.2 |

TABLE 8-continued

Factor VII assay—In vivo liver results

| Lipid | Neutral lipid[1] | Helper lipid | Stealth lipid[2,3] | Lipid ratio (molar ratio)[4] | N/P ratio | Final size (nm) | PDI | pKa | dose (mg/kg) | FVII inhib % |
|---|---|---|---|---|---|---|---|---|---|---|
| E0008 | DSPC | CHOL | AVANTI | 50/28/18/4 | 3.43 | 85 | 0.168 | 5.81 | 3 | 73 |
| E0008 | | CHOL | AVANTI | 50/0/46/4 | 3.43 | 84 | 0.214 | 5.81 | 3 | 84.5 |
| E0009 | | CHOL | AVANTI | 50/0/46/4 | 3.43 | 82 | 0.16 | 4.89 | 3 | 6.9 |
| E0009 | DSPC | CHOL | AVANTI | 50/28/18/4 | 3.43 | 83 | 0.2 | 4.89 | 3 | 38.4 |
| E0010 | | CHOL | AVANTI | 50/0/46/4 | 3.43 | 80 | 0.201 | 5.85 | 3 | 65.1 |
| E0010 | DSPC | CHOL | AVANTI | 50/28/18/4 | 3.43 | 90 | 0.184 | 5.85 | 3 | 46.8 |
| E0011 | DSPC | CHOL | AVANTI | 50/28/18/4 | 3.43 | 111 | 0.221 | 5.32 | 3 | 86.5 |
| E0011 | | CHOL | AVANTI | 50/0/46/4 | 3.43 | 108 | 0.23 | 5.32 | 3 | 92.3 |
| E0012 | DSPC | CHOL | AVANTI | 30/30/36/4 | 2.3 | 220 | 0.105 | | 3 | 9.3 |
| E0014 | | CHOL | GM-020 | 60/0/36/4 | 3 | 101.5 | 0.182 | 6.4 | 1 | 68.5 |
| E0014 | | CHOL | AVANTI | 50/0/46/4 | 3.43 | 148 | 0.05 | 6.4 | 3 | 97.4 |
| E0014 | DSPC | CHOL | AVANTI | 50/28/18/4 | 3.43 | 104 | 0.151 | 6.4 | 3 | 98.6 |
| E0014 | DSPC | CHOL | AVANTI | 50/28/18/4 | 3.43 | 104 | 0.151 | 6.4 | 1 | 72.1 |
| E0014 | DSPC | CHOL | AVANTI | 50/28/18/4 | 3.43 | 95 | 0.148 | 6.4 | 3 | 95.8 |
| E0014 | | CHOL | GM-020 | 60/0/36/4 | 3 | 94.6 | 0.092 | 6.4 | 3 | 94 |
| E0014 | | CHOL | GM-020 | 60/0/36/4 | 3 | 94.6 | 0.092 | 6.4 | 1 | 37.6 |
| E0014 | | CHOL | GM-020 | 60/0/34/6 | 3 | 85.8 | 0.106 | 6.4 | 3 | 96.6 |
| E0014 | | CHOL | GM-020 | 60/0/34/6 | 3 | 85.8 | 0.106 | 6.4 | 1 | 25 |
| E0014 | | CHOL | GM-020 | 60/0/38/2 | 3 | 141 | 0.122 | 6.4 | 3 | 96.2 |
| E0014 | | CHOL | GM-020 | 60/0/38/2 | 3 | 141 | 0.122 | 6.4 | 1 | 71.5 |
| E0015 | | CHOL | AVANTI | 50/0/46/4 | 3.43 | 130 | 0.05 | 7.39 | 3 | 77.1 |
| E0015 | DSPC | CHOL | AVANTI | 50/28/18/4 | 3.43 | 164 | 0.06 | 7.39 | 3 | 30.7 |
| E0016 | | CHOL | AVANTI | 50/0/46/4 | 3.43 | 178 | 0.206 | 5.85 | 3 | 59.9 |
| E0016 | DSPC | CHOL | AVANTI | 50/28/18/4 | 3.43 | 97 | 0.175 | 5.85 | 3 | 88.8 |
| E0017 | | CHOL | AVANTI | 50/0/46/4 | 3.43 | 97 | 0.19 | 6.46 | 3 | 96.5 |
| E0017 | DSPC | CHOL | AVANTI | 50/28/18/4 | 3.43 | 106 | 0.17 | 6.46 | 3 | 98.3 |
| E0017 | DSPC | CHOL | AVANTI | 50/28/18/4 | 3.43 | 106 | 0.17 | 6.46 | 1 | 53.8 |
| E0018 | DSPC | CHOL | AVANTI | 50/28/18/4 | 3.43 | 119 | 0.095 | 5.9 | 3 | 91.8 |
| E0018 | | CHOL | AVANTI | 50/0/46/4 | 3.43 | 103 | 0.113 | 5.9 | 3 | 98 |
| E0018 | | CHOL | AVANTI | 50/0/46/4 | 3.43 | 140 | 0.13 | 5.9 | 1 | 40.5 |
| E0019 | DSPC | CHOL | AVANTI | 50/28/18/4 | 3.43 | 143 | 0.065 | 6.75 | 3 | 76.7 |
| E0019 | | CHOL | AVANTI | 50/0/46/4 | 3.43 | 90.5 | 0.164 | 6.75 | 3 | 85.2 |
| E0019 | | CHOL | AVANTI | 50/0/46/4 | 3.43 | 180 | 0.19 | 6.75 | 1 | 33.7 |
| E0020 | | CHOL | AVANTI | 50/0/46/4 | 3.43 | 81 | 0.084 | 6.08 | 3 | 51.4 |
| E0020 | DSPC | CHOL | AVANTI | 50/28/18/4 | 3.43 | 83 | 0.138 | 6.08 | 3 | 62.4 |
| E0021 | | CHOL | AVANTI | 50/0/46/4 | 3.43 | 72 | 0.184 | 5.13 | 3 | 52.8 |
| E0021 | DSPC | CHOL | AVANTI | 50/28/18/4 | 3.43 | 85 | 0.22 | 5.13 | 3 | 24.5 |
| E0022 | | CHOL | AVANTI | 50/0/46/4 | 3.43 | 84 | 0.192 | | 3 | 87.8 |
| E0022 | DSPC | CHOL | AVANTI | 50/28/18/4 | 3.43 | 93 | 0.143 | | 3 | 49.4 |
| E0023 | | CHOL | AVANTI | 50/0/46/4 | 3.43 | 99 | 0.122 | 5.85 | 3 | 68 |
| E0023 | DSPC | CHOL | AVANTI | 50/28/18/4 | 3.43 | 95 | 0.221 | 5.85 | 3 | 59.1 |
| E0024 | | CHOL | AVANTI | 50/0/46/4 | 3.43 | 149 | 0.092 | 6.62 | 3 | 99.5 |
| E0024 | DSPC | CHOL | AVANTI | 50/28/18/4 | 3.43 | 100 | 0.148 | 6.62 | 3 | 99.9 |
| E0024 | DSPC | CHOL | AVANTI | 50/28/18/4 | 3.43 | 100 | 0.148 | 6.62 | 1 | 85.3 |
| E0024 | | CHOL | AVANTI | 50/0/46/4 | 3.43 | 125 | 0.08 | 6.62 | 1 | 95.7 |
| E0024 | | CHOL | S010 | 60/0/37/3 | 3 | 96.09 | 0.137 | 6.62 | 1 | 72.2 |
| E0024 | | CHOL | S006 | 60/0/37/3 | 3 | 98.53 | 0.12 | 6.62 | 1 | 83.8 |
| E0025 | | CHOL | AVANTI | 50/0/46/4 | 3.43 | 73 | 0.12 | 5.45 | 3 | 94.2 |
| E0025 | DSPC | CHOL | AVANTI | 50/28/18/4 | 3.43 | 97 | 0.22 | 5.45 | 3 | 63 |
| E0026 | | CHOL | AVANTI | 50/0/46/4 | 3.43 | 87 | 0.23 | 5.85 | 3 | 95.1 |
| E0027 | | CHOL | AVANTI | 50/0/46/4 | 3.43 | 65 | 0.15 | 5.71 | 3 | 30.3 |
| E0027 | DSPC | CHOL | AVANTI | 50/28/18/4 | 3.43 | 146 | 0.311 | 5.71 | 3 | 36.3 |
| E0028 | | CHOL | AVANTI | 50/0/46/4 | 3.43 | 68 | 0.125 | 4.8 | 3 | 38.7 |
| E0028 | DSPC | CHOL | AVANTI | 50/28/18/4 | 3.43 | 129 | 0.216 | 4.8 | 3 | 12.5 |
| E0029 | | CHOL | AVANTI | 50/0/46/4 | 3.43 | 113 | 0.08 | 4.95 | 3 | −19.1 |
| E0029 | DSPC | CHOL | AVANTI | 50/28/18/4 | 3.43 | 137 | 0.04 | 4.95 | 3 | 12.4 |
| E0030 | | CHOL | AVANTI | 50/0/46/4 | 3.43 | 155 | 0.08 | 5.38 | 3 | 12.4 |
| E0031 | | CHOL | AVANTI | 50/0/46/4 | 3.43 | 65 | 0.11 | 4.8 | 3 | 27.1 |
| E0031 | DSPC | CHOL | AVANTI | 50/28/18/4 | 3.43 | 108 | 0.23 | 4.8 | 3 | 36.7 |
| E0032 | | CHOL | AVANTI | 50/0/46/4 | 3.43 | 63 | 0.21 | 6.8 | 3 | 85.5 |
| E0032 | DSPC | CHOL | AVANTI | 50/28/18/4 | 3.43 | 87 | 0.18 | 6.8 | 3 | 64.5 |
| E0033 | | CHOL | AVANTI | 50/0/46/4 | 3.43 | 105 | 0.05 | | 3 | 15.3 |
| E0033 | DSPC | CHOL | AVANTI | 25/28/18/4 | 1.9 | 161 | 0.16 | | 3 | −36.4 |
| E0034 | | CHOL | AVANTI | 50/0/46/4 | 3.43 | 99 | 0.16 | | 3 | 88.1 |
| E0034 | DSPC | CHOL | AVANTI | 50/28/18/4 | 3.43 | 99 | 0.16 | | 3 | 81.3 |
| E0035 | | CHOL | AVANTI | 50/0/46/4 | 3.43 | 79 | 0.21 | 5.93 | 3 | 66.8 |
| E0035 | DSPC | CHOL | AVANTI | 50/28/18/4 | 3.43 | 103 | 0.2 | 5.93 | 3 | 22 |
| E0036 | | CHOL | AVANTI | 50/0/46/4 | 3.43 | 76 | 0.24 | 5.74 | 3 | −23.1 |
| E0036 | DSPC | CHOL | AVANTI | 50/28/18/4 | 3.43 | 122 | 0.12 | 5.74 | 3 | −47 |
| E0037 | | CHOL | AVANTI | 50/0/46/4 | 3.43 | 117 | 0.1 | | 3 | 66.2 |
| E0037 | DSPC | CHOL | AVANTI | 50/28/18/4 | 3.43 | 96 | 0.24 | | 3 | 69.3 |
| E0038 | | CHOL | AVANTI | 50/0/46/4 | 3.43 | 115 | 0.08 | | 3 | −6.2 |
| E0038 | DSPC | CHOL | AVANTI | 50/28/18/4 | 3.43 | 116 | 0.25 | | 3 | −2.4 |
| E0039 | | CHOL | AVANTI | 50/0/46/4 | 3.43 | 94 | 0.06 | 5.88 | 3 | −5.4 |

TABLE 8-continued

Factor VII assay—In vivo liver results

| Lipid | Neutral lipid[1] | Helper lipid | Stealth lipid[2,3] | Lipid ratio (molar ratio)[4] | N/P ratio | Final size (nm) | PDI | pKa | dose (mg/kg) | FVII inhib % |
|---|---|---|---|---|---|---|---|---|---|---|
| E0039 | DSPC | CHOL | AVANTI | 50/28/18/4 | 3.43 | 113 | 0.15 | 5.88 | 3 | −6.7 |
| E0040 | DSPC | CHOL | AVANTI | 50/28/18/4 | 3.43 | 87 | 0.21 | 6.13 | 3 | 91.8 |
| E0040 | | CHOL | AVANTI | 50/0/46/4 | 3.43 | 103 | 0.15 | 6.13 | 3 | 97.8 |
| E0040 | | CHOL | AVANTI | 50/0/46/4 | 3.43 | 101 | 0.17 | 6.13 | 1 | 49.2 |
| E0041 | | CHOL | AVANTI | 50/0/46/4 | 3.43 | 93 | 0.21 | 4.8 | 3 | 17.6 |
| E0041 | DSPC | CHOL | AVANTI | 50/28/18/4 | 3.43 | 95 | 0.37 | 4.8 | 3 | −7.4 |
| E0042 | | CHOL | AVANTI | 50/0/46/4 | 3.43 | 73 | 0.19 | 6.7 | 3 | 84.5 |
| E0042 | DSPC | CHOL | AVANTI | 50/28/18/4 | 3.43 | 83 | 0.11 | 6.7 | 3 | 49.1 |
| E0043 | DSPC | CHOL | AVANTI | 50/28/18/4 | 3.43 | 110 | 0.24 | 6.33 | 3 | 95.7 |
| E0043 | | CHOL | AVANTI | 50/0/46/4 | 3.43 | 76 | 0.15 | 6.33 | 3 | −11.7 |
| E0045 | DSPC | CHOL | AVANTI | 50/28/18/4 | 3.43 | 100 | 0.18 | 4.73 | 3 | 10.4 |
| E0045 | | CHOL | AVANTI | 50/0/46/4 | 3.43 | 103 | 0.25 | 4.73 | 3 | 90.7 |
| E0046 | | CHOL | AVANTI | 50/0/46/4 | 3.43 | 194 | 0.116 | 5.75 | 3 | 12.7 |
| E0047 | | CHOL | AVANTI | 50/0/46/4 | 3.43 | 112 | 0.061 | 5.55 | 3 | −3.4 |
| E0048 | | CHOL | AVANTI | 50/0/46/4 | 3.43 | 225 | 0.115 | 6.56 | 3 | 88.5 |
| E0049 | | CHOL | AVANTI | 50/0/46/4 | 3.43 | 237 | 0.09 | 6.85 | 3 | 78.8 |
| E0050 | DSPC | CHOL | AVANTI | 50/28/18/4 | 3.43 | 100 | 0.21 | 4.9 | 3 | −7.2 |
| E0050 | | CHOL | AVANTI | 50/0/46/4 | 3.43 | 103 | 0.097 | 4.9 | 3 | −10.4 |
| E0051 | | CHOL | AVANTI | 50/0/46/4 | 3.43 | 142.9 | 0.057 | 5.73 | 3 | 77.5 |
| E0051 | DSPC | CHOL | AVANTI | 50/28/18/4 | 3.43 | 157.7 | 0.131 | 5.73 | 3 | 17 |
| E0052 | DSPC | CHOL | AVANTI | 50/28/18/4 | 3.43 | 100.4 | 0.185 | 6.95 | 3 | 98.1 |
| E0052 | DSPC | CHOL | AVANTI | 50/28/18/4 | 3.43 | 100.4 | 0.185 | 6.95 | 1 | 69.8 |
| E0053 | DSPC | CHOL | AVANTI | 50/28/18/4 | 3.43 | 103.3 | 0.221 | 6.95 | 3 | 90.1 |
| E0053 | DSPC | CHOL | AVANTI | 50/28/18/4 | 3.43 | 103.3 | 0.221 | 6.95 | 1 | −9.4 |
| E0054 | DSPC | CHOL | AVANTI | 50/28/18/4 | 3.43 | 103 | 0.2 | 6.58 | 3 | 97.8 |
| E0054 | | CHOL | AVANTI | 50/0/46/4 | 3.43 | 96 | 0.13 | 6.58 | 3 | 98.9 |
| E0054 | DSPC | CHOL | AVANTI | 50/28/18/4 | 3.43 | 103 | 0.2 | 6.58 | 1 | 57.5 |
| E0054 | | CHOL | AVANTI | 50/0/46/4 | 3.43 | 96 | 0.13 | 6.58 | 1 | 63 |
| E0055 | DSPC | CHOL | AVANTI | 50/28/18/4 | 3.43 | 113 | 0.24 | 6.78 | 3 | 96.4 |
| E0055 | | CHOL | AVANTI | 50/0/46/4 | 3.43 | 380 | 0.22 | 6.78 | 3 | 69.8 |
| E0055 | DSPC | CHOL | AVANTI | 50/28/18/4 | 3.43 | 113 | 0.24 | 6.78 | 1 | 28.2 |
| E0055 | | CHOL | AVANTI | 50/0/46/4 | 3.43 | 380 | 0.22 | 6.78 | 1 | 14.8 |
| E0060 | | CHOL | GM-020 | 60/0/36/4 | 3 | 90.25 | 0.171 | 6.43 | 1 | 0.0 |
| E0061 | | CHOL | GM-020 | 60/0/36/4 | 3 | 139.4 | 0.073 | 6.28 | 1 | 52.6 |
| E0062 | | CHOL | GM-020 | 60/0/36/4 | 3 | 145.1 | 0.125 | 6.45 | 1 | 64.8 |
| E0063 | | CHOL | GM-020 | 60/0/36/4 | 3 | 155.5 | 0.09 | 6.48 | 1 | 33.3 |
| E0064 | | CHOL | GM-020 | 60/0/36/4 | 3 | 169.2 | 0.144 | 6.83 | 1 | 37.2 |
| E0065 | | CHOL | GM-020 | 60/0/36/4 | 3 | 153.01 | 0.148 | 6.8 | 1 | 41.1 |
| E0066 | | CHOL | GM-020 | 60/0/36/4 | 3 | 140.7 | 0.071 | 6.5 | 1 | 44.2 |
| E0068 | | CHOL | GM-020 | 60/0/36/4 | 3 | 174.0 | 0.041 | 4.82 | 2 | 28.6 |
| E0069 | | CHOL | GM-020 | 60/0/36/4 | 3 | 113.4 | 0.199 | 6.07 | 1 | 29 |
| E0070 | | CHOL | GM-020 | 60/0/36/4 | 3 | 150.9 | 0.045 | 6.40 | 1 | 50.3 |
| E0071 | | CHOL | GM-020 | 60/0/36/4 | 3 | 188.2 | 0.151 | 6.47 | 1 | 30.8 |
| E0073 | | CHOL | GM-020 | 60/0/36/4 | 3 | 130.1 | 0.118 | 5.66 | 1 | 37.4 |
| E0075 | | CHOL | GM-020 | 60/0/36/4 | 3 | 108.3 | 0.098 | 5.79 | 1 | 31.5 |
| E0076 | | CHOL | GM-020 | 60/0/36/4 | 3 | 89.47 | 0.143 | 5.85 | 1 | 29.3 |
| E0077 | | CHOL | GM-020 | 60/0/36/4 | 3 | 109.8 | 0.127 | 5.79 | 1 | 26.8 |
| E0078 | | CHOL | GM-020 | 60/0/36/4 | 3 | 122.6 | 0.098 | 5.72 | 1 | 51.9 |
| E0079 | | CHOL | GM-020 | 60/0/36/4 | 3 | 106.2 | 0.052 | 6.79 | 1 | 33.5 |
| E0082 | | CHOL | GM-020 | 60/0/36/4 | 3 | 105.1 | 0.303 | 6.81 | 1 | 49.7 |
| E0083 | | CHOL | GM-020 | 60/0/36/4 | 3 | 113.4 | 0.199 | 6.79 | 1 | 55.6 |
| E0084 | | CHOL | GM-020 | 60/0/36/4 | 3 | 112.1 | 0.1 | 7.27 | 1 | 60.7 |
| E0087 | | CHOL | GM-020 | 60/0/36/4 | 3 | 119.2 | 0.148 | 6.38 | 1 | 69 |
| E0088 | | CHOL | GM-020 | 60/0/36/4 | 3 | 110.7 | 0.080 | 5.79 | 1 | 50.8 |
| E0094 | | CHOL | GM-020 | 60/0/36/4 | 3 | 115.5 | 0.076 | 5.91 | 1 | 36.3 |
| E0095 | | CHOL | GM-020 | 60/0/36/4 | 3 | 125.1 | 0.091 | 5.84 | 1 | 13 |
| E0096 | | CHOL | GM-020 | 60/0/36/4 | 3 | 128.8 | 0.162 | 5.77 | 1 | 14.4 |
| E0115 | | CHOL | GM-020 | 60/0/36/4 | 3 | 162.5 | 0.098 | 6.41 | 1 | 68.8 |
| E0118 | DSPC | CHOL | AVANTI | 50/28/18/4 | 3.43 | 88 | 0.21 | 6.88 | 3 | 98.1 |
| E0118 | | CHOL | AVANTI | 50/0/46/4 | 3.43 | 93 | 0.23 | 6.88 | 3 | 99.2 |
| E0118 | | CHOL | AVANTI | 50/0/46/4 | 3.43 | 98 | 0.22 | 6.88 | 1 | 76.1 |
| E0170 | | CHOL | AVANTI | 50/0/46/4 | 3.43 | 170 | 0.05 | | 3 | 14.3 |
| E0170 | DSPC | CHOL | AVANTI | 50/28/18/4 | 3.43 | 133 | 0.095 | | 3 | 9.3 |
| E0171 | | CHOL | AVANTI | 50/0/46/4 | 3.43 | 90 | 0.18 | 5.85 | 3 | 54.1 |
| E0172 | | CHOL | AVANTI | 50/0/46/4 | 3.43 | 129 | 0.184 | 8.5 | 3 | 40.8 |
| E0172 | DSPC | CHOL | AVANTI | 50/28/18/4 | 3.43 | 170 | 0.181 | 8.5 | 3 | 21 |
| E0173 | | CHOL | AVANTI | 50/0/46/4 | 3.43 | 76 | 0.16 | 6.73 | 3 | 98.5 |
| E0173 | DSPC | CHOL | AVANTI | 50/28/18/4 | 3.43 | 98 | 0.17 | 6.73 | 3 | 90.9 |
| E0173 | | CHOL | AVANTI | 50/0/46/4 | 3.43 | 76 | 0.16 | 6.73 | 1 | 87.4 |

TABLE 8-continued

Factor VII assay—In vivo liver results

| Lipid | Neutral lipid[1] | Helper lipid | Stealth lipid[2,3] | Lipid ratio (molar ratio)[4] | N/P ratio | Final size (nm) | PDI | pKa | dose (mg/kg) | FVII inhib % |
|---|---|---|---|---|---|---|---|---|---|---|
| E0174 | DSPC | CHOL | AVANTI | 50/28/18/4 | 3.43 | 117 | 0.23 | 5.15 | 3 | 63.2 |
| E0174 |  | CHOL | AVANTI | 50/0/46/4 | 3.43 | 90 | 0.21 | 5.15 | 3 | 3.5 |

[1] wherein a blank cell indicates that no neutral lipid is present
[2] wherein AVANTI represents AVANTI 880150P
[3] wherein GM-020 represents GM-020 NOF
[4] wherein the order of the lipids types as they appear in the molar ratio corresponds to the order in which the lipids appear in the first four columns of the table. Where only three lipids are listed in the molar ratio, the neutral lipid is absent.

Example 72

Hep3B Tumor Studies

Hep3B tumors are established in female nude mice by sc injection of $7 \times 10^6$ cells in 100 ul PBS into the left flank. Mice are randomized into treatment groups 10-14 days after seeding as tumors reached an average size of 100 mm$^3$. siRNA formulated LNP formulations are administered at various dose levels intravenously via the lateral tail vein calculated on a mg siRNAs/kg basis according to individual animal weights (10 ml/kg injection volume). Mice are euthanized by $CO_2$ inhalation at various time points and the tumors are harvested for mRNA quantitation. Lipids with a wide range of pKa (5.3-6.6) are used in the LNP formulations. Tumors are measured in 2 dimensions (width×length) to assess tumor growth using digital calipers. Tumor volume is calculated using the equation [a×b×b/2], where a equals the largest diameter and b equals the smallest diameter.

Example 73

HepG2 Liver Tumor Studies

HepG2 tumors are established in female nude mice by sc injection of $5 \times 10^6$ cells in 100 ul PBS into the left flank. Mice are randomized into treatment groups 10-14 days after seeding as tumors reached an average size of 150 mm$^3$. siRNA formulated LNP formulations are administered at 3×3 mg/kg dose levels intravenously via the lateral tail vein calculated on a mg siRNAs/kg basis according to individual animal weights (10 ml/kg injection volume). Mice are euthanized by $CO_2$ inhalation at various time points and the tumors are harvested 24 hrs after the last dose for mRNA quantitation. Lipids with a wide range of pKa (5.3-6.6) are used in the LNP formulations. Tumors are measured in 2 dimensions (width×length) to assess tumor growth using digital calipers. Tumor volume is calculated using the equation [a×b×b/2], where a=largest diameter and b=smallest diameter.

Example 74

786-0 Renal Tumor Studies 786-0 tumors are established as described before by sc injection of $10 \times 10^6$ cells in 200 ul PBS. 4 weeks post implantation, the mice with the tumor size ranging from 200-250 mm$^3$ are randomized into treatment groups. siRNA formulated LNPs are then intravenously administered at either 5 or 10 mg/kg dose levels. 48 hrs after the single dose, tumors are collected for mRNA quantitation.

Example 75

Measurement of PLK-1 and GAPDH mRNA KD in Tumor Tissues

About 30-50 mg tumor tissue is homogenized in tissue lysis buffer in a Qiagen homogenizer followed by centrifugation to clarify lysates. Total RNA is isolated using RNeasy isolation kit (catalog number 74106) according to the manufacture's protocol. PLK-1 mRNA is analyzed by quantitative PCR and normalized to human GAPDH. Applied Biosystems human PLK-1 gene expression assay Hs00983229_m1 and human GAPDH endogenous control cat number 4326317E are used for mRNA detection.

The results for knock down ("KD") of PLK1 mRNA levels in the tumor experiments of Examples 72, 73, 74 and 75 are set out in the following Tables and calculated as percent inhibition (PLK1% inhibition). Results for targetting Hep3B liver tumors are reported in Table 9. Results for targetting HepG2 liver tumors are reported in Table 10. Results for targetting 786-0 renal tumors are reported in Table 11. The pKa in all tables refers to the pKa of the cationic lipid. Where multiple doses are indicated (e.g., 3×5), the first number indicates the number of doses given and the second number indicates the amount per dose in mg siRNA (biologically active agent) per kg mouse. In general the multiple doses are administered at 24 hour intervals, and tissues for mRNA quantitation are harvested 24 hours after the last dose.

TABLE 9

Hep3B Tumor In vivo Assay results

| Lipid ref. | Helper lipid | Neutral Lipid[1] | Stealth lipid | Lipid Ratio (molar ratio)[2] | N/P (ratio) | Final size (nm) | pKa | # doses × (mg/kg) | PLK1 inhibition % |
|---|---|---|---|---|---|---|---|---|---|
| E0008 | Chol |  | S011 | 60/38/2 | 4 | 93.11 | 5.81 | 1 × 5 | 85 |
| E0008 | Chol |  | S004 | 60/38/2 | 4 | 123.1 | 5.81 | 1 × 1 | 38 |
| E0011 | Chol | DSPC | S011 | 40/48/10/2 | 4 | 83.45 | 5.32 | 1 × 10 | 56 |
| E0011 | Chol |  | S019 | 60/38/2 | 4 | 110 | 5.32 | 1 × 1 | 36 |
| E0011 | Chol |  | S020 | 60/38/2 | 4 | 74.42 | 5.32 | 1 × 1 | 32 |
| E0011 | Chol |  | S011 | 60/38/2 | 4 | 84.58 | 5.32 | 1 × 10 | 67 |
| E0011 | Chol |  | S011 | 60/38/2 | 4 | 84.58 | 5.32 | 3 × 10 | 71 |
| E0011 | Chol |  | S011 | 60/38/2 | 4 | 84.58 | 5.32 | 3 × 5 | 68 |

TABLE 9-continued

Hep3B Tumor In vivo Assay results

| Lipid ref. | Helper lipid | Neutral Lipid[1] | Stealth lipid | Lipid Ratio (molar ratio)[2] | N/P (ratio) | Final size (nm) | pKa | # doses × (mg/kg) | PLK1 inhibition % |
|---|---|---|---|---|---|---|---|---|---|
| E0011 | Chol | DSPC | S004 | 40/48/10/2 | 4 | 85.09 | 5.32 | 1 × 10 | 65 |
| E0011 | Chol | DSPC | S012 | 40/48/10/2 | 4 | 91.46 | 5.32 | 1 × 10 | 18 |
| E0011 | Chol | DSPC | S002 | 40/48/10/2 | 4 | 89.73 | 5.32 | 1 × 10 | 37 |
| E0011 | Chol | DSPC | S003 | 40/48/10/2 | 4 | 100.5 | 5.32 | 1 × 10 | 42 |
| E0011 | Chol | DSPC | S011 | 40/53/5/2 | 4 | 100 | 5.32 | 1 × 10 | 60 |
| E0011 | Chol | DSPC | S011 | 40/43/15/2 | 4 | 94.21 | 5.32 | 1 × 10 | 44 |
| E0011 | Chol | DSPC | S011 | 40/38/20/2 | 4 | 95.4 | 5.32 | 1 × 10 | 38 |
| E0011 | Chol |  | S011 | 60/38/2 | 4 | 83.01 | 5.32 | 1 × 5 | 69 |
| E0011 | Chol |  | S011 | 60/38/2 | 4 | 83.02 | 5.32 | 1 × 2 | 46 |
| E0011 | Chol |  | S004 | 60/38/2 | 4 | 95.47 | 5.32 | 1 × 10 | 70 |
| E0011 | Chol |  | S004 | 60/38/2 | 4 | 95.47 | 5.32 | 3 × 5 | 67 |
| E0011 | Chol |  | S004 | 60/38/2 | 4 | 96.31 | 5.32 | 1 × 2 | 56 |
| E0011 | Chol |  | S004 | 60/38/2 | 4 | 96.31 | 5.32 | 1 × 5 | 66 |
| E0011 | Chol |  | S007 | 60/38/2 | 4 | 94.2 | 5.32 | 1 × 2 | 65 |
| E0011 | Chol |  | S009 | 60/38/2 | 4 | 98.41 | 5.32 | 1 × 2 | 64 |
| E0011 | Chol |  | S008 | 60/38/2 | 4 | 101.5 | 5.32 | 1 × 2 | 60 |
| E0011 | Chol |  | S005 | 60/38/2 | 4 | 95.26 | 5.32 | 1 × 2 | 52 |
| E0011 | Chol |  | S011 | 55/43/2 | 4 | 84.58 | 5.32 | 1 × 2 | 59 |
| E0011 | Chol |  | S011 | 55/43/2 | 4 | 84.58 | 5.32 | 1 × 5 | 66 |
| E0011 | Chol |  | S011 | 50/48/2 | 4 | 84.76 | 5.32 | 1 × 2 | 58 |
| E0011 | Chol |  | S011 | 50/48/2 | 4 | 84.76 | 5.32 | 1 × 5 | 67 |
| E0014 | Chol | DSPC | S011 | 40/48/10/2 | 4 | 82.21 | 6.4 | 1 × 10 | 22 |
| E0061 | Chol |  | S004 | 60/38/2 | 4 | 90.09 | 6.28 | 1 × 1 | 23 |
| E0024 | Chol | DSPC | S011 | 40/48/10/2 | 3 | 88.46 | 6.62 | 1 × 10 | 15 |
| E0024 | Chol |  | S004 | 60/38/0/2 | 3 | 120.6 | 6.62 | 4 × 5 | 23 |
| E0025 | Chol |  | S011 | 60/38/2 | 4 | 95.73 | 5.45 | 1 × 5 | 84 |
| E0025 | Chol | DSPC | S011 | 40/48/10/2 | 4 | 85.63 | 5.45 | 1 × 5 | 77 |
| E0025 | Chol | DSPC | S004 | 45/43/10/2 | 4 | 118.8 | 5.45 | 1 × 1 | 27 |
| E0026 | Chol |  | S011 | 60/38/2 | 4 | 105.8 | 5.85 | 1 × 5 | 75 |
| E0051 | Chol | DSPC | S011 | 40/48/10/2 | 4 | 85.77 | 5.73 | 1 × 10 | 17 |
| E0095 | Chol |  | S004 | 50/48/2 | 4 | 96.09 | 5.84 | 1 × 1 | 58 |
| E0095 | Chol |  | S004 | 50/48/2 | 4 | 96.09 | 5.84 | 1 × 0.1 | 23 |
| E0095 | Chol |  | S004 | 50/48/2 | 4 | 96.09 | 5.84 | 1 × 1 | 56 |
| E0075 | Chol |  | S011 | 60/38/2 | 4 | 124.5 | 5.79 | 1 × 5 | 75 |
| E0076 | Chol |  | S011 | 60/38/2 | 4 | 89.89 | 5.85 | 1 × 5 | 85 |
| E0076 | Chol |  | S004 | 50/48/2 | 4 | 86.03 | 5.85 | 1 × 1 | 54 |
| E0076 | Chol |  | S004 | 50/48/2 | 4 | 86.03 | 5.85 | 1 × 1 | 42 |
| E0076 | Chol | DSPC | S004 | 45/43/10/2 | 4 | 80.98 | 5.85 | 1 × 1 | 19 |
| E0076 | Chol | DSPC | S004 | 45/43/10/2 | 4 | 80.98 | 5.85 | 1 × 0.1 | 0 |
| E0077 | Chol |  | S011 | 60/38/2 | 4 | 120.8 | 5.79 | 1 × 5 | 77 |
| E0085 | Chol | DSPC | S004 | 45/43/10/2 | 4 | 76.8 | 5.32 | 1 × 1 | 22 |
| E0085 | Chol | DSPC | S004 | 50/43/5/2 | 4 | 87.74 | 5.32 | 1 × 1 | 30 |
| E0085 | Chol | DSPC | S004 | 50/43/5/2 | 4 | 87.74 | 5.32 | 1 × 1 | 34 |
| E0085 | Chol | DSPC | S004 | 50/43/5/2 | 4 | 87.74 | 5.32 | 1 × 0.1 | 53 |
| E0085 | Chol |  | S004 | 50/48/0/2 | 4 | 96.42 | 5.32 | 1 × 1 | 42 |
| E0085 | Chol | DSPC | S004 | 50/38/10/2 | 4 | 88.33 | 5.32 | 1 × 1 | 20 |
| E0085 | Chol | DSPC | S011 | 40/48/10/2 | 4 | 81.83 | 5.32 | 1 × 10 | 55 |
| E0085 | Chol |  | S004 | 60/38/2 | 4 | 90.06 | 5.32 | 1 × 2 | 62 |
| E0085 | Chol |  | S004 | 60/38/2 | 4 | 90.06 | 5.32 | 1 × 5 | 69 |
| E0088 | Chol |  | S011 | 60/38/2 | 4 | 146.2 | 5.79 | 1 × 5 | 71 |
| E0093 | Chol | DSPC | S011 | 40/48/10/2 | 4 | 82.42 | 4.85 | 1 × 10 | 2 |
| E0104 | Chol | DSPC | S004 | 45/43/10/2 | 4 | 87.59 | 6.1 | 1 × 1 | 48 |
| E0104 | Chol | DSPC | S004 | 45/43/10/2 | 4 | 87.59 | 6.1 | 1 × 0.1 | 34 |
| E0104 | Chol | DSPC | S004 | 50/43/5/2 | 4 | 92.19 | 6.1 | 1 × 1 | 34 |
| E0104 | Chol | DSPC | S004 | 50/43/5/2 | 4 | 92.19 | 6.1 | 1 × 0.1 | 22 |
| E0104 | Chol |  | S004 | 60/38/2 | 4 | 106.2 | 6.1 | 1 × 1 | 47 |
| E0104 | Chol |  | S004 | 50/48/2 | 3 | 96.19 | 6.1 | 1 × 1 | 48 |
| E0104 | Chol |  | S020 | 50/48/2 | 4 | 75.56 | 6.1 | 1 × 1 | 45 |
| E0104 | Chol |  | S004 | 50/48/2 | 4 | 90.77 | 6.1 | 1 × 0.1 | 29 |
| E0104 | Chol |  | S004 | 50/48/2 | 4 | 90.77 | 6.1 | 1 × 1 | 55 |
| E0104 | Chol |  | S004 | 50/48/2 | 4 | 95.05 | 6.1 | 1 × 1 | 50 |
| E0104 | Chol |  | S004 | 50/48/2 | 4 | 95.05 | 6.1 | 1 × 0.1 | 15 |
| E0104 | Chol |  | S004 | 50/48/2 | 4 | 95.05 | 6.1 | 1 × 1 | 50 |
| E0104 | Chol |  | S004 | 50/48/2 | 4 | 95.05 | 6.1 | 1 × 1 | 40 |
| E0104 | Chol |  | S004 | 50/48/2 | 4 | 90.87 | 6.1 | 1 × 1 | 56 |
| E0102 | Chol |  | S004 | 60/38/2 | 4 | 94.69 | 6.31 | 1 × 1 | 37 |
| E0102 | Chol |  | S004 | 60/38/2 | 4 | 94.69 | 6.31 | 1 × 1 | 47 |
| E0045 | Chol |  | S004 | 60/38/2 | 4 | 103.2 | 4.73 | 1 × 1 | 36 |
| E0119 | Chol |  | S004 | 50/48/2 | 4 | 99.37 | 5.82 | 1 × 1 | 40 |
| E0120 | Chol |  | S004 | 50/48/2 | 4 | 87 | 5.48 | 1 × 1 | 28 |
| E0125 | Chol |  | S004 | 50/48/2 | 4 | 94.13 | 5.53 | 1 × 1 | 36 |
| E0125 | Chol | DSPC | S004 | 50/43/5/2 | 4 | 92.84 | 5.53 | 1 × 1 | 20 |
| E0125 | Chol | DSPC | S004 | 50/38/10/2 | 4 | 101.5 | 5.53 | 1 × 1 | 34 |
| E0128 | Chol |  | S004 | 50/48/2 | 4 | 83.47 | 5.01 | 1 × 1 | 23 |

TABLE 9-continued

Hep3B Tumor In vivo Assay results

| Lipid ref. | Helper lipid | Neutral Lipid[1] | Stealth lipid | Lipid Ratio (molar ratio)[2] | N/P (ratio) | Final size (nm) | pKa | # doses × (mg/kg) | PLK1 inhibition % |
|---|---|---|---|---|---|---|---|---|---|
| E0151 | Chol | | S004 | 50/48/2 | 4 | 103.8 | 6.06 | 1 × 1 | 25 |
| E0151 | Chol | | S004 | 50/48/2 | 4 | 103.8 | 6.06 | 1 × 0.1 | 7 |
| E0152 | Chol | | S004 | 50/48/2 | 4 | 121.3 | 5.38 | 1 × 1 | 18 |
| E0160 | Chol | | S004 | 50/48/2 | 4 | 100.8 | 6.05 | 1 × 1 | 38 |
| E0161 | Chol | | S004 | 50/48/2 | 4 | 101.4 | 6.3 | 1 × 1 | 45 |
| E0167 | Chol | | S004 | 50/48/2 | 4 | 86.57 | 5.21 | 1 × 1 | 23 |
| E0175 | Chol | | S004 | 60/38/2 | 4 | 78.74 | 5.67 | 1 × 1 | 42 |
| E0175 | Chol | | S020 | 60/38/2 | 4 | 69.33 | 5.67 | 1 × 1 | 44 |
| E0175 | Chol | | S004 | 50/48/2 | 4 | 67.98 | 5.67 | 1 × 1 | 41 |
| E0175 | Chol | DSPC | S004 | 50/43/5/2 | 3.8 | 93.51 | 5.67 | 1 × 1 | 46 |
| E0175 | Chol | resorcinol[3] | S004 | 50/43/5/2 | 3.8 | 104.2 | 5.67 | 1 × 1 | 34 |
| E0176 | Chol | | S004 | 60/38/2 | 4 | 99.14 | 5.56 | 1 × 1 | 36 |
| E0177 | Chol | | S004 | 50/48/2 | 4 | 91.91 | 6.1 | 1 × 1 | 41 |
| E0177 | Chol | | S004 | 50/48/2 | 4 | 91.91 | 6.1 | 1 × 1 | 30 |
| E0177 | Chol | | S004 | 50/48/2 | 4 | 91.91 | 6.1 | 1 × 0.1 | 9 |
| E0177 | Chol | DSPC | S004 | 50/43/5/2 | 4 | 95.92 | 6.1 | 1 × 1 | 45 |
| E0177 | Chol | DOPC | S004 | 50/43/5/2 | 4 | 89.78 | 6.1 | 1 × 1 | 0 |
| E0177 | Chol | DSPC | S004 | 50/38/10/2 | 4 | 88.15 | 6.1 | 1 × 1 | 36 |
| E0178 | Chol | | S004 | 50/48/2 | 4 | 88.39 | 5.92 | 1 × 1 | 35 |
| E0178 | Chol | | S004 | 50/48/2 | 4 | 88.39 | 5.92 | 1 × 0.1 | 0 |
| E0178 | Chol | | S004 | 50/48/2 | 4 | 88.39 | 5.92 | 1 × 1 | 56 |
| E0178 | Chol | DSPC | S004 | 50/43/5/2 | 4 | 94.67 | 5.92 | 1 × 1 | 58 |
| E0178 | Chol | DSPC | S004 | 50/43/5/2 | 4 | 94.67 | 5.92 | 1 × 1 | 32 |
| E0179 | Chol | | S004 | 50/48/2 | 4 | 114.6 | 5.95 | 1 × 1 | 53 |
| E0180 | Chol | | S004 | 50/48/2 | 4 | 77.35 | | 1 × 1 | 16 |

[1] A blank cell indicates that the neutral lipid is omitted
[2] wherein the order of the lipids types as they appear in the molar ratio corresponds to the order in which the lipids appear in the first four columns of the table. Where only three lipids are listed in the molar ratio, the neutral lipid is absent.
[3] wherein "resorcinol" represents 5-heptadecylbenzene-1,3-diol.

TABLE 10

HepG2 Tumor In vivo Assay results

| Lipid ref. | Helper lipid | Neutral lipid[1] | Stealth lipid | Molar Lipid Ratio[2] | N/P ratio | Final size | pKa | # doses × (mg/kg) | PLK1 % inhibition |
|---|---|---|---|---|---|---|---|---|---|
| E0011 | Chol | | S018 | 60/38/2 | 4 | 113.2 | 5.32 | 3 × 3 | 16 |
| E0011 | Chol | | S019 | 60/38/2 | 4 | 110 | 5.32 | 3 × 3 | 13 |
| E0011 | Chol | | S020 | 60/38/2 | 4 | 74.42 | 5.32 | 3 × 3 | 29 |
| E0056 | Chol | | S004 | 50/48/2 | 4 | 77 | 6.33 | 3 × 3 | 0 |
| E0076 | Chol | | S004 | 50/48/2 | 4 | 86.03 | 5.85 | 3 × 3 | 35 |
| E0085 | Chol | DSPC | S004 | 45/43/10/2 | 4 | 76.8 | 5.32 | 3 × 3 | 40 |
| E0056 | Chol | | S004 | 50/48/2 | 4 | 96.09 | 5.84 | 3 × 3 | 16 |
| E0056 | Chol | | S004 | 50/48/2 | 4 | 96.09 | 5.84 | 3 × 3 | 30 |
| E0096 | Chol | | S004 | 50/48/2 | 4 | 94.91 | 5.77 | 3 × 3 | 17 |
| E0104 | Chol | DSPC | S004 | 45/43/10/2 | 4 | 87.59 | 6.1 | 3 × 3 | 32 |
| E0104 | Chol | DSPC | S004 | 50/43/5/2 | 4 | 92.19 | 6.1 | 3 × 3 | 36 |
| E0104 | Chol | DOPC | S004 | 50/43/5/2 | 4 | 125.1 | 6.1 | 3 × 3 | 19 |
| E0104 | Chol | | S004 | 50/48/2 | 4 | 95.05 | 6.1 | 3 × 3 | 34 |
| E0104 | Chol | | S004 | 50/48/2 | 4 | 90.87 | 6.1 | 3 × 3 | 30 |
| E0119 | Chol | | S004 | 50/48/2 | 4 | 99.37 | 5.82 | 3 × 3 | 22 |
| E0175 | Chol | | S004 | 60/38/2 | 4 | 78.74 | 5.67 | 3 × 3 | 49 |
| E0175 | Chol | DSPC | S004 | 50/43/5/2 | 3.8 | 93.51 | 5.67 | 3 × 3 | 30 |
| E0176 | Chol | | S004 | 60/38/2 | 4 | 99.14 | 5.56 | 3 × 3 | 37 |
| E0177 | Chol | | S004 | 50/48/2 | 4 | 91.91 | 6.1 | 3 × 3 | 30 |
| E0177 | Chol | DSPC | S004 | 50/43/5/2 | 4 | 95.92 | 6.1 | 3 × 3 | 44 |
| E0177 | Chol | DOPC | S004 | 50/43/5/2 | 4 | 89.78 | 6.1 | 3 × 3 | 24 |
| E0178 | Chol | DSPC | S004 | 50/43/5/2 | 4 | 94.67 | 5.92 | 3 × 3 | 0 |
| E0161 | Chol | | S004 | 50/48/2 | 4 | 101.4 | 6.3 | 3 × 3 | 0 |
| E0162 | Chol | | S004 | 50/48/2 | 4 | 114.4 | 6.07 | 3 × 3 | 0 |
| E0180 | Chol | | S004 | 50/48/2 | 4 | 77.35 | | 3 × 3 | 0 |

[1] A blank cell indicates that the neutral lipid is omitted
[2] wherein the order of the lipids types as they appear in the molar ratio corresponds to the order in which the lipids appear in the first four columns of the table. Where only three lipids are listed in the molar ratio, the neutral lipid is absent.

TABLE 11

786-0 Renal Tumor Assay results

| Lipid ref. | Helper lipid | Neutral lipid[1] | Stealth lipid | Lipid Ratio[2] | N/P ratio | Final size | pKa | # doses × (mg/kg) | PLKI % Inhibition |
|---|---|---|---|---|---|---|---|---|---|
| E0104 | Chol | | S004 | 50/48/2 | 4 | 95.05 | 6.1 | 1 × 5 | 55 |
| E0104 | Chol | DSPC | S004 | 45/43/10/2 | 4 | 87.59 | 6.1 | 1 × 10 | 50 |
| E0104 | Chol | | S004 | 50/48/2 | 4 | 95.05 | 6.1 | 1 × 10 | 50 |

[1] A blank cell indicates that the neutral lipid is omitted
[2] wherein the order of the lipids types as they appear in the molar ratio corresponds to the order in which the lipids appear in the first four columns of the table. Where only three lipids are listed in the molar ratio, the neutral lipid is absent.

In the above tables, the N/P ratio is equal to the following: (number of moles of cationic lipid initially formulated)/ (number of moles of siRNA initially formulated*total number of anionic charges per siRNA).

Example 76

Optimization of Lipid Formulations

Further optimization of the formulations utilizing cationic lipids and stealth lipids, e.g., as shown in the above tables, is considered within the knowledge of a skilled practitioner and may be done without undue experimentation. For example, formulations may be optimized for at least one parameter including but not limited to individual selection of, e.g., the pKa of the cationic lipid optimized for the type of cell or organ being targeted, the cationic lipid used, the stealth lipid used, the helper lipid, the neutral lipid used, whether the neutral lipid is present or absent, the ratio of the selected helper lipid, optional neutral lipid, stealth lipid and cationic lipid, the N/P ratio, the particle size, the dosage regimen, the dose given, the formulation method, and the like.

In one embodiment, when choosing the more optimal neutral lipid, a skilled practitioner would more often opt for DSPC than DOPC. In some embodiments, e.g., for E0177 in Table 9 and E0104 in Table 10, compositions that differed only by the choice of these two neutral lipids exhibit a lower KD or even zero KD when DOPC is used compared to when DSPC is used, with all other aspects considered equal. In certain compositions, omitting the neutral lipid altogether, e.g., for at least one formulation of E0085 in Table 9, results in a higher percent inhibition of PLK1 compared to having a neutral lipid present, or for E0011 where progressively decreasing the amount of DSPC in the formulations leads to progressively increasing percent knockdown.

Dose in mg/kg and dosage regimen, e.g., number of doses given and timing of said doses, may also be optimized. For example, in one experiment shown in Table 9, administering 0.1 mg/kg of a formulation with E0178 results in zero (0) % KD but administering 1.0 mg/kg provides 35% KD. If larger doses are not tolerated by a subject, a full treatment regimen may be administered as multiple smaller doses provided over several days, such in Table 9, wherein delivery of 1×10 mg/kg siRNA versus 3×5 mg/kg siRNA in formulations containing E0011 and S004 resulted in 70% KD and 67% KD, respectively.

Example 77

Liposomes for Delivery of Nucleic Acid Replicons

Various nucleic acid replicons, each about 10,000 nucleotides long, are delivered in liposomes as described below. Nucleic acid is encapsulated in liposomes made essentially by the methods of Jeffs et al. (2005) *Pharmaceutical Research* 22 (3):362-372 and Maurer et al. (2001) *Biophysical Journal*, 80: 2310-2326.

Reference liposomes are made of 10% DSPC (zwitterionic, i.e., neutral lipid), 40% DlinDMA (cationic lipid), 48% cholesterol (helper lipid) and 2% PEG-conjugated DMG (stealth lipid). The DlinDMA lipid (1,2-dilinoleyloxy-N,N-dimethyl-3-aminopropane) is synthesized using the procedure of Heyes et al. (2005) *J Controlled Release* 107:276-87. DSPC (1,2-Diastearoyl-sn-glycero-3-phosphocholine) is purchased from Genzyme. Cholesterol is obtained from Sigma-Aldrich. PEG-conjugated DMG (1,2-dimyristoyl-sn-glycero-3-phosphoethanolamine-N-[methoxy(polyethylene glycol), ammonium salt), DOTAP (1,2-dioleoyl-3-trimethylammonium-propane, chloride salt) and DC-chol(3β-[N-(N', N'dimethylaminoethane)-carbamoyl]cholesterol hydrochloride) are available from Avanti Polar Lipids.

Briefly, lipids are dissolved in ethanol (2 ml), replicon is dissolved in buffer (2 ml, 100 mM sodium citrate, pH 6) and these are mixed with 2 ml of buffer followed by 1 hour of equilibration. The mixture is diluted with 6 ml buffer then filtered. The resulting product contained liposomes, with ~95% encapsulation efficiency.

The percentage of encapsulated nucleic acid and the nucleic acid concentration are determined with a commercial kit. Liposomes are diluted 10× or 100× in 1X TE buffer (from kit) before addition of the dye. Separately, liposomes are diluted 10× or 100× in 1X TE buffer containing 0.5% Triton X before addition of the dye (to disrupt the liposomes and thus to assay total nucleic acid). Thereafter an equal amount of dye is added to each solution and then approximately 180 μL of each solution after dye addition is loaded in duplicate into a 96 well culture plate. The fluorescence (Ex 485 nm, Em 528 nm) is read on a microplate reader.

To assess in vivo expression of the nucleic acid a reporter enzyme (SEAP; secreted alkaline phosphatase) is encoded in the replicon. Expression levels are measured in sera diluted 1:4 in 1X Phospha-Light dilution buffer using a chemiluminescent alkaline phosphate substrate. 8-10 week old BALB/c mice (5/group) are injected intramuscularly on day 0, 50 μl per leg with 0.1 μg or 1 μg nucleic acid dose. The same vector is also administered without the liposomes (in PBS) at 1 μg.

Encapsulation increases SEAP levels by about ½ log at the 1 μg dose, and at day 6 expression from a 0.1 μg encapsulated dose matches levels seen with 1 μg unencapsulated dose. Thus expression increases when the nucleic acid is formulated in the liposomes relative to the naked nucleic acid control, even at a 10× lower dose.

Further SEAP experiments show a clear dose response in vivo, wherein expression is seen after delivery of as little as 1 ng nucleic acid. Experiments comparing expression from encapsulated and naked replicons indicate that 0.01 μg encapsulated nucleic acid is equivalent to 1 μg of naked nucleic acid. At a 0.5 µg dose of nucleic acid the encapsulated material can give a 12-fold higher expression at day 6; at a 0.1 µg dose levels can be 24-fold higher at day 6.

As an alternative to using the reference lipid (DlinDMA), cationic lipids of the invention are used. The reference liposomes are formed using DlinDMA (see above) as the cationic lipid. DlinDMA is replaced with various cationic lipids in series as described below and shown in Table. Two different types of each liposome are formed, using 2% PEG2000-DMG with either (01) 40% of the cationic lipid, 10% DSPC, and 48% cholesterol, or (02) 60% of the cationic lipid and 38% cholesterol. Thus a comparison of the (01) and (02) liposomes shows the effect of the neutral zwitterionic lipid.

These liposomes are tested with the SEAP reporter described above. The following Table 12 shows the size of the liposomes (Z average and polydispersity index), the % of nucleic acid encapsulation in each liposome, together with the SEAP activity detected at days 1 and 6 after injection. SEAP activity is relative to "DlinDMA (02)" liposomes made from DlinDMA, cholesterol and PEG-DMG.

TABLE 12

Liposome delivery of nucleic acid replicons

| E no. | Zav (pdI) | % encapsulation | SEAP day 1 | SEAP day 6 |
|---|---|---|---|---|
| DlinDMA (01) | 154.6 (0.131) | 95.5 | 80.9 | 71.1 |
| DlinDMA (02) | 162.0 (0.134) | 85.3 | 100 | 100 |
| Comparative (01) | 133.9 (0.185) | 96.5 | 57 | 45.7 |
| Comparative (02) | 134.6 (0.082) | 97.6 | 54.2 | 4.3 |
| E0014 (01) | 158.3 (0.212) | 62.0 | 65.7 | 44.9 |
| E0014 (02) | 164.2 (0.145) | 86 | 62.2 | 39.7 |
| E0024 (01) | 131.0 (0.145) | 74.0 | 91 | 154.8 |
| E0024 (02) | 134.6 (0.117) | 81.5 | 90.4 | 142.6 |
| E0026 (01) | 164.0 (0.162) | 76.0 | 76.9 | 329.8 |
| E0026 (02) | 177.8 (0.117) | 72.8 | 67.1 | 227.9 |
| E0084 (01) | 116.0 (0.180) | 79.8 | 25.5 | 12.4 |
| E0084 (02) | 136.3 (0.164) | 74.9 | 24.8 | 23.1 |
| E0065 (01) | 140.6 (0.184) | 77 | 26.5 | 163.3 |
| E0065 (02) | 138.6 (0.122) | 87 | 29.7 | 74.8 |
| E0078 (01) | 176.7 (0.185) | 50 | 76.5 | 187 |
| E0078 (02) | 199.5 (0.191) | 46.3 | 82.4 | 329.8 |
| E0069 (01) | 165.3 (0.169) | 72.2 | 65.1 | 453.9 |
| E0069 (02) | 179.5 (0.157) | 65 | 68.5 | 658.2 |
| E0108 (01) | 129.7 (0.184) | 78.4 | 113.4 | 47.8 |
| E0108 (02) | 147.6 (0.131) | 80.9 | 78.2 | 10.4 |
| E0115 (01) | 129.2 (0.186) | 71 | 113.6 | 242.2 |
| E0115 (02) | 139 (0198) | 75.2 | 71.8 | 187.2 |
| E0099 (01) | 135.7 (0.161) | 78.8 | 65 | 10 |
| E0099 (02) | 158.3 (0.287) | 69.4 | 78.8 | 8.2 |

Additional Aspects of the Invention

The invention comprises a composition comprising at least one cationic lipid, at least one helper lipid and at least one stealth lipid for delivery of a biologically active agent, wherein the biologically active agent is for delivery to a tissue or cell selected from: (a) the liver or liver cells, wherein the composition has a cationic lipid with a pKa of from about 6.2 or above; and (b) a tumor or tumor cell, wherein the composition has a cationic lipid with a pKa of from about 6.2 or below.

The invention comprises a composition comprising at least one cationic lipid, at least one helper lipid and at least one stealth lipid for delivery of a biologically active agent, wherein the biologically active agent is for delivery to a tissue or cell selected from: (a) the liver or liver cells, wherein the composition has a cationic lipid with a pKa of from about 5.1 to about 7.4; and (b) a tumor or tumor cell, wherein the composition has a cationic lipid with a pKa of from about 5.0 to about 6.7.

The invention comprises a composition of paragraphs [00707] or [00708], wherein the composition further comprises an optional neutral lipid.

The invention comprises the composition of any one of paragraphs [00707], [00708] or [00709], wherein the biologically active agent is in an amount effective for therapeutic treatment of a disease or disorder.

The invention comprises the composition of paragraphs [00710], wherein the biologically active agent is for delivery to the liver or a liver cell and the cationic lipid 1 has a pKa at least about 5.1 to about 7.4.

The invention comprises the composition of paragraph [00710], wherein the biologically active agent is for delivery to a tumor or tumor cells and the compound of paragraph 1 has a pKa of from about 5.0 to about 6.7.

The invention comprises the composition of paragraph [00712], wherein the cationic lipid has a pKa of from about 5.2 to about 6.3.

The invention comprises the composition of paragraph [00712], wherein the cationic lipid has a pKa of from about 5.4 to about 6.2.

The invention comprises the composition of paragraph [00712], wherein the cationic lipid has a pKa of from about 5.8 to about 6.1.

The invention comprises the composition of any one or more of paragraph [00712] through paragraph [00715], wherein the composition is optimized by selection of at least one of a stealth lipid, formulation method, N/P ratio, particle size, and molar ratio of the cationic lipid, an optional neutral lipid, helper lipid, stealth lipid and an optional alkyl resorcinol based lipid.

The invention comprises the composition of paragraph [00710], wherein the biologically active agent is for delivery to the liver or a liver cell, the composition comprising a formulation comprising at least one cationic lipid with a pKa of from about 5.1 to about 7.4.

The invention comprises the composition of paragraph [00717], wherein the cationic lipid has a pKa of from about 5.3 to about 7.3.

The invention comprises the composition of paragraph [00717], wherein the cationic lipid has a pKa of from about 5.9 to about 7.0.

The invention comprises the composition of paragraph [00717], wherein the cationic lipid has a pKa of from about 6.2 to about 6.8.

The invention comprises the composition of any one or more of paragraph [00717] through paragraph [00720], wherein the composition is optimized by selection of at least one of a stealth lipid, formulation method, N/P ratio, particle size, and molar ratio of the cationic lipid, an optional neutral lipid, helper lipid, stealth lipid and an optional alkyl resorcinol based lipid.

The invention comprises the composition of paragraph [00716], wherein the pKa of the cationic lipid is from about 5.4 to about 5.9 for delivery to Hep3B-like tumors.

The invention comprises the composition of paragraph [00716], wherein the pKa of the cationic lipid is from about 5.6 to about 6.1 for delivery to HepG2-like and 786-0-like tumors.

The invention comprises a method for the treatment of a disease or condition comprising the step of administering a therapeutically effective amount of a composition of any of paragraphs [00707] to [00723] to a patient in need thereof.

The invention comprises the method of paragraph [00724] wherein the disease or condition is a tumor, a disease of the liver, or a disease that is responsive to treatment with an RNAi construct.

The invention comprises the method of paragraph [00724] wherein the disease or condition is a tumor and the cationic lipid in the composition has a pKa of from about 5.0 to about 6.7.

The invention comprises the method of paragraph [00724] wherein the disease or condition is in the liver, and the cationic lipid in the composition has a pKa of from about 5.1 to about 7.4.

The invention comprises a compound of formula (I):

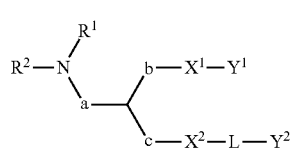

(I)

or a salt or pharmaceutically acceptable derivative thereof, wherein:
 $R^1$ and $R^2$ together with the nitrogen atom to which they are attached form an optionally substituted $C_{3-20}$-heterocycloalkyl, $C_{3-20}$-heterocycloalkenyl, $C_{3-20}$-heterocycloalkynyl or $C_{5-20}$-heteroaryl group;
 a is absent or optionally substituted $C_{1-4}$ alkylene;
 b is absent or optionally substituted $C_{1-4}$ alkylene;
 c is absent or optionally substituted $C_{1-4}$ alkylene;
 $X^1$ is O or S;
 $X^2$ is O or S;
 $Y^1$ is optionally substituted $C_{10-30}$alkenyl, $C_{10-30}$alkynyl, $C_{10-30}$heteroalkenyl or $C_{10-30}$heteroalkynyl;
 L is absent or —$(L^a)_d$—$(L^b)_e$—$(L^c)_f$—, wherein
  $L^a$ is optionally substituted $C_{1-15}$alkylene, $C_{1-15}$alkenylene, $C_{1-15}$alkynylene, $C_{1-15}$heteroalkylene, $C_{1-15}$heteroalkenylene or $C_{1-15}$heteroalkynylene;
  $L^b$ is optionally substituted $C_{6-14}$arylene or $C_{5-13}$heteroarylene;
  $L^c$ is optionally substituted $C_{1-15}$alkylene, $C_{1-15}$alkenylene, $C_{1-15}$alkynylene, $C_{1-15}$heteroalkylene, $C_{1-15}$heteroalkenylene or $C_{1-15}$heteroalkynylene;
  d is 0 or 1;
  e is 0 or 1; and
  f is 0 or 1; and
 $Y^2$ is an optionally substituted steroid.

The invention comprises the compound of paragraph [00728], wherein a is selected from optionally substituted $C_{1-2}$alkylene and optionally substituted $C_1$ alkylene.

The invention comprises the compound of paragraphs [00728] or [00729], wherein b is selected from optionally substituted $C_{0-2}$alkylene and optionally substituted $C_1$ alkylene.

The invention comprises the compound of any one of paragraphs [00728] to [00730], wherein c is absent or is optionally substituted $C_1$ alkylene.

The invention comprises the compound of any one of paragraphs [00728] to [00731], wherein a, b and c are unsubstituted.

The invention comprises the compound of any one of paragraphs [00728] to [00732], wherein $R^1$ and $R^2$ together with the nitrogen atom to which they are attached form an optionally substituted $C_{3-20}$-heterocycloalkyl, $C_{3-20}$-heterocycloalkenyl or $C_{3-20}$-heterocycloalkynyl group.

The invention comprises the compound of any one of paragraphs [00728] to [00733], wherein $R^1$ and $R^2$ together with the nitrogen atom to which they are attached form a compound selected from a cyclic optionally substituted $C_{5-16}$ group and a cyclic optionally substituted $C_{5-12}$ group.

The invention comprises the compound of paragraph [00734], wherein $R^1$ and $R^2$ together with the nitrogen atom to which they are attached form a cyclic optionally substituted $C_5$ group, $C_6$ group or $C_7$ group.

The invention comprises the compound of any one of paragraphs [00728] to [00735], wherein $R^1$ and $R^2$ together with the nitrogen atom to which they are attached are selected from at least one of the head groups $H^1$ to $H^{52}$.

The invention comprises the compound of any one of paragraphs [00728] to [00736], wherein $X^1$ is O.

The invention comprises the compound of any one of paragraphs [00728] to [00737], wherein $X^2$ is O.

The invention comprises the compound of any one of paragraphs [00728] to [00738], wherein L comprises at least one heteroatom.

The invention comprises the compound of paragraph [00739], wherein L comprises at least one O atom.

The invention comprises the compound of any one of paragraphs [00728] to [00740], wherein $L^c$ is selected from one of formulae $L^{c-i}$ to $L^{c-xxxxiii}$:

| | |
|---|---|
| $L^{c-i}$ | —(CH$_2$)$_2$O(CH$_2$)$_2$— |
| $L^{c-ii}$ | —(CH$_2$)$_4$— |
| $L^{c-iii}$ | —CO(CH$_2$)$_2$CO— |
| $L^{c-iv}$ | —CO— |
| $L^{c-v}$ | —COCH$_2$OCH$_2$CO— |
| $L^{c-vi}$ | —(CH$_2$)$_2$O(CH$_2$)$_2$NHCO— |
| $L^{c-vii}$ | —(CH$_2$)$_3$O(CH$_2$)$_3$— |
| $L^{c-viii}$ | —(CH$_2$)$_2$— |
| $L^{c-ix}$ | —(CH$_2$)$_2$O(CH$_2$)$_2$O(CH$_2$)$_2$O(CH$_2$)$_2$— |
| $L^{c-x}$ | —(CH$_2$)$_2$O(CH$_2$)$_2$O(CH$_2$)$_2$— |
| $L^{c-xi}$ | 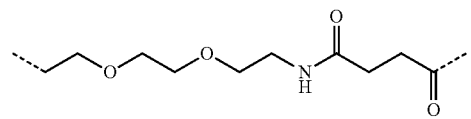 |
| $L^{c-xii}$ | 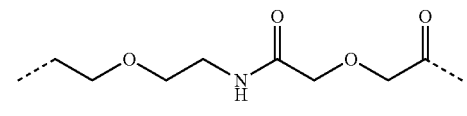 |
| $L^{c-xiii}$ | 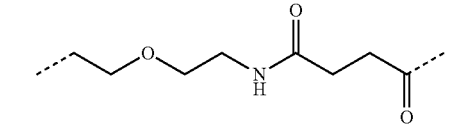 |
| $L^{c-xiv}$ | 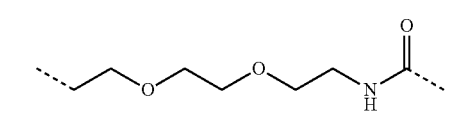 |
| $L^{c-xv}$ | —(CH$_2$)$_2$O(CH$_2$)$_2$OCH(CH$_3$)— |
| $L^{c-xvi}$ | —(CH$_2$)$_2$O(CH$_2$)$_2$OC(=O)(CH$_2$)$_2$CO— |
| $L^{c-xvii}$ | —(CH$_2$)$_2$OC(=O)(CH$_2$)$_2$CO— |
| $L^{c-xviii}$ | —(CH$_2$)$_2$O(CH$_2$)$_2$OCO— |
| $L^{c-xix}$ | —(CH$_2$)$_2$NHC(=O)CH$_2$OCH$_2$C(=O)— |
| $L^{c-xx}$ | —(CH$_2$)$_2$NHC(=O)(CH$_2$)$_2$C(=O)— |
| $L^{c-xxi}$ | —(CH$_2$)$_2$NHC(=O)— |
| $L^{c-xxii}$ | —(CH$_2$)$_2$NHC(=O)CH$_2$NHC(=O)— |

| | |
|---|---|
| $L^{c\text{-}xxiii}$ | —(CH$_2$)$_2$NHC(=O)CH(side-chain-1)NHC(=O)—, 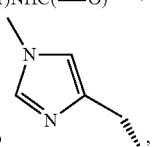 wherein side-chain-1 represents the group the dashed line representing the bond to the rest of the molecule; |
| $L^{c\text{-}xxiv}$ | —(CH$_2$)$_2$OC(=O)— |
| $L^{c\text{-}xxv}$ | —(CH$_2$)$_2$O(CH$_2$)$_2$OC(=O)CH$_2$— |
| $L^{c\text{-}xxvi}$ | —(CH$_2$)$_2$OC(=O)CH$_2$— |
| $L^{c\text{-}xxvii}$ | —(CH$_2$)$_2$OC(=O)CH$_2$NHC(=O)— |
| $L^{c\text{-}xxviii}$ | —(CH$_2$)$_2$OC(=O)(CH$_2$)$_2$NHC(=O)— |
| $L^{c\text{-}xxix}$ | 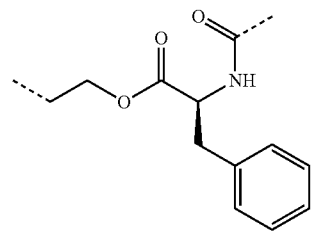 |
| $L^{c\text{-}xxx}$ | 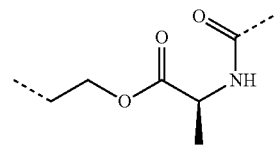 |
| $L^{c\text{-}xxxi}$ | 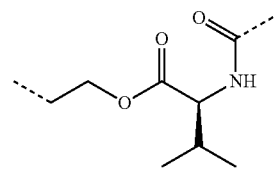 |
| $L^{c\text{-}xxxii}$ | 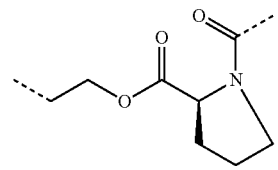 |
| $L^{c\text{-}xxxiii}$ | 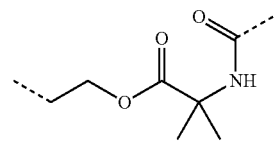 |
| $L^{c\text{-}xxxiv}$ | 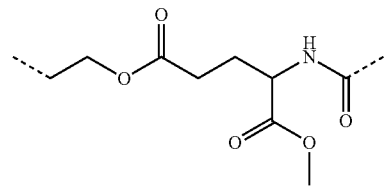 |
| $L^{c\text{-}xxxv}$ | 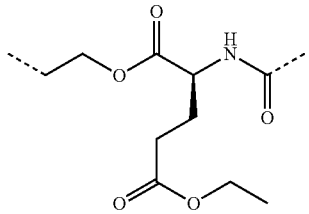 |
| $L^{c\text{-}xxxvi}$ | —(CH$_2$)$_2$OCO$_2$(CH$_2$)$_2$— |
| $L^{c\text{-}xxxvii}$ | —(CH$_2$)$_2$OC(=O)CH$_2$OCH$_2$C(=O)— |
| $L^{c\text{-}xxxviii}$ | —(CH$_2$)$_2$OC(=O)(CH$_2$)$_3$C(=O)— |
| $L^{c\text{-}xxxix}$ | —(CH$_2$)$_3$OC(=O)(CH$_2$)$_2$C(=O)— |
| $L^{c\text{-}xxxx}$ | 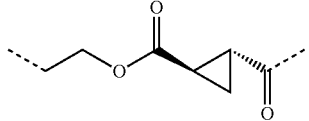 |
| $L^{c\text{-}xxxxi}$ | 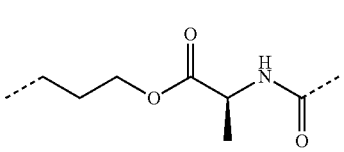 |
| $L^{c\text{-}xxxxii}$ | —(CH$_2$)$_2$OCH$_2$C(=O)— |
| $L^{c\text{-}xxxxiii}$ | 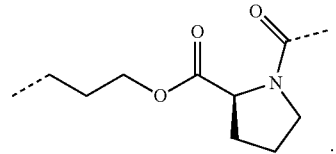 |

The invention comprises the compound of any one of paragraphs [00728] to [00741], wherein d is 0; e is 0, and f is 1.

The invention comprises the compound of any one of paragraphs [00728] to [00742], wherein $Y^1$ is a $C_{12\text{-}28}$ group.

The invention comprises the compound of any one of paragraphs [00728] to [00743], wherein $Y^1$ has at least one alkene group.

The invention comprises the compound of paragraph [00744], wherein $Y^1$ has at least one cis unsaturated alkene group.

The invention comprises the compound of any one of paragraphs [00728] to [00742], wherein $Y^1$ is selected from $Y^{1\text{-}i}$ to $Y^{1\text{-}vii}$.

The invention comprises the compound of any one of paragraphs [00728] to [00746], wherein $Y^2$ is linked to L via an oxygen atom on the optionally substituted steroid.

The invention comprises the compound of paragraph [00747], wherein $Y^2$ is a sterol in which the hydrogen atom of the hydroxy group at the 3-position of the A steroid ring has been removed.

The invention comprises the compound of paragraph [00747], wherein the sterol is selected from the group consisting of: annasterol; avenasterol; beta-sitosterol; brassicasterol; calciferol; campesterol; chalinosterol; chinasterol; cholestanol; cholesterol; coprostanol; cycloartenol; dehydrocholesterol; desmosterol; dihydrocalciferol; dihydrocholesterol; dihydroergosterol; dinosterol; epicholesterol; ergosterol; fucosterol; hexahydrolumisterol; hexaol; hydroxycholesterol; lanosterol; lumisterol; parkeol; poriferasterol; saringosterol; sitostanol; sitosterol; stigmastanol; stigmasterol; weinbersterol; zymosterol; sterol bile acids (including one or more selected from cholic acid; chenodeoxycholic acid; glycocholic acid; taurocholic acid; deoxycholic acid, and lithocholic acid); and/or a salt or a pharmaceutically acceptable derivative thereof.

The invention comprises the compound of paragraph [00749], wherein the sterol is cholesterol.

The invention comprises the compound of paragraph [00728] comprising formula (II):

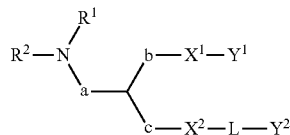

or a salt or pharmaceutically acceptable derivative thereof, wherein:
- $R^1$ and $R^2$ together with the nitrogen atom to which they are attached form an optionally substituted $C_{3-20}$-heterocycloalkyl, $C_{3-20}$-heterocycloalkenyl, $C_{3-20}$-heterocycloalkynyl or $C_{5-20}$-heteroaryl group;
- a is absent or optionally substituted $C_{1-4}$ alkylene;
- b is absent or optionally substituted $C_{1-4}$ alkylene;
- c is absent or optionally substituted $C_{1-4}$ alkylene;
- $X^1$ is O or S;
- $X^2$ is O or S;
- $Y^1$ is optionally substituted $C_{10-30}$alkenyl, $C_{10-30}$alkynyl, $C_{10-30}$heteroalkenyl or $C_{10-30}$heteroalkynyl;
- L is $—(L^a)_d—(L^b)_e—(L^c)_f—$, wherein
  - $L^a$ is optionally substituted $C_{1-15}$alkylene, $C_{1-15}$alkenylene, $C_{1-15}$alkynylene, $C_{1-15}$heteroalkylene, $C_{1-15}$heteroalkenylene or $C_{1-15}$heteroalkynylene;
  - $L^b$ is optionally substituted $C_{6-14}$arylene or $C_{5-13}$heteroarylene;
  - $L^c$ is optionally substituted $C_{1-15}$alkylene, $C_{1-15}$alkenylene, $C_{1-15}$alkynylene, $C_{1-15}$heteroalkylene, $C_{1-15}$heteroalkenylene or $C_{1-15}$heteroalkynylene;
  - d is 0 or 1;
  - e is 0 or 1; and
  - f is 0 or 1;
- provided that L comprises one or more heteroatoms, and $Y^2$ is an optionally substituted steroid.

The invention comprises the compound of paragraph [00728] comprising formula (III):

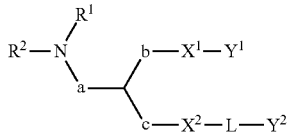

or a salt or pharmaceutically acceptable derivative thereof, wherein:
- $R^1$ and $R^2$ together with the nitrogen atom to which they are attached form an optionally substituted $C_{3-20}$-heterocycloalkyl, $C_{3-20}$-heterocycloalkenyl, $C_{3-20}$-heterocycloalkynyl or $C_{5-20}$-heteroaryl group;
- a is methylene;
- b is methylene;
- c is absent;
- $X^1$ is O or S;
- $X^2$ is O or S;
- $Y^1$ is optionally substituted $C_{10-30}$alkenyl, $C_{10-30}$alkynyl, $C_{10-30}$heteroalkenyl or $C_{10-30}$heteroalkynyl;
- L is $—(L^a)_d—(L^b)_e—(L^c)_f—$, wherein
  - $L^a$ is optionally substituted $C_{1-15}$alkylene, $C_{1-15}$alkenylene, $C_{1-15}$alkynylene, $C_{1-15}$heteroalkylene, $C_{1-15}$heteroalkenylene or $C_{1-15}$heteroalkynylene;
  - $L^b$ is optionally substituted $C_{6-14}$arylene or $C_{5-13}$heteroarylene;
  - $L^c$ is optionally substituted $C_{1-15}$alkylene, $C_{1-15}$alkenylene, $C_{1-15}$alkynylene, $C_{1-15}$heteroalkylene, $C_{1-15}$heteroalkenylene or $C_{1-15}$heteroalkynylene;
  - d is 0 or 1;
  - e is 0 or 1; and
  - f is 0 or 1; and
- $Y^2$ is an optionally substituted steroid.

The invention comprises the compound of paragraph [00728] comprising formula (IV):

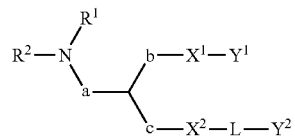

or a salt or pharmaceutically acceptable derivative thereof, wherein:
- $R^1$ and $R^2$ together with the nitrogen atom to which they are attached form an optionally substituted $C_{3-20}$-heterocycloalkyl, $C_{3-20}$-heterocycloalkenyl, $C_{3-20}$-heterocycloalkynyl or $C_{5-20}$-heteroaryl group;
- a is methylene;
- b is methylene;
- c is absent;
- $X^1$ is O or S;
- $X^2$ is O or S;
- $Y^1$ is optionally substituted $C_{10-30}$alkenyl, $C_{10-30}$alkynyl, $C_{10-30}$heteroalkenyl or $C_{10-30}$heteroalkynyl;
- L is $—(L^a)_d—(L^b)_e—(L^c)_f—$, wherein
  - $L^a$ is optionally substituted $C_{1-15}$alkylene, $C_{1-15}$alkenylene, $C_{1-15}$alkynylene, $C_{1-15}$heteroalkylene, $C_{1-15}$heteroalkenylene or $C_{1-15}$heteroalkynylene;
  - $L^b$ is optionally substituted $C_{6-14}$arylene or $C_{5-13}$heteroarylene;
  - $L^c$ is optionally substituted $C_{1-15}$alkylene, $C_{1-15}$alkenylene, $C_{1-15}$alkynylene, $C_{1-15}$heteroalkylene, $C_{1-15}$heteroalkenylene or $C_{1-15}$heteroalkynylene;
  - d is 0 or 1;
  - e is 0 or 1; and
  - f is 0 or 1;
- provided that L comprises one or more heteroatoms, and $Y^2$ is an optionally substituted steroid.

The invention comprises the compound of paragraph [00728] comprising formula (V):

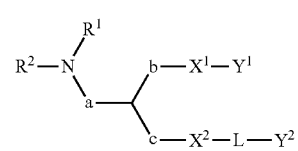

or a salt or pharmaceutically acceptable derivative thereof, wherein:
R$^1$ and R$^2$ together with the nitrogen atom to which they are attached form an optionally substituted C$_{3-20}$-heterocycloalkyl, C$_{3-20}$-heterocycloalkenyl, C$_{3-20}$-heterocycloalkynyl or C$_{5-20}$-heteroaryl group;
a is methylene;
b is methylene;
c is absent;
X$^1$ is O;
X$^2$ is O;
Y$^1$ is optionally substituted C$_{10-30}$alkenyl, C$_{10-30}$alkynyl, C$_{10-30}$heteroalkenyl or C$_{10-30}$heteroalkynyl;
L is —(L$^a$)$_d$—(L$^b$)$_e$—(L$^c$)$_f$—, wherein
L$^a$ is optionally substituted C$_{1-15}$alkylene, C$_{1-15}$alkenylene, C$_{1-15}$alkynylene, C$_{1-15}$heteroalkylene, C$_{1-15}$heteroalkenylene or C$_{1-15}$heteroalkynylene;
L$^b$ is optionally substituted C$_{6-14}$arylene or C$_{5-13}$heteroarylene;
L$^c$ is optionally substituted C$_{1-15}$alkylene, C$_{1-15}$alkenylene, C$_{1-15}$alkynylene, C$_{1-15}$heteroalkylene, C$_{1-15}$heteroalkenylene or C$_{1-15}$heteroalkynylene;
d is 0 or 1;
e is 0 or 1; and
f is 0 or 1;
provided that L comprises one or more heteroatoms, and Y$^2$ is an optionally substituted steroid.

The invention comprises the compound of paragraph [00728] comprising formula (VI):

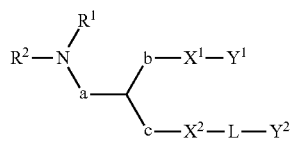

(VI)

or a salt or pharmaceutically acceptable derivative thereof, wherein:
R$^1$ and R$^2$ together with the nitrogen atom to which they are attached form an optionally substituted C$_{3-20}$-heterocycloalkyl, C$_{3-20}$-heterocycloalkenyl, C$_{3-20}$-heterocycloalkynyl or C$_{5-20}$-heteroaryl group;
a is methylene;
b is methylene;
c is absent;
X$^1$ is O;
X$^2$ is O;
Y$^1$ is optionally substituted C$_{10-30}$alkenyl, C$_{10-30}$alkynyl, C$_{10-30}$heteroalkenyl or C$_{10-30}$heteroalkynyl;
L is —L$^c$—, wherein
L$^c$ is optionally substituted C1-15heteroalkylene, C1-15heteroalkenylene or C1-15heteroalkynylene; and
Y$^2$ is an optionally substituted steroid.

The invention comprises the compound of paragraph [00728] comprising formula (VII):

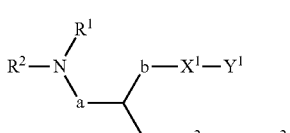

(VII)

or a salt or pharmaceutically acceptable derivative thereof, wherein:
R$^1$ and R$^2$ together with the nitrogen atom to which they are attached form an optionally substituted C$_{3-20}$-heterocycloalkyl, C$_{3-20}$-heterocycloalkenyl, C$_{3-20}$-heterocycloalkynyl or C$_{5-20}$-heteroaryl group;
a is methylene;
b is methylene;
c is absent;
X$^1$ is O;
X$^2$ is O;
Y$^1$ is an optionally substituted C$_{16-22}$ alkenyl group;
L is —L$^c$—, wherein
L$^c$ is optionally substituted C$_{1-15}$heteroalkylene, C$_{1-15}$heteroalkenylene or C$_{1-15}$heteroalkynylene; and
Y$^2$ is an optionally substituted steroid.

The invention comprises the compound of paragraph [00728] comprising formula (VIII):

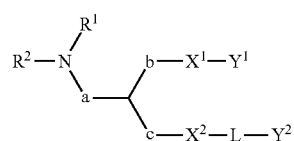

(VIII)

or a salt or pharmaceutically acceptable derivative thereof, wherein:
R$^1$ and R$^2$ together with the nitrogen atom to which they are attached form an optionally substituted C$_{3-20}$-heterocycloalkyl, C$_{3-20}$-heterocycloalkenyl, C$_{3-20}$-heterocycloalkynyl or C$_{5-20}$-heteroaryl group;
a is methylene;
b is methylene;
c is absent;
X$^1$ is O;
X$^2$ is O;
Y$^1$ is an optionally substituted C$_{16-22}$ alkenyl group;
L is —L$^c$—, wherein
L$^c$ is optionally substituted C$_{1-15}$heteroalkylene, C$_{1-15}$heteroalkenylene or C$_{1-15}$heteroalkynylene; and
Y$^2$ is cholesterol connected through the hydroxy group at the 3-position of the A steroid ring, the hydrogen atom of said hydroxy group being absent.

The invention comprises the compound of paragraph [00728] comprising formula (IX):

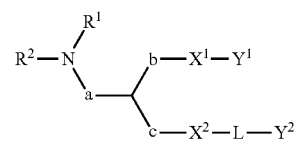

(IX)

or a salt or pharmaceutically acceptable derivative thereof, wherein:
R$^1$ and R$^2$ together with the nitrogen atom to which they are attached form an optionally substituted C$_{3-20}$-heterocycloalkyl, C$_{3-20}$-heterocycloalkenyl, C$_{3-20}$-heterocycloalkynyl or C$_{5-20}$-heteroaryl group;
a is methylene;
b is methylene;
c is absent;
X$^1$ is O or S;

$X^2$ is O or S;

$Y^1$ is optionally substituted $C_{10-30}$alkenyl, $C_{10-30}$alkynyl, $C_{10-30}$heteroalkenyl or $C_{10-30}$heteroalkynyl;

L is $—(L^a)_d—(L^b)_e—(L^c)_f—$, wherein $L^a$ is optionally substituted $C_{1-15}$alkylene, $C_{1-15}$alkenylene, $C_{1-15}$alkynylene, $C_{1-15}$heteroalkylene, $C_{1-15}$heteroalkenylene or $C_{1-15}$heteroalkynylene;

$L^b$ is optionally substituted $C_{6-14}$arylene or $C_{5-13}$heteroarylene;

$L^c$ is optionally substituted $C_{1-15}$alkylene, $C_{1-15}$alkenylene, $C_{1-15}$alkynylene, $C_{1-15}$heteroalkylene, $C_{1-15}$heteroalkenylene or $C_{1-15}$heteroalkynylene;

d is 0 or 1;

e is 0 or 1; and f is 0 or 1;

provided that L comprises one or more heteroatoms, and $Y^2$ is an optionally substituted steroid; and wherein the pKa of the compound is from about 5.1 to about 7.4.

The invention comprises the compound of paragraph [00728] comprising formula (X):

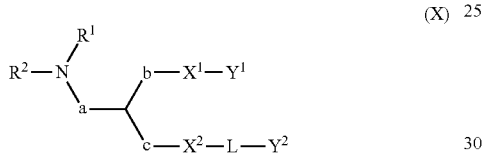

(X)

or a salt or pharmaceutically acceptable derivative thereof, wherein:

$R^1$ and $R^2$ together with the nitrogen atom to which they are attached form an optionally substituted $C_{3-20}$-heterocycloalkyl, $C_{3-20}$-heterocycloalkenyl, $C_{3-20}$-heterocycloalkynyl or $C_{5-20}$-heteroaryl group;

a is methylene;

b is methylene;

c is absent;

$X^1$ is O or S;

$X^2$ is O or S;

$Y^1$ is optionally substituted $C_{10-30}$alkenyl, $C_{10-30}$alkynyl, $C_{10-30}$heteroalkenyl or $C_{10-30}$heteroalkynyl;

L is $—(L^a)_d—(L^b)_e—(L^c)_f—$, wherein $L^a$ is optionally substituted $C_{1-15}$alkylene, $C_{1-15}$alkenylene, $C_{1-15}$alkynylene, $C_{1-15}$heteroalkylene, $C_{1-15}$heteroalkenylene or $C_{1-15}$heteroalkynylene;

$L^b$ is optionally substituted $C_{6-14}$arylene or $C_{5-13}$heteroarylene;

$L^c$ is optionally substituted $C_{1-15}$alkylene, $C_{1-15}$alkenylene, $C_{1-15}$alkynylene, $C_{1-15}$heteroalkylene, $C_{1-15}$heteroalkenylene or $C_{1-15}$heteroalkynylene;

d is 0 or 1;

e is 0 or 1; and f is 0 or 1;

provided that L comprises one or more heteroatoms, and $Y^2$ is an optionally substituted steroid; and wherein the pKa of the compound is from about 5.0 to about 6.7.

The invention comprises a compound of any one of formulas I through X in paragraphs [00728] through [00759], wherein the compound is selected from any one or more of E0001-E0171 and E0175-E0180.

The invention comprises a stealth lipid of formula (XI)

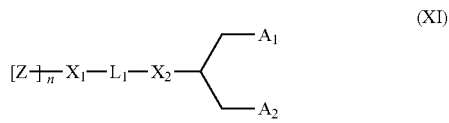

(XI)

or a salt or pharmaceutically acceptable derivative thereof, wherein

Z is a hydrophilic head group component selected from PEG and polymers based on poly(oxazoline), poly(ethylene oxide), poly(vinyl alcohol), poly(glycerol), poly(N-vinylpyrrolidone), poly[N-(2-hydroxypropyl)methacrylamide] and poly(amino acid)s, wherein the polymer may be linear or branched, and wherein the polymer may be optionally substituted;

wherein Z is polymerized by n subunits;

n is a number-averaged degree of polymerization between 10 and 200 units of Z, wherein n is optimized for different polymer types;

$L_1$ is an optionally substituted $C_{1-10}$ alkylene or $C_{1-10}$heteroalkylene linker including zero, one, two or more of an ether (e.g., —O—), ester (e.g., —C(O)O—), succinate (e.g., —O(O)C—$CH_2$—$CH_2$—C(O)O—)), carbamate (e.g., —OC(O)—NR'—), carbonate (e.g., —OC(O)O—), ketone (e.g., —C—C(O)—C—), carbonyl (e.g., —C(O)—), urea (e.g., —NRC(O)NR'—), amine (e.g., —NR'—), amide (e.g., —C(O)NR'—), imine (e.g., —C(NR')—), thioether (e.g., —S—), xanthate (e.g., —OC(S)S—), and phosphodiester (e.g., —OP(O)$_2$O—); any of which may be substituted by zero, one or more Z groups;

wherein R' is independently selected from H, —NH—, —O—, —S—, a phosphate or an optionally substituted $C_{1-10}$ alkylene;

$X_1$ and $X_2$ are independently selected from a carbon or a heteroatom selected from —NH—, —O—, —S— or a phosphate;

$A_1$ and $A_2$ are independently selected from a $C_{6-30}$ alkyl, $C_{6-30}$ alkenyl, and $C_{6-30}$ alkynyl, wherein $A_1$ and $A_2$ may be the same or different, or wherein $A_1$ and $A_2$ together with the carbon atom to which they are attached form an optionally substituted steroid.

The invention comprises the stealth lipid of paragraph [00761] comprising formula (XII)

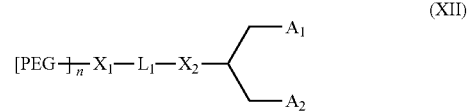

(XII)

or a salt or pharmaceutically acceptable derivative thereof, wherein

PEG is a poly(ethylene glycol) subunit, wherein the PEG may be linear or branched;

n is a number-averaged degree of polymerization between 10 and 200 units of PEG, preferably about 23 units, about 45 units or about 68 units;

$L_1$ is an optionally substituted $C_{1-10}$ heteroalkylene linker containing one, two or more of an ether, ester, succinate, carbamate, carbonate, ketone, carbonyl, urea, amine, amide, imine, thioether, xanthate, and phosphodiester; any of which may be substituted by zero, one or more PEG groups;

$X_1$ and $X_2$ are independently selected from carbon or oxygen;

$A_1$ and $A_2$ are independently selected from a $C_{6-30}$ alkyl, $C_{6-30}$ alkenyl, and $C_{6-30}$ alkynyl, wherein $A_1$ and $A_2$ may be the same or different, or wherein $A_1$ and $A_2$ together with the carbon atom to which they are attached form an optionally substituted steroid.

The invention comprises a compound of any one of paragraphs [00761] and [00762], wherein the compound is selected from any one or more of S001 though S009 and S012 through S026.

The invention comprises the compound of any one of paragraphs [00728] to [00760], wherein the pKa of the compound is from about 5.1 to about 7.4, for use in a formulation for delivery of a biologically active agent to the liver or a liver cell.

The invention comprises the compound of any one of paragraphs [00728] to [00760], wherein the pKa of the compound is about 6.2 or above, for use in a formulation for delivery of a biologically active agent to the liver or a liver cell.

The invention comprises the compound of paragraph [00765], wherein the pKa of the compound is from about 5.9 to about 7.0, for use in a formulation for delivery of a biologically active agent to the liver or a liver cell.

The invention comprises the compound of any one of paragraphs [00728] to [00760], wherein the pKa of the compound is from about 5.0 to about 6.7, for use in a formulation for delivery of a biologically active agent to a tumor or a tumor cell.

The invention comprises the compound of any one of paragraphs [00728] to [00760], wherein the pKa of the compound is from about 5.4 to about 6.2, for use in a formulation for delivery of a biologically active agent to a tumor or a tumor cell.

The invention comprises the compound of any one of paragraphs [00728] to [00760], wherein the pKa of the compound is about 6.2 or below, for use in a formulation for delivery of a biologically active agent to a tumor or a tumor cell.

The invention comprises the compound of any of paragraphs [00728] to [00769] for use in a formulation for delivery of a biologically active agent for therapy.

The invention comprises a composition comprising one or more compounds of any one of paragraphs [00728] to [00770] for use in a formulation for delivery of a biologically active agent for therapy.

The invention comprises the composition of paragraph [00771] further comprising at least one additional lipid component in addition to the compound of any one of paragraphs [00728] to [00770].

The invention comprises the composition of any one of paragraphs [00707] to [00723] and paragraph [00772] comprising a lipid formulation comprising one or more lipid components, wherein the lipid component is selected from the group consisting of one or more of a cationic lipid, an optional neutral lipid, a helper lipid, a stealth lipid and an optional alkyl resorcinol based lipid.

The invention comprises the composition of paragraph [00773], wherein the stealth lipid is selected from a stealth lipid of formula XI or formula XII.

The invention comprises the composition of paragraph [00773], wherein the composition is optimized for at least one parameter including but not limited to individual selection of the pKa of the cationic lipid optimized for the type of cell or organ being targeted, the cationic lipid used, the stealth lipid used, the helper lipid, the neutral lipid used, whether the neutral lipid is present or absent, the ratio of the selected helper lipid, optional neutral lipid, stealth lipid and cationic lipid, the N/P ratio, the particle size, the dosage regiment, the dose given, the formulation method, and the like.

The invention comprises the composition of any one of paragraphs [00707] to [00723] and paragraphs [00771] to [00775], further comprising a biologically active agent.

The invention comprises the composition of paragraph [00776] wherein said biologically active agent is selected from the group consisting of antibodies, cholesterol, hormones, antivirals, peptides, polypeptides, proteins, nucleoproteins, chemotherapeutics, low molecular weight drugs, vitamins, co-factors, nucleosides, nucleoside derivatives, nucleotides, oligonucleotides, enzymatic nucleic acids, antisense nucleic acids, triplex forming oligonucleotides, 2,5-A antisense chimeras, allozymes, aptamers, decoy RNA molecules and analogs thereof, and small nucleic acid molecules, such as an RNA interfering agent (RNAi), short interfering nucleic acid (siNA), short interfering RNA (siRNA), double-stranded RNA (dsRNA), micro-RNA (miRNA), and short hairpin RNA (shRNA).

The invention comprises the composition of paragraph [00777] wherein said biologically active agent is a nucleoside or nucleoside derivative.

The invention comprises the composition of paragraph [00778] wherein said biologically active agent is selected from an RNAi, an siNA, an RNAi inhibitor, a miRNA, an siRNA and a shRNA.

The invention comprises the composition of paragraph [00773], wherein the cationic lipid is selected from one or more of the cationic lipids of E0007, E0008, E0011, E0014, E0015, E0016, E0017, E0018, E0019, E0022, E0024, E0025, E0026, E0032, E0034, E0040, E0042, E0043, E0045, E0048, E0049, E0051, E0052, E0053, E0054, E0055 and E0118.

The invention comprises the composition of paragraph [00773], wherein the cationic lipid is selected from the cationic lipids of E0008, E0011, E0025, E0026, E0075, E0076, E0077, E0085, E0088, E0095, E0104, E0178 and E0179.

The invention comprises the composition of paragraph [00773], the composition comprising at least one cationic lipid selected from E0008, E0011, E0025, E0026, E0075, E0076, E0077, E0085, E0088, E0095, E0104, E0178 and E0179.

The invention comprises the composition of paragraph [00773], the composition comprising at least one cationic lipid selected from E0011, E0025, E0026, E0075, E0076, E0077 and E0088.

The invention comprises the composition of paragraph [00773], wherein the stealth lipid is selected from the stealth lipids of S001, S002, S003, S004, S005, S006, S007, S008, S009, S010, S011, S012, S013, S014, S015, S016, S017, S018, S019, S020, S021, S022, S023, S024, S025 and S026.

The invention comprises any one or more of the above compounds, formulations and/or compositions, which further comprises a pharmaceutically acceptable carrier.

The invention comprises a kit comprising any one or more of the above compounds, formulations and compositions, and instructions for use.

The invention comprises a method for the treatment of a disease or condition in a subject in need thereof, the method comprising the step of administering a therapeutically effective amount of a biologically active agent in a formulation comprising one or more compositions of any of paragraphs [00707] to [00723] and paragraphs [00771] to [00784].

The invention comprises a method for delivering a biologically active agent to a cell or tissue, which method comprises administering the composition of any one of paragraphs [00707] to [00723] and paragraphs [00771] to [00784] to the cell or tissue.

The invention comprises the method of paragraph [00788] wherein the disease or condition is a tumor, a disease of the liver, or a disease that is responsive to treatment with an RNAi construct.

The invention comprises the method of paragraph [00788] wherein the disease or condition is a tumor and the cationic lipid in the composition has a pKa of from about 5.0 to about 6.7.

The invention comprises the method of paragraph [00788] wherein the disease or condition is a tumor and the cationic lipid in the composition has a pKa of from about 6.2 or below.

The invention comprises the method of paragraph [00788] wherein the disease or condition is a tumor and the cationic lipid in the composition has a pKa of from about 5.0 to about 6.7.

The invention comprises the method of paragraph [00788] wherein the disease or condition is in the liver, and the cationic lipid in the composition has a pKa of from about 5.1 to about 7.4.

The invention comprises the method of paragraphs [00787] to [00793] wherein said biologically active agent is selected from the group consisting of antibodies, cholesterol, hormones, antivirals, peptides, polypeptides, proteins, nucleoproteins, chemotherapeutics, low molecular weight drugs, vitamins, co-factors, nucleosides, nucleoside derivatives, nucleotides, oligonucleotides, enzymatic nucleic acids, antisense nucleic acids, triplex forming oligonucleotides, 2,5-A antisense chimeras, allozymes, aptamers, decoy RNA molecules and analogs thereof, and small nucleic acid molecules, such as an RNA interfering agent (RNAi), short interfering nucleic acid (siNA), short interfering RNA (siRNA), double-stranded RNA (dsRNA), micro-RNA (miRNA), and short hairpin RNA (shRNA).

The invention comprises the method of paragraph [00794] wherein said biologically active agent is a nucleoside or nucleoside derivative.

The invention comprises the method of paragraph [00795] wherein said biologically active agent is selected from an RNAi, an siNA, an RNAi inhibitor, a miRNA, an siRNA and a shRNA.

Unless defined otherwise, the technical and scientific terms used herein have the same meaning as that usually understood by a specialist familiar with the field to which the invention belongs.

Unless indicated otherwise, it is assumed that all other methods, steps, techniques and manipulations that are not specifically described in detail can be performed and have been performed in a manner known to the skilled person. Reference is e.g., made to the standard handbooks and the general background art and to the further references cited therein.

Claims to the invention are non-limiting and are provided below.

Although particular embodiments and claims have been disclosed herein in detail, this has been done by way of example for purposes of illustration only, and is not intended to be limiting with respect to the scope of the appended claims, or the scope of subject matter of claims of any corresponding future application. In particular, it is contemplated by the inventors that various substitutions, alterations, and modifications may be made to the invention without departing from the spirit and scope of the invention as defined by the claims. The choice of starting material, biological material of interest, or liposome assembly method is believed to be a matter of routine for a person of ordinary skill in the art with knowledge of the embodiments described herein. Other aspects, advantages, and modifications considered to be within the scope of the following claims. Redrafting of claim scope in later filed corresponding applications may be due to limitations by the patent laws of various countries and should not be interpreted as giving up subject matter of the claims.

Table of Sequences

| SEQ ID NO: | Sequence (5' to 3') | Type |
|---|---|---|
| 1 | UUu AAU UGA AAC cAA GAc Auu | Artificial |
| 2 | uGu cuu GGu uuc AAu uAA Auu | Artificial |
| 3 | UAU UUA AgG AGG GUG AuC Uuu | Artificial |
| 4 | AGA Uca cCC Ucc uuA AAU auu | Artificial |

We claim:

1. A stealth lipid of formula (XI)

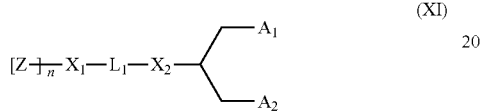

or a salt or pharmaceutically acceptable derivative thereof, wherein:

Z is a hydrophilic head group component selected from PEG and polymers based on poly(oxazoline), poly(ethyleneoxide), poly(vinyl alcohol), poly(glycerol), poly(N-vinylpyrrolidone), poly[N-(2-hydroxypropyl)methacrylamide] and poly(amino acid)s, wherein the polymer may be linear or branched, and wherein the polymer may be optionally substituted;

wherein Z is polymerized by n subunits;

n is a number-averaged degree of polymerization between 10 and 200 units of Z, wherein n is optimized for different polymer types;

$L_1$ is an optionally substituted $C_{1-10}$ heteroalkylene linker including one, two or more of an ester (e.g., —C(O)O—), succinate (e.g., —O(O)C—$CH_2$—$CH_2$—C(O)O—)), carbamate (e.g., —OC(O)—NR'—), carbonate (e.g., —OC(O)O—), ketone (e.g., —C—C(O)—C—), carbonyl (e.g., —C(O)—), urea (e.g., —NRC(O)NR'—), amine (e.g., —NR'—), amide (e.g., —C(O)NR'—), imine (e.g., —C(NR')—), thioether (e.g., —S—), xanthate (e.g., —OC(S)S—), and phosphodiester (e.g., —OP(O)$_2$O—); any of which may be substituted by zero, one or more Z groups;

wherein R' is independently selected from —H, —NH—, —$NH_2$, —O—, —S—, a phosphate or an optionally substituted $C_{1-10}$ alkylene;

$X_1$ and $X_2$ are independently selected from a carbon or a heteroatom selected from —NH—, —O—, —S— or a phosphate; and $A_1$ and $A_2$ are independently selected from a $C_{6-30}$ alkyl, $C_{6-30}$ alkenyl, and $C_{6-30}$ alkynyl, wherein $A_1$ and $A_2$ may be the same or different.

2. The stealth lipid, or a salt or pharmaceutically acceptable derivative thereof, according to claim 1, is of formula (XII)

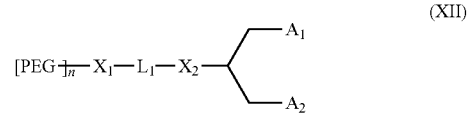

wherein

PEG is a poly(ethylene glycol) subunit, wherein the PEG may be linear or branched;

n is a number-averaged degree of polymerization between 10 and 200 units of PEG;

$L_1$ is an optionally substituted $C_{1-10}$ heteroalkylene linker containing one, two or more of an ester, succinate, carbamate, carbonate, ketone, carbonyl, urea, amine, amide, imine, thioether, xanthate, and phosphodiester; any of which may be substituted by zero, one or more PEG groups;

$X_1$ and $X_2$ are independently selected from carbon or oxygen; and $A_1$ and $A_2$ are independently selected from a $C_{6-30}$ alkyl, $C_{6-30}$ alkenyl, and $C_{6-30}$ alkynyl, wherein $A_1$ and $A_2$ may be the same or different.

3. The stealth lipid, or a salt or pharmaceutically acceptable derivative thereof, according to claim 1 or claim 2, wherein the stealth lipid is selected from:

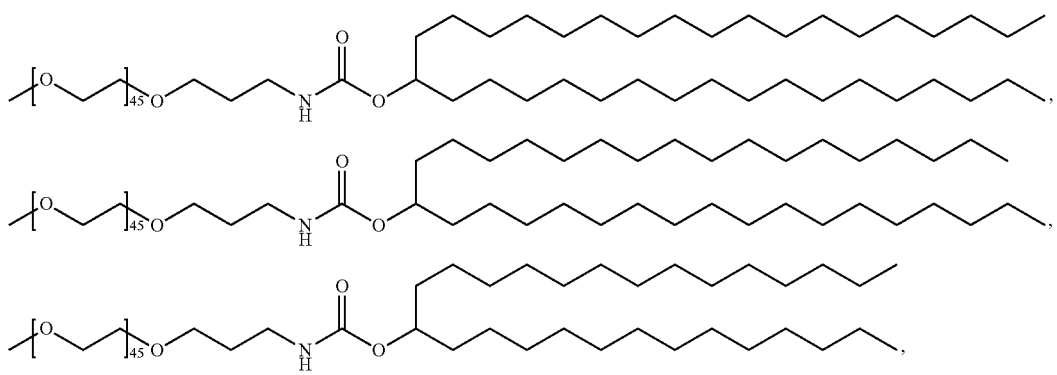

-continued
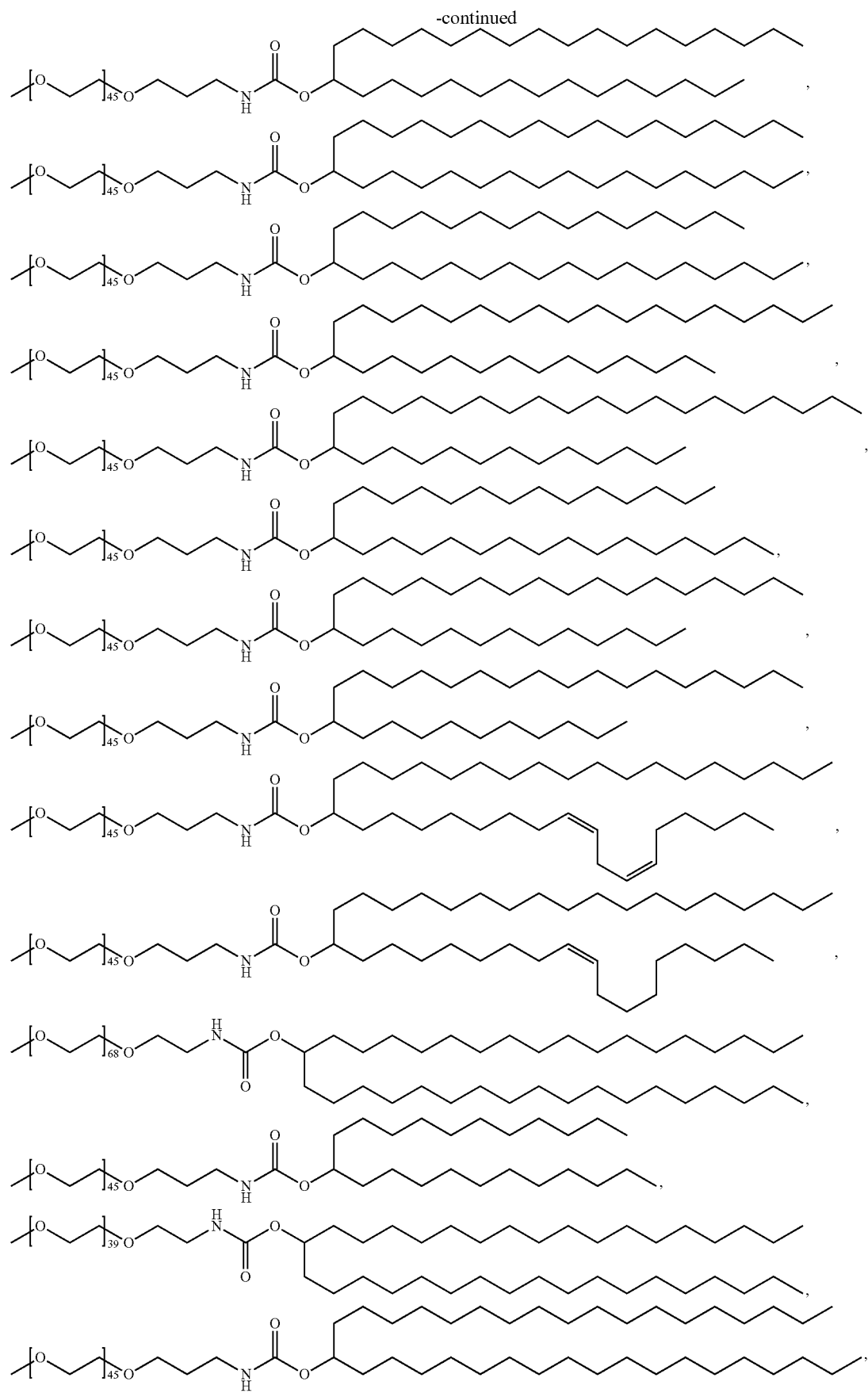

-continued

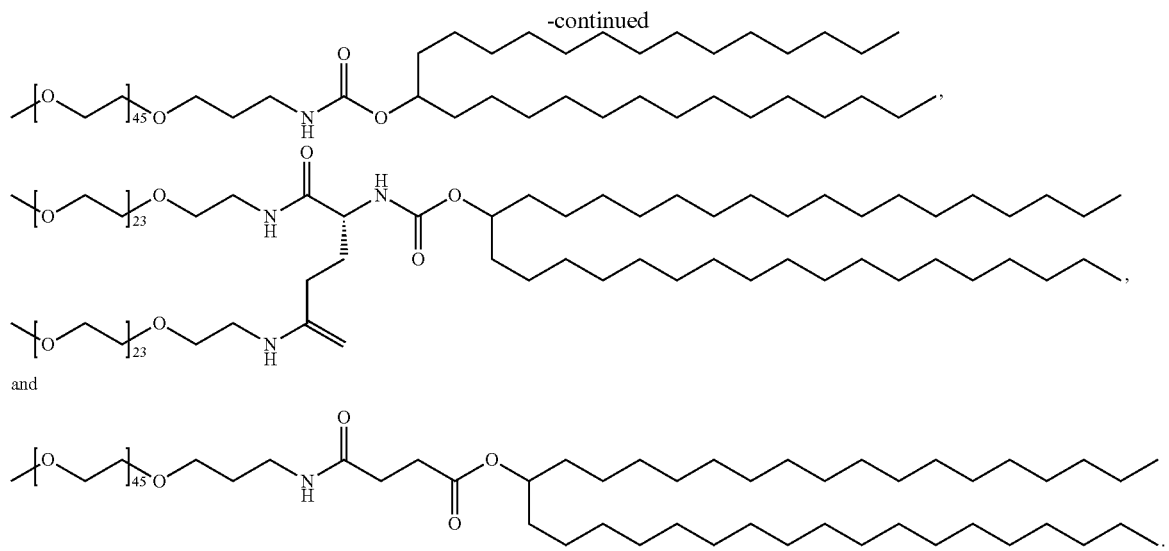

and

4. The stealth lipid, or a salt or pharmaceutically acceptable derivative thereof, according to claim 1 or claim 2, wherein the stealth lipid is

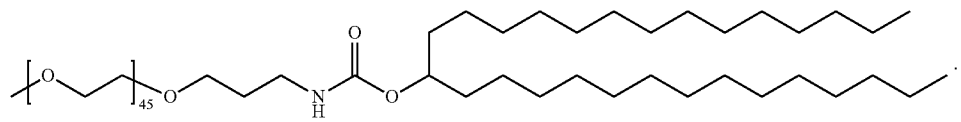

5. A method for the treatment of a disease or condition comprising the step of administering a therapeutically effective amount of a stealth lipid according to claim 1 to a patient in need thereof.

6. The method of claim 5 wherein the disease or condition is a cancer, a disease of the liver, or a disease that is responsive to treatment with an RNAi construct.

7. A method for the treatment of a disease or condition in a subject in need thereof, the method comprising the step of administering a therapeutically effective amount of a biologically active agent in a formulation comprising a stealth lipid according to claim 1 or claim 2.

8. The method of claim 7 wherein the disease or condition is a tumor, a disease of the liver, or a disease that is responsive to treatment with an RNAi construct.

* * * * *